(12) United States Patent
Chamberlain et al.

(10) Patent No.: US 7,338,959 B2
(45) Date of Patent: Mar. 4, 2008

(54) DIAMINO-PYRIMIDINES AND THEIR USE AS ANGIOGENESIS INHIBITORS

(75) Inventors: Stanley Dawes Chamberlain, Durham, NC (US); Mui Cheung, Durham, NC (US); Holly Kathleen Emerson, Durham, NC (US); Neil W. Johnson, Collegeville, PA (US); Kristen Elizabeth Nailor, Durham, NC (US); Douglas McCord Sammond, Durham, NC (US); Marcus Semones, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 473 days.

(21) Appl. No.: 10/506,447

(22) PCT Filed: Feb. 28, 2003

(86) PCT No.: PCT/US03/06022

§ 371 (c)(1),
(2), (4) Date: Sep. 1, 2004

(87) PCT Pub. No.: WO03/074515

PCT Pub. Date: Sep. 12, 2003

(65) Prior Publication Data

US 2005/0234083 A1    Oct. 20, 2005

Related U.S. Application Data

(60) Provisional application No. 60/360,741, filed on Mar. 1, 2002.

(51) Int. Cl.
*C07D 239/48* (2006.01)
*C07D 403/12* (2006.01)
*C07D 403/14* (2006.01)
*A61K 31/506* (2006.01)
*A61K 31/4184* (2006.01)
*A61P 35/00* (2006.01)

(52) U.S. Cl. .................. 514/275; 544/323; 544/324
(58) Field of Classification Search ................ 544/323, 544/324; 514/275
See application file for complete search history.

(56) References Cited

FOREIGN PATENT DOCUMENTS

| WO | 97/19065 | 5/1997 |
|----|----------|--------|
| WO | 00/12089 | 3/2000 |
| WO | 02/59110 | 8/2002 |

OTHER PUBLICATIONS

West, Anthony R., Solid State Chemistry and its Applications, Wiley, New York, 1988, pp. 358 & 365.*
Vippagunta et al., Advanced Drug Delivery Reveiws 48: 3-26, 2001.*
Sennlaub et al., The Journal of Clinical Investigation 107(6): 717-725, 2001.*
Connell et al. Exp. Opin. Ther. Patents (2001) 11(1):77-144, especially p. 109 closing paragraph.*
Klement et al., The Journal of Clinical Investigation 105(8): R15-R24, 2000.*

* cited by examiner

*Primary Examiner*—Venkataraman Balasubramanian
(74) *Attorney, Agent, or Firm*—John L. Lemanowicz; Jennifer L. Fox

(57) ABSTRACT

Benzimidazole derivatives, which are useful as TIE-2 and/or VEGFR-2 inhibitors are described herein. The described invention also includes methods of making such benzimidazole derivatives as well as methods of using the same in the treatment of hyperproliferative diseases.

33 Claims, No Drawings

DIAMINO-PYRIMIDINES AND THEIR USE AS ANGIOGENESIS INHIBITORS

This application is filed pursuant to 35 U.S.C. § 371 as a United States National Phase Application of International Application No. PCT/US03/06022 filed Feb. 28, 2003, which claims priority from U.S. 60/360,741 filed Mar. 1, 2002.

BACKGROUND OF THE INVENTION

The present invention relates to benzimidazole derivatives, compositions and medicaments containing the same, as well as processes for the preparation and use of such compounds, compositions and medicaments. Such benzimidazole derivatives are useful in the treatment of diseases associated with inappropriate angiogenesis.

The process of angiogenesis is the development of new blood vessels, generally capillaries, from pre-existing vasculature. Angiogenesis is defined as involving (i) activation of endothelial cells; (ii) increased vascular permeability; (iii) subsequent dissolution of the basement membrane and extravisation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and (vii) deposition of basement membrane and recruitment of perivascular cells to newly formed vessels. Normal angiogenesis is activated during tissue growth, from embryonic development through maturity, and then enters a period of relative quiescence during adulthood. Normal angiogensesis is also activated during wound healing, and at certain stages of the female reproductive cycle. Inappropriate angiogenesis has been associated with several disease states including various retinopathies; ischemic disease; atherosclerosis; chronic inflammatory disorders; and cancer. The role of angiogenesis in disease states is discussed, for instance, in Fan et al, Trends in Pharmacol Sci. 16: 54-66; Shawver et al, DDT Vol. 2, No. 2 Feb. 1997; Folkmann, 1995, Nature Medicine 1:27-31.

In cancer, the growth of solid tumors has been shown to be angiogenesis dependent. (See Folkmann, J., J. Nat'l. Cancer Inst., 1990, 82, 4-6.) Consequently, the targeting of pro-angiogenic pathways in cancer treatment is a strategy being widely pursued in order to provide new therapeutics in these areas of great, unmet medical need. The role of tyrosine kinases involved in angiogenesis and in the vascularization of solid tumors has drawn interest. Until recently most interest in this area has focused on growth factors such as vascular endothelial growth factor (VEGF) and its receptors termed vascular endothelial growth factor receptor(s) (VEGFR). VEGF, a polypeptide, is mitogenic for endothelial cells in vitro and stimulates angiogenic responses in vivo. VEGF has also been linked to inappropriate angiogenesis (Pinedo, H. M. et al The Oncologist, Vol. 5, No. 90001, 1-2, Apr. 2000). VEGFR(s) are protein tyrosine kinases (PTKs). PTKs catalyze the phosphorylation of specific tyrosyl residues in proteins involved in the regulation of cell growth and differentiation. (A. F. Wilks, Progress in Growth Factor Research, 1990, 2, 97-111; S. A. Courtneidge, Dev. Supp.l, 1993, 57-64; J. A. Cooper, Semin. Cell Biol., 1994, 5(6), 377-387; R. F. Paulson, Semin. Immunol., 1995, 7(4), 267-277; A. C. Chan, Curr. Opin. Immunol., 1996, 8(3), 394-401).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. et al J. Cell Biol. 1995:129:895-898). Of particular interest is VEGFR-2, which is a transmembrane receptor PTK expressed primarily in endothelial cells. Activation of VEGFR-2 by VEGF is a critical step in the signal transduction pathway that initiates tumor angiogenesis. VEGF expression may be constitutive to tumor cells and can also be upregulated in response to certain stimuli. One such stimuli is hypoxia, where VEGF expression is upregulated in both tumor and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3-10, Apr. 2000).

Angiopoieten 1 (Ang1), a ligand for the endothelium-specific receptor tyrosine kinase TIE-2, is a novel angiogenic factor (Davis et al, Cell, 1996, 87:1161-1169; Partanen et al, Mol. Cell Biol, 12:1698-1707 (1992); U.S. Pat. Nos. 5,521,073; 5,879,672; 5,877,020; and 6,030,831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of an EGF-like domain and an immunoglobulin (IG) like domain, which consists of extracellular folding units, stabilized by intra-chain disulfide bonds (Partanen et al Curr. Topics Microbiol. Immunol., 1999, 237:159-172). Unlike VEGF, which functions during the early stages of vascular development, Ang1 and its receptor TIE-2 function in the later stages of vascular development, i.e., during vascular remodeling (remodeling refers to formation of a vascular lumen) and maturation (Yancopoulos et al, Cell, 1998, 93:661-664; Peters, K. G., Circ. Res., 1998, 83(3): 342-3; Suri et al, Cell 87, 1171-1180 (1996)).

Consequently, inhibition of TIE-2 would be expected to serve to disrupt remodeling and maturation of new vasculature initiated by angiogenesis thereby disrupting the angiogenic process. Furthermore, inhibition at the kinase domain binding site of VEGFR-2 would block phosphorylation of tyrosine residues and serve to disrupt initiation of angiogenesis. Presumably then, inhibition of TIE-2 and/or VEGFR-2 should prevent tumor angiogenesis and serve to retard or eradicate tumor growth. Accordingly, a treatment for cancer or other disorders associated with inappropriate angiogenesis could be provided.

The present inventors have discovered novel benzimidazole compounds, which are inhibitors of TIE-2 and/or VEGFR-2 kinase activity. Such benzimidazole derivatives are useful in the treatment of disorders, including cancer, associated with inappropriate angiogenesis.

BRIEF SUMMARY OF THE INVENTION

In one aspect of the present invention, there is provided a compound of Formula (I):

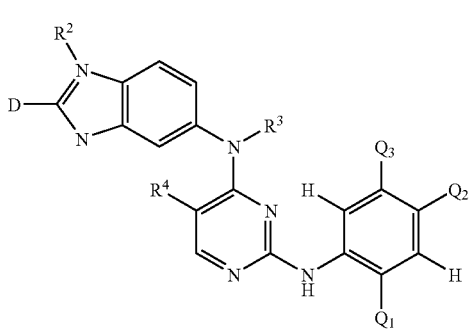 (I)

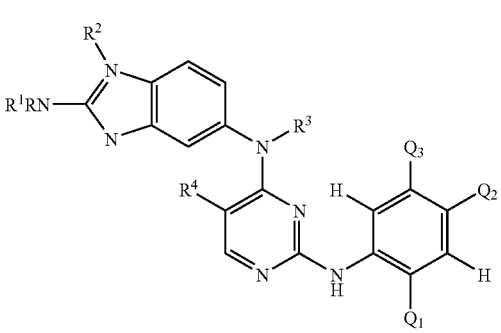 (II)

or a salt, solvate, or physiologically functional derivative thereof:

wherein:

D is —NRR$^1$, —OR, —SR, —S(O)R, or —S(O)$_2$R;

R is hydrogen, $C_1$-$C_8$ alkyl, $C_3$-$C_7$ cycloalkyl, aralkyl, aryl, heteroaryl, —C(O)NR$^1$R$^1$, —C(O)OR$^1$, acyl, aroyl, or heteroaroyl;

R$^1$ is hydrogen, $C_1$-$C_8$ alkyl, $C_3$-$C_7$ cycloalkyl, aralkyl, or aryl;

R$^2$ is $C_1$-$C_6$ alkyl or $C_3$-$C_7$ cycloalkyl;

R$^3$ is hydrogen, $C_1$-$C_4$ alkyl, $C_1$-$C_4$ haloalkyl, aralkyl, cyanoalkyl, —(CH$_2$)$_p$C=CH(CH$_2$)$_t$H, —(CH$_2$)$_p$C≡C(CH$_2$)$_t$H, or $C_3$-$C_7$ cycloalkyl;

p is 1, 2, or 3;

t is 0 or 1;

R$^4$ is hydrogen, halo, or cyano;

Q$_1$ is hydrogen, halo, $C_1$-$C_2$ haloalkyl, $C_1$-$C_2$ alkyl, $C_1$-$C_2$ alkoxy, or $C_1$-$C_2$ haloalkoxy;

Q$_2$ is A$^1$ or A$^2$;

Q$_3$ is A$^1$ when Q$_2$ is A$^2$ and Q$_3$ is A$^2$ when Q$_2$ is A$^1$;

wherein

A$^1$ is hydrogen, halo, $C_1$-$C_3$ alkyl, $C_1$-$C_3$ haloalkyl, —OR$^5$, and

A$^2$ is the group defined by -(Z)$_m$-(Z$^1$)-(Z$^2$), wherein

Z is CH$_2$ and m is 0, 1, 2, or 3, or

Z is NR$^5$ and m is 0 or 1, or

Z is oxygen and m is 0 or 1, or

Z is CH$_2$NR$^6$ and m is 0 or 1;

Z$^1$ is S(O)$_2$, S(O), or C(O); and

Z$^2$ is $C_1$-$C_4$ alkyl, cycloalkyl, heterocyclyl, —NR$_8$R$^9$, aryl, arylamino, aralkyl, aralkoxy, or heteroaryl;

R$^5$ and R$^6$ are each independently selected from hydrogen, hydroxyl, alkoxy, aryloxy, aralkoxy, $C_1$-$C_4$ alkyl, $C_3$-$C_7$ cycloalkyl, heterocyclyl, —S(O)$_2$R$^7$, or —C(O)R$^7$;

R$^7$ is $C_1$-$C_4$ alkyl, or $C_3$-$C_7$ cycloalkyl;

R$^8$ is hydrogen, hydroxyl, $C_1$-$C_6$ alkyl, $C_1$-$C_6$ alkoxy, aryloxy, aralkoxy, $C_3$-$C_7$ cycloalkyl, or $C_3$-$C_7$ cycloalkoxy; and R$^9$ is hydrogen, $C_1$-$C_6$ alkyl, $C_3$-$C_7$ cycloalkyl, aryl, acyl, carbamoyl, or heterocyclyl.

In a second aspect of the present invention, there is provided a compound of Formula (II):

or a salt, solvate, or physiologically functional derivative thereof:

wherein:

R is hydrogen, $C_1$-$C_8$ alkyl, $C_3$-$C_7$ cycloalkyl, aralkyl, aryl, heteroaryl, —C(O)NR$^1$R$^1$, —C(O)OR$^1$, acyl, aroyl, or heteroaroyl;

R$^1$ is hydrogen, $C_1$-$C_8$ alkyl, $C_3$-$C_7$ cycloalkyl, aralkyl, or aryl;

R$^2$ is $C_1$-$C_6$ alkyl or $C_3$-$C_7$ cycloalkyl;

R$^3$ is hydrogen, $C_1$-$C_4$ alkyl, $C_1$-$C_4$ haloalkyl, aralkyl, cyanoalkyl, —(CH$_2$)$_p$C=CH(CH$_2$)$_t$H, —(CH$_2$)$_p$C≡C(CH$_2$)$_t$H, or $C_3$-$C_7$ cycloalkyl;

p is 1, 2, or 3;

t is 0 or 1;

R$^4$ is hydrogen, halo, or cyano;

Q$_1$ is hydrogen, halo, $C_1$-$C_2$ haloalkyl, $C_1$-$C_2$ alkyl, $C_1$-$C_2$ alkoxy, or $C_1$-$C_2$ haloalkoxy;

Q$_2$ is A$^1$ or A$^2$;

Q$_3$ is A$^1$ when Q$_2$ is A$^2$ and Q$_3$ is A$^2$ when Q$_2$ is A$^1$;

wherein

A$^1$ is hydrogen, halo, $C_1$-$C_3$ alkyl, $C_1$-$C_3$ haloalkyl, —OR$^5$, and

A$^2$ is the group defined by -(Z)$_m$-(Z$^1$)-(Z$^2$), wherein

Z is CH$_2$ and m is 0, 1, 2, or 3, or

Z is NR$^5$ and m is 0 or 1, or

Z is oxygen and m is 0 or 1, or

Z is CH$_2$NR$^6$ and m is 0 or 1;

Z$^1$ is S(O)$_2$, S(O), or C(O); and

Z$^2$ is $C_1$-$C_4$ alkyl, cycloalkyl, heterocyclyl, —NR$^8$R$^9$, aryl, arylamino, aralkyl, aralkoxy, or heteroaryl;

R$^5$ and R$^6$ are each independently selected from hydrogen, hydroxyl, alkoxy, aryloxy, aralkoxy, $C_1$-$C_4$ alkyl, $C_3$-$C_7$ cycloalkyl, heterocyclyl, —S(O)$_2$R$^7$, or —C(O)R$^7$;

R$^7$ is $C_1$-$C_4$ alkyl, or $C_3$-$C_7$ cycloalkyl;

R$^8$ is hydrogen, hydroxyl, $C_1$-$C_6$ alkyl, $C_1$-$C_6$ alkoxy, aryloxy, aralkoxy, $C_3$-$C_7$ cycloalkyl, or $C_3$-$C_7$ cycloalkoxy; and R$^9$ is hydrogen, $C_1$-$C_6$ alkyl, $C_3$-$C_7$ cycloalkyl, aryl, acyl, carbamoyl, or heterocyclyl.

In a third aspect of the present invention, there is provided a pharmaceutical composition comprising a therapeutically effective amount of a compound of formula (I) or a salt, solvate, or a physiologically functional derivative thereof and one or more of pharmaceutically acceptable carriers, diluents and excipients.

In a fourth aspect of the present invention, there is provided a method of treating a disorder in a mammal, said disorder being mediated by at least one of inappropriate TIE-2 and VEGFR-2 activity, comprising: administering to said mammal a therapeutically effective amount of a compound of formula (I) or a salt, solvate or a physiologically functional derivative thereof.

In a fifth aspect of the present invention, there is provided a compound of formula (I), or a salt, solvate, or a physiologically functional derivative thereof for use in therapy.

In a sixth aspect of the present invention, there is provided the use of a compound of formula (I), or a salt, solvate, or a physiologically functional derivative thereof in the preparation of a medicament for use in the treatment of a disorder mediated by at least one of inappropriate TIE-2 and VEGFR-2 activity.

In a seventh aspect of the present invention, there is provided a method of treating a disorder in a mammal, said disorder being mediated by at least one of inappropriate TIE-2 and VEGFR-2 activity, comprising: administering to said mammal therapeutically effective amounts of (i) a compound of formula (I), or a salt, solvate or physiologically functional derivative thereof and (ii) an agent to inhibit growth factor receptor function.

In an eighth aspect of the present invention, there is provided a method of treating a disorder in a mammal, said disorder being characterized by inappropriate angiogenesis, comprising: administering to said mammal a therapeutically effective amount of a compound of formula (I), or a salt, solvate or physiologically functional derivative thereof.

DETAILED DESCRIPTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight or branched chain hydrocarbon radical having from one to twelve carbon atoms, optionally substituted with substituents selected from the group consisting of $C_1$-$C_6$ alkyl, $C_1$-$C_6$ hydroxyalkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aryl, aryloxy, heteroaryl, aminosulfonyl optionally substituted by alkyl, nitro, cyano, halogen, or $C_1$-$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the terms "$C_1$-$C_3$ alkyl", "$C_1$-$C_4$ alkyl", "$C_1$-$C_6$ alkyl" and "$C_1$-$C_8$ alkyl" refer to an alkyl group, as defined above, containing at least 1, and at most 3, 4, 6, or 8, carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, n-hexyl, and n-septyl.

As used herein, the term "alkylene" refers to a straight or branched chain divalent hydrocarbon radical having from one to ten carbon atoms, optionally substituted with substituents selected from the group which includes $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and $C_1$-$C_6$ perfluoroalkyl, multiple degrees of substitution being allowed. Examples of "alkylene" as used herein include, but are not limited to, methylene, ethylene, n-propylene, n-butylene, and the like.

As used herein, the term "$C_1$-$C_3$ alkylene" refers to an alkylene group, as defined above, which contains at least 1, and at most 3, carbon atoms respectively. Examples of "$C_1$-$C_3$ alkylene" groups useful in the present invention include, but are not limited to, methylene, ethylene, and n-propylene.

As used herein, the term "halogen" refers to fluorine (F), chlorine (Cl), bromine (Br), or iodine (I) and the term "halo" refers to the halogen radicals fluoro (—F), chloro (—Cl), bromo (—Br), and iodo (—I).

As used herein, the terms "$C_1$-$C_2$ haloalkyl", "$C_1$-$C_3$ haloalkyl", "$C_1$-$C_4$ haloalkyl", and "$C_1$-$C_6$ haloalkyl" refer to an alkyl group as defined above containing at least 1, and at most 2, 3, 4, or 6, carbon atoms respectively substituted with at least one halo group, halo being as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo.

As used herein, the term "cycloalkyl" refers to a non-aromatic cyclic hydrocarbon ring. In a like manner the term "$C_3$-$C_7$ cycloalkyl" refers to a non-aromatic cyclic hydrocarbon ring having from three to seven carbon atoms and which optionally includes a $C_1$-$C_6$ alkyl linker through which it may be attached. The $C_1$-$C_6$ alkyl group is as defined above. Exemplary "$C_3$-$C_7$ cycloalkyl" groups useful in the present invention include, but are not limited to, cyclopropyl, cyclobutyl, cyclopentyl, cyclohexyl and cycloheptyl.

As used herein, the term "heterocyclic" or the term "heterocyclyl" refers to a three to twelve-membered non-aromatic heterocyclic ring, being saturated or having one or more degrees of unsaturation, containing one or more heteroatom substitutions selected from S, S(O), S(O)$_2$, O, or N, optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or $C_1$-$C_6$ perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, piperidine, piperazine, 2,4-piperazinedione, pyrrolidine, imidazolidine, pyrazolidine, morpholine, thiomorpholine, tetrahydrothiopyran, tetrahydrothiophene, and the like.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino optionally substituted by alkyl or acyl, carboxy, tetrazolyl, carbamoyl optionally substituted by alkyl, aryl, or heteroaryl, aminosulfonyl optionally substituted by alkyl, acyl, aroyl, aroylamino, heteroaroyl, acyloxy, aroyloxy, heteroaroyloxy, alkoxycarbonyl, nitro, cyano, halogen, heteroaryl, heterocyclyl, aryl optionally substituted with aryl, halogen, $C_1$-$C_6$ alkyl, $C_1$-$C_6$ haloalkyl, or $C_1$-$C_6$ alkylsulfonyl, ureido, arylurea, alkylurea, cycloalkylurea, alkylthiourea, aryloxy, or aralkoxy, multiple degrees of substitution being allowed. Examples of "aryl" groups include, but are not limited to, phenyl, 2-naphthyl, 1-naphthyl, biphenyl, as well as substituted derivatives thereof.

As used herein, the term "aralkyl" refers to an aryl or heteroaryl group, as defined herein, attached through a $C_1$-$C_3$ alkylene linker, wherein the $C_1$-$C_3$ alkylene is as defined herein. Examples of "aralkyl" include, but are not limited to, benzyl, phenylpropyl, 2-pyridylmethyl, 3-isoxazolylmethyl, 5-methyl, 3-isoxazolylmethyl, and 2-imidazoyly ethyl.

As used herein, the term "heteroaryl" refers to a monocyclic five to seven membered aromatic ring, or to a fused bicyclic or tricyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl, or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "alkoxy" refers to the group $R_aO$—, where $R_a$ is alkyl as defined above and the term "$C_1$-$C_6$ alkoxy" refers to an alkoxy group as defined herein wherein the alkyl moiety contains at least 1, and at most 6, carbon atoms. Exemplary $C_1$-$C_6$ alkoxy groups useful in the present invention include, but are not limited to, methoxy, ethoxy, n-propoxy, isopropoxy, n-butoxy, and t-butoxy.

As used herein, the term "amino" refers to the group —$NH_2$.

As used herein the term "alkylamino" refers to the group —$NHR_a$ wherein $R_a$ is alkyl as defined above.

As used herein the term "arylamino" refers to the group —$NHR_a$ wherein $R_a$ is aryl as defined above.

As used herein the term "aralkylamino" refers to the group —$NHR_a$ wherein $R_a$ is an aralkyl group as defined above.

As used herein the term "aralkoxy" refers to the group $R_bR_aO$—, where $R_a$ is alkylene and $R_b$ is aryl or heteroaryl all as defined above.

As used herein the term "aryloxy" refers to the group $R_aO$—, where $R_a$ is aryl or heteroaryl both as defined above.

As used herein the term "ureido" refers to the group —$NHC(O)NH_2$.

As used herein, the term "arylurea" refers to the group —$NHC(O)NHR_a$ wherein $R_a$ is aryl as defined above.

As used herein, the term "arylthiourea" refers to the group —$NHC(S)NHR_a$ wherein $R_a$ is aryl as defined above.

As used herein, the term "alkylurea" refers to the group —$NHC(O)NHR_a$ wherein $R_a$ is alkyl as defined above.

As used herein, the term "cycloalkylurea" refers to the group —$NHC(O)NHR_a$ wherein $R_a$ is cycloalkyl as defined above.

As used herein, the term "$C_3$-$C_7$ cycloalkoxy" refers to the group $R_aO$—, where $R_a$ is $C_3$-$C_7$ cycloalkyl as defined above. Exemplary $C_3$-$C_7$ cycloalkoxy groups useful in the present invention include, but are not limited to, cyclobutoxy, and cyclopentoxy.

As used herein, the term "haloalkoxy" refers to the group $R_aO$—, where $R_a$ is haloalkyl as defined above and the term "$C_1$-$C_6$ haloalkoxy" refers to a haloalkoxy group as defined herein wherein the haloalkyl moiety contains at least 1, and at most 6, carbon atoms. Exemplary $C_1$-$C_6$ haloalkoxy groups useful in the present invention include, but is not limited to, trifluoromethoxy.

As used herein, the term "alkylsulfanyl" refers to the group $R_aS$—, where $R_a$ is alkyl as defined above and the term "$C_1$-$C_6$ alkylsulfanyl" refers to an alkylsulfanyl group as defined herein wherein the alkyl moiety contains at least 1, and at most 6, carbon atoms.

As used herein, the term "haloalkylsulfanyl" refers to the group $R_aS$—, where $R_a$ is haloalkyl as defined above and the term "$C_1$-$C_6$ haloalkylsulfanyl" refers to a haloalkylsulfanyl group as defined herein wherein the alkyl moiety contains at least 1, and at most 6, carbon atoms.

As used herein, the term "alkylsulfenyl" refers to the group $R_aS(O)$—, where $R_a$ is alkyl as defined above and the term "$C_1$-$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group $R_aS(O)_2$—, where $R_a$ is alkyl as defined above and the term "$C_1$-$C_6$ alkylsulfonyl" refers to an alkylsulfonyl group as defined herein wherein the alkyl moiety contains at least 1, and at most 6, carbon atoms.

As used herein, the term "alkylsulfonylamino" refers to the group —$NHS(O)_2R_a$ wherein $R_a$ is alkyl as defined above and the term "$C_1$-$C_6$ alkylsulfonylamino" refers to an alkylsulfonylamino group as defined herein wherein the alkyl moiety contains at least 1, and at most 6, carbon atoms.

As used herein, the term "arylsulfonylamino" refers to the group —$NHS(O)_2R_a$ wherein $R_a$ is aryl as defined above.

As used herein, the term "alkylcarboxyamide" refers to the group —$NHC(O)R_a$ wherein $R_a$ is alkyl, amino, or amino substituted with alkyl, aryl or heteroaryl as described above.

As used herein the term "alkylcarboxy" refers to the group —$C(O)R_a$ wherein $R_a$ is alkyl as described above.

As used herein, the term "oxo" refers to the group =O.

As used herein, the term "mercapto" refers to the group —SH.

As used herein, the term "carboxy" refers to the group —C(O)OH.

As used herein, the term "cyano" refers to the group —CN.

As used herein the term "cyanoalkyl" refers to the group —$CNR_a$, wherein $R_a$ is alkyl as defined above. Exemplary "cyanoalkyl" groups useful in the present invention include, but are not limited to, cyanomethyl, cyanoethyl, and cyanoisopropyl.

As used herein, the term "aminosulfonyl" refers to the group —S(O)$_2$NH$_2$.

As used herein, the term "carbamoyl" refers to the group —C(O)NH$_2$.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$— or —SO$_2$—.

As used herein, the term "acyl" refers to the group R$_a$C(O)—, where R$_a$ is alkyl, cycloalkyl, or heterocyclyl as defined herein.

As used herein, the term "aroyl" refers to the group R$_a$C(O)—, where R$_a$ is aryl as defined herein.

As used herein, the term "aroylamino" refers to the group R$_a$C(O)NH—, where R$_a$ is aryl as defined herein.

As used herein, the term "heteroaroyl" refers to the group R$_a$C(O)—, where R$_a$ is heteroaryl as defined herein.

As used herein, the term "alkoxycarbonyl" refers to the group R$_a$OC(O)—, where R$_a$ is alkyl as defined herein.

As used herein, the term "acyloxy" refers to the group R$_a$C(O)O—, where R$_a$ is alkyl, cycloalkyl, or heterocyclyl as defined herein.

As used herein, the term "aroyloxy" refers to the group R$_a$C(O)O—, where R$_a$ is aryl as defined herein.

As used herein, the term "heteroaroyloxy" refers to the group R$_a$C(O)O—, where R$_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted. Also, it is understood that any tautomers and mixtures of tautomers of the compounds of formula (I) are included within the scope of the compounds of formula (I).

It is to be understood that reference to compounds of formula (I) and (II) above, following herein, refers to compounds within the scope of formula (I) and (II) as defined above with respect to D, $Q_1$, $Q_2$, $Q_3$, $A^1$, $A^2$, Z, $Z^1$, $Z^2$, $R_1$, $R^2$, $R^3$, $R^4$, $R_5$, $R^6$, $R^7$, $R^8$, and $R^9$ unless specifically limited otherwise.

In one embodiment, D is —NRR$^1$. In one embodiment, D is —NRR$^1$, wherein R is $C_1$-$C_8$ alkyl, aryl, or aralkyl and R$^1$ is hydrogen. In a preferred embodiment, D is —NRR$^1$, wherein R is methyl, isopropyl, benzyl, or phenyl and R$^1$ is hydrogen. In another embodiment, D is —NRR$^1$, wherein R is hydrogen, $C_1$-$C_8$ alkyl, $C_3$-$C_7$ cycloalkyl. In another embodiment, D is —NRR$^1$, wherein R is $C_3$-$C_7$ cycloalkyl. In a further embodiment, D is —NRR$^1$, wherein R is —C(O)NR$^1$R$^1$. In another embodiment, D is —NRR$^1$, wherein R is C(O)OR$^1$. In still another embodiment, D is —NRR$^1$, wherein R is acyl. In another embodiment, D is —NRR$^1$, wherein R is aroyl. In still another embodiment, D is —NRR$^1$, wherein R is heteroaroyl.

In one embodiment, R$^2$ is $C_1$-$C_8$ alkyl. In a preferred embodiment, R$^2$ is methyl.

In one embodiment, R$^3$ is hydrogen, $C_1$-$C_4$ alkyl, cyanoalkyl, or —(CH$_2$)$_p$C≡C(CH$_2$)$_t$H. In a preferred embodiment, R$^3$ is hydrogen, methyl, ethyl, isopropyl, cyanomethyl, or —(CH$_2$)$_p$C≡C(CH$_2$)$_t$H, wherein p is 1 and t is 0. In a more preferred embodiment, R$^3$ is methyl.

In one embodiment, R$^4$ is hydrogen or halo. In a preferred embodiment, R$^4$ is hydrogen.

In another embodiment, $Q_1$ is hydrogen, halo, $C_1$-$C_2$ alkyl or $C_1$-$C_2$ alkoxy. In a preferred embodiment, $Q_1$ is hydrogen, chloro, methyl, or methoxy.

In one embodiment, $Q_2$ is A$^1$ and $Q_3$ is A$^2$. In an alternative embodiment, $Q_2$ is A$^2$ and $Q_3$ is A$^1$.

In one embodiment, $Q_2$ is A$^2$ and $Q_3$ is A$^1$, wherein A$^1$ is hydrogen, halo, or $C_1$-$C_3$ haloalkyl and A$^2$ is the group defined by -(Z)$_m$-(Z$^1$)-(Z$^2$), wherein Z is CH$_2$ and m is 0 or 1; Z$^1$ is S(O)$_2$; and Z$^2$ is $C_1$-$C_4$ alkyl or NR$_8$R$^9$ and wherein R$^8$ is hydrogen $C_1$-$C_4$alkyl, or alkoxy and R$^9$ is hydrogen, $C_1$-$C_4$alkyl, or alkoxy. In a preferred embodiment, $Q_2$ is A$^2$ and $Q_3$ is A$^1$, wherein A$^1$ is hydrogen or chloro and A$^2$ is the group defined by -(Z)$_m$-(Z$^1$)-(Z$^2$), wherein Z is CH$_2$ and m is 0 or 1; Z$^1$ is S(O)$_2$; and Z$^2$ is methyl or —NH$_2$.

In one embodiment, $Q_2$ is A$^1$ and $Q_3$ is A$^2$, wherein A$^1$ is hydrogen, halo, or $C_1$-$C_3$ alkyl and A$^2$ is the group defined by -(Z)$_m$-(Z$^1$)-(Z$^2$), wherein Z is CH$_2$ and m is 0 or 1; Z$^1$ is S(O)$_2$; and Z$^2$ is $C_1$-$C_4$ alkyl or NR$^8$R$^9$, and wherein R$^8$ is hydrogen $C_1$-$C_4$alkyl, or alkoxy and R$^9$ is hydrogen, $C_1$-$C_4$alkyl, or alkoxy. In a preferred embodiment, $Q_2$ is A$^1$ and $Q_3$ is A$^2$, wherein A$^1$ is hydrogen, methyl, or chloro and A$^2$ is the group defined by -(Z)$_m$-(Z$^1$)-(Z$^2$), wherein Z is CH$_2$ and m is 0 or 1; Z$^1$ is S(O)$_2$; and Z$^2$ is NR$^8$R$^9$, wherein R$^8$ is methoxy and R$^9$ is hydrogen.

In a preferred embodiment, D is —NRR$^1$, wherein R is $C_1$-$C_8$ alkyl, aryl, or aralkyl and R$^1$ is hydrogen; R$^2$ is $C_1$-$C_8$ alkyl. R$^2$ is methyl; R$^3$ is methyl; R$^4$ is hydrogen; $Q_1$ is hydrogen, chloro, methyl, or methoxy; $Q_2$ is A$^2$ and $Q_3$ is A$^1$, wherein A$^1$ is hydrogen or chloro and A$^2$ is the group defined by -(Z)$_m$-(Z$^1$)-(Z$^2$), wherein Z is CH$_2$ and m is 0 or 1; Z$^1$ is S(O)$_2$; and Z$^2$ is methyl or —NH$_2$.

In a preferred embodiment, D is —NRR$^1$, wherein R is C$_1$-C$_8$ alkyl, aryl, or aralkyl and R$^1$ is hydrogen; R$^2$ is C$_1$-C$_8$ alkyl. R$^2$ is methyl; R$^3$ is methyl; R$^4$ is hydrogen; Q$_1$ is hydrogen, chloro, methyl, or methoxy; Q$_2$ is A$^1$ and Q$_3$ is A$^2$, wherein A$^1$ is hydrogen, methyl, or chloro and A$^2$ is the group defined by -(Z)$_m$-(Z$^1$)-(Z$^2$), wherein Z is CH$_2$ and m is 0 or 1; Z$^1$ is S(O)$_2$; and Z$^2$ is NR$^8$R$^9$, wherein R$^8$ is methoxy and R$^9$ is hydrogen.

Specific examples of compounds of the present invention include the following:

N$^2$-Isopropyl-N$^5$,1-dimethyl-N$^5$-[2-({4-[(methylsulfonyl)methyl]phenyl}amino)pyrimidin-4-yl]-1H-benzimidazole-2,5-diamine;

N$^2$-Isopropyl-N$^5$,1-dimethyl-N$^5$-[2-({4-[(methylsulfonyl)methyl]phenyl}amino)pyrimidin-4-yl]-1H-benzimidazole-2,5-diamine;

1-{4-[(4-{Methyl[1-methyl-2-(methylamino)-1H-benzimidazol-5-yl]amino}pyrimidin-2-yl)amino]phenyl}methanesulfonamide;

N$^2$-benzyl-N$^5$,1-dimethyl-N$^5$-[2-({4-[(methylsulfonyl)methyl]phenyl}amino)pyrimidin-4-yl]-1H-benzimidazole-2,5-diamine;

N$^5$,1-Dimethyl-N$^5$-[2-({4-[(methylsulfonyl)methyl]phenyl}amino)pyrimidin-4-yl]-N$^2$-phenyl-1H-benzimidazole-2,5-diamine; and 5-({4-[[2-(Benzylamino)-1-methyl-1H-benzimidazol-5-yl](methyl)amino]pyrimidin-2-yl}amino)-N-methoxy-2-methylbenzenesulfonamide;

or a salt, solvate, or physiologically functional derivative thereof.

Further specific examples of compounds of the present invention include the following:

3-{4-[(2-benzylamino-1-methyl-1H-benzoimidazol-5-yl)-methyl-amino]-pyrimidin-2-ylamino}-benzenesulfonamide;

5-{4-[(2-benzylamino-1-methyl-1H-benzoimidazol-5-yl)-methyl-amino]-pyrimidinylamino}-2-methyl-benzenesulfonamide;

(4-{4-[(2-benzylamino-1-methyl-1H-benzoimidazol-5-yl)-methyl-amino]-pyrimidin-2-ylamino}-phenyl)-methanesulfonamide;

2-(4-{4-[(2-benzylamino-1-methyl-1H-benzoimidazol-5-yl)-methyl-amino]-pyrimidin-2-ylamino}-phenyl)-ethanesulfonic acid methylamide;

3-(4-{[2-(4-fluoro-benzylamino)-1-methyl-1H-benzoimidazol-5-yl]-methyl-amino}-pyrimidin-2-ylamino)-benzenesulfonamide;

5-(4-{[2-(4-fluoro-benzylamino)-1-methyl-1H-benzoimidazol-5-yl]-methyl-amino}-pyrimidin-2-ylamino)-2-methyl-benzenesulfonamide;

N$^2$-(4-fluoro-benzyl)-N$^5$-[2-(4-methanesulfonylmethyl-phenylamino)-pyrimidin-4-yl]-1,N$^5$-dimethyl-1H-benzoimidazole-2,5-diamine;

[4-(4-{[2-(4-fluoro-benzylamino)-1-methyl-1H-benzoimidazol-5-yl]-methyl-amino}-pyrimidin-2-ylamino)-phenyl]-methanesulfonamide;

2-[4-(4-{[2-(4-fluoro-benzylamino)-1-methyl-1H-benzoimidazol-5-yl]-methyl-amino}-pyrimidin-2-ylamino)-phenyl]-ethanesulfonic acid methylamide;

3-(4-{[2-(4-methoxy-benzylamino)-1-methyl-1H-benzoimidazol-5-yl]-methyl-amino}-pyrimidin-2-ylamino)-benzenesulfonamide;

5-(4-{[2-(4-methoxy-benzylamino)-1-methyl-1H-benzoimidazol-5-yl]-methyl-amino}-pyrimidin-2-ylamino)-2-methyl-benzenesulfonamide;

N$^5$-[2-(4-methanesulfonymethyl-phenylamino)-pyrimidin-4-yl]-N$^2$-(4-methoxy-benzyl)-1,N$^5$-dimethyl-1H-benzoimidazole-2,5-diamine;

[4-(4-{[2-(4-methoxy-benzylamino)-1-methyl-1H-benzoimidazol-5-yl]-methyl-amino}-pyrimidin-2-ylamino)-phenyl]-methanesulfonamide;

2-[4-(4-{[2-(4-methoxy-benzylamino)-1-methyl-1H-benzoimidazol-5-yl]-methylamino}-pyrimidin-2-ylamino)-phenyl]-ethanesulfonic acid methylamide;

5-(4-{[2-(3-fluoro-benzylamino)-1-methyl-1H-benzoimidazol-5-yl]-methyl-amino}-pyrimidin-2-ylamino)-2-methyl-benzenesulfonamide;

3-(4-{[2-(3-fluoro-benzylamino)-1-methyl-1H-benzoimidazol-5-yl]-methyl-amino}-pyrimidin-2-ylamino)-benzenesulfonamide;

N$^2$-(3-fluoro-benzyl)-N$^5$-[2-(4-methanesulfonylmethyl-phenylamino)-pyrimidin-4-yl]-1,N$^5$-dimethyl-1H-benzoimidazole-2,5-diamine;

[4-(4-{[2-(3-fluoro-benzylamino)-1-methyl-1H-benzoimidazol-5-yl]-methyl-amino}-pyrimidin-2-ylamino)-phenyl]-methanesulfonamide;

2-[4-(4-{[2-(3-fluoro-benzylamino)-1-methyl-1H-benzoimidazol-5-yl]-methyl-amino}-pyrimidin-2-ylamino)-phenyl]-ethanesulfonic acid methylamide;

3-(4-{[2-(4-chloro-benzylamino)-1-methyl-1H-benzoimidazol-5-yl]-methyl-amino}-pyrimidin-2-ylamino)-benzenesulfonamide;

5-(4-{[2-(4-chloro-benzylamino)-1-methyl-1H-benzoimidazol-5-yl]-methyl-amino}-pyrimidin-2-ylamino)-2-methyl-benzenesulfonamide;

2-[4-(4-{[2-(4-chloro-benzylamino)-1-methyl-1H-benzoimidazol-5-yl]-methyl-amino}-pyrimidin-2-ylamino)-phenyl]-ethanesulfonic acid methylamide;

N$^2$-(4-chloro-benzyl)-N$^5$-[2-(4-methanesulfonylmethyl-phenylamino)-pyrimidin-4-yl]-1,N$^5$-dimethyl-1H-benzoimidazole-2,5-diamine;

3-{4-[(2-benzylamino-1-ethyl-1H-benzoimidazol-5-yl)-methyl-amino]-pyrimidin-2-ylamino}-benzenesulfonamide;

5-{4-[(2-benzylamino-1-ethyl-1H-benzoimidazol-5-yl)-methyl-amino]-pyrimidin-2-ylamino}-2-methyl-benzenesulfonamide;

N$^2$-benzyl-1-ethyl-N$^5$-[2-(4-methanesulfonylmethyl-phenylamino)-pyrimidin-4-yl]-N$^5$-methyl-1H-benzoimidazole-2,5-diamine;

(4-{4-[(2-benzylamino-1-ethyl-1H-benzoimidazol-5-yl)-methyl-amino]-pyrimidin-2-ylamino}-phenyl)-methanesulfonamide;

3-(4-{[2-(2-fluoro-benzylamino)-1-methyl-1H-benzoimidazol-5-yl]-methyl-amino}-pyrimidin-2-ylmethyl)-benzenesulfonamide;

5-(4-{[2-(2-fluoro-benzylamino)-1-methyl-1H-benzoimidazol-5-yl]-methyl-amino}-pyrimidin-2-ylamino)-2-methyl-benzenesulfonamide;

[4-(4-{[2-(2-fluoro-benzylamino)-1-methyl-1H-benzoimidazol-5-yl]-methyl-amino}-pyrimidin-2-ylamino)-phenyl]-methanesulfonamide;

2-(4-{4-[(2-benzylamino-1-ethyl-1H-benzoimidazol-5-yl)-methyl-amino]-pyrimidin-2-ylamino}-phenyl)-ethanesulfonic acid methylamide;

3-(4-{methyl-[1-methyl-2-(1-phenyl-ethylamino)-1H-benzoimidazol-5-yl]-amino}-pyrimidin-2-ylamino)-benzenesulfonamide;

2-methyl-5-(4-{methyl-[1-methyl-2-(1-phenyl-ethylamino)-1H-benzoimidazol-5-yl]-amino}-pyrimidin-2-ylamino)-benzenesulfonamide;

N⁵-[2-(4-methanesulfonylmethyl-phenylamino)-pyrimidin-4-yl]-1,N⁵-dimethyl-N²-(1-phenyl-ethyl)-1H-benzoimidazole-2,5-diamine;

[4-(4-{methyl-[1-methyl-2-(1-phenyl-ethylamino)-1H-benzoimidazol-5-yl]-amino}-pyrimidin-2-ylamino)-phenyl]-methanesulfonamide;

3-(4-{[2-(3-chloro-benzylamino)-1-methyl-1H-benzoimidazol-5-yl]-methyl-amino}-pyrimidin-2-ylamino)-benzenesulfonamide;

3-(4-{[2-(3-chloro-benzylamino)-1-methyl-1H-benzoimidazol-5-yl]-methyl-amino}-pyrimidin-2-ylamino)-benzenesulfonamide;

[4-(4-{[2-(4-chloro-benzylamino)-1-methyl-1H-benzoimidazol-5-yl]-methyl-amino}-pyrimidin-2-ylamino)-phenyl]-methanesulfonamide;

methanesulfonic acid-3-(4-{[2-(4-chloro-benzylamino)-1-methyl-1H-benzoimidazol-5-yl]-methyl-amino}-pyrimidin-2-ylamino)-phenyl ester;

N⁵-{2-[4-(2-methanesulfonyl-ethyl)-phenylamino]-pyrimidin-4-yl}-N²-(4-methoxy-benzyl)-1,N⁵-dimethyl-1H-benzoimidazole-2,5-diamine;

N⁵-{2-[3-(2-methanesulfonyl-ethyl)-phenylamino]-pyrimidin-4-yl}-N²-(4-methoxy-benzyl)-1,N⁵-dimethyl-1H-benzoimidazole-2,5-diamine;

N⁵-{2-[4-(1-methanesulfonyl-ethyl)-phenylamino]-pyrimidin-4-yl}-N²-(4-methoxy-benzyl)-1,N⁵-dimethyl-1H-benzoimidazole-2,5-diamine;

N⁵-[2-(3-methanesulfonylmethyl-phenylamino)-pyrimidin-4-yl]-N²-(4-methoxy-benzyl)-1,N⁵-dimethyl-1H-benzoimidazole-2,5-diamine;

N²-benzyl-N⁵-[2-(3-methanesulfonylmethyl-phenylamino)-pyrimidin-4-yl]-1,N⁵-dimethyl-1H-benzoimidazole-2,5-diamine;

N⁵-[2-(3-methanesulfonylmethyl-phenylamino)-pyrimidin-4-yl]-1,N⁵-dimethyl-N²-(1-phenyl-ethyl)-1H-benzoimidazole-2,5-diamine;

N⁵-{2-[3-(2-methanesulfonyl-ethyl)-phenylamino]-pyrimidin-4-yl}-1,N⁵-dimethyl-N²-(1-phenyl-ethyl)-1H-benzoimidazole-2,5-diamine;

N⁵-{2-[4-(2-methanesulfonyl-ethyl)-phenylamino]-pyrimidin-4-yl}-1,N⁵-dimethyl-N²-(1-phenyl-ethyl)-1H-benzoimidazole-2,5-diamine;

2-methyl-5-(4-{methyl-[1-methyl-2-(4-methyl-benzylamino)-1H-benzoimidazol-5-yl]-amino}-pyrimidin-2-ylamino)-benzenesulfonamide;

N⁵-[2-(4-methanesulfonyl methyl-phenylamino)-pyrimidin-4-yl]-1,N⁵-dimethyl-N²-(4-methyl-benzyl)-1H-benzoimidazole-2,5-diamine;

N⁵-[2-(3-methanesulfonylmethyl-phenylamino)-pyrimidin-4-yl]-1,N⁵-dimethyl-N²-(4-methyl-benzyl)-1H-benzoimidazole-2,5-diamine;

N⁵-{2-[4-(2-methanesulfonyl-ethyl)-phenylamino]-pyrimidin-4-yl}-1,N⁵-dimethyl-N²-(4-methyl-benzyl)-1H-benzoimidazole-2,5-diamine;

N⁵-{2-[3-(2-methanesulfonyl-ethyl)-phenylamino]-pyrimidin-4-yl}-1,N⁵-dimethyl-N²-(4-methyl-benzyl)-1H-benzoimidazole-2,5-diamine; and N⁵-{2-[4-(1-methanesulfonyl-ethyl)-phenylamino]-pyrimidin-4-yl}-1,N⁵-dimethyl-N²-(4-methyl-benzyl)-1H-benzoimidazole-2,5-diamine;

or a salt, solvate, or physiologically functional derivative thereof.

Still further specific examples of compounds of the present invention include the following:

(1-methyl-5-{methyl-[2-(3-sulfamoyl-phenylamino)-pyrimidin-4-yl]-amino}-1H-benzoimidazol-2-yl)-phenyl-carbamic acid tert-butyl ester;

3-{4-[methyl-(1-methyl-2-phenylamino-1H-benzoimidazol-5-yl)-amino]-pyrimidin-2-ylamino}-benzenesulfonamide;

(1-methyl-5-{methyl-[2-(4-methyl-3-sulfamoyl-phenylamino)-pyrimidin-4-yl]-amino}-1H-benzoimidazol-2-yl)-phenyl-carbamic acid tert-butyl ester;

N⁵-[2-(3-methanesulfonyl-4-methyl-phenylamino)-pyrimidin-4-yl]-1,N⁵-dimethyl-N²-phenyl-1H-benzoimidazole-2,5-diamine;

N⁵-[2-(4-methanesulfonylmethyl-phenylamino)-pyrimidin-4-yl]-1,N⁵-dimethyl-N²-phenyl-1H-benzoimidazole-2,5-diamine;

(4-{4-[methyl-(1-methyl-2-phenylamino-1H-benzoimidazol-5-yl)-amino]-pyrimidin-2-ylamino}-phenyl)-methanesulfonamide;

methanesulfonic acid 4-{4-[methyl-(1-methyl-2-phenylamino-1H-benzoimidazol-5-yl)-amino]-pyrimidin-2-ylamino}-phenyl ester;

3-(4-{[2-(4-fluoro-phenylamino)-1-methyl-1H-benzoimidazol-5-yl]-methyl-amino}-pyrimidin-2-ylamino)-benzenesulfonamide;

5-(4-{[2-(4-fluoro-phenylamino)-1-methyl-1H-benzoimidazol-5-yl]-methyl-amino}-pyrimidin-2-ylamino)-2-methyl-benzenesulfonamide;

N²-(4-fluoro-phenyl)-N⁵-[2-(4-methanesulfonylmethyl-phenylamino)-pyrimidin-4-yl]-1,N⁵-dimethyl-1H-benzoimidazole-2,5-diamine;

[4-(4-{[2-(4-fluoro-phenylamino)-1-methyl-1H-benzoimidazol-5-yl]-methyl-amino}-pyrimidin-2-ylamino)-phenyl]-methanesulfonamide;

methanesulfonic acid 4-(4-{[2-(4-fluoro-phenylamino)-1-methyl-1H-benzoimidazol-5-yl]-methyl-amino}-pyrimidin-2-ylamino)-phenyl ester;

methanesulfonic acid 3-(4-{[2-(4-fluoro-phenylamino)-1-methyl-1H-benzoimidazol-5-yl]-methyl-amino}-pyrimidin-2-ylamino)-phenyl ester;

N⁵-[2-(4-methanesulfonylmethyl-phenylamino)-pyrimidin-4-yl]-1,N⁵-dimethyl-N²-p-tolyl-1H-benzoimidazole-2,5-diamine;

[4-(4-{[2-(4-tert-butyl-phenylamino)-1-methyl-1H-benzoimidazol-5-yl]-methyl-amino}-pyrimidin-2-ylamino)-phenyl]-methanesulfonamide;

3-(4-{[2-(4-tert-butyl-phenylamino)-1-methyl-1H-benzoimidazol-5-yl]-methyl-amino}-pyrimidin-2-ylamino)-benzenesulfonamide;

5-(4-{[2-(4-tert-butyl-phenylamino)-1-methyl-1H-benzoimidazol-5-yl]-methyl-amino}-pyrimidin-2-ylamino)-2-methyl-benzenesulfonamide;

N²-(4-tert-butyl-phenyl)-N⁵-[2-(4-methanesulfonylmethyl-phenylamino)-pyrimidin-4-yl]-1,N⁵-dimethyl-1H-benzoimidazole-2,5-diamine;

(5-{[2-(4-methanesulfonylmethyl-phenylamino)-pyrimidin-4-yl]-methyl-amino}-1-methyl-1H-benzoimidazol-2-yl)-(4-methoxy-phenyl)-carbamic acid tert-butyl ester;

N⁵-[2-(4-methanesulfonylmethyl-phenylamino)-pyrimidin-4-yl]-N²-(4-methoxy-phenyl)-1,N⁵-dimethyl-1H-benzoimidazole-2,5-diamine;

(4-methoxy-phenyl)-(1-methyl-5-{methyl-[2-(4-sulfamoyl-methyl-phenylamino)-pyrimidin-4-yl]-amino}-1H-benzoimidazol-2-yl)-carbamic acid tert-butyl ester;

[4-(4-{[2-(4-methoxy-phenylamino)-1-methyl-1H-benzoimidazol-5-yl]-methyl-amino}-pyrimidin-2-ylamino)-phenyl]-methanesulfonamide;

(5-{[2-(3-methanesulfonylmethyl-phenylamino)-pyrimidin-4-yl]-methyl-amino}-1-methyl-1H-benzoimidazol-2-yl)-(4-methoxy-phenyl)-carbamic acid tert-butyl ester;

N⁵-[2-(3-methanesulfonylmethyl-phenylamino)-pyrimidin-4-yl]-N²-(4-methoxy-phenyl)-1,N⁵-dimethyl-1H-benzoimidazole-2,5-diamine;

[5-({2-[4-(1-methanesulfonyl-ethyl)-phenylamino]-pyrimidin-4-yl}-methyl-amino)-1-methyl-1H-benzoimidazol-2-yl]-(4-methoxy-phenyl)-carbamic acid tert-butyl ester;

N⁵-{2-[4-(1-methanesulfonyl-ethyl)-phenylamino]-pyrimidin-4-yl}-N²-(4-methoxy-phenyl)-1,N⁵-dimethyl-1H-benzoimidazole-2,5-diamine; and N⁵-{2-[3-(1-methanesulfonyl-ethyl)-phenylamino]-pyrimidin-4-yl}-N²-(4-methoxy-phenyl)-1,N⁵-dimethyl-1H-benzoimidazole-2,5-diamine;

or a salt, solvate, or physiologically functional derivative thereof.

Additional specific examples of compounds of the present invention include the following:

3-{4-[(2-isopropylamino-1-methyl-1H-benzoimidazol-5-yl)-methyl-amino]-pyrimidin-2-ylamino}-benzenesulfonamide;

2-chloro-5-{4-[(2-isopropylamino-1-methyl-1H-benzoimidazol-5-yl)-methyl-amino]-pyrimidin-2-ylamino}-benzenesulfonamide;

5-{4-[(2-isopropylamino-1-methyl-1H-benzoimidazol-5-yl)-methyl-amino]-pyrimidin-2-ylamino}-2-methyl-benzenesulfonamide;

2-(4-{4-[(2-isopropylamino-1-methyl-1H-benzoimidazol-5-yl)-methyl-amino]-pyrimidin-2-ylamino}-phenyl)-ethanesulfonic acid methylamide;

methanesulfonic acid 4-{4-[(2-isopropylamino-1-methyl-1H-benzoimidazol-5-yl)-methyl-amino]-pyrimidin-2-ylamino}-phenyl ester;

methanesulfonic acid 3-{4-[(2-isopropylamino-1-methyl-1H-benzoimidazol-5-yl)-methyl-amino]-pyrimidin-2-ylamino}-phenyl ester;

N²-isopropyl-N⁵-[2-(3-methanesulfonylmethyl-phenylamino)-pyrimidin-4-yl]-1,N⁵-dimethyl-1H-benzoimidazole-2,5-diamine;

3-[4-(1-methyl-2-phenethylamino-1H-benzoimidazol-5-ylamino)-pyrimidin-2-ylamino]-benzenesulfonamide;

2-methyl-5-{4-[methyl-(1-methyl-2-phenethylamino-1H-benzoimidazol-5-yl)-amino]-pyrimidin-2-ylamino}-benzenesulfonamide;

(4-{4-[methyl-(1-methyl-2-phenethylamino-1H-benzoimidazol-5-yl)-amino]-pyrimidin-2-ylamino}-phenyl)-methanesulfonamide;

N⁵-[2-(4-methanesulfonylmethyl-phenylamino)-pyrimidin-4-yl]-1,N⁵-dimethyl-N²-phenethyl-1H-benzoimidazole-2,5-diamine;

2-(4-{4-[methyl-(1-methyl-2-phenethylamino-1H-benzoimidazol-5-yl)-amino]-pyrimidin-2-ylamino}-phenyl)-ethanesulfonic acid methylamide;

N²-tert-Butyl-N⁵-[2-(4-methanesulfonylmethyl-phenylamino)-pyrimidin-4-yl]-1,N⁵-dimethyl-1H-benzoimidazole-2,5-diamine;

N²-cyclohexyl-N⁵-[2-(4-methanesulfonylmethyl-phenylamino)-pyrimidin-4-yl]-1,N⁵-dimethyl-1H-benzoimidazole-2,5-diamine;

5-{4-[(2-cyclohexylamino-1-methyl-1H-benzoimidazol-5-yl)-methyl-amino]-pyrimidin-2-ylamino}-2-methyl-benzenesulfonamide;

N²-cyclohexyl-N⁵-{2-[3-(2-methanesulfonyl-ethyl)-phenylamino]-pyrimidin-4-yl}-1,N⁵-dimethyl-1H-benzoimidazole-2,5-diamine;

N²-cyclohexyl-N⁵-{2-[4-(2-methanesulfonyl-ethyl)-phenylamino]-pyridin-4-yl}-1,N⁵-dimethyl-1H-benzoimidazole-2,5-diamine;

N²-cyclohexyl-N⁵-{2-[4-(1-methanesulfonyl-ethyl)-phenylamino]-pyrimidin-4-yl}-1,N⁵-dimethyl-1H-benzoimidazole-2,5-diamine;

2-methyl-5-{4-[methyl-(1-methyl-2-methylamino-1H-benzoimidazol-5-yl)-amino]-pyrimidin-2-ylamino}-benzenesulfonamide;

(4-{4-[methyl-(1-methyl-2-methylamino-1H-benzoimidazol-5-yl)-amino]-pyrimidin-2-ylamino}-phenyl)-methanesulfonamide;

3-{4-[methyl-(1-methyl-2-methylamino-1H-benzoimidazol-5-yl)-amino]-pyrimidin-2-ylamino}-benzenesulfonamide;

N⁵-[2-(3-methanesulfonylmethyl-phenylamino)-pyrimidin-4-yl]-1,N²,N⁵-trimethyl-1H-benzoimidazole-2,5-diamine; and (4-{4-[(1-ethyl-2-methylamino-1H-benzoimidazol-5-yl)-methyl-amino]-pyrimidin-2-ylamino}-phenyl)-methanesulfonamide;

or a salt, solvate, or physiologically functional derivative thereof.

Additional specific examples of compounds of the present invention include the following:

N¹-methyl-N⁵-[2-(4-Methanesulfonylmethyl-phenylamino)-pyrimidin-4-yl]-N⁵-methyl-N²-(4-trifluoromethyl-phenyl)-1H-benzoimidazole-2,5-diamine;

N²-(3-chloro-phenyl)-N⁵-[2-(4-methanesulfonylmethyl-phenylamino)-pyrimidin-4-yl]-N¹,N⁵-dimethyl-1H-benzoimidazole-2,5-diamine;

N²-(4-chloro-phenyl)-N⁵-[2-(4-methanesulfonylmethyl-phenylamino)-pyrimidin-4-yl]-N¹,N⁵-dimethyl-1H-benzoimidazole-2,5-diamine;

N²-(2,4-dichloro-phenyl)-N⁵-[2-(4-methanesulfonylmethyl-phenylamino)-pyrimidin-4-yl]-N¹,N⁵-dimethyl-1H-benzoimidazole-2,5-diamine;

N²-(2,5-dichloro-phenyl)-N⁵-[2-(4-methanesulfonylmethyl-phenylamino)-pyrimidin-4-yl]-N¹,N⁵-dimethyl-1H-benzoimidazole-2,5-diamine;

N²-(2-chloro-4-trifluoromethyl-phenyl)-N⁵-[2-(4-methanesulfonylmethyl-phenylamino)-pyrimidin-4-yl]-N¹,N⁵-dimethyl-1H-benzoimidazole-2,5-diamine;

N²-(2-chloro-5-trifluoromethyl-phenyl)-N⁵-[2-(4-methanesulfonylmethyl-phenylamino)-pyrimidin-4-yl]-N¹,N⁵-dimethyl-1H-benzoimidazole-2,5-diamine;

N⁵-[2-(4-methanesulfonylmethyl-phenylamino)-pyrimidin-4-yl]-N¹,N⁵-dimethyl-N²-(4-morpholin-4-yl-phenyl)-1H-benzoimidazole-2,5-diamine;

N²-(3-fluoro-phenyl)-N⁵-[2-(4-methanesulfonylmethyl-phenylamino)-pyrimidin-4-yl]-N¹,N⁵-dimethyl-1H-benzoimidazole-2,5-diamine;

N²-(2,4-difluoro-phenyl)-N⁵-[2-(4-methanesulfonylmethyl-phenylamino)-pyrimidin-4-yl]-N¹,N⁵-dimethyl-1H-benzoimidazole-2,5-diamine;

N²-(2-chloro-4-fluoro-phenyl)-N⁵-[2-(4-methanesulfonylmethyl-phenylamino)-pyrimidin-4-yl]-N¹,N⁵-dimethyl-1H-benzoimidazole-2,5-diamine;

N²-(4-chloro-2-fluoro-phenyl)-N⁵-[2-(4-methanesulfonylmethyl-phenylamino)-pyrimidin-4-yl]-N¹,N⁵-dimethyl-1H-benzoimidazole-2,5-diamine;

N²-(2-chloro-5-fluoro-phenyl)-N⁵-[2-(4-methanesulfonylmethyl-phenylamino)-pyrimidin-4-yl]-N¹,N⁵-dimethyl-1H-benzoimidazole-2,5-diamine;

N²-(2-fluoro-4-methyl-phenyl)-N⁵-[2-(4-methanesulfonylmethyl-phenylamino)-pyrimidin-4-yl]-N¹,N⁵-dimethyl-1H-benzoimidazole-2,5-diamine;

N²-(2-fluoro-phenyl)-N⁵-[2-(4-methanesulfonylmethyl-phenylamino)-pyrimidin-4-yl]-N¹,N⁵-dimethyl-1H-benzoimidazole-2,5-diamine;

N²-(2-fluoro-5-trifluoromethyl-phenyl)-N⁵-[2-(4-methane-sulfonylmethyl-phenylamino)-pyrimidin-4-yl]-N¹,N⁵-dimethyl-1H-benzoimidazole-2,5-diamine;

4-{4-[methyl-(1-methyl-2-methylsulfanyl-1H-benzoimidazol-5-yl)-amino]-pyrimidin-2-ylamino}-benzene sulfonamide;

4-{4-[(2-methanesulfinyl-1-methyl-1H-benzoimidazol-5-yl)-methyl-amino]-pyrimidin-2-ylamino}-benzensulfonamide;

4-(4-{methyl-[1-methyl-2-(4-trifluoromethyl-phenylamino)-1H-benzoimidazol-5-yl]-amino}-pyrimidin-2-ylamino)-benzenesulfonamide;

(methyl-nitro-1H-benzoimidazol-2-yl)-(3-trifluoromethyl-phenyl)-amine;

(methyl-nitro-1H-benzoimidazol-2-yl)-(3-trifluoromethyl-phenyl)-carbamic acid dimethyl-ethyl ester;

(amino-methyl-1-benzoimidazol-2-yl)-(3-trifluoromethyl-phenyl)-carbamic acid dimethyl-ethyl ester;

[(2-chloro-pyrimidin-4-yl)-methyl-amino]-methyl-1H-benzoimidazol-2-yl}-(3-trifluoromethyl-phenyl)-carbamic acid dimethyl-ethyl ester; and N⁵-[2-(4-methanesulfonylmethyl-phenylamino)-pyrimidin-4-yl]-N¹,N⁵-dimethyl-N²-(3-trifluoromethyl-phenyl)-1H-benzoimidazole-2,5-diamine;

or a salt, solvate, or physiologically functional derivative thereof.

Further additional specific examples of compounds of the present invention include the following:

N²-(5-tert-butyl-isoxazol-3-yl)-N⁵[2-(4-methanesulfonylmethyl-phenylamino)-pyrimidin-4-yl]-1,N⁵-dimethyl-1H-methyl-amino-benzoimidazole-2,5-diamine;

N²-(5-tert-butyl-isoxazol-3-yl)-N⁵-[2-(4-methanesulfonylmethyl-phenylamino)-pyrimidin-4-yl]-1-methyl-1-1H-benzoimidazole-2,5-diamine;

N²-(5-tert-butyl-isoxazol-3-yl)-N⁵-[2-(3-methanesulfonylmethyl-phenylamino)-pyrimidin-4-yl]-1-methyl-1H-benzoimidazole-2,5-diamine;

N²-(5-tert-butyl-isoxazol-3-yl)-N⁵-[2-(3-methanesulfonylmethyl-phenylamino)-pyrimidin-4-yl]-1,N⁵-dimethyl-1-H-benzoimidazole-2,5-diamine;

N²-(5-tert-butyl-isoxazol-3-yl)-N⁵-[2-(3-methanesulfonyl-4-methyl-phenylamino)-pyrimidin-4-yl]-1-methyl-1-1H-benzoimidazole-2,5-diamine;

5-(4-{[2-(5-tert-butyl-isoxazol-3-ylamino)-1-methyl-1-H-benzoimidazol-5-yl]-methyl-amino}-pyrimidin-2-ylamino)-2-methyl-benzenesulfonamide;

N²-(6-fluoro-4-H benzo[1,3]dioxin-8-ylmethyl)-N⁵-[2-(3-methanesulfonyl-4-methyl-phenylamino)-pyrimidin-4-yl]-1-methyl-1H-benzoimidazole-2,5-diamine; and N²-(5-tert-butyl-isoxazol-3-yl)-1-methyl-N⁵-{2-[3-(morpholine-4-sulfonyl)-phenylamino]-pyrimidin-4-yl}-1H-benzoimidazole-2,5-diamine;

or a salt, solvate, or physiologically functional derivative thereof.

Further additional specific examples of compounds of the present invention include the following:

N-(1-methyl-5-{methyl[2-({4-[(methylsulfonyl)methyl]phenyl}amino)pyrimidin-4-yl]amino}-1H-benzimidazol-2-yl)-N'-phenylurea;

N-(1-methyl-5-{methyl[2-({4-[(methylsulfonyl)methyl]phenyl}amino)pyrimidin-4-yl]amino}-1H-benzimidazol-2-yl)benzamide;

N-(1-methyl-5-{methyl[2-({4-[(methylsulfonyl)methyl]phenyl}amino)pyrimidin-4-yl]amino}-1H-benzimidazol-2-yl)indoline-1-carboxamide;

N-(5-tert-butylisoxazol-3-yl)-N'-(1-methyl-5-{methyl[2-({4-[(methylsulfonyl)methyl]phenyl}amino)pyrimidin-4-yl]amino}-1H-benzimidazol-2-yl)urea;

N-(1-methyl-5-{methyl[2-({4-[(methylsulfonyl)methyl]phenyl}amino)pyrimidin-4-yl]amino}-1H-benzimidazol-2-yl)-2-phenylacetamide;

N-(1-methyl-5-{methyl[2-({4-[(methylsulfonyl)methyl]phenyl}amino)pyrimidin-4-yl]amino}-1H-benzimidazol-2-yl)-1-phenylcyclopropanecarboxamide;

N-(1-methyl-5-{methyl[2-({4-[(methylsulfonyl)methyl]phenyl}amino)pyrimidin-4-yl]amino}-1H-benzimidazol-2-yl)isonicotinamide;

N-(1-methyl-5-{methyl[2-({4-[(methylsulfonyl)methyl]phenyl}amino)pyrimidin-4-yl]amino}-1H-benzimidazol-2-yl)cyclohexanecarboxamide;

2-(benzyloxy)-N-(1-methyl-5-{methyl[2-({4-[(methylsulfonyl)methyl]phenyl}amino)pyrimidin-4-yl]amino}-1H-benzimidazol-2-yl)acetamide;

2-(3-methylisoxazol-5-yl)-N-(1-methyl-5-{methyl[2-({4-[(methylsulfonyl)methyl]phenyl}amino)pyrimidin-4-yl]amino}-1H-benzimidazol-2-yl)acetamide; and 3-[(dimethylamino)methyl]-N-(1-methyl-5-{methyl[2-({4-[(methylsulfonyl)methyl]phenyl}amino)pyrimidin-4-yl]amino}-1H-benzimidazol-2-yl)benzamide;

or a salt, solvate, or physiologically functional derivative thereof.

Further additional specific examples of compounds of the present invention include the following:

N-({[3-(4-methanesulfonylmethyl-phenylamino)-phenyl]-methyl-amino}-methyl-1H-benzoimidazol-2-yl)-C-thiophen-2-yl-acetamide;

C-fluoro-N-({[3-(3-methanesulfonylmethyl-phenylamino)-phenyl]-methyl-amino}-methyl-1H-benzoimidazol-2-yl)-trifluoromethyl-benzamide;

difluoro-N-({[2-(3-methanesulfonylmethyl-phenylamino)-pyrimidin-4-yl]-methyl-amino}-methyl-1H-benzoimidazol-2-yl)-benzamide;

N-({[2-(3-methanesulfonylmethyl-phenylamino)-pyrimidin-4-yl]-methyl-amino}-methyl-1H-benzoimidazol-2-yl)-3,5-bis-trifluoromethyl-benzamide;

cyclohexanecarboxylic acid ({[2-(3-methanesulfonylmethyl-phenylamino)-pyrimidin-4-yl]-methyl-amino}-methyl-1H-benzoimidazol-2-yl)-amide;

N-({[2-(3-methanesulfonylmethyl-phenylamino)-pyrimidin-4-yl]-methyl-amino}-methyl-1H-benzoimidazol-2-yl)-methyl-benzamide;

N-({[2-(3-methanesulfonylmethyl-phenylamino)-pyrimidin-4-yl]-methyl-amino}-methyl-1H-benzoimidazol-2-yl)-4-methoxy-benzamide;

C-(chloro-trifluoromethyl-phenyl)-N-({[2-(3-methanesulfonylmethyl-phenylamino)-pyrimidin-4-yl]-methyl-amino}-methyl-1H-benzoimidazol-2-yl)-acetamide;

(3,5-bis-trifluoromethyl-phenyl)-N-({[2-(3-methanesulfonylmethyl-phenylamino)-pyrimidin-4-yl]-methyl-amino}-methyl-1H-benzoimidazol-2-yl)-acetamide;

N-(5-{[2-(3-methanesulfonylmethyl-phenylamino)-pyrimidin-4-yl]-methyl-amino}-1-methyl-1H-benzoimidazol-2-yl)-2-(3-trifluoromethylsulfanyl-phenyl)-acetamide;

(2,4-bis-trifluoromethyl-phenyl)-N-({[2-(3-methanesulfonylmethyl-phenylamino)-pyrimidin-4-yl]-methyl-amino}-methyl-1H-benzoimidazol-2-yl)-acetamide;

(2-fluoro-5-trifluoromethyl-phenyl)-N-({[2-(3-methanesulfonylmethyl-phenylamino)-pyrimidin-4-yl]-methyl-amino}-methyl-1H-benzoimidazol-2-yl)-acetamide;

3H-benzotriazole-5-carboxylic acid ({[2-(3-methanesulfonylmethyl-phenylamino)-pyrimidin-4-yl]-methyl-amino}-methyl-1H-benzoimidazol-2-yl)-amide;

3H-benzoimidazole-5-carboxylic acid ({[2-(3-methanesulfonylmethyl-phenylamino)-pyrimidin-4-yl]-methylamino}-methyl-1H-benzoimidazol-2-yl)-amide;

thiophene-2-carboxylic acid ({[2-(3-methanesulfonylmethyl-phenylamino)-pyrimidin-4-yl]-methyl-amino}-methyl-1H-benzoimidazol-2-yl)-amide;

thiophene-3-carboxylic acid ({[2-(3-methanesulfonylmethyl-phenylamino)-pyrimidin-4-yl]-methyl-amino}-methyl-1H-benzoimidazol-2-yl)-amide;

N-({[2-(3-methanesulfonylmethyl-phenylamino)-pyrimidin-4-yl]-methyl-amino}-methyl-1H-benzoimidazol-2-yl)-C-thiophen-2-yl-acetamide;

3-methyl-thiophene-2-carboxylic acid ({[2-(4-methanesulfonylmethyl-phenylamino)-pyrimidin-4-yl]-methyl-amino}-methyl-1H-benzoimidazol-2-yl)-amide;

furan-3-carboxylic acid ({[2-(4-methanesulfonylmethyl-phenylamino)-pyrimidin-4-yl]-methyl-amino}-methyl-1H-benzoimidazol-2-yl)-amide;

3-methyl-furan-2-carboxylic acid ({[2-(4-methanesulfonylmethyl-phenylamino)-pyrimidin-4-yl]-methyl-amino}-methyl-1H-benzoimidazol-2-yl)-amide;

N-({[2-(4-methanesulfonylmethyl-phenylamino)-pyrimidin-4-yl]-methyl-amino}-methyl-1H-benzoimidazol-2-yl)-2-(3-methyl-isoxazol-5-yl)-acetamide;

C-(chloro-trifluoromethyl-phenyl)-N-({[2-(4-methanesulfonylmethyl-phenylamino)-pyrimidin-4-yl]-methyl-amino}-methyl-1H-benzoimidazol-2-yl)-acetamide;

N-(5-{[2-(4-methanesulfonylmethyl-phenylamino)-pyrimidin-4-yl]-methyl-amino}-1-methyl-1H-benzoimidazol-2-yl)-2-(3-trifluoromethylsulfanyl-phenyl)-acetamide;

C-(fluoro-trifluoromethyl-phenyl)-N-({[2-(4-methanesulfonylmethyl-phenylamino)-pyrimidin-4-yl]-methyl-amino}-methyl-1H-benzoimidazol-2-yl)-acetamide;

N-({[2-(4-methanesulfonylmethyl-phenylamino)-pyrimidin-4-yl]-methyl-amino}-methyl-1H-benzoimidazol-2-yl)-dimethyl-butyramide;

2-propyl-pentanoic acid ({[2-(4-methanesulfonylmethyl-phenylamino)-pyrimidin-4-yl]-methyl-amino}-methyl-1H-benzoimidazol-2-yl)-amide;

N-({[2-(4-methanesulfonylmethyl-phenylamino)-pyrimidin-4-yl]-methyl-amino}-methyl-1H-benzoimidazol-2-yl)-isobutyramide;

cyclopropanecarboxylic acid ({[2-(4-methanesulfonylmethyl-phenylamino)-pyrimidin-4-yl]-methyl-amino}-methyl-1H-benzoimidazol-2-yl)-amide;

N-({[2-(4-methanesulfonylmethyl-phenylamino)-pyrimidin-4-yl]-methyl-amino}-methyl-1H-benzoimidazol-2-yl)-4-methoxy-benzamide;

4-methoxy-N-(methyl-{methyl-[2-(4-methyl-3-sulfamoyl-phenylamino)-pyrimidin-4-yl]-amino}-1H-benzoimidazol-2-yl)-benzamide;

furan-2-carboxylic acid ({[2-(4-methanesulfonylmethyl-phenylamino)-pyrimidin-4-yl]-methyl-amino}-methyl-1H-benzoimidazol-2-yl)-amide;

N-(methyl-{methyl-[2-(4-methyl-3-sulfamoyl-phenylamino)-pyrimidin-4-yl]-amino}-1H-benzoimidazol-2-yl)-C-thiophen-2-yl-acetamide;

C-(chloro-trifluoromethyl-phenyl)-N-(methyl-{methyl-[2-(4-methyl-3-sulfamoyl-phenylamino)-pyrimidin-4-yl]-amino}-1H-benzoimidazol-2-yl)-acetamide;

4-methoxy-N-[methyl-(methyl-{2-[3-(morpholine-4-sulfonyl)-phenylamino]-pyrimidin-4-yl}-amino)-1H-benzoimidazol-2-yl]-benzamide;

N-[methyl-(methyl-{2-[3-(morpholine-4-sulfonyl)-phenylamino]-pyrimidin-4-yl}-amino)-1H-benzoimidazol-2-yl]-C-thiophen-2-yl-acetamide;

thiophene-2-carboxylic acid[methyl-(methyl-{2-[3-(morpholine-4-sulfonyl)-phenylamino]-pyrimidin-4-yl}-amino)-1H-benzoimidazol-2-yl]-amide;

furan-2-carboxylic acid[methyl-(methyl-{2-[3-(morpholine-4-sulfonyl)-phenylamino]-pyrimidin-4-yl}-amino)-1H-benzoimidazol-2-yl]-amide;

N-({[2-(3-methanesulfonylmethyl-phenylamino)-pyrimidin-4-yl]-methyl-amino}-methyl-1H-benzoimidazol-2-yl)-2-(3-methyl-isoxazol-5-yl)-acetamide;

furan-2-carboxylic acid ({[2-(3-methanesulfonylmethyl-phenylamino)-pyrimidin-4-yl]-methyl-amino}-methyl-1H-benzoimidazol-2-yl)-amide;

2-(3-methyl-isoxazol-5-yl)-N-[methyl-(methyl-{2-[3-(morpholine-4-sulfonyl)-phenylamino]-pyrimidin-4-yl}-amino)-1H-benzoimidazol-2-yl]-acetamide;

3-methyl-furan-2-carboxylic acid ({[2-(3-methanesulfonylmethyl-phenylamino)-pyrimidin-4-yl]-methyl-amino}-methyl-1H-benzoimidazol-2-yl)-amide;

N-[methyl-(methyl-{2-[3-(4-methyl-piperazine-1-sulfonyl)-phenylamino]-pyrimidin-4-yl}-amino)-1H-benzoimidazol-2-yl]-C-thiophen-2-yl-acetamide;

thiophene-2-carboxylic acid[methyl-(methyl-{2-[3-(4-methyl-piperazine-1-sulfonyl)-phenylamino]-pyrimidin-4-yl}-amino)-1H-benzoimidazol-2-yl]-amide;

furan-2-carboxylic acid[methyl-(methyl-{2-[3-(4-methyl-piperazine-1-sulfonyl)-phenylamino]-pyrimidin-4-yl}-amino)-1H-benzoimidazol-2-yl]-amide;

2-(3-methyl-isoxazol-5-yl)-N-[methyl-(methyl-{2-[3-(4-methyl-piperazine-1-sulfonyl)-phenylamino]-pyrimidin-4-yl}-amino)-1H-benzoimidazol-2-yl]-acetamide;

N-({[2-(3-methanesulfonylmethyl-phenylamino)-pyrimidin-4-yl]-methyl-amino}-methyl-1H-benzoimidazol-2-yl)-dimethyl-butyramide;

N-({[2-(3-methanesulfonylmethyl-phenylamino)-pyrimidin-4-yl]-methyl-amino}-methyl-1H-benzoimidazol-2-yl)-propionamide;

pentanoic acid ({[2-(3-methanesulfonylmethyl-phenylamino)-pyrimidin-4-yl]-methyl-amino}-methyl-1H-benzoimidazol-2-yl)-amide;

N-({[2-(3-methanesulfonylmethyl-phenylamino)-pyrimidin-4-yl]-methyl-amino}-methyl-1H-benzoimidazol-2-yl)-butyramide;

phenyl-N-({[2-(4-methanesulfonylmethyl-phenylamino)-pyrimidin-4-yl]-methyl-amino}-methyl-1H-benzoimidazol-2-yl)-acetamide;

phenylcyclopropanecarboxylic acid ({[2-(4-methanesulfonylmethyl-phenylamino)-pyrimidin-4-yl]-methyl-amino}-methyl-1H-benzoimidazol-2-yl)-amide;

1-(2,5-difluoro-phenyl)-cyclopropanecarboxylic acid ({[2-(4-methanesulfonylmethyl-phenylamino)-pyrimidin-4-yl]-methyl-amino}-methyl-1H-benzoimidazol-2-yl)-amide;

1-(4-chloro-phenyl)-cyclopropanecarboxylic acid ({[2-(4-methanesulfonylmethyl-phenylamino)-pyrimidin-4-yl]-methyl-amino}-methyl-1H-benzoimidazol-2-yl)-amide;

2-(4-fluoro-phenyl)-N-({[2-(4-methanesulfonylmethyl-phenylamino)-pyrimidin-4-yl]-methyl-amino}-methyl-1H-benzoimidazol-2-yl)-acetamide;

(3,5-bistrifluoromethyl-phenyl)-N-({[2-(4-methanesulfonylmethyl-phenylamino)-pyrimidin-4-yl]-methyl-amino}-methyl-1H-benzoimidazol-2-yl)-acetamide;

(3,4-dichlorophenyl)-N-({[2-(4-methanesulfonylmethyl-phenylamino)-pyrimidin-4-yl]-methyl-amino}-methyl-1H-benzoimidazol-2-yl)-acetamide;

1-(2,5-difluorophenyl)-cyclopropanecarboxylic acid ({[2-(3-methanesulfonylmethyl-phenylamino)-pyrimidin-4-yl]-methyl-amino}-methyl-1H-benzoimidazol-2-yl)-amide;

(2,5-difluorophenyl)-N-({[2-(3-methanesulfonylmethyl-phenylamino)-pyrimidin-4-yl]-methyl-amino}-methyl-1H-benzoimidazol-2-yl)-acetamide;

(3,4-dichlorophenyl)-N-({[2-(3-methanesulfonylmethyl-phenylamino)-pyrimidin-4-yl]-methyl-amino}-methyl-1H-benzoimidazol-2-yl)-acetamide;

1-(2,5-difluorophenyl)-cyclopropanecarboxylic acid ({[2-(5-ethanesulfonyl-2-methoxy-phenylamino)-pyrimidin-4-yl]-methyl-amino}-methyl-1H-benzoimidazol-2-yl)-amide;

(2,5-difluorophenyl)-N-({[2-(5-ethanesulfonyl-2-methoxy-phenylamino)-pyrimidin-4-yl]-methyl-amino}-methyl-1H-benzoimidazol-2-yl)-acetamide;

1-(3,4-dichlorophenyl)-cyclopropanecarboxylic acid ({[2-(5-ethanesulfonyl-2-methoxy-phenylamino)-pyrimidin-4-yl]-methyl-amino}-methyl-1H-benzoimidazol-2-yl)-amide;

3,4-dichlorophenyl-N-({[2-(5-ethanesulfoyl-2-methoxy-phenylamino)-pyrimidin-4-yl]-methyl-amino}-methyl-1H-benzoimidazol-2-yl)-acetamide;

1-(2,5-difluorophenyl)-cyclopropanecarboxylic acid (methyl-{methyl-[2-(4-methyl-3-sulfamoyl-phenylamino)-pyrimidin-4-yl]-amino}-1H-benzoimidazol-2-yl)-amide;

1-(3,4-dichlorophenyl)-cyclopropanecarboxylic acid (methyl-{methyl-[2-(4-methyl-3-sulfamoyl-phenylamino)-pyrimidin-4-yl]-amino}-1H-benzoimidazol-2-yl)-amide;

(3,4-dichlorophenyl)-N-(methyl-{methyl-[2-(4-methyl-3-sulfamoyl-phenylamino)-pyrimidin-4-yl]-amino}-1H-benzoimidazol-2-yl)-acetamide;

2-(2,3-dimethoxyphenyl)-N-(5-{[2-(4-methanesulfonylmethyl-phenylamino)-pyrimidin-4-yl]-methyl-amino}-1-methyl-1H-benzoimidazol-2-yl)-acetamide;

2-(2-methoxyphenyl)-N-(5-{[2-(4-methanesulfonylmethyl-phenylamino)-pyrimidin-4-yl]-methyl-amino}-1-methyl-1H-benzoimidazol-2-yl)-acetamide;

2-(3-methoxyphenyl)-N-(5-{[2-(4-methanesulfonylmethyl-phenylamino)-pyrimidin-4-yl]-methyl-amino}-1-methyl-1H-benzoimidazol-2-yl)-acetamide;

2-(3-methoxyphenyl)-N-(5-{[2-(4-methanesulfonylmethyl-phenylamino)-pyrimidin-4-yl]-methyl-amino}-1-methyl-1H-benzoimidazol-2-yl)-acetamide;

2-(2-fluorophenyl)-N-({[2-(4-methanesulfonylmethyl-phenylamino)-pyrimidin-4-yl]-methyl-amino}-methyl-1H-benzoimidazol-2-yl)-acetamide;

2-(3-fluorophenyl)-N-({[2-(4-methanesulfonylmethyl-phenylamino)-pyrimidin-4-yl]-methyl-amino}-methyl-1H-benzoimidazol-2-yl)-acetamide;

(2,5-difluorophenyl)-N-({[2-(4-methanesulfonylmethyl-phenylamino)-pyrimidin-4-yl]-methyl-amino}-methyl-1H-benzoimidazol-2-yl)-acetamide;

(2,3-difluorophenyl)-N-({[2-(4-methanesulfonylmethyl-phenylamino)-pyrimidin-4-yl]-methyl-amino}-methyl-1H-benzoimidazol-2-yl)-acetamide;

2-(3,4-dimethoxyphenyl)-N-(5-{[2-(4-methanesulfonylmethyl-phenylamino)-pyrimidin-4-yl]-methyl-amino}-1-methyl-1H-benzoimidazol-2-yl)-acetamide;

(2,5-difluorophenyl)-N-(methyl-{methyl-[2-(4-methyl-3-sulfamoyl-phenylamino)-pyrimidin-4-yl]-amino}-1H-benzoimidazol-2-yl)-acetamide;

1-(3,4-dichloro-phenyl)-cyclopropanecarboxylic acid ({[2-(3-methanesulfonylmethyl-phenylamino)-pyrimidin-4-yl]-methyl-amino}-methyl-1H-benzoimidazol-2-yl)-amide;

2-(2-chlorophenyl)-N-({[2-(4-methanesulfonylmethyl-phenylamino)-pyrimidin-4-yl]-methyl-amino}-methyl-1H-benzoimidazol-2-yl)-acetamide;

2-(3-chlorophenyl)-N-({[2-(4-methanesulfonylmethyl-phenylamino)-pyrimidin-4-yl]-methyl-amino}-methyl-1H-benzoimidazol-2-yl)-acetamide;

2-(4-chlorophenyl)-N-({[2-(4-methanesulfonylmethyl-phenylamino)-pyrimidin-4-yl]-methyl-amino}-methyl-1H-benzoimidazol-2-yl)-acetamide;

2-(3,5-dimethoxyphenyl)-N-(5-{[2-(4-methanesulfonylmethyl-phenylamino)-pyrimidin-4-yl]-methyl-amino}-1-methyl-1H-benzoimidazol-2-yl)-acetamide;

2-(2,5-dimethoxyphenyl)-N-(5-{[2-(4-methanesulfonylmethyl-phenylamino)-pyrimidin-4-yl]-methyl-amino}-1-methyl-1H-benzoimidazol-2-yl)-acetamide;

(2,5-dichlorophenyl)-N-({[2-(4-methanesulfonylmethyl-phenylamino)-pyrimidin-4-yl]-methyl-amino}-methyl-1H-benzoimidazol-2-yl)-acetamide;

N-({[2-(4-methanesulfonylmethyl-phenylamino)-pyrimidin-4-yl]-methyl-amino}-methyl-1H-benzoimidazol-2-yl)-methyl-C-phenyl-butyramide;

(3,5-dimethylphenyl)-N-({[2-(4-methanesulfonylmethyl-phenylamino)-pyrimidin-4-yl]-methyl-amino}-methyl-1H-benzoimidazol-2-yl)-acetamide;

N-({[2-(4-methanesulfonylmethyl-phenylamino)-pyrimidin-4-yl]-methyl-amino}-methyl-1H-benzoimidazol-2-yl)-phenyl-isobutyramide; and benzo[1,3]dioxol-5-yl-N-({[2-(4-methanesulfonylmethyl-phenylamino)-pyrimidin-4-yl]-methyl-amino}-methyl-1H-benzoimidazol-2-yl)-acetamide;

or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or, solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinyl pyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as combination with surgical therapy and radiotherapy. Combination therapies according to the present invention thus comprise the administration of at least one compound of formula (I) or a pharmaceutically acceptable salt or solvate thereof, or a physiologically functional derivative thereof, and the use of at least one other cancer treatment method. Preferably, combination therapies according to the present invention comprise the administration of at least one compound of formula (I) or a pharmaceutically acceptable salt or solvate thereof, or a physiologically functional derivative thereof, and at least one other pharmaceutically active agent, preferably an anti-neoplastic agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

The compounds of the Formula (I) or salts, solvates, or physiologically functional derivatives thereof and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I) or salts, solvates, or physiologically functional derivatives thereof with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts, solvates or physiologically functional derivatives thereof of formula I include the following:

(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; gemcitabine; fluoropyrimidines such as 5-fluorouracil and fluorodeoxyuridine; antimetabolites such as allopurinol, fludurabine, methotrexate, cladrabine, cytarabine, mercaptopurine and thioguanine; and camptothecins such as 9-amino camptothecin, irinotecan, topotecan, CPT-11 and the various optical forms of 7-(4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumour antibiotics such as doxorubicin, daunomycin, epirubicin, idarubicin, mitomycin-C, dacttinomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestogens; urokinase plasminogen activator receptor function inhibitors; growth factor function inhibitors such as inhibitors of the functions of hepatocyte growth factor; erb-B2, erb-B4, epidermal growth factor receptor (EGFR), platelet derived growth factor receptor (PDGFR), vascular endothelial growth factor receptor (VEGFR, and TIE-2 (other than those VEGFR and TIE-2 inhibitors described in the present invention); and other tyrosine kinase inhibitors such as inhibitors of CDK2 and CDK4 inhibitors.

The compounds of formula (I) and salts, solvates and physiological functional derivatives thereof, are believed to have anticancer activity as a result of inhibition of the protein kinase TIE-2 and/or VEGFR-2 and its effect on selected cell lines whose growth is dependent on TIE-2 and/or VEGFR-2 protein kinase activity.

The present invention thus also provides compounds of formula (I) and pharmaceutically acceptable salts or solvates thereof, or physiologically functional derivatives thereof, for use in medical therapy, and particularly in the treatment of disorders mediated by at least one of inappropriate TIE-2 and VEGFR-2 activity.

The inappropriate TIE-2 and/or VEGFR-2 activity referred to herein is any TIE-2 and/or VEGFR-2 activity that deviates from the normal TIE-2 and/or VEGFR-2 activity expected in a particular mammalian subject. Inappropriate TIE-2 and/or VEGFR-2 activity may take the form of, for instance, an abnormal increase in activity, or an aberration in the timing and or control of TIE-2 and/or VEGFR-2 activity. Such inappropriate activity may result then, for example, from overexpression or mutation of the protein kinase leading to inappropriate or uncontrolled activation. Furthermore, it is also understood that unwanted TIE-2 and/or VEGFR-2 activity may reside in an abnormal source, such as a malignancy. That is, the level of TIE-2 and/or VEGFR-2 activity does not have to be abnormal to be considered inappropriate, rather the activity derives from an abnormal source. In a like manner, the inappropriate angiogenesis referred to herein is any angiogenic activity that deviates from the normal angiogenic activity expected in a particular mammalian subject. Inappropriate angiogenesis may take the form of, for instance, an abnormal increase in activity, or an aberration in the timing and or control of angiogenic activity. Such inappropriate activity may result then, for example, from overexpression or mutation of a protein kinase leading to inappropriate or uncontrolled activation. Furthermore, it is also understood that unwanted angiogenic activity may reside in an abnormal source, such as a malignancy. That is, the level of angiogenic activity does not have to be abnormal to be considered inappropriate, rather the activity derives from an abnormal source.

The present invention is directed to methods of regulating, modulating, or inhibiting TIE-2 and/or VEGFR-2 for the prevention and/or treatment of disorders related to unregulated TIE-2 and/or VEGFR-2 activity. In particular, the compounds of the present invention can also be used in the treatment of certain forms of cancer. Furthermore, the compounds of the present invention can be used to provide additive or synergistic effects with certain existing cancer chemotherapies, and/or be used to restore effectiveness of certain existing cancer chemotherapies and radiation.

The compounds of the present invention are also useful in the treatment of one or more diseases afflicting mammals which are characterized by cellular proliferation in the area of disorders associated with neo-vascularization and/or vascular permeability including blood vessel proliferative disorders including arthritis and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, organ transplant rejection and glomerulopathies; and metabolic disorders include psoriasis, diabetes mellitus, chronic wound healing, inflammation and neurodegenerative diseases.

A further aspect of the invention provides a method of treatment of a mammal suffering from a disorder mediated by at least one of inappropriate TIE-2 and VEGFR-2 activity, including susceptible malignancies, which includes administering to said subject an effective amount of a compound of formula (I) or a pharmaceutically acceptable salt, solvate, or a physiologically functional derivative thereof. In a preferred embodiment, the disorder is a susceptible cancer.

A further aspect of the invention provides a method of treatment of a mammal suffering from cancer which includes administering to said subject an effective amount of a compound of formula (I) or a pharmaceutically acceptable salt or solvate thereof, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by at least one of inappropriate TIE-2 and VEGFR-2 activity. In a preferred embodiment, the disorder is a susceptible cancer.

A further aspect of the present invention provides the use of a compound of formula (I), or a pharmaceutically acceptable salt or solvate thereof, or a physiologically functional derivative thereof, in the preparation of a medicament for the treatment of cancer and malignant tumors.

The mammal requiring treatment with a compound of the present invention is typically a human being.

In another embodiment, therapeutically effective amounts of the compounds of formula (I) or salts, solvates or physiologically derived derivatives thereof and agents which inhibit growth factor receptor function may be administered in combination to a mammal for treatment of a disorder mediated by at least one of inappropriate TIE-2 and VEGFR-2 activity, for instance in the treatment of cancer. Such growth factor receptors include, for example, EGFR, PDGFR, erbB2, erbB4, VEGFR, and/or TIE-2. Growth factor receptors and agents that inhibit growth factor receptor function are described, for instance, in Kath, John C., Exp. Opin. Ther. Patents (2000) 10(6): 803-818 and in Shawver et al DDT Vol 2, No. 2 February 1997.

The compounds of the formula (I) or salts, solvates, or physiologically functional derivatives thereof and the agent for inhibiting growth factor receptor function may be employed in combination concomitantly or sequentially in any therapeutically appropriate combination. The combination may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

In another aspect of the present invention, there is provided a method of treating a disorder in a mammal, said disorder being mediated by inappropriate angiogenesis, including: administering to said mammal a therapeutically effective amount of a compound of formula (I), or a salt, solvate or physiologically functional derivative thereof. In one embodiment, the inappropriate angiogenic activity is due to at least one of inappropriate VEGFR1, VEGFR2, VEGFR3, or TIE-2 activity. In another embodiment, the inappropriate angiogenesis is due to inappropriate VEGFR2 and TIE-2 activity. In a further embodiment, the method further includes administering a therapeutically effective amount of a VEGFR2 inhibitor along with the compounds of formula (I) or salts, solvates or physiologically functional derivatives thereof. Preferably the disorder is a susceptible cancer.

In another aspect of the present invention, there is provided the use of a compound of formula (I), or a salt, solvate or physiologically functional derivative thereof in the preparation of a medicament for use in treating a disorder in a mammal, said disorder being characterized by inappropriate angiogenesis. In one embodiment, the inappropriate angiogenic activity is due to at least one of inappropriate VEGFR1, VEGFR2, VEGFR3 or TIE-2 activity. In another embodiment, the inappropriate angiogenesis is due to inappropriate VEGFR2 and TIE-2 activity. In a further embodiment, the use further includes use of a VEGFR2 inhibitor to prepare said medicament.

The combination of a compound of formula (I) or salts, solvates, or physiologically functional derivatives thereof with a VEGFR2 inhibitor may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley Et Sons). These groups are removed at a convenient stage of the compound synthesis using methods that are readily apparent to those skilled in the art. The selection of processes as well as the reaction conditions and order of their execution shall be consistent with the preparation of compounds of Formula (I). Those skilled in the art will recognize if a stereocenter exists in compounds of Formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of Formula I can be prepared according to the synthetic sequences illustrated in Schemes 1, 2, 3, 4, and 5 and further detailed in the Examples section following.

Scheme 1 illustrates the synthetic scheme for the preparation of N-alkyl and N-benzyl 2-aminobenzimidazole derivatives of Formula I. That is, those compounds of formula I wherein D is —NRR$^1$. In this scheme R is hydrogen, R$^1$ is as defined above, and Q represents 1 or more substituents as defined by Q$_1$, Q$_2$, and Q$_3$ above.

Scheme 1

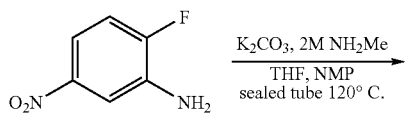

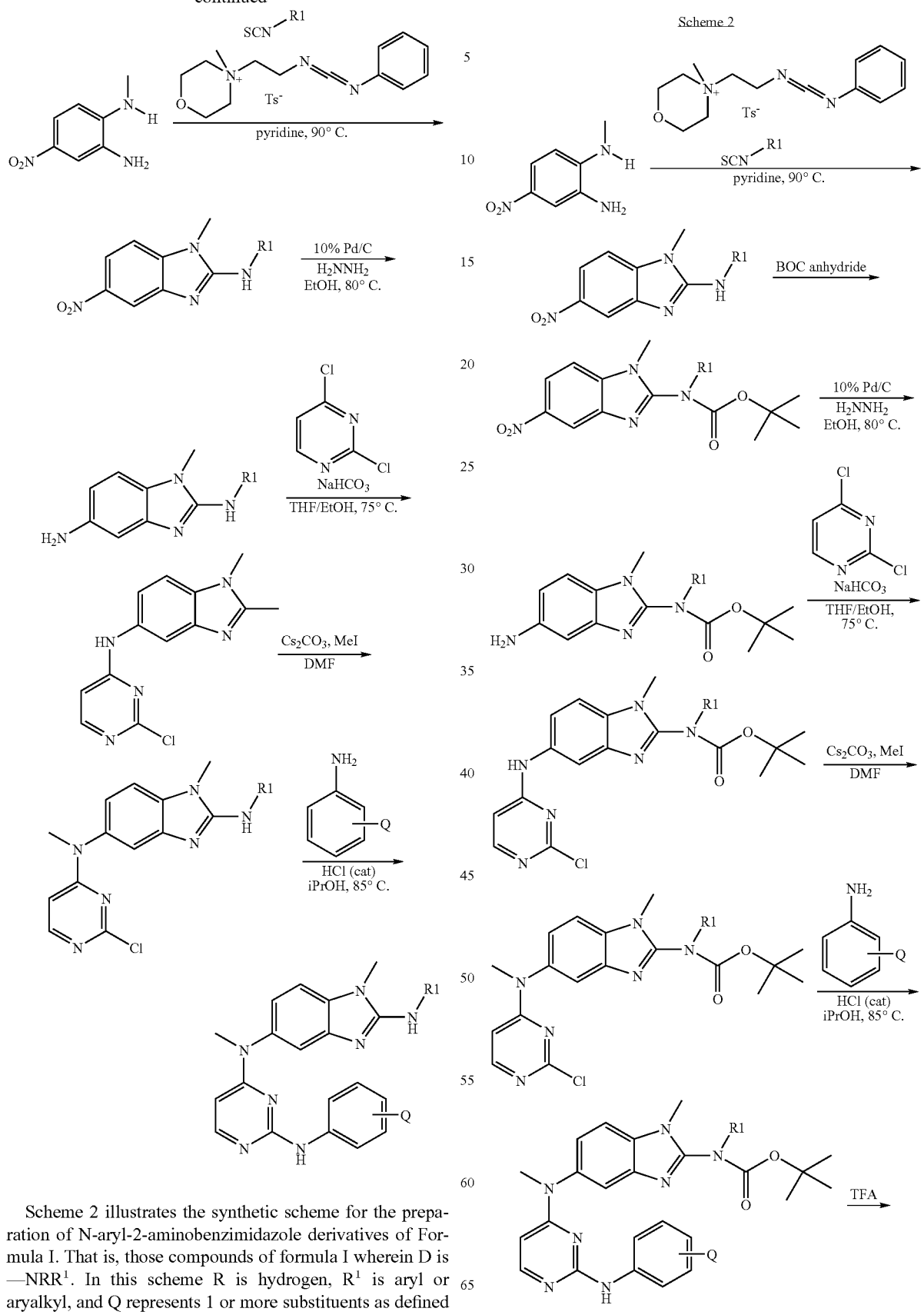
Scheme 2 illustrates the synthetic scheme for the preparation of N-aryl-2-aminobenzimidazole derivatives of Formula I. That is, those compounds of formula I wherein D is —NRR$^1$. In this scheme R is hydrogen, R$^1$ is aryl or aryalkyl, and Q represents 1 or more substituents as defined by Q$_1$, Q$_2$, and Q$_3$ above.

-continued

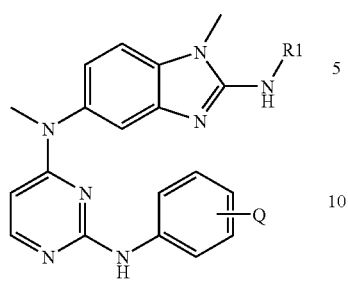

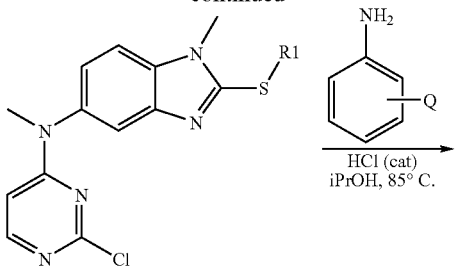

Scheme 3 illustrates the synthetic scheme for the preparation of alkyl-thiobenzimidazole derivatives of Formula I. That is, those compounds of formula I wherein D is —SR$^1$, —S(O)R$^1$, or —S(O)$_2$R$^1$. In this scheme R$^1$ is as defined above, n is 1 or 2, and Q represents 1 or more substituents as defined by Q$_1$, Q$_2$, and Q$_3$ above.

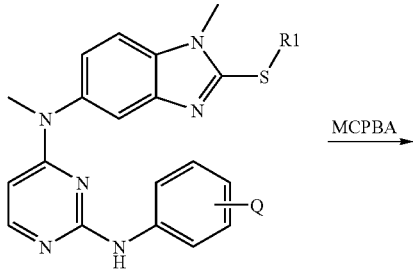

Scheme 4 illustrates the synthetic scheme for the preparation of tailpieces of the aminobenzimidazole derivatives of Formula I. That is, those compounds of formula I wherein Q represents 1 or more substituents as defined by Q$_1$, Q$_2$, Q$_3$ above. Also, R$^8$ and R$^9$ are as defined above.

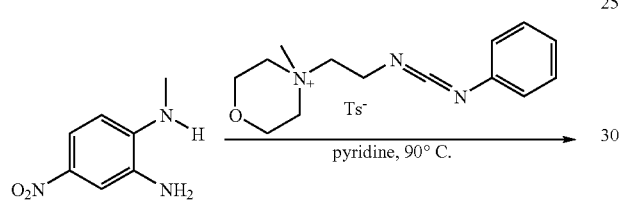

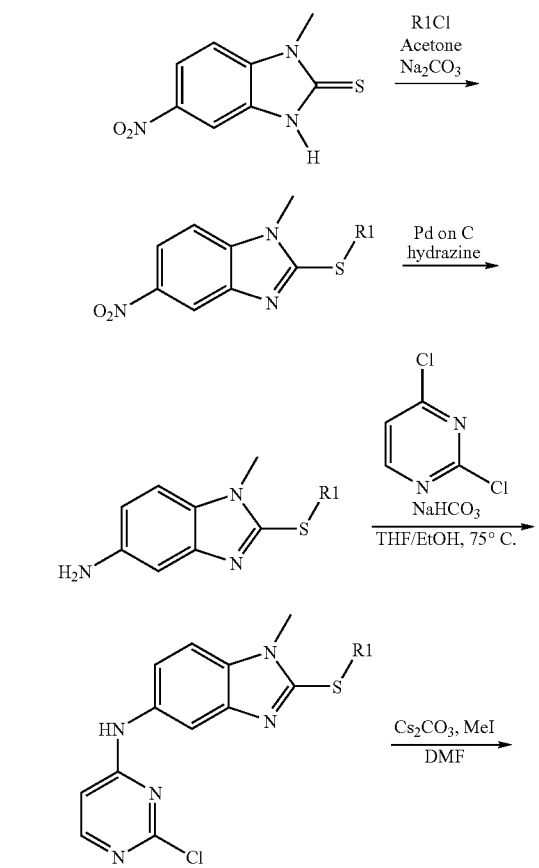

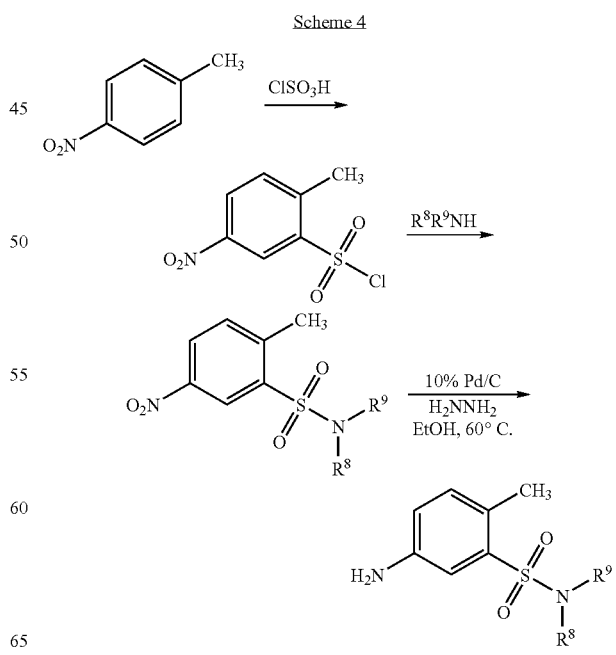

Scheme 5 illustrates the synthetic scheme for the preparation of 2-alkoxy, 2-phenoxy, and 2-thiophenoxy benzimidazole derivatives of Formula I. That is, those compounds of formula I wherein X is a heteroatom of D as defined above, $R^1$ is alkoxy, aryloxy, or aralkoxy, n is 1 or 2, and Q represents 1 or more substituents as defined by $Q_1$, $Q_2$, and $Q_3$ above.

Scheme 5

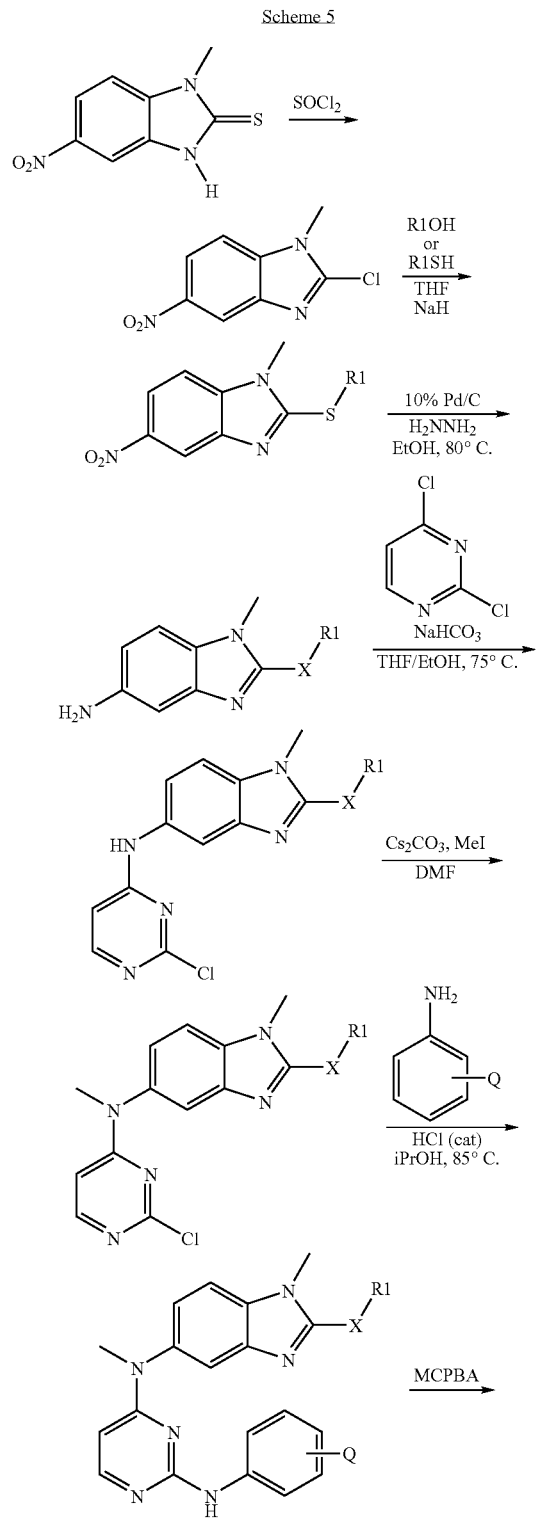

Scheme 6 illustrates the synthetic scheme for the preparation of benzimidazole heteroaryl amine derivatives of formula (I), wherein oxazole is utilized as a specific heteroaryl group:

Scheme 6

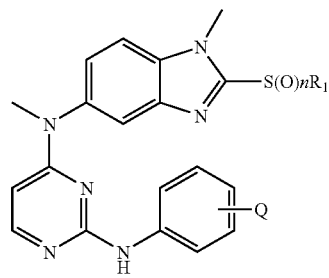

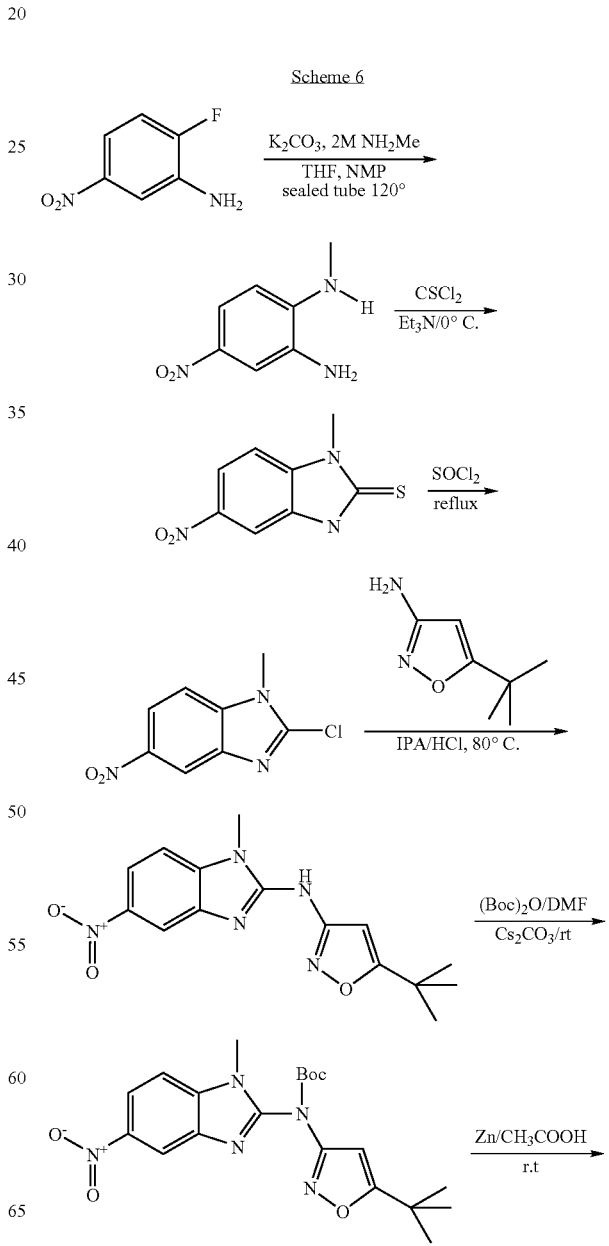

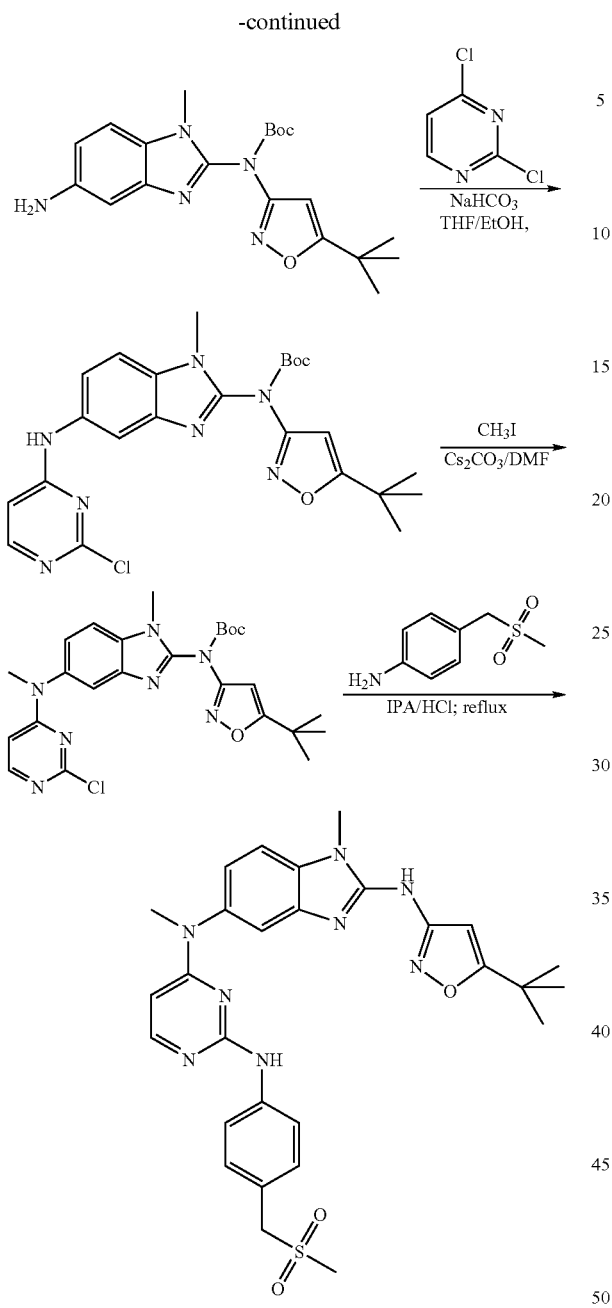
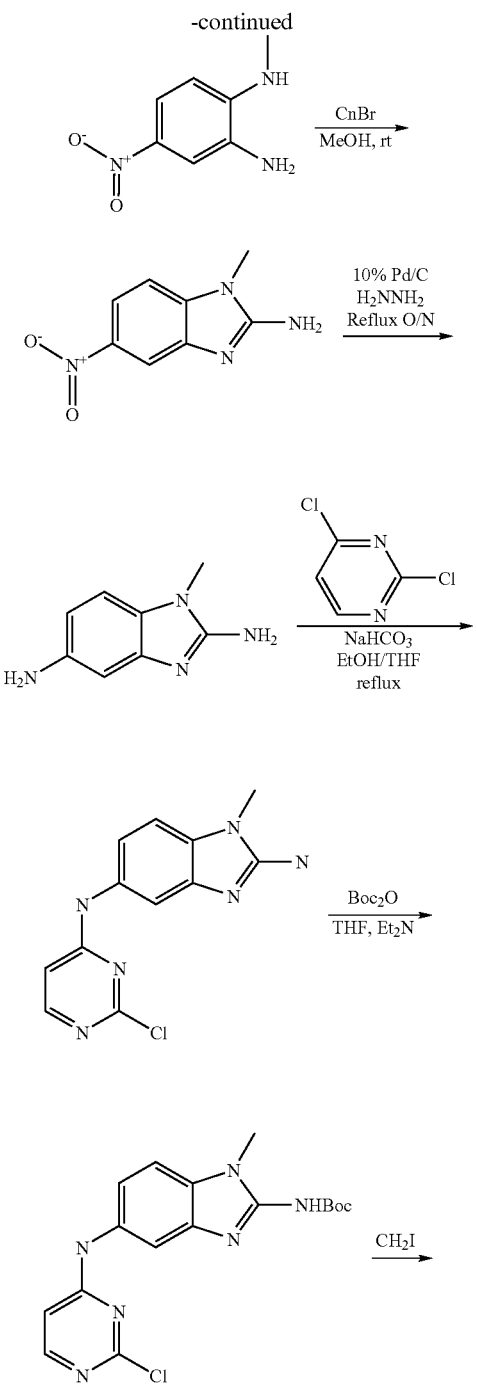
Scheme 7 following illustrates a synthetic scheme for the preparation of benzimidazole amides of formula (I) and (II). $R^1$ is as defined above and Q represents $Q_1$, $Q_2$, and/or $Q_3$ as defined above.
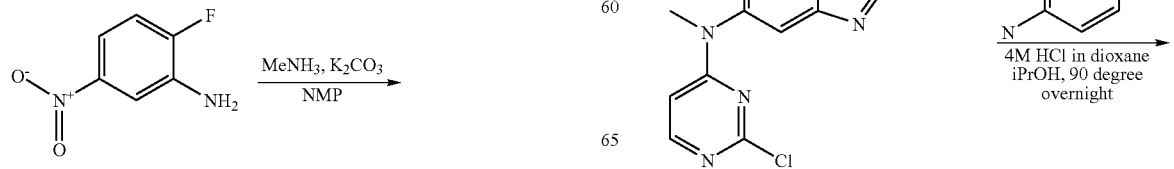

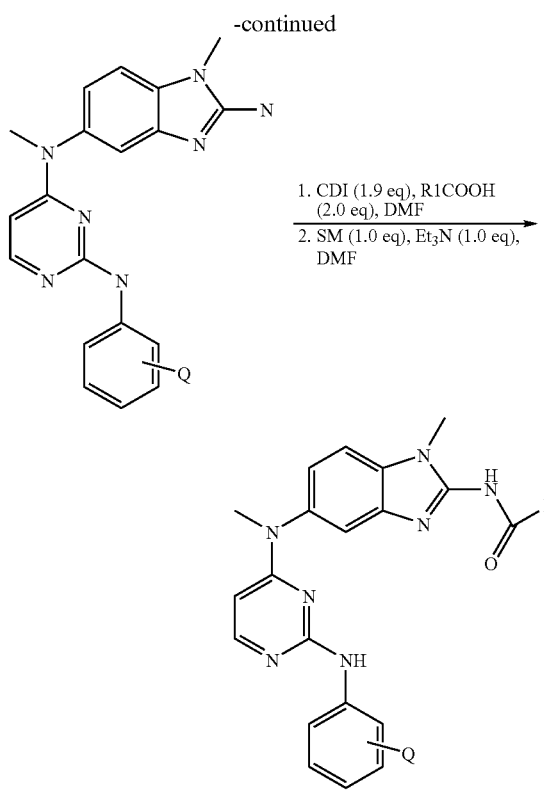

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification.

Specifically, the following abbreviations may be used in the examples and throughout the specification:

g (grams); mg (milligrams);
L (liters); mL (milliliters);
µL (microliters); psi (pounds per square inch);
M (molar); mM (millimolar);
i. v. (intravenous); Hz (Hertz);
MHz (megahertz); mol (moles);
mmol (millimoles); rt (room temperature);
min (minutes); h (hours);
mp (melting point); TLC (thin layer chromatography);
T$_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); AcOEt (ethyl acetate);
DME (1,2-dimethoxyethane); DCM (dichloromethane);
DCE (dichloroethane); DMF (N,N-dimethylformamide);
DMPU (N,N'-dimethylpropyleneurea); (CDI (1,1-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid; EDC (ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin)
ATP (adenosine triphosphate); HRP (horseradish peroxidase);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluronium hexafluorophosphate).
HEPES (4-(2-hydroxyethyl)-1-piperazine ethane sulfonic acid);
DPPA (diphenylphosphoryl azide);
fHNO$_3$ (fumed HNO$_3$); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Varian VXR-300, a Varian Unity-300, a Varian Unity-400 instrument, a Brucker AVANCE-400, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

HPLC were recorded on a Gilson HPLC or Shimazu HPLC system by the following conditions. Column: 50×4.6 mm (id) stainless steel packed with 5 µm Phenomenex Luna C-18; Flow rate: 2.0 mL/min; Mobile phase: A phase=50 mM ammonium acetate (pH 7.4), B phase=acetonitrile, 0-0.5 min (A: 100%, B: 0%), 0.5-3.0 min (A: 100-0%, B: 0-100%), 3.0-3.5 min (A: 0%, B: 100%), 3.5-3.7 min (A: 0-100%, B: 100-0%), 3.7-4.5 min (A: 100%, B: 0%); Detection: UV 254 nm; Injection volume: 3 µL.

Low-resolution mass spectra (MS) were recorded on a JOEL JMS-AX505HA, JOEL SX-102, or a SCIEX-APliii spectrometer; LC-MS were recorded on a micromass 2MD and Waters 2690; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Additional mass spectra were run on an open access LC/MS system using electrospray ionization. LC conditions: 4.5% to 90% CH$_3$CN (0.02% TFA) in 3.2 min with a 0.4 min hold and 1.4 min re-equilibration; detection by MS, UV at 214 nm, and a light scattering detector (ELS). Column: 1×40 mm Aquasil (C18).

Most of the reactions were monitored by thin-layer chromatography on 0.25 mm E. Merck silica gel plates (60F-254), visualized with UV light, 50% ethanolic phosphomolybdic acid or p-anisaldehyde solution. Flash column chromatography was performed on silica gel (230-400 mesh, Merck).

Intermediate Example 1

$N^5$-(2-chloropyrimidin-4-yl)-$N^2$-isopropyl-$N^5$,1-dimethyl-1H-benzimidazole-2,5-diamine

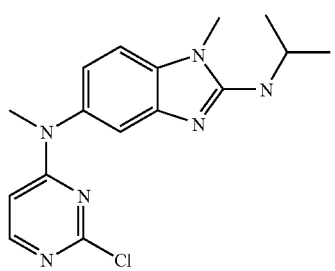

A. $N^1$-Methyl-4-nitro-benzene-1,2-diamine

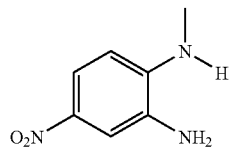

To a solution of 2-fluoro-5-nitroaniline (5 g, 32 mmol) in 40 ml N-methylpyrrolidinone in a sealed reaction vessel was added potassium carbonate (9.0 g, 50.0 mmol) and a solution of methyl amine (32 ml, 2M in THF) and the reaction was heated to 120° C. After 16 h, the reaction mixture was cooled to room temperature and poured into 400 ml of water. The resulting precipitate was filtered and dried to give the title compound as a red solid. $^1$H NMR (300 MHz, $d_6$-DMSO) δ7.54 (dd, J=8.7 and 2.7 Hz, 1H), 7.39 (d, J=2.7 Hz, 1H), 6.41 (d, J=8.7 Hz, 1H), 6.13 (s, 1H), 5.08 (s, 2H), 2.83 (s, 3H).

B. N-isopropyl-1-methyl-5-nitro-1H-benzimidazol-2-amine

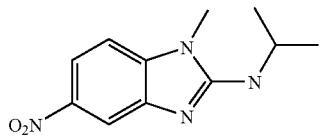

To a solution of $N^1$-methyl-4-nitro-benzene-1,2-diamine (2.0 g, 12.0 mmol) in pyridine (20 ml) was added isopropyl isothiocyanate (1.41 g, 13.2 mmol) and the mixture was heated to 90° C. After 1 h, 1-cyclohexyl-3-(2-morpholinoethyl)carbodiimide metho-p-toluenesulfonate (6.6 g, 15.6 mmol) was added and the mixture was heated at 90° C. After 16 h, the reaction mixture was cooled to rt, filtered and concentrated to a red residue. This was dissolved in EtOAc and washed with water (4×125 ml). The organic layer was dried over $MgSO_4$ and concentrated to an orange solid. MeOH was added, and the solid was filtered and dried to give the title compound as an orange solid (2.4 g, 85%). $^1$H NMR (300 MHz, $d_6$-DMSO) δ7.88 (dd, J=8.7 and 2.4 Hz), 7.30 (d, J=8.7 Hz, 1H), 6.89 (d, J=7.5 Hz, 1H), 4.08 (m, 1H), 3.56 (s, 3), 1.25 (d, J=6.6 Hz, 6H). MS (ESI) m/z=235 [M+H]$^+$.

C. $N^2$-isopropyl-1-methyl-1H-benzimidazole-2,5-diamine

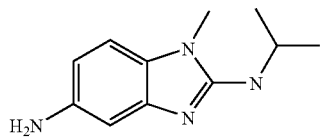

To a solution of isopropyl-(1-methyl-5-nitro-1H-benzimidazol-2-yl)-amine (2.15 g, 9.2 mmol) and 10% Pd/C (500 mg) in ethanol (60 ml) was added hydrazine (5 ml) and the reaction was heated to 80° C. After TLC showed the starting material to be consumed, the reaction was cooled to rt and passed through a plug of celite. The filtrate was concentrated to give the title compound as an off-white solid. $^1$H NMR (300 MHz, $d_6$-DMSO) δ 6.75 (d, J=8.1 Hz, 1H), 6.45 (d, J=1.8 Hz, 1H), 6.20 (dd, J=8.1 and 2.1 Hz, 1H), 6.06 (d, J=7.8 Hz, 1H), 4.43 (br s, 2H), 3.96 (m, 1H), 3.35 (s, 3H), 1.19 (d, J=6.6 Hz, 6H).

D. $N_5$-(2-Chloropyrimidin-4-yl)-$N^2$-isopropyl-$N^5$,1-dimethyl-1H-benzimidazole-2,5-diamine

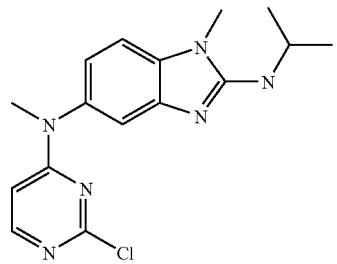

To a solution of $N^2$-isopropyl-1-methyl-1H-benzimidazole-2,5-diamine (1.46 g, 7.2 mmol) in THF (7 ml) and ethanol (21 ml) was added $NaHCO_3$ (1.81 g, 21.6 mmol) and 2,4-dichloropyrimidine (2.68 g, 18 mmol) and the reaction was heated to 75° C. After 5 h, the reaction was filtered hot and concentrated to a gray foam. Ether was added and the solid was filtered and dried to give $N^5$-(2-chloro-pyrimidin-4-yl)-$N^2$-isopropyl-1-methyl-1H-benzimidazole-2,5-diamine as an off-white solid. $N^5$-(2-chloro-pyrimidin-4-yl)-$N^2$-isopropyl-1-methyl-1H-benzimidazole-2,5-diamine was dissolved in DMF (21 ml) and cesium carbonate (6.84 g, 21 mmol) was added After 15 min, iodomethane (0.70 ml, 11.2 mmol) was added, and the reaction was stirred at rt. After TLC showed the starting material to be consumed, the reaction was diluted with water. The aqueous layer was extracted with EtOAc. The combined organic layers were washed with water, dried over $MgSO_4$ and concentrated to a red foam. The crude material was purified with silica gel to give the title compound as a white solid (1.10 g, 46% over two steps). $^1$H NMR (300 MHz, $d_6$-DMSO) δ 7.87 (d, J=6.0 Hz, 1H), 7.22 (d, J=8.1 Hz, 1H), 7.11 (1.8 Hz, 1H), 6.82 (dd, J=8.1 and 1.8 Hz, 1H), 6.53 (d, J=7.5 Hz, 1H), 6.09 (d, J=6.0 Hz, 1H), 4.04 (m, 1H), 3.51 (s, 3H), 3.37 (s, 3H), 1.23 (d, J=6.6 Hz, 6H). MS (ESI) m/z=331 [M+H]$^+$.

Intermediate Example 2

$N^5$-(2-Chloropyrimidin-4-yl)-$N^2$,$N^5$,1-trimethyl-1H-benzimidazole-2,5-diamine

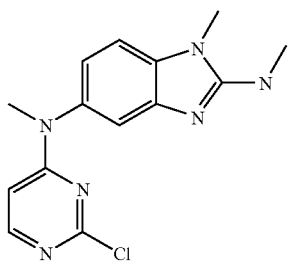

A. Methyl-(1-methyl-5-nitro-1H-benzimidazol-2-yl)-amine

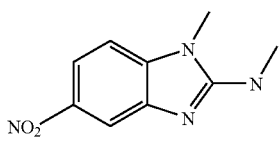

$N^1$-methyl-4-nitro-benzene-1,2-diamine (2.0 g, 12.0 mmol) and methyl isothiocyanate (0.90 ml, 13.2 mmol) were coupled using the procedure of example one part B to give the title compound as a yellow solid (1.32 g, 53%). $^1$H NMR (300 MHz, $d_6$-DMSO) δ 7.98 (d, J=2.1 Hz, 1H), 7.90 (dd, J=8.7 and 2.4 Hz, 1H), 7.32 (d, J=8.7 Hz, 1H), 7.15 (m, 1H), 3.55 (d, 3H), 2.95 (d, J=4.5 Hz, 3H).

B. $N^2$,1-Dimethyl-1H-benzimidazole-2,5-diamine

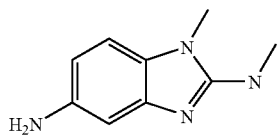

Methyl-(1-methyl-5-nitro-1H-benzimidazol-2-yl)-amine was reduced using the procedure of example one part C to give the title compound as a white solid. $^1$H NMR (300 MHz, $CD_3OD$) δ 7.50 (m, 2H), 7.31 (dd, J=8.7 and 2.1 Hz, 1H), 3.13 (s, 3H). MS (ESI) m/z=163 [M+H]$^+$.

C. $N^5$-(2-Chloropyrimidin-4-yl)-$N^2$,$N^5$,1-trimethyl-1H-benzimidazole-2,5-diamine

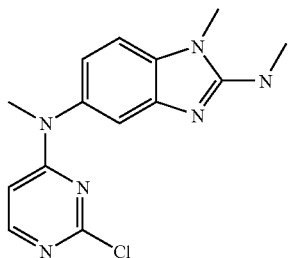

$N^2$,1-Dimethyl-1H-benzimidazole-2,5-diamine was coupled and methylated according to the procedure of example one part D to give the title compound as a white solid. $^1$H NMR (400 MHz, $d_6$-DMSO) δ 7.85 (d, J=6.0 Hz, 1H), 7.21 (d, J=8.0 Hz, 1H), 6.92 (dd, J=8.4 and 2.0 Hz, 1H), 6.77 (m, 1H), 6.07 (br s, 1H), 3.48 (s, 3H), 3.36 (s, 3H), 2.89 (d, J=4.4 Hz, 3H).

Intermediate Example 3

$N^2$-Benzyl-$N^5$-(2-chloropyrimidin-4-yl)-$N^5$,1-dimethyl-1H-benzimidazole-2,5-diamine

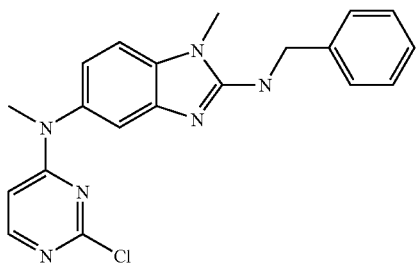

A. N-Benzyl-1-methyl-5-nitro-1H-benzimidazol-2-amine

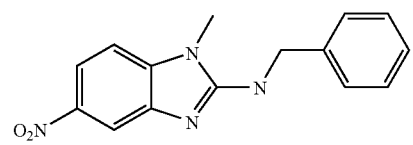

$N^1$-Methyl-4-nitro-benzene-1,2-diamine (2.0 g, 12.0 mmol) and benzyl isothiocyanate (1.75 ml, 13.2 mmol) were coupled using the procedure of example one part B to give the title compound as a yellow solid (2.4 g, 71%). $^1$H NMR (300 MHz, $d_6$-DMSO) δ 7.97 (d, J=2.4 Hz, 1H), 7.90 (dd, J=8.7 and 2.4 Hz, 1H), 7.77 (t, J=5.7 Hz, 1H), 7.21-7.41 (m, 6H), 4.63 (d, J=5.7 Hz, 2H), 3.62 (s, 3H) ppm.

B. $N^2$-Benzyl-1-methyl-1H-benzimidazole-2,5-diamine

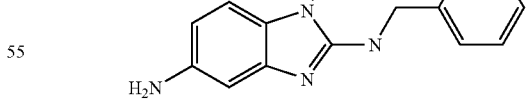

N-Benzyl-1-methyl-5-nitro-1H-benzimidazol-2-amine (2.4 g, 8.5 mmol) was reduced using the procedure of example one part C to give the title compound as a white foam (2.01 g, 94%). $^1$H NMR (300 MHz, DMSO) δ 7.28-7.39 (m, 4H), 7.22 (m, 1H), 7.01 (t, J=5.7 Hz, 1H), 6.79 (d, J=8.1 Hz, 1H), 6.44 (d, J=1.8 Hz, 1H), 6.23 (dd, J=8.2 and 1.9 Hz, 1H), 4.54 (d, J=5.7 Hz, 2H), 3.42 (s, 3H).

C. N²-Benzyl-N⁵-(2-chloropyrimidin-4-yl)-N⁵,1-dimethyl-1H-benzimidazole-2,5-diamine

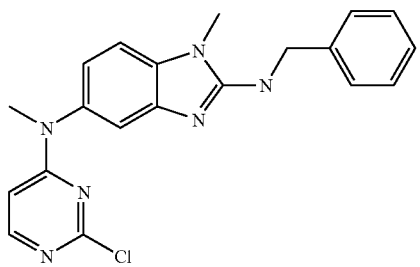

N²-Benzyl-1-methyl-1H-benzimidazole-2,5-diamine (2.01 g, 8 mmol) was coupled and methylated according to the procedure of example one part D to give the title compound as a white solid (1.20 g, 40%). ¹H NMR (300 MHz, d₆-DMSO) δ 7.86 (d, J=6.0 Hz, 1H), 7.23-7.46 (m, 7H), 7.11 (d, J=1.8 Hz, 1H), 6.84 (dd, J=8.2 and 1.9 Hz, 1H), 6.08 (d, J=5.4 Hz, 1H), 4.60 (d, J=5.7 Hz, 2H), 3.57 (s, 3H), 3.36 (s, 3H). MS (ESI) m/z=379 [M+H]⁺.

Intermediate Example 4

Tert-butyl 5-[(2-chloropyrimidin-4-yl)(methyl) amino]-1-methyl-1H-benzimidazol-2-yl(phenyl) carbamate

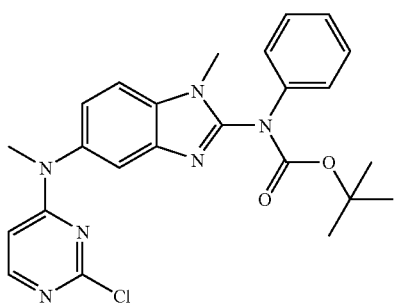

A. 1-Methyl-5-nitro-N-phenyl-1H-benzimidazol-2-amine

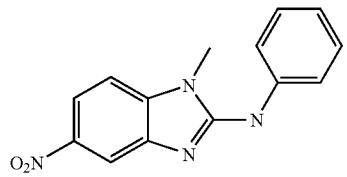

A solution of phenyl isothiocyanate (1.58 ml, 13.2 mmol) and 1-cyclohexyl-3-(2-morpholinoethyl)carbodiimide metho-p-toluenesulfonate (6.6 g, 15.6 mmol) was stirred in pyridine (20 ml) at 90° C. After 2 hours, N¹-methyl-4-nitrobenzene-1,2-diamine was added and the reaction was heated overnight. The reaction was cooled and concentrated to a red solid. This was dissolved in EtOAc and washed with water. The organic layer was dried over MgSO₄ and concentrated to a red solid. This was stirred in MeOH, filtered, and dried to give the title compound as an orange solid (1.97 g, 62%). ¹H NMR (300 MHz, d₆-DMSO) δ 8.23 (s, 1H), 8.17 (d, J=1.8 Hz, 1H), 8.02 (dd, J=8.7 and 2.1 Hz, 1H), 7.89 (d, J=8.1 Hz, 2H), 7.50 (d, J=8.7 Hz, 1H), 7.36 (m, 2H), 7.02 (m, 1H), 3.79 (s, 1H) ppm. MS (ESI) m/z=269 [M+H]⁺.

B. tert-butyl 1-methyl-5-nitro-1H-benzimidazol-2-yl(phenyl)carbamate

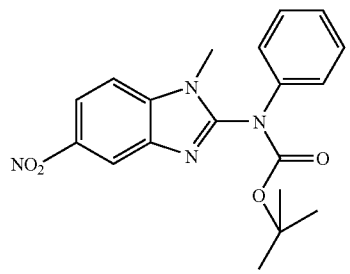

To a solution of methyl-5-nitro-N-phenyl-1H-benzimidazol-2-amine (1.97 g, 7.4 mmol) in THF (30 ml) was added cesium carbonate (4.82 g, 14.8 mmol) and di-tert-butyl dicarbonate (2.42 g, 11.1 mmol) and the reaction was stirred at rt for 16 h. The reaction was diluted with water and extracted with EtOAc. The combined organic layers were washed with water, dried over MgSO₄ and concentrated to a yellow solid. The crude material was purified through silica gel to give the title compound as a yellow solid (1.11 g, 41%). ¹H NMR (300 MHz, d₆-DMSO) δ 8.50 (d, J=2.4 Hz, 1H), 8.23 (dd, J=9.0 and 2.1 Hz, 1H), 7.84 (d, J=9.0 Hz, 1H), 7.40 (m, 4H), 7.29 (m, 1H), 3.83 (s, 3H), 1.40 (s, 9H) ppm.

C. Tert-butyl 5-amino-1-methyl-1H-benzimidazol-2-yl(phenyl)carbamate

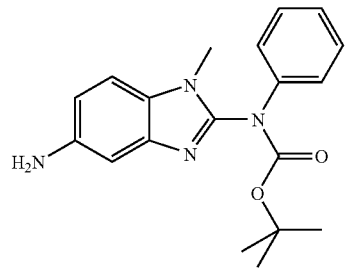

Tert-butyl 1-methyl-5-nitro-1H-benzimidazol-2-yl(phenyl)carbamate (1.11 g, 3 mmol) was reduced by the procedure of example one part C to give the title compound as a white solid (1.03 g, >95%). ¹H NMR (300 MHz, d₆-DMSO) δ 7.31-7.40 (m, 4H), 7.19-7.26 (m, 2H), 6.70 (d, J=1.8 Hz, 1H), 6.63 (dd, J=8.1 and 1.8 Hz, 1H), 4.78 (br s, 2H), 3.60 (s, 3H), 1.39 (s, 9H).

D. Tert-butyl 5-[(2-chloropyrimidin-4-yl)amino]-1-methyl-1H-benzimidazol-2-yl(phenyl)carbamate

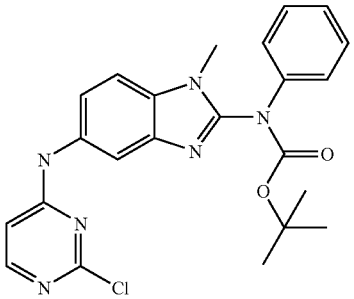

To a solution of tert-butyl 5-amino-1-methyl-1H-benzimidazol-2-yl(phenyl)carbamate (1.03 g, 3.0 mmol) in THF (3 ml) and ethanol (9 ml) was added NaHCO₃ (0.76 g, 9.0 mmol) and 2,4-dichloropyrimidine (0.89 g, 6.0 mmol) and the reaction was heated to 75° C. After 5 h, the reaction was filtered hot and concentrated to a gray foam. The crude material was purified on silica gel to give the title compound as a white foam (0.98 g, 73%). $^1$H NMR (300 MHz, d$_6$-DMSO) δ 10.00 (s, 1H), 8.10 (d, J=5.7 Hz, 1H), 7.89 (s, 1H), 7.58 (d, J=9.0 Hz, 1H), 7.36-7.39 (m, 5H), 7.24-7.34 (m, 1H), 6.70 (d, J=6.0 Hz, 1H), 3.73 (s, 3H), 1.40 (s, 9H).

E. Tert-butyl 5-[(2-chloropyrimidin-4-yl)(methyl)amino]-1-methyl-1H-benzimidazol-2-yl(phenyl)carbamate

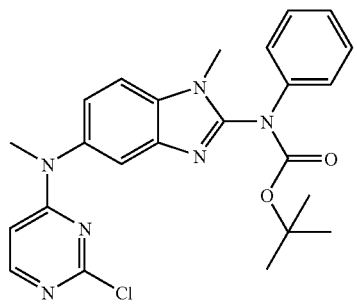

Tert-butyl 5-[(2-chloropyrimidin-4-yl)amino]-1-methyl-1H-benzimidazol-2-yl(phenyl)carbamate (0.97 g, 2.2 mmol) was dissolved in DMF (10 ml) and cesium carbonate (2.15 g, 6.6 mmol) was added. After 15 min, iodomethane (0.20 ml, 3.3 mmol) was added, and the reaction was stirred at rt. After TLC showed the starting material to be consumed, the reaction was diluted with water. The aqueous layer was extracted with EtOAc. The combined organic layers were washed with water, dried over MgSO$_4$ and concentrated to a red foam. The crude material was purified through silica gel to give the title compound as a white solid (0.80 g, 78% over two steps). $^1$H NMR (300 MHz, d$_6$-DMSO) δ 7.90 (d, J=6.3 Hz, 1H), 7.72 (d, J=8.7 Hz, 1H), 7.60 (d, J=1.8 Hz, 1H), 7.38 (m, 4H), 7.25-7.29 (m, 2H), 6.17 (d, J=5.7 Hz, 1H), 3.78 (s, 3H), 3.41 (s, 3H), 1.41 (s, 9H). MS (ESI) m/z=465 [M+H]$^+$.

Intermediate Example 5

N-Methoxy-2-methyl-5-nitrobenzenesulfonamide

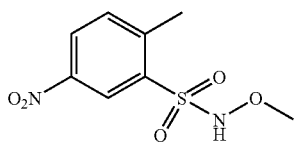

4-Nitrotoluene (15 g, 73 mmol) was added to cold chlorosulfonic acid (25 mL, 365 mmol) in 0.5 g portions over a period of 10 min. The solution was stirred in the ice bath for 10 min then placed in a 65° C. oil bath and heated to 7 h open to the air. The resulting dark brown solution was cooled to rt, then slowly poured onto an ice water solution (400 mL). The aqueous suspension was extracted with EtOAc. The organics were dried with MgSO$_4$, and concentrated to a brown oil, which was dissolved in 1,4-dioxane (100 mL) and combined with methoxylamine hydrochloride (50 mL of a 25% aqueous solution, 165 mmol, Aldrich). This solution was cooled in an ice bath, and treated with triethylamine (30 mL), then stirred at rt for 18 hr. Ice water was added (100 mL) and the solution was extracted with EtOAc. The organics were dried with MgSO$_4$, and concentrated to a brown solid (16 g, 67 mmol). $^1$H NMR (300 MHz, d$_6$-DMSO) δ 10.9 (s, 1H), 8.58 (s, 1H), 8.42 (d, J=8.4 Hz, 1H), 7.76 (d, J=8.4 Hz, 1H), 3.68 (s, 3H), 2.72 (s, 3H).

Intermediate Example 6

5-Amino-N-methoxy-2-methylbenzenesulfonamide

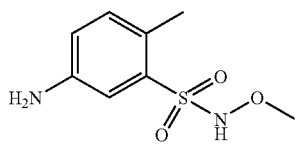

N-Methoxy-2-methyl-5-nitrobenzenesulfonamide (0.5 g, 2 mmol) was combined with 10% palladium on carbon (0.05 g), ethanol (10 mL), and hydrazine (1 mL) and heated at reflux for 18 h. The solution was filtered through celite, concentrated, and purified on silica gel with methanol in dichloromethane. Product was an off white solid (0.28 g, 1.3 mmoL). $^1$H NMR (300 MHz, d$_6$-DMSO) δ10.3 (s, 1H), 7.11 (s, 1H), 7.02 (d, J=8.2 Hz, 1H), 6.7 (d, J=8.2 Hz, 1H), 5.37 (s, 2H), 3.57 (s, 3H), 2.38 (s, 3H).

Intermediate Example 7

N$^5$-(2-Chloro-pyrimidin-4-yl)-N$^2$-(4-fluoro-benzyl)-1,N$^5$-dimethyl-1H-benzoimidazole-2,5-diamine

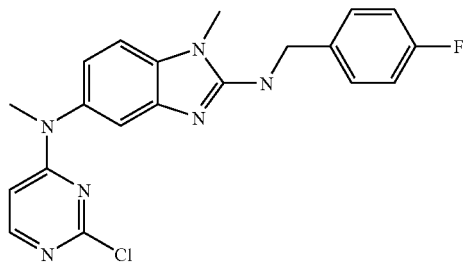

A. (4-Fluoro-benzyl)-(1-methyl-5-nitro-1H-benzoimidazol-2-yl)-amine

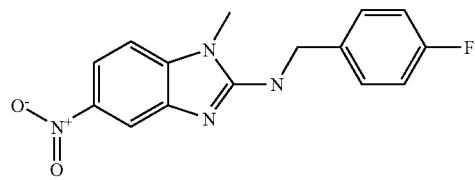

N$^1$-Methyl-4-nitro-benzene-1,2-diamine (2.0 g, 12 mmol) and 4-fluorobenzyl isothiocyante (2.21 g, 13.2 mmol) were coupled using the procedure of intermediate example one part B to give the title compound as a yellow solid (2.16 g, 60%). $^1$H NMR (300 MHz, d$_6$-DMSO) δ 7.96 (d, J=1.8 Hz, 1H), 7.89 (dd, J=6.6 and 1.8 Hz, 1H), 7.76 (t, J=4.5 Hz, 1H), 7.42 (m, 2H), 7.34 (d, J=6.6 Hz, 1H), 7.13 (t, J=6.6 Hz 2H), 4.59 (d, J=4.5 Hz, 2H), 3.60 (s, 3H).

B. N$^2$-(4-Fluoro-benzyl)-1-methyl-1H-benzoimidazole-2,5-diamine

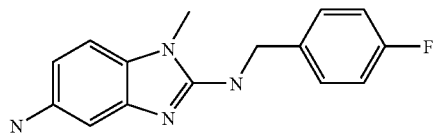

(4-Fluoro-benzyl)-(1-methyl-5-nitro-1H-benzoimidazol-2-yl)-amine (2.16 g, 7.2 mmol) was reduced using the procedure of intermediate example one part C to give the title compound as a white solid (1.77 g, 70%). $^1$H NMR (300 MHz, d$_6$-DMSO) δ 7.39-7.44 (m, 2H), 7.10-7.16 (m, 2H), 6.96-6.99 (m, 1H), 6.79 (d, J=8.1 Hz, 1H), 6.44 (d, J=2.1 Hz, 1H), 6.23 (dd, J=8.1 and 1.8 Hz, 1H), 4.51 (s, 2H), 3.93 (s, 2H), 3.41 (s, 3H).

C. $N^5$-(2-Chloro-pyrimidin-4-yl)-$N^2$-(4-fluoro-benzyl)-1,$N^5$-dimethyl-1H-benzoimidazole-2,5-diamine

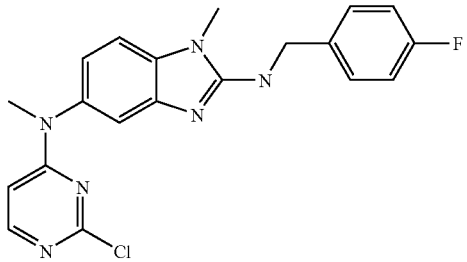

$N^2$-(4-Fluoro-benzyl)-1-methyl-1H-benzoimidazole-2,5-diamine was coupled and methylated according to the procedure of intermediate example one part D to give the title compound as a white solid (603 mg, 23% over two steps). $^1$H NMR (300 MHz, $d_6$-DMSO) δ 7.86 (d, J=6.0 Hz, 1H), 7.40-7.47 (m, 3H), 7.26 (d, J=8.1 Hz, 1H), 7.11-7.17 (m, 3H), 6.85 (dd, J=8.1 and 1.8 Hz, 1H), 6.08 (d, J=5.4 Hz, 1H), 4.57 (d, J=5.7 Hz, 2H), 3.56 (s, 3H), 3.37 (s, 3H). MS (ESI) m/z=397 [M+H]$^+$.

Intermediate Example 8

$N^5$-(2-Chloro-pyrimidin-4-yl)-$N^2$-(4-methoxy-benzyl)-1,$N^5$-dimethyl-1H-benzoimidazole-2,5-diamine

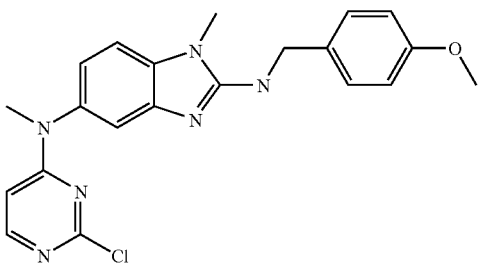

A. (4-Methoxy-benzyl)-(1-methyl-5-nitro-1H-benzoimidazol-2-yl)-amine

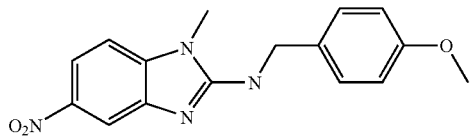

$N^1$-Methyl-4-nitro-benzene-1,2-diamine (2.0 g, 12 mmol) and 4-methoxybenzyl isothiocyante (2.37 g, 13.2 mmol) were coupled using the procedure of intermediate example one part B to give the title compound as a yellow solid (2.00 g, 41%). $^1$H NMR (300 MHz, $d_6$-DMSO) δ 7.98 (d, J=2.1 Hz, 1H), 7.90 (dd, J=8.7 and 2.1 Hz, 1H), 7.68 (t, J=5.7 Hz, 1H), 7.32-7.35 (m, 3H), 6.859 (d, J=8.7 Hz, 2H), 4.55 (d, J=5.7 Hz, 2H), 3.72 (s, 3H), 3.61 (s, 3H).

B. $N^2$-(4-Methoxy-benzyl)-1-methyl-1H-benzoimidazole-2,5-diamine

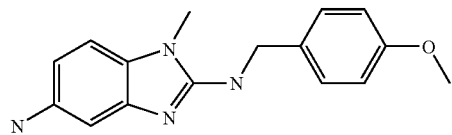

(4-Methoxy-benzyl)-(1-methyl-5-nitro-1H-benzoimidazol-2-yl)-amine (1.99 g, 4.9 mmol) was reduced using the procedure of intermediate example one part C to give the title compound as a white solid (1.68 g, 91%). $^1$H NMR (300 MHz, $d_6$-DMSO) δ 7.30 (d, J=8.1 Hz, 2H), 6.87 (m, 3H), 6.78 (d, J=8.4 Hz, 1H), 6.45 (s, 1H), 6.22 (d, J=8.1 Hz, 1H), 4.45 (d, J=2.1 Hz, 2H), 4.21 (br s, 2H), 3.71 (s, 3H), 3.39 (s, 3H).

C. $N^5$-(2-Chloro-pyrimidin-4-yl)-$N^2$-(4-methoxy-benzyl)-1,$N^5$-dimethyl-1H-benzoimidazole-2,5-diamine

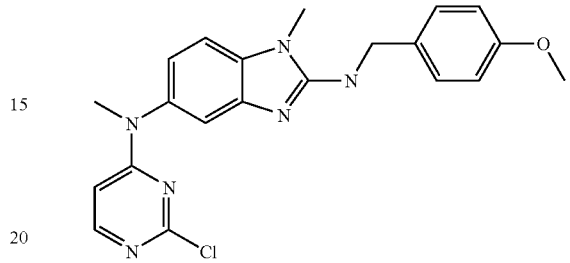

$N^2$-(4-Methoxy-benzyl)-1-methyl-1H-benzoimidazole-2,5-diamine was coupled and methylated according to the procedure of intermediate example one part D to give the title compound as an off-white solid (910 mg, 51% over two steps). $^1$H NMR (300 MHz, $d_6$-DMSO) δ 7.86 (d, J=6.0 Hz, 1H), 7.30-7.37 (m, 3H), 7.24 (d, J=8.1 Hz, 1H), 7.11 (d, J=1.5 Hz, 1H), 6.82-6.89 (M, 3H), 6.09 (d, J=5.4 Hz, 1H), 4.52 (d, J=5.7 Hz, 2H), 3.72 (s, 3H), 3.55 (s, 3H), 3.37 (s, 3H). MS (ESI) m/z=409 [M+H]$^+$.

Intermediate Example 9

$N^5$-(2-Chloro-pyrimidin-4-yl)-$N^2$-(3-fluoro-benzyl)-1,$N^5$-dimethyl-1H-benzoimidazole-2,5-diamine

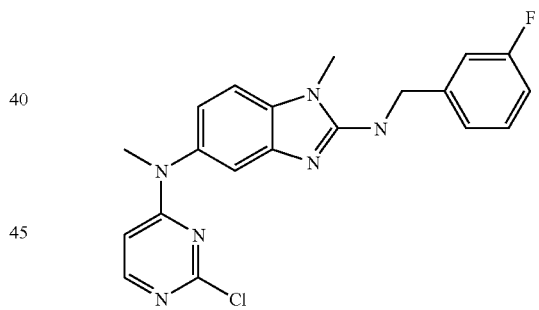

A. (3-Fluoro-benzyl)-(1-methyl-5-nitro-1H-benzoimidazol-2-yl)-amine

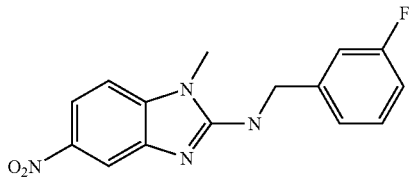

$N^1$-Methyl-4-nitro-benzene-1,2-diamine (1.4 g, 8.4 mmol) and 3-fluorobenzyl isothiocyante (1.26 ml, 9.2 mmol) were coupled using the procedure of intermediate example one part B to give the title compound as a yellow solid (1.40 g, 56%). $^1$H NMR (300 MHz, $d_6$-DMSO) δ 7.98 (d, J=2.1 Hz, 1H), 7.92 (dd, J=8.4 and 2.1 Hz, 1H), 7.81 (t, J=5.7 Hz, 1H), 7.34-7.41 (m, 2H), 7.20-7.25 (M, 2H), 7.07 (td, J=8.7 and 2.4 Hz, 1H), 4.65 (d, J=5.7 Hz, 2H), 3.64 (s, 3H).

B. N²-(3-Fluoro-benzyl)-1-methyl-1H-benzoimidazole-2,5-diamine

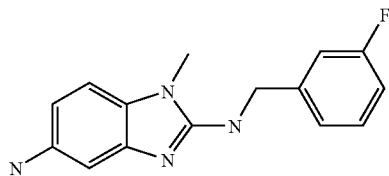

(3-Fluoro-benzyl)-(1-methyl-5-nitro-1H-benzoimidazol-2-yl)-amine (1.39 g, 4.6 mmol) was reduced using the procedure of intermediate example one part C to give the title compound as a white solid (1.12 g, 90%). ¹H NMR (300 MHz, d₆-DMSO) δ 7.30-7.38 (m, 1H), 7.16-7.22 (m, 2H), 7.00-7.06 (M, 2H), 6.79 (d, J=8.4 Hz, 1H), 6.43 (d, J=1.8 Hz, 1H), 6.23 (dd, J=8.1 and 2.1 Hz, 1H), 4.54 (d, J=4.5 Hz, 2H), 4.42 (br s, 2H), 3.42 (s, 3H).

C. N⁵-(2-Chloro-pyrimidin-4-yl)-N²-(3-fluoro-benzyl)-1,N⁵-dimethyl-1H-benzoimidazole-2,5-diamine

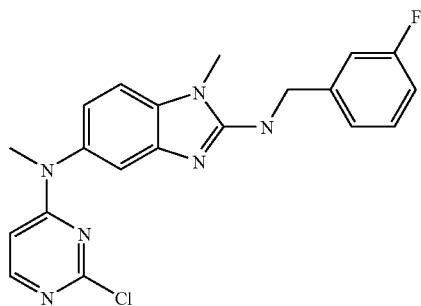

N²-(3-Fluoro-benzyl)-1-methyl-1H-benzoimidazole-2,5-diamine was coupled and methylated according to the procedure of intermediate example one part D to give the title compound as a yellow solid. ¹H NMR (300 MHz, d₆-DMSO) δ 7.85 (d, J=6.0 Hz, 1H), 7.48 (t, J=6.0 Hz, 1H), 7.32-7.39 (m, 1H), 7.17-7.27 (m, 3H), 7.11 (d, J=1.8 Hz, 1H), 7.04 (m, 1H), 6.85 (dd, J=8.1 and 1.8 Hz, 1H), 6.07 (d, J=5.7 Hz 1H), 4.60 (d, J=6.0 Hz, 2H), 3.58 (s, 3H), 3.36 (s, 3H).

Intermediate Example 10

N²-(4-Chloro-benzyl)-N⁵-(2-chloro-pyrimidin-4-yl)-1,N⁵-dimethyl-1H-benzoimidazole-2,5-diamine

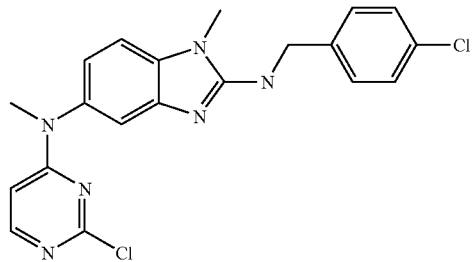

A. (4-Chloro-benzyl)-(1-methyl-5-nitro-1H-benzoimidazol-2-yl)-amine

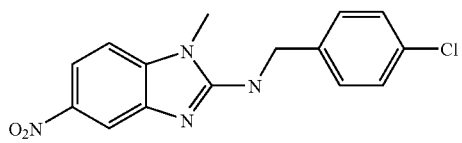

N¹-Methyl-4-nitro-benzene-1,2-diamine (2.0 g, 12.0 mmol) and 4-chlorobenzyl isothiocyante (2.42 g, 13.2 mmol) were coupled using the procedure of intermediate example one part B to give the title compound as a yellow solid (2.82 g, 74%). ¹H NMR (300 MHz, d₆-DMSO) δ 7.96 (d, J=2.1 Hz, 1H), 7.90 (dd, J=8.7 and 2.4 Hz, 1H), 7.98 (t, J=6.0 Hz, 1H), 7.33-7.43 (m, 5H), 4.60 (d, J=5.7 Hz, 2H), 3.61 (s, 3H). MS (ESI) m/z=317 [M+H]⁺.

B. N²-(4-Chloro-benzyl)-1-methyl-1H-benzoimidazole-2,5-diamine

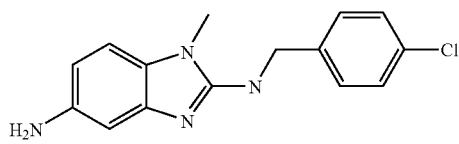

(4-Chloro-benzyl)-(1-methyl-5-nitro-1H-benzoimidazol-2-yl)-amine (2.82 g, 8.9 mmol) was reduced following the procedure of intermediate example one part C to give the title compound as a white solid (2.43 g, 96%). ¹H NMR (300 MHz, d₆-DMSO) δ 733-7.41 (m, 4H), 7.00 (m, 1H), 6.78 (d, J=8.1 Hz, 1H), 6.43 (d, J=1.8 Hz, 1H), 6.22 (dd, J=8.4 and 1.8 Hz, 1H), 4.51 (m, 2H), 3.40 (s, 3H).

C. N²-(4-Chloro-benzyl)-N⁵-(2-chloro-pyrimidin-4-yl)-1,N⁵-dimethyl-1H-benzoimidazole-2,5-diamine

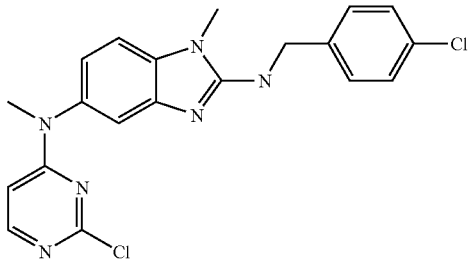

N²-(4-Chloro-benzyl)-1-methyl-1H-benzoimidazole-2,5-diamine (2.43 g, 8.5 mmol) was coupled and methylated according to the procedure of intermediate example one part D to give the title compound as a pink solid (1.93 g, 55%). ¹H NMR (300 MHz, d₆-DMSO) δ 7.85 (d, J=6.0 Hz, 1H), 7.47 (t, J=5.7 Hz, 1H), 7.34-7.42 (M, 4H), 7.25 (d, J=8.4 Hz, 1H), 7.10 (s, 1H), 6.83 (d, J=8.4 Hz, 1H), 6.01 (D, J=4.8 Hz, 1H), 4.57 (d, J=5.7 Hz, 2H), 3.56 (s, 3H), 3.35 (s, 3H). MS (ESI) m/z=413 [M+H]⁺.

Intermediate Example 11

N²-Benzyl-N⁵-(2-chloro-pyrimidin-4-yl)-1-ethyl-N⁵-methyl-1H-benzoimidazole-2,5-diamine

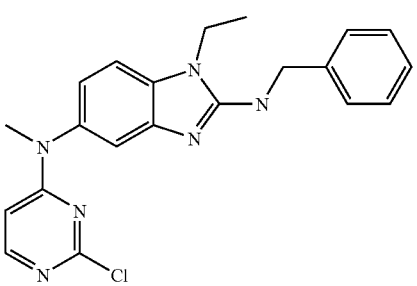

A. N-Ethyl-4-nitro-benzene-1,2-diamine

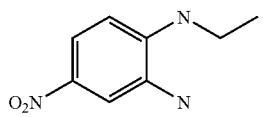

2-fluoro-5-nitroaniline (5 g, 32 mmol) and a solution of ethyl amine (32 ml, 2M in THF) were coupled according to the procedure of intermediate example one part A to give the title compound as a dark red solid 4.16 g, 72%). $^1$H NMR (300 MHz, $d_6$-DMSO) δ7.51 (dd, J=8.7 and 2.7 Hz, 1H), 7.38 (d, J=2.7 Hz, 1H), 6.44 (d, J=8.7 Hz, 1H), 5.86 (t, J=4.6 Hz, 1H), 5.15 (s, 2H), 3.20 (m, 2H), 1.21 (t, J=7.2 Hz, 3H).

B. Benzyl-(1-ethyl-5-nitro-1H-benzoimidazol-2-yl)-amine

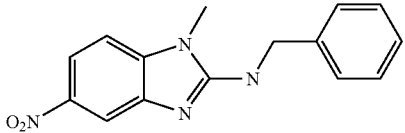

N-Ethyl-4-nitro-benzene-1,2-diamine (2.0 g, 11.0 mmol) and benzyl isothiocyante (1.60 ml, 12.1 mmol) were coupled using the procedure of intermediate example one part B to give the title compound as a yellow solid (2.0 g, 61%). $^1$H NMR (300 MHz, $d_6$-DMSO) δ 7.96 (d, J=2.1 Hz, 1H), 7.89 (dd, J=8.7 and 2.1 Hz, 1H), 7.80 (t, J=5.7 Hz, 1H), 7.21-7.39 (m, 6H), 4.63 (d, J=5.7 Hz, 2H), 4.16 (q, J=6.9 Hz, 2H), 1.24 (t, J=6.9 Hz, 3H).

C. $N^2$-Benzyl-1-ethyl-1H-benzoimidazole-2,5-diamine

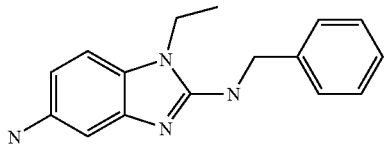

Benzyl-(1-ethyl-5-nitro-1H-benzoimidazol-2-yl)-amine (2.0 g, 6.7 mmol) was reduced following the procedure of intermediate example one part C to give the title compound as a white solid (1.6 g, 90%). $^1$H NMR (300 MHz, $d_6$-DMSO) δ 7.24-7.38 (m, 4H), 7.21 (M, 1H), 6.99 (m, 1H), 6.80 (d, J=8.1 Hz, 1H), 6.44 (d, J=1.8 Hz, 1H), 6.22 (dd, J=8.1 and 1.8 Hz, 1H), 4.55 (s, 2H), 4.20 (br s, 2H), 3.94 (q, J=7.2 Hz, 2H), 1.17 (t, J=7.2 Hz, 3H).

D. $N^2$-Benzyl-$N^5$-(2-chloro-pyrimidin-4-yl)-1-ethyl-$N^5$-methyl-1H-benzoimidazole-2,5-diamine

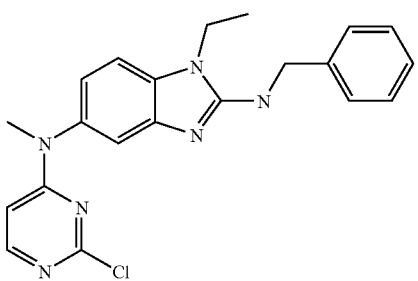

$N^2$-Benzyl-1-ethyl-1H-benzoimidazole-2,5-diamine (1.6 g, 6 mmol) was coupled and methylated following the procedure of intermediate example one part D to give the title compound as a white solid. $^1$H NMR (300 MHz, $d_6$-DMSO) δ 7.86 (d, J=6.0 Hz, 1H), 7.47 (t, J=6.0 Hz, 1H), 7.22-7.39 (m, 6H), 7.11 (d, J=1.8 Hz, 1H), 6.84 (dd, J=8.1 and 1.8 Hz, 1H), 6.11 (d, J=5.7 Hz, 1H), 4.61 (d, J=5.7 Hz, 2H), 4.11 (q, J=7.2 Hz, 2H), 3.37 (s, 3H), 1.25 (t, J=7.2 Hz, 3H). MS (ESI) m/z=393 [M+H]$^+$.

Intermediate Example 12

$N^5$-(2-Chloro-pyrimidin-4-yl)-$N^2$-(2-fluoro-benzyl)-1,$N^5$-dimethyl-1H-benzoimidazole-2,5-diamine

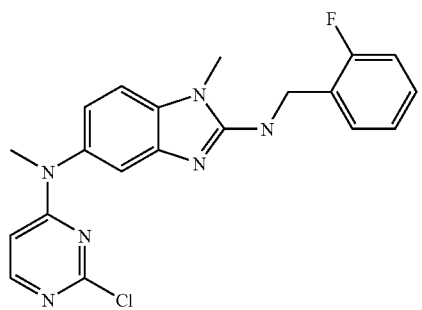

A. (2-Fluoro-benzyl)-(1-methyl-5-nitro-1H-benzoimidazol-2-yl)-amine

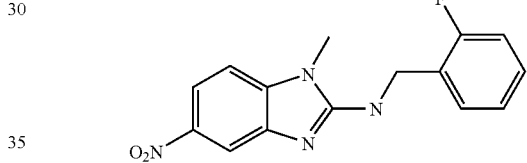

$N^1$-Methyl-4-nitro-benzene-1,2-diamine (2.0 g, 12 mmol) and 2-fluorobenzyl isothiocyante (1.81 ml, 13.2 mmol) were coupled using the procedure of intermediate example one part B to give the title compound as a yellow solid (2.0 g, 56%). $^1$H NMR (300 MHz, $d_6$-DMSO) δ 7.98 (s, 1H), 7.92 (d, J=8.7 Hz, 1H), 7.76 (t, J=5.7 Hz, 1H), 7.47 (m, 1H), 7.28-7.38 (m, 2H), 7.13-7.23 (m, 2H), 4.67 (d, J=5.7 Hz, 2H), 3.64 (s, 3H). MS (ESI) m/z=543 [M+H]$^+$.

B. $N^2$-(2-Fluoro-benzyl)-1-methyl-1H-benzoimidazole-2,5-diamine

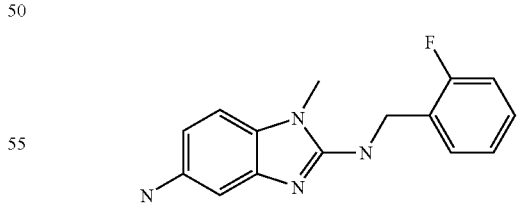

(2-Fluoro-benzyl)-(1-methyl-5-nitro-1H-benzoimidazol-2-yl)-amine was reduced following the procedure of intermediate example one part C to give the title compound as a white solid (1.74 g, 97%). $^1$H NMR (300 MHz, $d_6$-DMSO) δ 7.42-7.47 (m, 1H), 7.26-7.30 (m, 1H), 7.11-7.10 (m, 2H), 6.97-7.01 (m, 1H), 6.80 (d, J=8.1 Hz, 1H), 6.44 (d, J=2.1 Hz, 1H), 6.24 (dd, J=8.2 and 2.2 Hz, 1H), 5.00 (br s, 2H) 4.58 (m, 2H), 3.43 (s, 3H).

C. N⁵-(2-Chloro-pyrimidin-4-yl)-N²-(2-fluoro-benzyl)-1, N⁵-dimethyl-1H-benzoimidazole-5-diamine

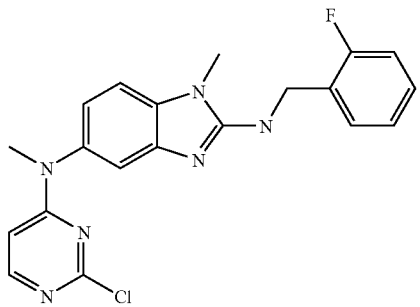

N²-(2-Fluoro-benzyl)-1-methyl-1H-benzoimidazole-2,5-diamine was coupled and methylated according to the procedure of intermediate example one part D to give the title compound as a white solid. ¹H NMR (300 MHz, d₆-DMSO) δ 7.86 (d, J=6.3 Hz, 1H), 7.41-7.48 (M, 2H), 7.26-7.31 (m, 2H), 7.12-7.22 (m, 3H), 6.86 (dd, J=8.1 and 1.8 Hz, 1H), 6.08 (d, J=5.7 Hz, 1H), 4.64 (d, J=5.7 Hz, 2H), 3.59 (s, 3H), 3.37 (s, 3H). MS (ESI) m/z=397 [M+H]⁺.

Intermediate Example 13

N⁵-(2-Chloro-pyrimidin-4-yl)-1,N⁵-dimethyl-N²-(1-phenyl-ethyl)-1H-benzoimidazole-2,5-diamine

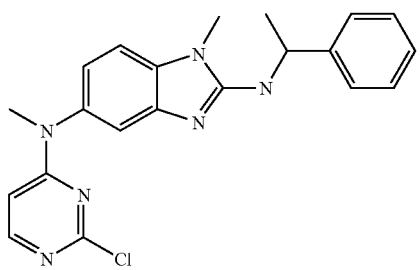

A. (1-Methyl-5-nitro-1H-benzoimidazol-2-yl)-(1-phenyl-ethyl)-amine

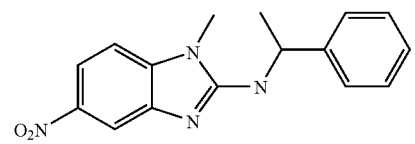

N¹-Methyl-4-nitro-benzene-1,2-diamine (2.0 g, 12 mmol) and 1-phenylethyl isothiocyante (2.15 g, 13.2 mmol) were coupled using the procedure of intermediate example one part B to give the title compound as a yellow solid (1.2 g, 34%). ¹H NMR (300 MHz, d₆-DMSO) δ 7.87-7.94 (m, 2H), 7.44-7.52 (m, 3H), 7.29-7.34 (m, 3H), 7.21 (m, 1H), 5.18 (m, 1H), 3.65 (s, 3H), 1.55 (d, J=6.9 Hz, 3H).

B. 1-Methyl-N²-(1-phenyl-ethyl)-1H-benzoimidazole-2,5-diamine

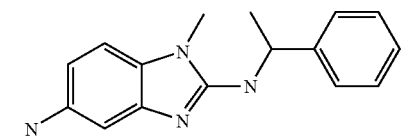

(1-Methyl-5-nitro-1H-benzoimidazol-2-yl)-(1-phenyl-ethyl)-amine was reduced following the procedure of intermediate example one part C to give the title compound as a white solid (1.2 g, 97%). ¹H NMR (300 MHz, d₆-DMSO) δ 7.42 (d, J=7.5 Hz, 2H), 7.27-7.32 (m, 2H), 7.18-7.21 (m, 1H), 6.70-6.78 (m, 2H), 6.40 (d, J=1.8 Hz, 1H), 6.21 (dd, J=8.2 and 2.0 Hz, 1H), 5.09 (m, 1H), 4.37 (br s, 2H), 3.44 (s, 3H), 1.49 (d, J=7.2 Hz, 3H).

C. N⁵-(2-Chloro-pyrimidin-4-yl)-1,N⁵-dimethyl-N²-(1-phenyl-ethyl)-1H-benzoimidazole-2,5-diamine

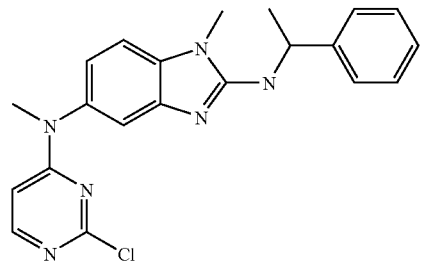

1-Methyl-N²-(1-phenyl-ethyl)-1H-benzoimidazole-2,5-diamine was coupled and methylated according to the procedure of intermediate example one part D to give the title compound as a yellow foam. ¹H NMR (300 MHz, d₆-DMSO) δ 7.84 (d, J=6.3 Hz, 1H), 7.44 (d, J=7.5 Hz, 2H), 7.28-7.34 (m, 2H), 7.16-7.25 (m, 3H), 7.07 (d, J=1.8 Hz, 1H), 6.83 (dd, J=8.1 and 1.8 Hz, 1H), 6.06 (d, J=5.7 Hz, 1H), 5.14 (m, 1H), 3.60 (s, 3H), 3.35 (s, 3H). MS (ESI) m/z=393 [M+H]⁺.

Intermediate Example 14

N⁵-(2-Chloro-pyrimidin-4-yl)-1,N⁵-dimethyl-N²-(4-methyl-benzyl)-1H-benzoimidazole-2,5-diamine hydrochloride

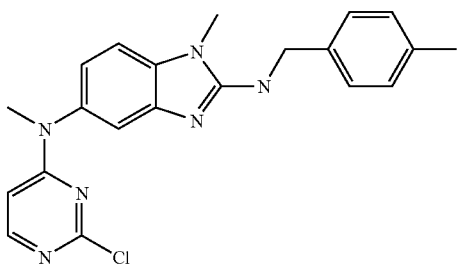

A. (4-Methyl-benzyl)-(1-methyl-5-nitro-1H-benzoimidazol-2-yl)-amine

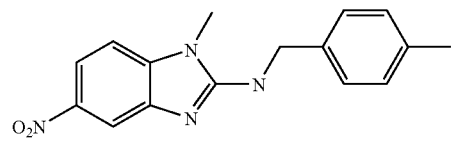

N¹-Methyl-4-nitro-benzene-1,2-diamine (2.0 g, 12 mmol) and 4-methylbenzyl isothiocyante (2.15 g, 13.2 mmol) were coupled using the procedure of intermediate example one part B to give the title compound as a yellow solid (2.1 g, 59%). ¹H NMR (300 MHz, d₆-DMSO) δ 7.97 (d, J=2.4 Hz, 1H), 7.90 (dd, J=8.7 and 2.1 Hz, 1H), 7.71 (t, J=6.0H, 1H), 7.34 (d, JH=8.7 Hz, 1H), 7.28 (d, J=7.8 Hz, 2H), 7.13 (d, J=8.1 Hz, 2H), 4.58 (d, J=6.0 Hz, 2H), 3.61 (s, 3H), 2.27 (s, 3H).

B. 1-Methyl-N²-(4-methyl-benzyl)-1H-benzoimidazole-2,5-diamine

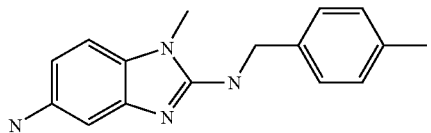

(4-Methyl-benzyl)-(1-methyl-5-nitro-1H-benzoimidazol-2-yl)-amine was reduced following the procedure of intermediate example one part C to give the title compound as a white solid (1.8 g, 95%). ¹H NMR (300 MHz, d₆-DMSO) δ 7.26 (d, J=8.1 Hz, 2H), 7.11 (d, J=7.8 Hz, 2H), 6.88 (t, J=6.0 Hz, 1H), 6.77 (d, J=8.1 Hz, 1H), 6.43 (d, J=1.8 Hz, 1H), 6.22 (dd, J=8.1 and 2.1 Hz, 1H), 4.48 (d, J=5.7 Hz, 2H), 4.37 (s, 2H), 3.40 (s, 3H), 2.26 (s, 3H).

C. N⁵-(2-Chloro-pyrimidin-4-yl)-1,N⁵-dimethyl-N²-(4-methyl-benzyl)-1H-benzoimidazole-2,5-diamine

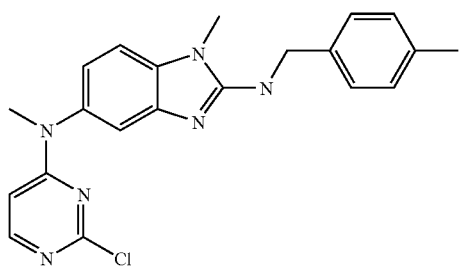

1-Methyl-N²-(4-methyl-benzyl)-1H-benzoimidazole-2,5-diamine was coupled and methylated according to the procedure of intermediate example one part D to give the title compound as a white solid. ¹H NMR (300 MHz, d₆-DMSO) δ 7.86 (d, J=6.0 Hz, 1H), 7.38 (t, J=6.0 Hz, 1H), 7.23-7.28 (m, 3H), 7.11-7.13 (m, 3H), 6.84 (dd, J=8.1 and 1.8 Hz, 1H), 6.08 (d, J=5.4 Hz, 1H), 4.54 (d, J=5.7 Hz, 2H), 3.56 (s, 3H), 3.37 (s, 3H), 2.26 (s, 3H). MS (ESI) m/z=393 [M+H]⁺.

Intermediate Example 15

N²-(3-Chloro-benzyl)-N⁵-(2-chloro-pyrimidin-4-yl)-1,N⁵-dimethyl-1H-benzoimidazole-2,5-diamine

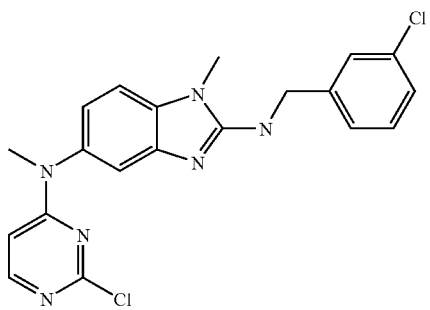

A. (3-Chloro-benzyl)-(1-methyl-5-nitro-1H-benzoimidazol-2-yl)-amine

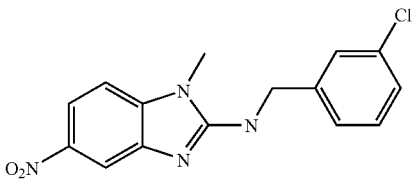

N¹-Methyl-4-nitro-benzene-1,2-diamine (2.0 g, 12.0 mmol) and 3-chlorobenzyl isothiocyante (1.94 ml, 13.2 mmol) were coupled using the procedure of intermediate example one part B to give the title compound as a yellow solid (2.2 g, 58%). ¹H NMR (300 MHz, d₆-DMSO) δ 7.98 (d, J=2.1 Hz, 1H), 7.90-7.93 (m, 1H), 7.82 (t, J=5.7 Hz, 1H), 7.46 (s, 1H), 7.30-7.38 (m, 4H), 4.63 (d, J=5.7 Hz, 2H), 3.64 (s, 3H).

B. N²-(3-Chloro-benzyl)-1-methyl-1H-benzoimidazole-2,5-diamine

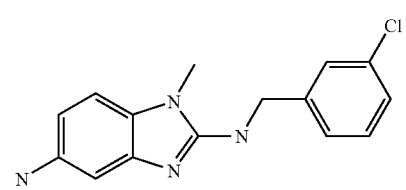

(3-Chloro-benzyl)-(1-methyl-5-nitro-1H-benzoimidazol-2-yl)-amine was reduced following the procedure of intermediate example one part C to give the title compound as a white solid (0.67 g, 34%). ¹H NMR (300 MHz, d₆-DMSO) δ 7.22-7.43 (m, 5H), 6.80 (m, 1H), 6.44 (d, J=1.8 Hz, 1H), 6.23 (m, 1H), 4.54 (s, 2H), 3.42 (s, 3H).

C. N²-(3-Chloro-benzyl)-N⁵-(2-chloro-pyrimidin-4-yl)-1,N⁵-dimethyl-1H-benzoimidazole-2,5-diamine

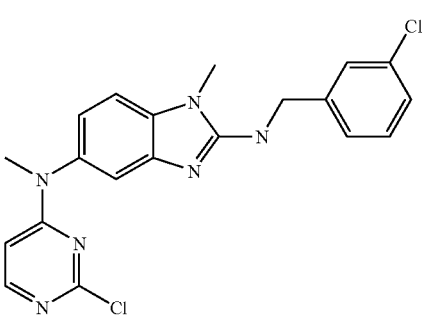

N²-(3-Chloro-benzyl)-1-methyl-1H-benzoimidazole-2,5-diamine was coupled and methylated according to the procedure of intermediate example one part D to give the title compound as a white solid. ¹H NMR (300 MHz, d₆-DMSO) δ 7.86 (d, J=6.0 Hz, 1H), 7.24-7.52 (m, 6H), 7.12 (m, 1H), 6.86 (dd, J=8.1 and 2.1 Hz, 1H), 6.09 (d, J=5.4 Hz, 1H), 4.60 (d, J=5.7 Hz, 2H), 3.58 (s, 3H), 3.37 (s, 3H). MS (ESI) m/z=413 [M+H]⁺.

Intermediate Example 16

3-amino-benzenesulfonamide

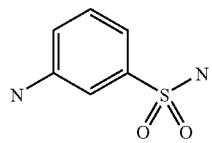

The title compound is commercially available: CAS # 98-18-0.

Intermediate Example 17

5-amino-2-methyl-benzenesulfonamide

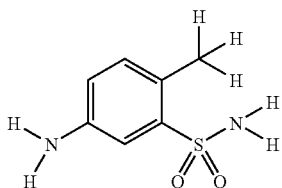

The title compound is described in the literature: CAS # 6973-09-7.

Intermediate Example 18

4-[(methylsulfonyl)methyl]aniline

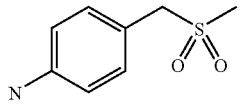

The title compound is described in the literature: CAS # 24176-70-3.

Intermediate Example 19

(4-amino-phenyl)-methanesulfonamide

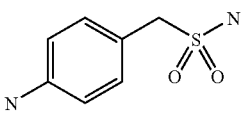

The title compound is described in the literature: CAS # 4403-84-3.

Intermediate Example 20

2-(4-amino-phenyl)-ethanesulfonic acid methylamide

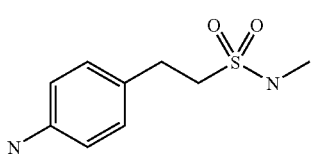

The title compound is described in the literature: CAS # 98623-16-6.

Intermediate Example 21

4-(2-Methanesulfonyl-ethyl)-phenylamine

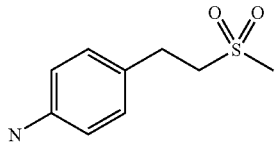

Synthesis of the title compound is described in International Patent Application PCT/US 03/03816 filed Feb. 7, 2003.

Intermediate Example 22

3-Methanesulfonylmethyl-phenylamine

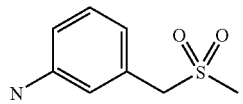

The title compound is described in the literature: CAS #261925-02-4.

Intermediate Example 23

Methanesulfonic acid 3-amino-phenylester

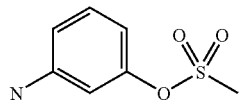

The title compound is described in the literature: CAS # 38164-50-0.

Intermediate Example 24

3-(2-methanesulfonyl-ethyl)-phenylamine

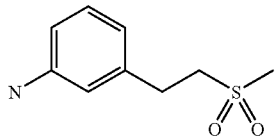

Synthesis of the title compound is described in International Patent Application PCT/US 03/03816 filed Feb. 7, 2003.

Intermediate Example 25

4-(1-methanesulfonyl-ethyl)-phenylamine

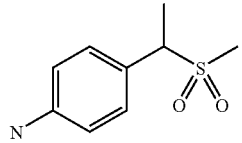

Synthesis of the title compound is described in International Patent Application PCT/US 03/03816 filed Feb. 7, 2003.

Intermediate Example 26

{5-[(2-Chloro-pyrimidin-4-yl)-methyl-amino]-1-methyl-1H-benzoimidazol-2-yl}-(4-fluoro-phenyl)-carbamic acid tert-butyl ester

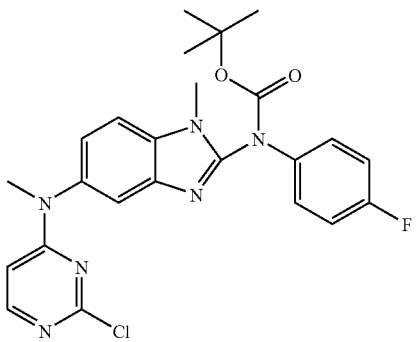

A. (4-Fluoro-phenyl)-(1-methyl-5-nitro-1H-benzoimidazol-2-yl)-amine

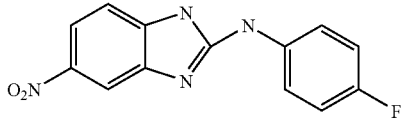

$N^1$-Methyl-4-nitro-benzene-1,2-diamine (2.0 g, 12 mmol) and 4-fluorophenyl isothiocyante (1.58 ml, 13.2 mmol) were coupled using the procedure of intermediate example four part A to give the title compound as a yellow solid (1.49 g, 43%). $^1$H NMR (300 MHz, $d_6$-DMSO) δ 9.29 (s, 1H), 8.17 (m, 1H), 8.01-8.04 (m, 1H), 7.89-7.90 (m, 2H), 7.49-7.52 (M, 1H), 7.18-7.25 (m, 2H), 3.79 (s, 3H).

B. (1-Methyl-5-nitro-1H-benzoimidazol-2-yl)-phenyl-carbamic acid tert-butyl ester

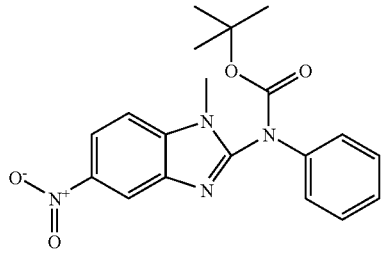

(4-Fluoro-phenyl)-(1-methyl-5-nitro-1H-benzoimidazol-2-yl)-amine (1.49 g, 5.2 mmol) was protected following the procedure of intermediate example four part B to give the title compound as a light yellow solid (1.08 g, 54%). $^1$H NMR (300 MHz, $d_6$-DMSO) δ 8.50 (d, J=2.1 Hz, 1H), 8.23 (dd, J=9.0 and 2.1 Hz, 1H), 7.85 (d, J=9.0 Hz, 1H), 7.47-7.51 (M, 2H), 7.22-7.27 (m, 2H), 3.84 (s, 3H), 1.40 (s, 9H).

C. (5-Amino-1-methyl-1H-benzoimidazol-2-yl)-(4-fluoro-phenyl)-carbamic acid tert-butyl ester

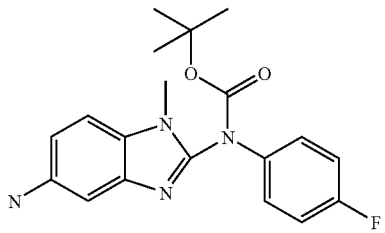

(1-Methyl-5-nitro-1H-benzoimidazol-2-yl)-phenyl-carbamic acid tert-butyl ester (1.08 g, 2.8 mmol) was reduced by the procedure of intermediate example one part C to give the title compound as a white solid (0.99 g, 99%). $^1$H NMR (300 MHz, $d_6$-DMSO) δ 7.39-7.44 (M, 2H), 7.17-7.23 (M, 3H), 6.70 (d, J=1.5 Hz, 1H), 6.63 (dd, J=8.5 and 2.0 Hz, 1H), 4.78 (s, 2H), 3.61 (s, 3H).

D. [5-(2-Chloro-pyrimidin-4-ylamino)-1-methyl-1H-benzoimidazol-2-yl]-(4-fluoro-phenyl)-carbamic acid tert-butyl ester

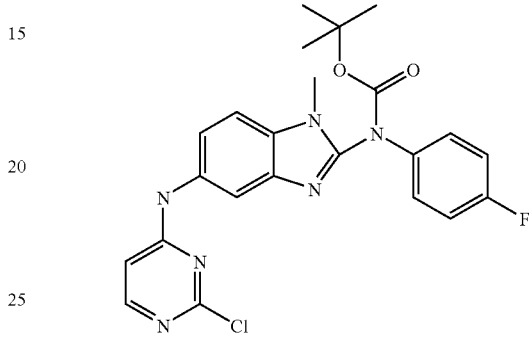

(5-Amino-1-methyl-1H-benzoimidazol-2-yl)-(4-fluoro-phenyl)-carbamic acid tert-butyl ester (0.99 g, 2.8 mmol) was coupled according to the procedure of intermediate example four part D to give the title compound as a white solid (1.00 g, 76%). $^1$H NMR (300 MHz, $d_6$-DMSO) δ 10.00 (s, 1H), 8.10 (d, J=6.0 Hz, 1H), 7.89 (m, 1H), 7.58 (d, J=8.4 Hz, 1H), 7.44-7.49 (m, 2H), 7.34 (d, J=8.7 Hz, 1H), 7.20-7.26 (m, 2H), 6.69 (d, J=6.0 Hz, 1H), 3.74 (s, 3H), 1.40 (s, 9H).

E. {5-[(2-Chloro-pyrimidin-4-yl)-methyl-amino]-1-methyl-1H-benzoimidazol-2-yl}-(4-fluoro-phenyl)-carbamic acid tert-butyl ester

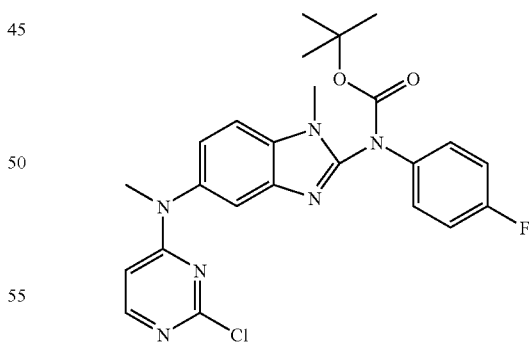

[5-(2-Chloro-pyrimidin-4-ylamino)-1-methyl-1H-benzoimidazol-2-yl]-(4-fluoro-phenyl)-carbamic acid tert-butyl ester was methylated according to the procedure of intermediate example four part E to give the title compound as an orange foam. $^1$H NMR (300 MHz, $d_6$-DMSO) δ 7.91 (d, J=6.0 Hz, 1H), 7.72 (d, J=8.4 Hz, 1H), 7.61 (d, J=1.5 Hz, 1H), 7.45-7.50 (M, 2H), 7.20-7.29 (M, 3H), 6.17 (d, J=5.7 Hz, 1H), 3.79 (s, 3H), 3.41 (s, 3H), 1.42 (s, 9H). MS (ESI) m/z=483 [M+H]$^+$.

Intermediate Example 27

{5-[(2-Chloro-pyrimidin-4-yl)-methyl-amino]-1-methyl-1H-benzoimidazol-2-yl}-p-tolyl-carbamic acid tert-butyl ester

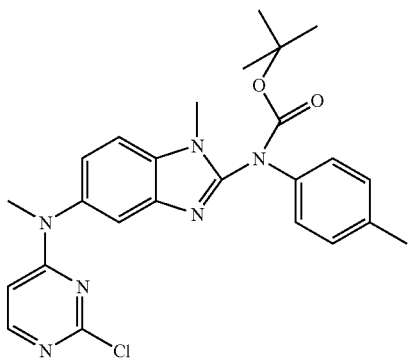

A. (1-Methyl-5-nitro-1H-benzoimidazol-2-yl)-p-tolyl-amine

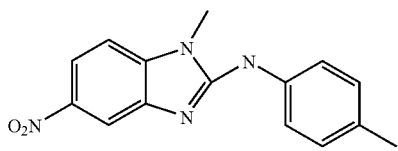

$N^1$-Methyl-4-nitro-benzene-1,2-diamine (2.5 g, 15 mmol) and p-tolyl isothiocyante (2.46 g, 16.5 mmol) were coupled using the procedure of intermediate example four part A to give the title compound as a yellow solid (1.99 g, 470%). $^1$H NMR (300 MHz, $d_6$-DMSO) δ 9.14 (s, 1H), 8.15 (d, J=2.1 Hz, 1H), 8.00 (dd, J=8.7 and 2.1 Hz, 1H), 7.76 (d, J=8.4 Hz, 2H), 7.47 (d, J=8.7 Hz, 1H), 7.16 (d, J=8.4 Hz, 2H), 3.77 (s, 3H), 2.28 (s, 3H).

B. (1-Methyl-5-nitro-1H-benzoimidazol-2-yl)-p-tolyl-carbamic acid tert-butyl ester

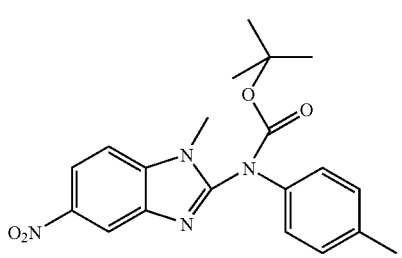

(1-Methyl-5-nitro-1H-benzoimidazol-2-yl)-p-tolyl-amine (2.0 g, 7.1 mmol) was protected following the procedure of intermediate example four part B to give the title compound as a light yellow solid (1.50 g, 55%). $^1$H NMR (300 MHz, $d_6$-DMSO) δ 8.49 (d, J=2.1 Hz, 1H), 8.22 (dd, J=9.0 and 2.1 Hz, 1H), 7.83 (d, J=9.3 Hz, 1H), 7.28 (d, J=8.4 Hz, 2H), 7.20 (d, J=8.1 Hz, 2H), 3.82 (s, 3H), 2.29 (s, 3H), 1.40 (s, 9H). MS (ESI) m/z=405 [M+Na]$^+$.

C. (5-Amino-1-methyl-1H-benzoimidazol-2-yl)-p-tolyl-carbamic acid tert-butyl ester

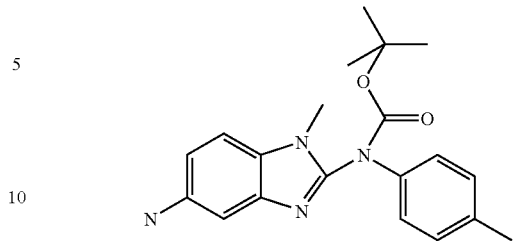

(1-Methyl-5-nitro-1H-benzoimidazol-2-yl)-p-tolyl-carbamic acid tert-butyl ester (1.50 g, 3.9 mmol) was reduced by the procedure of intermediate example one part C to give the title compound as a white solid (1.31 g, 96%). $^1$H NMR (300 MHz, $d_6$-DMSO) δ 7.14-7.23 (m, 5H), 6.69 (d, J=1.5 Hz, 1H), 6.62 (dd, J=8.5 and 1.9 Hz, 1H), 4.77 (s, 2H), 3.58 (s, 3H), 2.27 (s, 3H), 1.38 (s, 9H).

D. [5-(2-Chloro-pyrimidin-4-ylamino)-1-methyl-1H-benzoimidazol-2-yl]-p-tolyl-carbamic acid tert-butyl ester

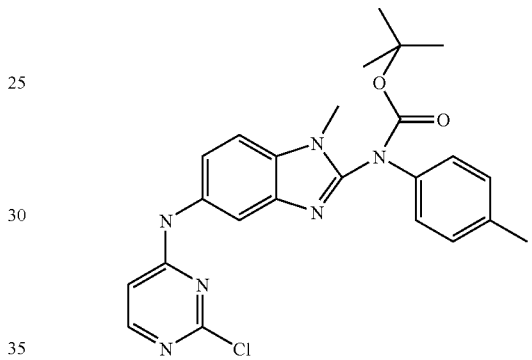

(5-Amino-1-methyl-1H-benzoimidazol-2-yl)-p-tolyl-carbamic acid tert-butyl ester (1.31 g, 3.7 mmol) was coupled according to the procedure of intermediate example four part D to give the title compound as a white solid (0.75 g, 44%). $^1$H NMR (300 MHz, $d_6$-DMSO) δ 10.00 (s, 1H), 8.10 (d, J=6.0 Hz, 1H), 7.87 (s, 1H), 7.57 (d, J=8.7 Hz, 1H), 7.34 (d, J=8.7 Hz, 1H), 7.26 (d, J=8.4 Hz, 2H), 7.18 (d, J=8.4 Hz, 2H), 6.69 (d, J=6.0 Hz, 1H), 3.72 (s, 3H), 2.28 (s, 3H), 1.40 (s, 9H). MS (ESI) m/z=465 [M+H]$^+$.

E. {5-[(2-Chloro-pyrimidin-4-yl)-methyl-amino]-1-methyl-1H-benzoimidazol-2-yl}-p-tolyl-carbamic acid tert-butyl ester

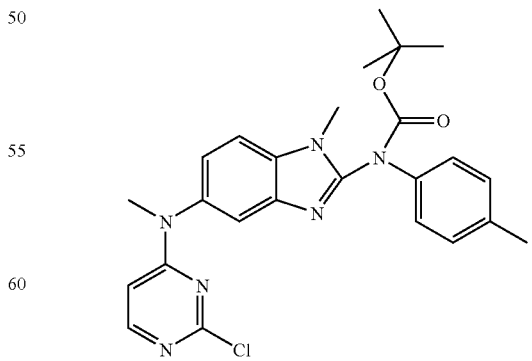

[5-(2-Chloro-pyrimidin-4-ylamino)-1-methyl-1H-benzoimidazol-2-yl]-p-tolyl-carbamic acid tert-butyl ester (0.75 g, 1.62 mmol) was methylated according to the procedure of intermediate example four part E to give the title compound as a white solid. $^1$H NMR (300 MHz, d$_6$-DMSO) δ 7.91 (d, J=6.0 Hz, 1H), 7.71 (d, J=8.4 Hz, 1H), 7.59 (d, J=1.2 Hz, 1H), 7.27 (d, J=8.4 Hz, 3H), 7.19 (d, J=8.4 Hz, 2H), 6.17 (d, J=5.4 Hz, 1H), 3.76 (s, 3H), 3.41 (s, 3H), 2.28 (s, 3H), 1.41 (s, 9H). MS (ESI) m/z=479 [M+H]$^+$.

Intermediate Example 28

(4-tert-Butyl-phenyl)-{5-[(2-chloro-pyrimidin-4-yl)-methyl-amino]-1-methyl-1H-benzoimidazol-2-yl}-carbamic acid tert-butyl ester

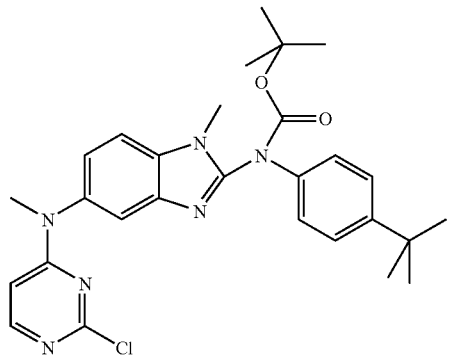

A. (4-tert-Butyl-phenyl)-(1-methyl-5-nitro-1H-benzoimidazol-2-yl)-amine

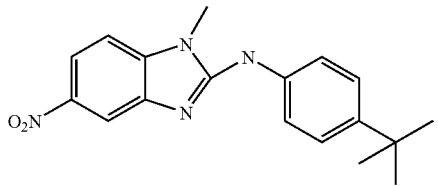

N$^1$-Methyl-4-nitro-benzene-1,2-diamine (1.89 g, 11.3 mmol) and p-tert-butylphenyl isothiocyante (2.37 g, 12.4 mmol) were coupled using the procedure of intermediate example four part A to give the title compound as a yellow solid (1.39 g, 38%). $^1$H NMR (300 MHz, d$_6$-DMSO) δ 9.17 (s, 1H), 8.14 (d, J=2.7 Hz, 1H), 8.00 (dd, J=9.0 and 2.4 Hz, 1H), 7.76 (d, J=8.7 Hz, 2H), 7.48 (d, J=9.0 Hz, 1H), 7.37 (d, J=8.7 Hz, 2H), 3.78 (s, 3H), 1.29 (s, 9H).

B. (4-tert-Butyl-phenyl)-(1-methyl-5-nitro-1H-benzoimidazol-2-yl)-carbamic acid tert-butyl ester

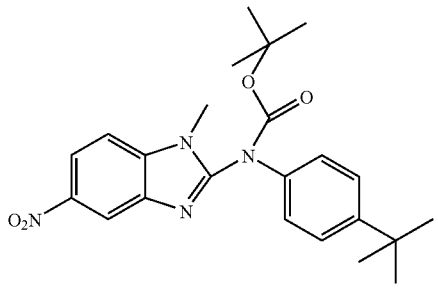

(4-tert-Butyl-phenyl)-(1-methyl-5-nitro-1H-benzoimidazol-2-yl)-amine (1.38 g, 4.3 mmol) was protected following the procedure of intermediate example four part B to give the title compound as a light yellow solid (0.86 g, 47%). $^1$H NMR (300 MHz, d$_6$-DMSO) δ 8.49 (d, J=2.1 Hz, 1H), 8.23 (dd, J=9.0 and 2.1 Hz, 1H), 7.84 (d, J=9.3 Hz, 1H), 7.41 (d, J=8.4 Hz, 2H), 7.31 (d, J=8.7 Hz, 2H), 3.83 (s, 3H), 1.40 (s, 9H), 1.26 (s, 9H).

C. (5-Amino-1-methyl-1H-benzoimidazol-2-yl)-(4-tert-butyl-phenyl)-carbamic acid tert-butyl ester

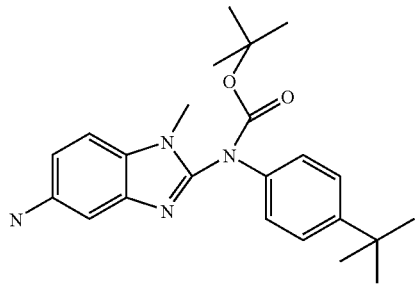

(4-Tert-Butyl-phenyl)-(1-methyl-5-nitro-1H-benzoimidazol-2-yl)-carbamic acid tert-butyl ester (0.86 g, 2.1 mmol) was reduced by the procedure of intermediate example one part C to give the title compound as a white solid (0.81 g, 98%). $^1$H NMR (300 MHz, d$_6$-DMSO) δ 7.37 (d, J=8.4 Hz, 2H), 7.18-7.25 (m, 2H), 6.69 (d, J=1.8 Hz, 1H), 6.62 (dd, J=8.7 and 2.1 Hz, 1H), 4.78 (s, 2H), 3.60 (s, 3H), 1.38 (s, 9H), 1.25 (s, 9H).

D. (4-tert-Butyl-phenyl)-[5-(2-chloro-pyrimidin-4-ylamino)-1-methyl-1H-benzoimidazol-2-yl]-carbamic acid tert-butyl ester

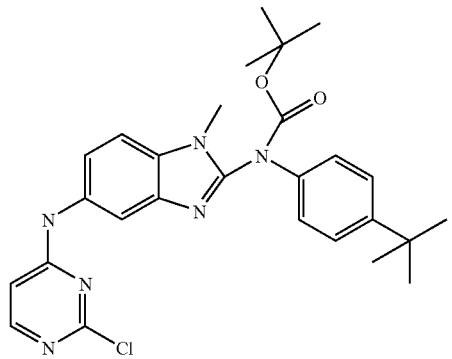

(5-Amino-1-methyl-1H-benzoimidazol-2-yl)-(4-tert-butyl-phenyl)-carbamic acid tert-butyl ester (0.81 g, 2.1 mmol) was coupled according to the procedure of intermediate example four part D to give the title compound as a white solid (0.76 g, 72%). $^1$H NMR (300 MHz, d$_6$-DMSO) δ 10.00 (s, 1H), 8.10 (d, J=5.7 Hz, 1H), 7.88 (s, 1H), 7.57 (d, J=8.7 Hz, 1H), 7.27-7.41 (m, 6H), 6.69 (d, J=6.0 Hz, 1H), 3.73 (s, 3H), 1.40 (s, 9H), 1.26 (s, 9H).

E. (4-tert-Butyl-phenyl)-{5-[(2-chloro-pyrimidin-4-yl)-methyl-amino]-1-methyl-1H-benzoimidazol-2-yl}-carbamic acid tert-butyl ester

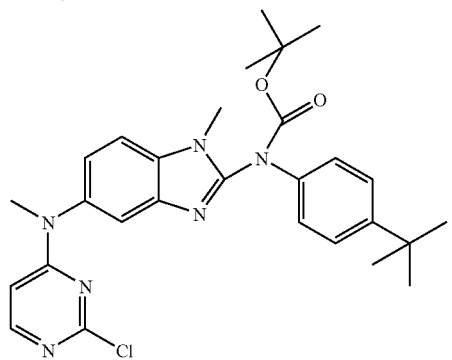

(4-tert-Butyl-phenyl)-[5-(2-chloro-pyrimidin-4-ylamino)-1-methyl-1H-benzoimidazol-2-yl]-carbamic acid tert-butyl ester (0.76 g, 1.50 mmol) was methylated according to the procedure of intermediate example four part E to give the title compound as a white solid. $^1$H NMR (300 MHz, d$_6$-DMSO) δ 7.90 (d, J=6.0 Hz, 1H), 7.72 (d, J=8.7 Hz, 1H), 7.60 (d, J=1.5 Hz, 1H), 7.40 (d, J=8.7 Hz, 2H), 7.25-7.31 (m, 3H), 7.16 (d, J=5.7 Hz, 1H), 3.78 (s, 3H), 3.41 (s, 3H), 1.41 (s, 9H), 1.26 (s, 9H). MS (ESI) m/z=521 [M+H]$^+$.

Intermediate Example 29

N$^5$-(2-Chloro-pyrimidin-4-yl)-N$^2$-(4-methoxy-phenyl)-1, N$^5$-dimethyl-1H-benzoimidazole-2,5-diamine

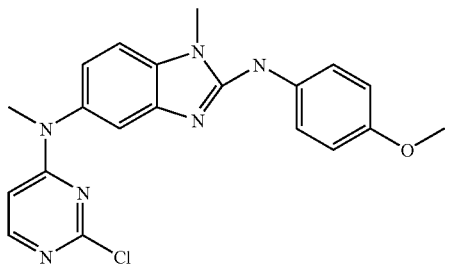

A. (4-Methoxy-phenyl)-(1-methyl-5-nitro-1H-benzoimidazol-2-yl)-amine

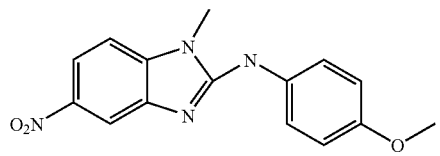

N$^1$-Methyl-4-nitro-benzene-1,2-diamine (2.0, 12.0 mmol) and p-methoxyphenyl isothiocyante (1.82 ml, 13.2 mmol) were coupled using the procedure of intermediate example four part A to give the title compound as a yellow solid (1.88 g, 53%). $^1$H NMR (300 MHz, d$_6$-DMSO) δ 9.08 (s, 1H), 8.12 (d, J=2.1 Hz, 1H), 7.99 (dd, J=8.7 and 2.1 Hz, 1H), 7.76 (d, J=9.0 Hz, 2H), 7.46 (d, J=9.0 Hz, 1H), 6.95 (d, J=9.0 Hz, 2H), 3.76 (s, 3H), 3.75 (s, 3H). MS (ESI) m/z=299 [M+H]$^+$.

B. (4-Methoxy-phenyl)-(1-methyl-5-nitro-1H-benzoimidazol-2-yl)-carbamic acid tert-butyl ester

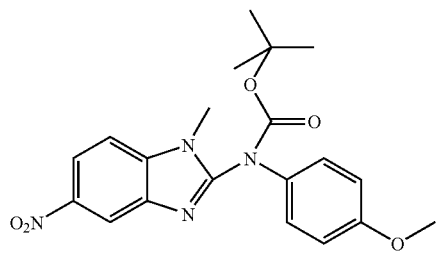

(4-Methoxy-phenyl)-(1-methyl-5-nitro-1H-benzoimidazol-2-yl)-amine (1.88 g, 6.3 mmol) was protected following the procedure of intermediate example four part B to give the title compound as a light yellow solid (1.09 g, 43%). $^1$H NMR (300 MHz, d$_6$-DMSO) δ 8.48 (d, J=2.1 Hz, 1H), 8.22 (dd, J=9.0 and 2.1 Hz, 1H), 7.82 (d, J=9.0 Hz, 1H), 7.35 (d, J=9.0 Hz, 2H), 6.94 (d, J=8.7 Hz, 2H), 3.83 (s, 3H), 3.74 (s, 3H), 1.40 (s, 9H). MS (ESI) m/z=399 [M+H]$^+$.

C. (5-Amino-1-methyl-1H-benzoimidazol-2-yl)-(4-methoxy-phenyl)-carbamic acid tert-butyl ester

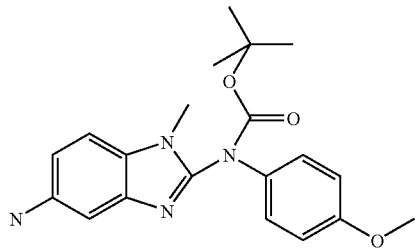

(4-Methoxy-phenyl)-(1-methyl-5-nitro-1H-benzoimidazol-2-yl)-carbamic acid tert-butyl ester (1.09 g, 2.7 mmol) was reduced by the procedure of intermediate example one part C to give the title compound as a white solid (1.05 g, 98%). $^1$H NMR (300 MHz, d$_6$-DMSO) δ 7.28 (d, J=8.7 Hz, 2H), 7.18 (d, J=8.4 Hz, 1H), 6.91 (d, J=9.0 Hz, 2H), 6.68 (d, J=1.5 Hz, 1H), 6.61 (dd, J=8.4 and 1.5 Hz, 1H), 4.76 (s, 2H), 3.73 (s, 3H), 3.60 (s, 3H), 1.38 (s, 9H).

D. [5-(2-Chloro-pyrimidin-4-ylamino)-7-methyl-1H-benzoimidazol-2-yl]-(4-methoxy-phenyl)-carbamic acid tert-butyl ester

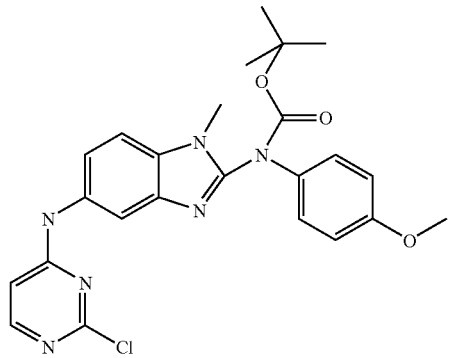

(5-Amino-1-methyl-1H-benzoimidazol-2-yl)-(4-methoxy-phenyl)-carbamic acid tert-butyl ester (1.05 g, 2.85 mmol) was coupled according to the procedure of intermediate example four part D to give the title compound as a white solid (0.96 g, 70%). $^1$H NMR (300 MHz, d$_6$-DMSO) δ 9.99(s, 1H), 8.09 (d, J=6.0 Hz, 1H), 7.87 (br s, 1H), 7.56 (d, J=8.7 Hz, 1H), 7.33 (d, J=9.0 Hz, 2H), 6.93 (d, J=9.0 Hz, 2H), 6.69 (d, J=6.0 Hz, 1H), 3.74 (s, 3H), 3.73 (s, 3H), 1.39 (s, 9H). MS (ESI) m/z=481 [M+H]$^+$.

E. {5-[(2-Chloro-pyrimidin-4-yl)-methyl-amino]-1-methyl-1H-benzoimidazol-2-yl}-(4-methoxy-phenyl)-carbamic acid tert-butyl ester

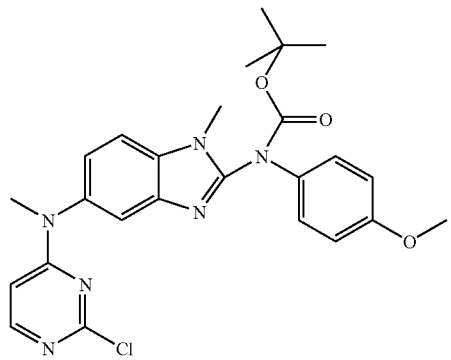

[5-(2-Chloro-pyrimidin-4-ylamino)-1-methyl-1H-benzoimidazol-2-yl]-(4-methoxy-phenyl)-carbamic acid tert-butyl ester was methylated according to the procedure of intermediate example four part E to give the title compound as a white solid. ¹H NMR (300 MHz, d₆-DMSO) δ 7.90 (d, J=6.0 Hz, 1H), 7.70 (d, J=8.4 Hz, 1H), 7.59 (d, J=1.8 Hz, 1H), 7.34 (d, J=9.0 Hz, 2H), 7.26 (dd, J=8.5 and 1.9 Hz, 1H), 6.93 (d, J=9.0 Hz, 2H), 6.16 (d, J=5.4 Hz, 1H), 3.78 (s, 3H), 3.74 (s, 3H), 3.41 (s, 3H), 1.41 (s, 9H). MS (ESI) m/z=495 [M+H]⁺.

Intermediate Example 30

$N^5$-(2-Chloro-pyrimidin-4-yl)-1,$N^5$-dimethyl-$N^2$-phenethyl-1H-benzoimidazole-2,5-diamine

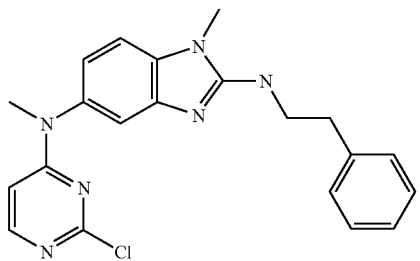

A. (1-Methyl-5-nitro-1H-benzoimidazol-2-yl)-phenethylamine

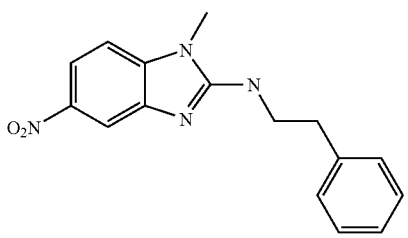

$N^1$-methyl-4-nitro-benzene-1,2-diamine (2.0 g, 12.0 mmol) and phenethyl isothiocyanate (2.15 g, 13.2 mmol) were coupled using the procedure of intermediate example one part B to give the title compound as a yellow solid (2.36 g, 66%). ¹H NMR (300 MHz, d₆-DMSO) δ 8.01 (d, J=2.1 Hz, 1H), 7.90 (dd, J=8.7 and 2.4 Hz, 1H), 7.21-7.35 (m, 7H), 3.58-3.65 (m, 2H), 3.56 (s, 3H), 2.93-2.98 (m, 2H) ppm.

B. 1-Methyl-$N^2$-phenethyl-1H-benzoimidazole-2,5-diamine

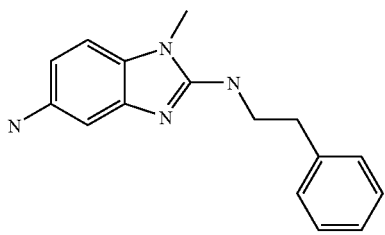

(1-Methyl-5-nitro-1H-benzoimidazol-2-yl)-phenethylamine (2.36 g, 8 mmol) was reduced using the procedure of intermediate example one part C to give the title compound as a white solid (1.98 g, 93%). ¹H NMR (300 MHz, CD₃OD) δ.

C. $N^5$-(2-Chloro-pyrimidin-4-yl)-1,$N^5$-dimethyl-$N^2$-phenethyl-1H-benzoimidazole-2,5-diamine

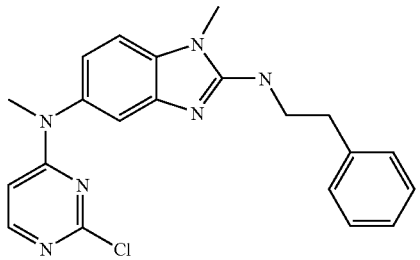

$N^2$,1-Dimethyl-1H-benzimidazole-2,5-diamine was coupled and methylated according to the procedure of intermediate example one part D to give the title compound as a white solid (1.43 g, 49% over 2 steps). ¹H NMR (300 MHz, d₆-DMSO) δ 7.87 (d, J=6.0 Hz, 1H), 7.20-7.34 (m, 6H), 7.15 (d, J=2.1 Hz, 1H), 6.97 (t, J=5.4 Hz, 1H), 6.84 (dd, J=8.4 and 1.8 Hz, 1H), 6.10 (d, J=5.7 Hz, 1H), 3.54-3.61 (m, 2H), 3.50 (s, 3H), 3.38 (s, 3H), 2.92-2.97 (M, 2H) ppm. MS (ESI) m/z=393 [M+H]⁺.

Intermediate Example 31

$N^2$-Tert-Butyl-$N^5$-(2-chloro-pyrimidin-4-yl)-1,$N^5$-dimethyl-1H-benzoimidazole-2,5-diamine

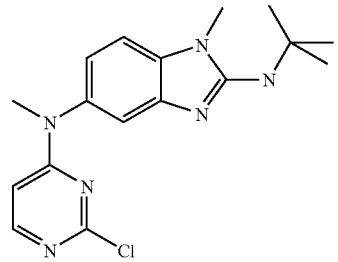

A. Tert-Butyl-(1-methyl-5-nitro-1H-benzoimidazol-2-yl)-amine

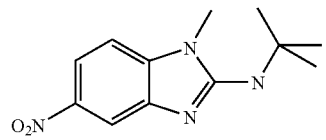

$N^1$-methyl-4-nitro-benzene-1,2-diamine (2.0 g, 12.0 mmol) and tert-butyl isothiocyanate (1.67 ml, 13.2 mmol) were coupled using the procedure of intermediate example one part B to give the title compound as a yellow solid. ¹H NMR (300 MHz, d₆-DMSO) d 8.01 (d, J=2.1 Hz, 1H), 7.90 (dd, J=8.7 and 2.1 Hz, 1H), 7.32 (d, J=8.7 Hz, 1H), 6.41 (s, 1H), 3.58 (s, 3H), 1.48 (s, 9H) ppm.

B. $N^2$-Tert-Butyl-1-methyl-1H-benzoimidazole-2,5-diamine

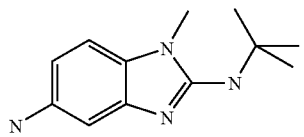

Tert-Butyl-(1-methyl-5-nitro-1H-benzoimidazol-2-yl)-amine (700 mg, 2.8 mmol) was reduced using the procedure of intermediate example one part C to give the title compound as a brown solid (240 mg, 39%). ¹H NMR (300 MHz, CD$_3$OD) δ 6.76 (d, J=8.1 Hz, 1H), 6.48 (d, J=1.8 Hz, 1H), 622 (dd, J=8.1 and 1.8 Hz, 1H), 5.64 (s, 1H), 4.40 (br s, 2H), 3.36 (s, 3H), 1.43 (s, 9H) ppm.

C. N$^2$-Tert-Butyl-N$^5$-(2-chloro-pyrimidin-4-yl)-1,N$^5$-dimethyl-1H-benzoimidazole-2,5-diamine

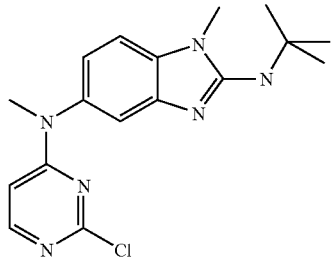

N$^2$-Tert-Butyl-1-methyl-1H-benzoimidazole-2,5-diamine (240 mg, 1.1 mmol) was coupled and methylated according to the procedure of intermediate example one part D to give the title compound as a white solid (348 mg, 92% over 2 steps). $^1$H NMR (300 MHz, d$_6$-DMSO) δ 7.86 (d, J=6.0 Hz, 1H), 7.23 (d, J=8.4 Hz, 1H), 7.16 (d, J=1.8 Hz, 1H), 6.84 (dd, J=8.1 and 1.8 Hz, 1H), 6.08 (br s, 2H), 3.52 (s, 3H), 3.38 (s, 3H), 1.46 (s, 9H) ppm. MS (ESI) m/z=345 [M+H]$^+$.

Intermediate Example 32

N$^5$-(2-Chloro-pyrimidin-4-yl)-N$^2$-cyclohexyl-1,N$^5$-dimethyl-1H-benzoimidazole-2,5-diamine

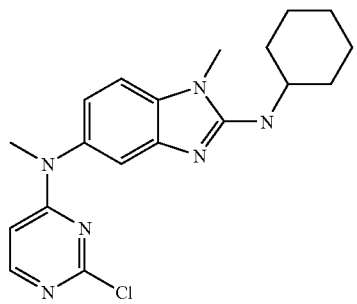

A. Cyclohexyl-(1-methyl-5-nitro-1H-benzoimidazol-2-yl)-amine

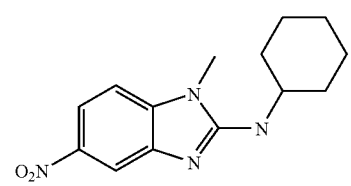

N$^1$-methyl-4-nitro-benzene-1,2-diamine (2.0 g, 12.0 mmol) and cylcohexyl isothiocyanate (1.80 ml, 13.2 mmol) were coupled using the procedure of intermediate example one part B to give the title compound as a yellow solid (2.41 g, 73%). $^1$H NMR (300 MHz, d$_6$-DMSO) δ 7.98 (d, J=2.4 Hz, 1H), 7.88 (dd, J=8.7 and 2.4 Hz, 1H), 7.30 (d, J=8.7 Hz, 1H), 6.88 (d, J=7.8 Hz, 1H), 3.74 (m, 1H), 3.56 (s, 3H), 2.00 (M, 2H), 1.75 (m, 2H), 1.63 (m, 1H), 1.25-1.36 (M, 4H), 1.17 (M, 1H) ppm.

B. N$^2$-Cyclohexyl-1-methyl-1H-benzoimidazole-2,5-diamine

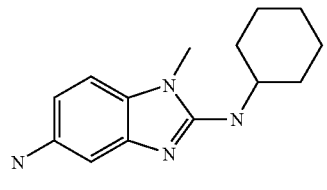

Cyclohexyl-(1-methyl-5-nitro-1H-benzoimidazol-2-yl)-amine (2.4 g, 8.8 mmol) was reduced using the procedure of intermediate example one part C to give the title compound as a white solid (2.05 g, 95%). $^1$H NMR (300 MHz, d$_6$-DMSO) δ 6.74 (d, J=8.1 Hz, 1H), 6.44 (d, J=1.8 Hz, 1H), 6.20 (dd, J=8.2 and 2.0 Hz, 1H), 6.05 (d, J=7.5 Hz, 1H), 4.32 (br s, 2H), 3.62 (m, 1H), 3.35 (s, 3H), 1.96-1.99 (m, 2H), 1.71-1.75 (m, 2H), 1.60-1.67 (m, 1H), 1.03-1.34 (m, 5H) ppm. MS (ESI) m/z=245 [M+H]$^+$.

C. N$^5$-(2-Chloro-pyrimidin-4-yl)-N$^2$-cyclohexyl-1,N$^5$-dimethyl-1H-benzoimidazole-2,5-diamine

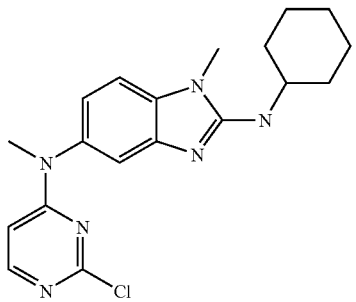

N$^2$-Cyclohexyl-1-methyl-1H-benzoimidazole-2,5-diamine (2.03 g, 8.3 mmol) was coupled and methylated according to the procedure of intermediate example one part D to give the title compound as a white solid (2.45 g, 80% over 2 steps). $^1$H NMR (300 MHz, d$_6$-DMSO) δ 7.87 (d, J=6.3 Hz, 1H), 7.21 (d, J=8.4 Hz, 1H), 7.11 (d, J=1.8 Hz, 1H), 6.82 (dd, J=8.2 and 2.0 Hz, 1H), 6.52 (d, J=7.8 Hz, 1H), 6.09 (d, J=5.7 Hz, 1H), 3.70 (m, 1H), 3.51 (s, 3H), 3.37 (s, 3H), 1.99 (m, 2H), 1.74 (m, 2H), 1.62 (m, 1H), 1.14-1.31 (m, 5H) ppm. MS (ESI) m/z=371 [M+H]$^+$.

Intermediate Example 33

N$^5$-(2-Chloro-pyrimidin-4-yl)-1-ethyl-N$^2$,N$^5$-dimethyl-1H-benzoimidazole-2,5-diamine

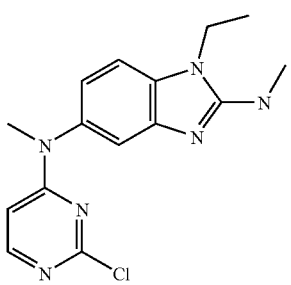

A. (1-Ethyl-5-nitro-1H-benzoimidazol-2-yl)-methyl-amine

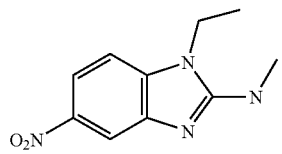

N-Ethyl-4-nitro-benzene-1,2-diamine (2.0 g, 11.0 mmol) and methyl isothiocyante (0.83 ml, 12.1 mmol) were coupled using the procedure of intermediate example one part B to give the title compound as a yellow solid (0.99 g, 41%). $^1$H NMR (300 MHz, d$_6$-DMSO) δ 7.99 (d, J=2.4 Hz, 1H), 7.90 (dd, J=8.7 and 2.1 Hz, 1H), 7.36 (d, J=8.7 Hz, 1H), 7.16 (m, 1H), 4.08 (q, J=7.2 Hz, 2H), 2.96 (d, J=4.5 Hz, 3H), 1.21 (t, J=7.2 Hz, 3H). MS (ESI) m/z=221 [M+H]$^+$.

B. 1-Ethyl-N$^2$-methyl-1H-benzoimidazole-2,5-diamine

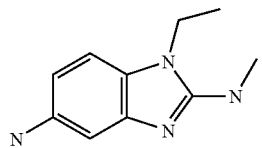

(1-Ethyl-5-nitro-1H-benzoimidazol-2-yl)-methyl-amine (0.99 g, 4.5 mmol) was reduced by the procedure of intermediate example one part C to give the title compound as a white solid (0.95 g, >95%). $^1$H NMR (300 MHz, d$_6$-DMSO) δ 6.78 (d, J=8.4 Hz, 1H), 6.47 (d, J=1.8 Hz, 1H), 6.32 (br s, 1H), 6.21 (dd, J=8.4 and 1.8 Hz, 1H), 4.15 (br s, 2H), 3.85 (q, J=7.1 Hz, 2H), 2.86 (s, 3H), 1.13 (t, J=7.1 Hz, 3H). MS (ESI) m/z=191 [M+H]$^+$.

C. N$^5$-(2-Chloro-pyrimidin-4-yl)-1-ethyl-N$^2$,N$^5$-dimethyl-1H-benzoimidazole-2,5-diamine

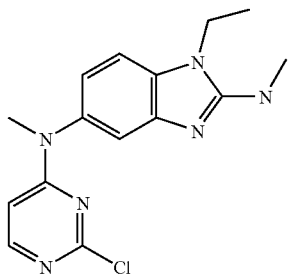

1-Ethyl-N$^2$-methyl-1H-benzoimidazole-2,5-diamine (0.95 g, 4.9 mmol) was coupled and methylated according to the procedure of intermediate example one part D to give the title compound as a white solid. $^1$H NMR (300 MHz, d$_6$-DMSO) δ 7.88 (d, J=6.0 Hz, 1H), 7.26 (d, J=8.1 Hz, 1H), 7.13 (d, J=108 Hz, 1H), 6.78-6.85 (m, 2H), 6.11 (d, J=5.7 Hz, 1H), 4.02 (q, J=7.1 Hz, 2H), 3.38 (s, 3H), 2.92 (d, J=4.5 Hz, 3H), 1.21 (t, J=7.1 Hz, 3H). MS (ESI) m/z=317 [M+H]$^+$.

Intermediate Example 34

1-Methyl-5-nitro-1,3-dihydro-benzoimidazole-2-thione

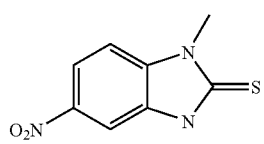

A solution of thiophosgene (2.3 ml, 30 mmol) in THF (300 ml) was added dropwise to a solution containing N$^1$-Methyl-4-nitro-benzene-1,2-diamine (5.01 g, 30 mmol) and Et$_3$N (9.2 ml, 66 mmol) in THF (300 ml) at 0° C. over 90 min. After stirring at 0° C. for another 1 hr, the mixture was allowed to warm to room temperature. The mixture was then concentrated to about 100 ml, water (200 ml) was added, the mix was stirred for 20 min, the product was collected by filtration and washed with small amount of cold CH$_2$Cl$_2$, after drying left 5.16 g as a mustard yellow solid: LC/MS (m/e) at 210.0 [M+H]$^+$, Rt at 1.49 min.

Intermediate Example 35

1-Methyl-2-methylsulfanyl-5-nitro-1H-benzoimidazole

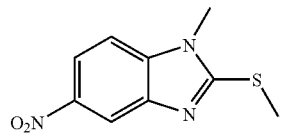

A mixture of 1-Methyl-5-nitro-1,3-dihydro-benzoimidazole-2-thione (5.16 g, 24.7 mmol), Na$_2$CO$_3$ (2.88 g, 27.2 mmol) and MeI (3.68 g, 25.94 mmol) in acetone (150 ml) was refluxed overnight. The mix was filtered hot and the filtrate was concentrated to about 50 ml, the product was collected by filtration and washed with a small amount of cold CH$_2$Cl$_2$, drying left 4.58 g as a mustard yellow solid: LC/MS(m/e) at 224.0 [M+H]$^+$, Rt at 1.55 min.

Intermediate Example 36

1-Methyl-2-methylsulfanyl-11H-benzoimidazol-5-ylamine

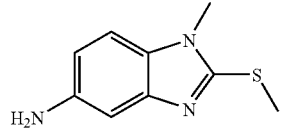

Zinc (9.52 g, 145.6 mmol) was added to a mix of 1-Methyl-2-methylsulfanyl-5-nitro-1H-benzoimidazole (4.64 g, 20.8 mmol) in EtOH (100 ml) and glacial acetic acid (200 ml), the resulting mix was stirred at room temperature for 2 hr. and filtered, the filtrate was concentrated, the residual was taken into water (100 ml) and neutralized by NaOH and the product was extracted by CH$_2$Cl$_2$ until all product was extracted from aqueous. The combined extracts were washed with brine, drying and concentrated gave 3.86 g as dust pink solid: LC/MS(m/e) at 194.0 [M+H]$^+$, Rt at 1.02 min.

Intermediate Example 37

(2-Chloro-pyrimidin-4-yl)-methyl-(1-methyl-2-methylsulfanyl-1H-benzoimidazol-5-yl)-amine

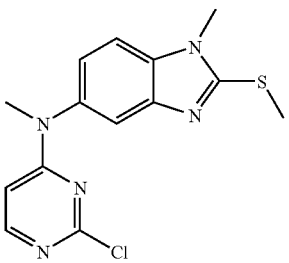

Follow the procedure of Intermediate Example 1D, replacing N$^2$-isopropyl-1-methyl-1H-benzoimidazole-2,5-diamine by 1-Methyl-2-methylsulfanyl-11H-benzoimidazol-5-ylamine gave the title compound as a white solid: LC/MS(m/e) at 320.0 [M+H]$^+$, Rt at 1.53 min.

Intermediate Example 38

N²-(4-Methanesulfonylmethyl-phenyl)-N⁴-methyl-N⁴-(1-methyl-2-methylsulfanyl-1H-benzoimidazol-5-yl)-pyrimidine-2,4-diamine

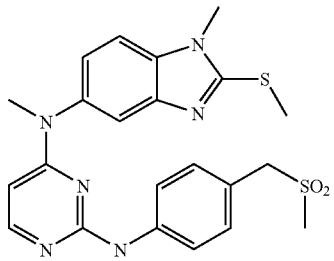

A mixture of (2-Chloro-pyrimidin-4-yl)-methyl-(1-methyl-2-methylsulfanyl-1H-benzoimidazol-5-yl)-amine (3.19 g, 10 mmol), 4-Methanesulfonylmethyl-phenylamine (1.85 g, 10 mmol) and (833 ul, 12N, 10 mmol) was refluxed in isopropanol (100 ml) overnight. The mixture was then concentrated to dryness and the residual was taken into MeOH and stirred with NaHCO₃ (3 g) at room temperature for 20 min. and filtered, the filtrate was concentrated and the residual was purified by silica flash gave 3.35 g as a pale yellow solid: LC/MS(m/e) 469.2 [M+H]⁺, Rt at 1.37 min.

Intermediate Example 39

N⁴-(2-Methanesulfonyl-1-methyl-1H-benzoimidazol-5-yl)-N²-(4-methanesulfonylmethyl-phenyl)-N⁴-methyl-pyrimidine-2,4-diamine

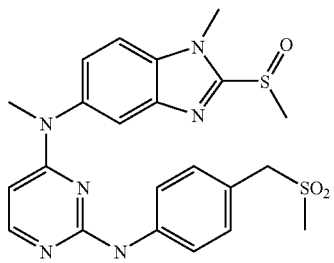

mCPBA (1.27 g, 5.61 mmol) was added to a solution of N²-(4-methanesulfonylmethyl-phenyl)-N⁴-methyl-N⁴-(1-methyl-2-methylsulfanyl-1H-benzoimidazol-5-yl)-pyrimidine-2,4-diamine (2.4 g, 5.1 mmol) in CHCl₃ (60 ml) at −20° C. The resulting mixture was stirred at −20° C. for 6 hr and diluted by CHCl₃, washed with NaHCO₃ (10%, ×4), all extracts were combined and washed by brine, drying and concentrated, the residual was purified by silica flash gave 1.22 g as a light yellow solid: LC/MS(m/e) 485 [M+H]⁺, Rt at 1.29 min.

Intermediate Example 40

N¹-Methyl-4-nitro-benzene-1,2-diamine

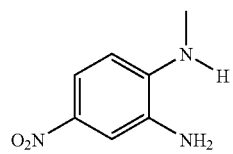

To a solution of 2-fluoro-5-nitroaniline (3.0 g, 19.2 mmol) in 24 ml N-methylpyrrolidinone in a sealed reaction vessel was added potassium carbonate (5.4 g, 30.0 mmol) and a solution of methyl amine (20 ml, 2M in THF) and the reaction was heated to 120° C. After 16 h, the reaction mixture was cooled to room temperature and poured into 200 ml of water. The resulting precipitate was filtered and dried to give the title compound as a red solid. MS (ESI) m/z=168 [M+H].

Intermediate Example 41

1-Methyl-5-nitro-1,3-dihydro-benzimidazole-2-thione

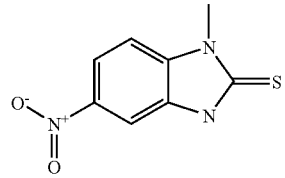

To a solution of N¹-Methyl-4-nitro-benzene-1,2-diamine (1.0 g, 6.0 mmol) and triethylamine 2.5 ml (18 mmol) in THF (60 ml) was added thiophosgene (0.46 ml, 6.0 mmol) at 0° C. After 1 h, the reaction mixture was warmed up to rt and was stirred at room temperature for 3 h. After the starting material was consumed, the reaction was filtered. The collected solid was washed with EtOAc:Hexane=1:1 (10 ml×2) and water. The resulting yellow solid was dried to give the title compound (0.82 g, 66%). MS (ESI) m/z=209 [M+H].

Intermediate Example 42

2-Chloro-1-methyl-5-nitro-1H-benzoimidazole

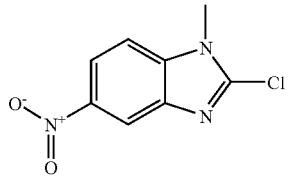

The compound 1-Methyl-5-nitro-1,3-dihydro-benzoimidazole-2-thione (5.8 g, 27.9 mmol) was heated to reflux with SOCl₂ (30 ml) overnight. The reaction mixture was cooled to room temperature and poured into 300 ml of ice water and extracted with CH₂Cl₂. The organic layers was washed with 10% NaHCO₃ water solution, brine, dried over Na₂SO₄ and concentrated to give the title compound as a yellow solid. MS (ESI) m/z=212 [M+H].

Intermediate Example 43

(5-tert-Butyl-isoxazol-3-yl)-(1-methyl-5-nitro-1-H-benzoimidazol-2-yl)-amine

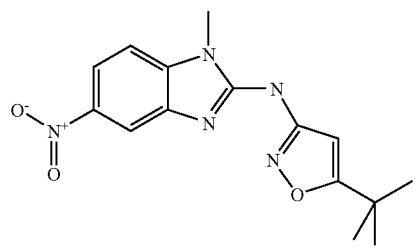

To a solution of 2-Chloro-1-methyl-5-nitro-1H-benzoimidazole (200 mg, 0.19 mmol) and 5-tert-Butyl-isoxazol-3-ylamine (265 mg, 1.90 mmol) in isopropanol (15 ml) was added a solution of HCl (3 drops, 4.0 m in dioxane). The reaction was heated to 80° C. and after 20 h. the reaction mixture was cooled to rt. The solvent was evaporated to dryness and the resultant solid was dissolved in EtOAc and neutralized by a 10% NaHCO₃ water solution. The combined organic layers were washed with water, dried over MgSO₄ and concentrated to give a foam. The crude material was purified through silica gel to give the title compound as a yellow solid (190 mg, 63%). MS (ESI) m/z=316 [M+H].

Intermediate Example 44

N-(5-tert-Butyl-isoxazol-3-yl)-2,2-dimethyl-N-(1-methyl-5-nitro-1-H-benzoimidazol-2-yl)-propinamide

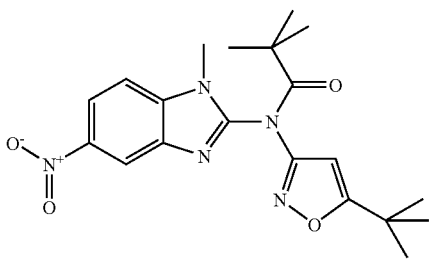

To a solution of (1.97 g, 7.4 mmol) (5-tert-Butyl-isoxazol-3-yl)-(1-methyl-5-nitro-1-H-benzoimidazol-2-yl)-amine (439 mmol, 1.38 mmol) in THF (30 ml) was added cesium carbonate (906 mg, 2.78 mmol) and di-tert-butyl dicarbonate THF solution (2.1 ml, 2.09 mmol 1M THF solution). The reaction was stirred at rt for 16 h and then the reaction was diluted with water and extracted with EtOAc. The combined organic layers were washed with water, dried over MgSO₄ and concentrated to afford a yellow oil. The crude material was purified through silica gel to give the title compound as a yellow solid (190 mg, 33%). MS (ESI) m/z=416 [M+H].

Intermediate Example 45

N-(5-Amino-1-methyl-1-H-benzoimidazol-2-yl)-N-(5-tert-Butyl-isoxazol-3-yl)-2,2-dimethyl-propinamide

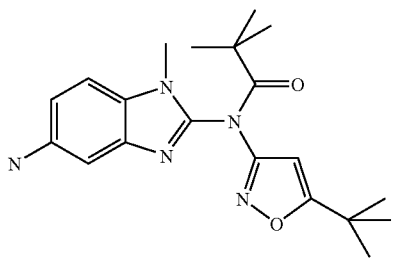

To a solution of N-(5-tert-butyl-isoxazol-3-yl)-2,2-dimethyl-N-(1-methyl-5-nitro-1-H-benzoimidazol-2-yl)-propinamide (190 mg, 0.48 mmol) in acetic acid (12 ml and ethanol 3 ml) was added zinc powder (290 mg). The reaction mixture was stirred at room temperature until the starting material was consumed, and then the reaction was filtered. The solvent was evaporated to give a brown residue that was then dissolved in CH₂Cl₂ and washed with a 10% NaHCO₃ water solution and brine. The organic layers was dried over MgSO₄ and concentrated to title compound as a yellow solid (140 mg, 73%). MS (ESI) m/z=450 [M+H].

Intermediate Example 46

N-(5-tert-butyl-isoxazol-3-yl)-2,2-dimethyl-N-[1-methyl-5-(2-methyl-pyrimidin-4-ylamino)-1H-benzoimidazol-2-yl]-propionamide

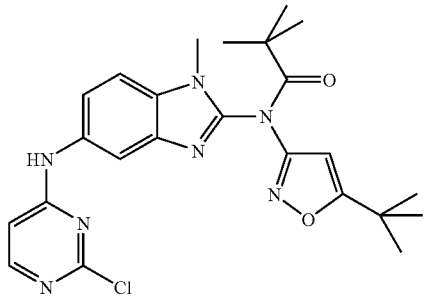

To a solution of N-(5-amino-1-methyl-1-H-benzoimidazol-2-yl)-N-(5-tert-butyl-isoxazol-3-yl)-2,2-dimethyl-propinamide (149 mg, 0.39 mmol) in THF (3 ml) and ethanol (9 ml) was added NaHCO₃ (66 mg, 0.78 mmol) and 2,4-dichloropyrimidine (78 mg, 0.52 mmol) and the reaction was heated to 75° C. After 5 h, the reaction was filtered hot and concentrated to give a brown residue. The crude material was diluted with ether and the title compound was precipitated out by the addition of hexane (140 mg, 73%). MS (ESI) m/z=498 [M+H].

Intermediate Example 47

N-(5-tert-butyl-isoxazol-3-yl)-N-{5-[(2-chloro-pyrimidin-4-yl)-methyl-amino]-1-methyl-1 Hbenzoimidazole-2-yl}-2,2-dimethyl propionamide

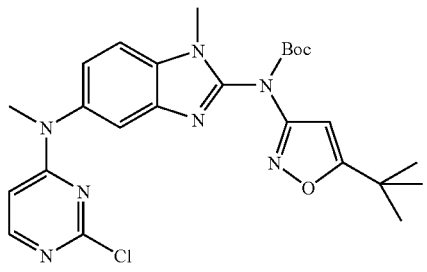

N-(5-tert-Butyl-isoxazol-3-yl)-2,2-dimethyl-N-[1-methyl-5-(2-methyl-pyrimidin-4-ylamino)-1H-benzoimidazol-2-yl]-propionamide (200 mg, 0.37 mmol) was dissolved in DMF (10 ml) and cesium carbonate (244 mg, 0.75 mmol) was added. After 15 min, iodomethane (25 ul, 0.41 mmol) was added, and the reaction was stirred at rt. until the starting material was consumed. The reaction was diluted with water and the aqueous layer was extracted with EtOAc. The combined organic layers were washed with water, dried over Na₂SO₄ and concentrated to afford a white solid (195 mg 96%). MS (ESI) m/z=512 [M+H]⁺.

Intermediate Example 48

1-methyl-5-nitro-1H-benzimidazol-2-amine

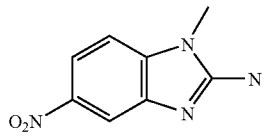

To a solution of $N^1$-methyl-4-nitro-benzene-1,2-diamine (200 mg, 1.20 mmol) in methanol (12 ml) was added cyanogen bromide (190.1 mg, 1.79 mmol). After stirring at room temperature for 16 h, the methanol was removed in vacuo and the resulting solid was stirred with diethyl ether (40 ml) for 5 minutes. The resulting hydrobromide salt of the title compound was filtered and air-dried.

$^1$H NMR (300 MHz, $d_6$-DMSO) δ 7.91 (s, 1H), 7.88 (d, J=8.6 Hz, 1H), 7.31 (d, J=8.5 Hz, 1H), 6.96 (s, 2H), 3.57 (s, 3H).

Intermediate Example 49

1-methyl-1H-benzimidazole-2,5-diamine

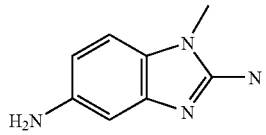

The title compound was prepared utilizing the procedure of Intermediate Example 1C, except that 1-methyl-5-nitro-1H-benzimidazol-2-amine was used as a starting material.

$^1$H NMR (400 MHz, $d_6$-DMSO) δ 6.72 (d, J=8.6 Hz, 1H), 6.37 (s, 1H), 6.17 (d, J=8.1 Hz, 1H), 6.04 (m, 2H), 4.36 (br s, 2H), 3.34 (s, 3H).

Intermediate Example 50

$N^5$-(2-chloropyrimidin-4-yl)-1-methyl-1H-benzimidazole-2,5-diamine

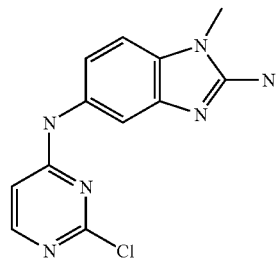

The title compound was prepared utilizing the procedure of Intermediate Example 1D, except that 1-methyl-1H-benzimidazole-2,5-diamine was used a starting material.

$^1$H NMR (300 MHz, $d_6$-DMSO) δ 9.75 (s, 1H), 8.02 (d, J=5.9 Hz, 1H), 7.29 (br s, 1H), 7.09 (d, J=8.3 Hz, 1H), 6.93 (br m, 1H), 6.58 (d, J=5.2 Hz, 1H), 6.44 (s, 2H), 3.47 (s, 3H).

Intermediate Example 51 tert-butyl 5-[(2-chloropyrimidin-4-yl)amino]-1-methyl-1H-benzimidazol-2-ylcarbamate

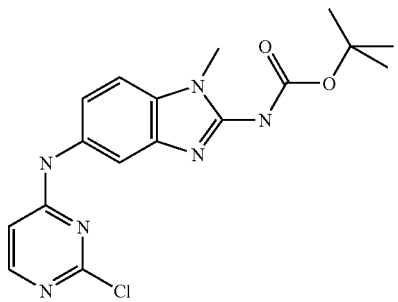

To a solution of $N^5$-(2-chloropyrimidin-4-yl)-1-methyl-1H-benzimidazole-2,5-diamine (200 mg, 0.728 mmol) in THF (10 ml), was added triethylamine (0.101 ml, 0.728 mmol) and di-tert-butyl dicarbonate (175 mg, 0.801 mmol). After stirring 16 h at roomtemperature, the reaction was diluted with water and extracted with EtOAc. The combined organic layers were washed with water, dried over $MgSO_4$ and concentrated in vacuo. $^1$H NMR (400 MHz, $d_6$-DMSO) δ 9.92 (s, 1H), 8.09 (d, J=5.8 Hz, 1H), 7.74 (br s, 1H), 7.21-7.19 (m, 2H), 7.02 (d, J=8.2 Hz, 1H), 6.66 (d, J=5.9 Hz, 1H), 3.24 (s, 3H), 1.61 (s, 9H).

Intermediate Example 52 tert-butyl 5-[(2-chloropyrimidin-4-yl)(methyl)amino]-1-methyl-1H-benzimidazol-2-ylcarbamate

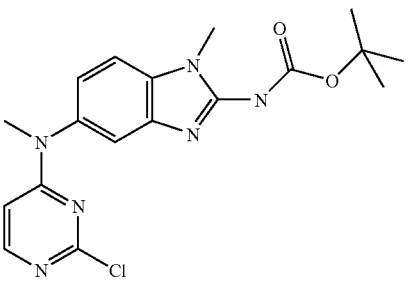

The title compound was prepared utilizing the procedure of Intermediate Example 4E, except that tert-butyl 5-[(2-chloropyrimidin-4-yl)amino]-1-methyl-1H-benzimidazol-2-ylcarbamate was used as a starting material.

$^1$H NMR (400 MHz, $d_6$-DMSO) δ 7.98 (d, J=6.0 Hz, 1H), 7.44 (s, 1H), 7.21-7.16 (m, 3H), 6.31 (d, J=5.8 Hz, 1H), 3.38 (s, 3H), 3.29 (s, 3H), 1.58 (s, 9H).

Intermediate Example 53

N⁵,1-dimethyl-N⁵-[2-({4-[(methylsulfonyl)methyl] phenyl}amino)pyrimidin-4-yl]-1H-benzimidazole-2,5-diamine

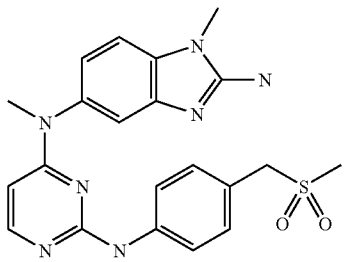

The title compound was prepared utilizing the procedure of Scheme 1 and Example 1, except that N⁵-(2-Chloropyrimidin-4-yl)-N²,N⁵,1-dimethyl-1H-benzimidazole-2,5-diamine was used as a starting material.

¹H NMR (400 MHz, d₆-DMSO) δ 9.23 (s, 1H), 7.81-7.78 (m, 3H), 7.25-7.19 (m, 3H), 7.04 (m, 1H), 6.82 (m, 1H), 6.56 (br s, 2H), 5.65 (d, J=5.9 Hz, 1H), 4.36 (s, 2H), 3.53 (s, 3H), 3.44 (s, 3H), 2.86 (s, 3H). MS (ESI) m/z=438 [M+H]⁺.

Intermediate Example 54

N⁵-(2-Chloro-pyrimidin-4-yl)-1,N⁵-dimethyl-1H-benzoimidazole-2,5-diamine

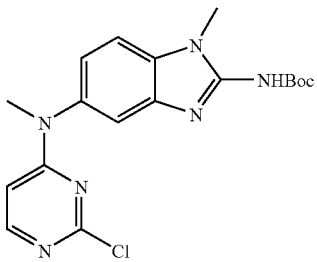

A. 1-Methyl-5-nitro-1H-benzoimidazol-2-ylamine

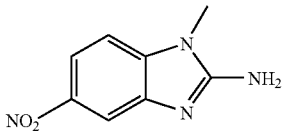

To a solution of N¹-Methyl-4-nitro-benzene-1,2-diamine (5 g, 30 mmol) in MeOH was added bromide isothiocyanate (4.4 g, 42 mmol) and the mixture was stirred at rt. After 16 h. 6N NaOH solution was added to the reaction mixture until Ph~10 and MeOH was then removed in vacuo. H₂O was added and the solid was filtered and dried to give the title compound as an off white solid (5.2 g, 90%). MS (ESI) m/z=193 [M+H]⁺.

B. 1-Methyl-1H-benzoimidazole-2,5-diamine

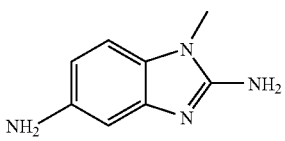

To a solution of 1-Methyl-5-nitro-1H-benzoimidazol-2-ylamine (0.19 g, 1 mmol) 10% Pd/C (50 mg) in ethanol (10 ml) was added hydrazine (0.5 ml) and the reaction was heated to 80° C. After TLC showed the starting material to be consumed, the reaction was cooled to rt and passed through a plug of celite. The filtrate was concentrated to give the title compound as an off-white solid. MS (ESI) m/z=163 [M+H]⁺.

C. N⁵-(2-Chloro-pyrimidin-4-yl)-1-methyl-1H-benzoimidazole-2,5-diamine

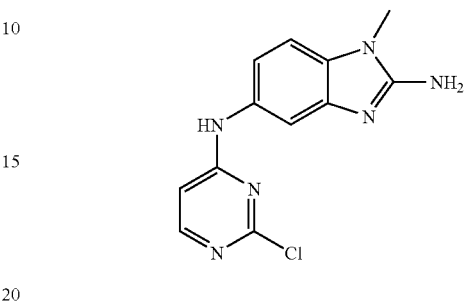

To a solution of 1-Methyl-1H-benzoimidazole-2,5-diamine (0.63 g, 3.89 mmol) in THF (4 ml) and ethanol (12 ml) was added NaHCO₃ (0.98 g, 11.67 mmol) and 2,4-dichloropyrimidine (1.45 g, 9.7 mmol) and the reaction was heated to 80° C. After 5 h, the reaction was filtered hot and concentrated to a gray foam. Ether was added and the solid was filtered and dried to give N⁵-(2-Chloro-pyrimidin-4-yl)-1-methyl-1H-benzoimidazole-2,5-diamine as an red solid. MS (ESI) m/z=275 [M+H]⁺.

D. {[(2-Chloro-pyrimidin-4-yl)-methyl-amino]-methyl-H-benzoimidazol-2-yl}-carbamic acid tert-butyl ester

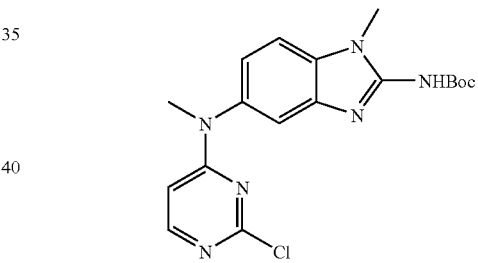

To a solution of N⁵-(2-Chloro-pyrimidin-4-yl)-1-methyl-1H-benzoimidazole-2,5-diamine (137 mg, 0.5 mmol) in THF (17 ml) was added triethylamine (0.7 ml, 0.5 mmol) and di-tert-butyl dicarbonate 1 M in THF (0.5 ml, 0.5 mmol) and the reaction was stirred at rt for 16 h. The reaction was diluted with water and extracted with CH₂Cl₂. The combined organic layers were washed with water, dried over MgSO₄ and concentrated to an off white solid.

This solid was dissolved in DMF (2 ml) and cesium carbonate (0.2 g, 0.626 mmol) was added, the reaction mixture was stirred at rt. After 15 min, iodomethane (0.022 ml, 0.344 mmol) was added, and the reaction was stirred at rt. After TLC showed the starting material to be consumed, the reaction was diluted with water. The aqueous layer was extracted with CH₂Cl₂. The combined organic layers were washed with water, dried over MgSO₄ and concentrated to a red foam. The crude material was purified with silica gel chromatography to give the title compound as a white solid (0.058 mg, 45% over two steps). MS (ESI) m/z=389 [M+H]⁺.

Intermediate Example 55

3-(Morpholine-4-sulfonyl)-phenylamine

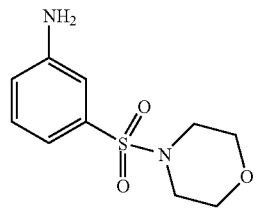

Morpholine (2.2 ml, 25 mmol) was slowly added to 3-Nitro-benzenesulfonyl chloride (5.5 g, 25 mmol) in $CH_2Cl_2$ at 0° C. The reaction was warmed up to rt in 0.5 h. After $CH_2Cl_2$ was removed in vacuo, saturated $NaHCO_3$ solution was added and the solid was filtered and dried to give 4-(3-Nitro-benzenesulfonyl)-morpholine as an off white solid (5.9 g, 87%). MS (ESI) m/z=273 $[M+H]^+$.

4-(3-Nitro-benzenesulfonyl)-morpholine (5.9 g, 21.7 mmol) was combined with 10% palladium on carbon (1 g), ethanol (60 mL), and hydrazine (5 mL) and heated at reflux for 18 h. The solution was filtered through celite, concentrated, and cooled to 0° C. Product precipitated out an colorless crystal (4.7 g, 89%). MS (ESI) m/z=243 $[M+H]^+$.

Intermediate Example 56

3-(4-Methyl-piperazine-1-sulfonyl)-phenylamine

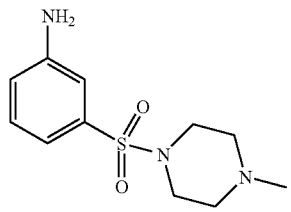

The title compound was prepared following the procedure of intermediate Example 2 with to 3-Nitro-benzenesulfonyl chloride (4.4 g, 20 mmol) and N-methyl-piperazine (2.2 ml 20 mmol) as an off white solid (3.6 g, 70%). MS (ESI) m/z=256 $[M+H]^+$.

Intermediate Example 57

4-Amino-N,N-dimethyl-benzenesulfonamide

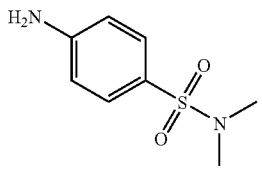

The title compound was prepared following the procedure of intermediate Example 2 with to 3-Nitro-benzenesulfonyl chloride (6.6 g, 30 mmol) dimethylamine 2M in MeOH (15 ml, 30 mmol) as an off white solid (4.8 g, 70%). MS (ESI) m/z=232 $[M+H]^+$.

Example 1

$N^2$-isopropyl-$N^5$,1-dimethyl-$N^5$-[2-({4-[(methylsulfonyl)methyl]phenyl}amino)pyrimidin-4-yl]-1H-benzimidazole-2,5-diamine hydrochloride

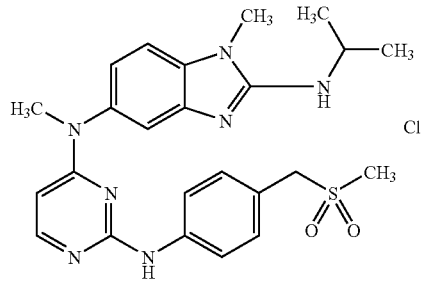

To a solution of $N^5$-(2-chloropyrimidin-4-yl)-$N^2$-isopropyl-$N^5$,1-dimethyl-1H-benzimidazole-2,5-diamine (83 mg, 0.25 mmol) and 4-[(methylsulfonyl)methyl]aniline (46 mg, 0.25 mmol) in ethanol (2.5 ml) was added a solution of HCl (0.25 ml, 1M in diethyl ether), and the reaction was heated to 70° C. After 5 h, the precipitate was filtered off and washed with ethanol and dried to give the title compound as a white solid (104 mg, 87%). $^1$H NMR (300 MHz, $d_6$-DMSO) δ 10.1 (s, 1H), 8.74 (m, 1H), 7.93 (d, J=6.6 Hz, 1H), 7.60-7.65 (m, 3H), 7.41 (s, 1H), 7.24-7.29 (m, 3H), 5.90 (s, 1H), 4.39 (s, 2H), 4.09 (m, 1H), 3.69 (s, 3H), 3.49 (s, 3H), 2.87 (s, 3H), 1.33 (d, J=6.6 Hz, 6H) ppm. MS (ESI) m/z=480 $[M+H]^+$.

Example 2

$N^2$-Isopropyl-$N^5$,1-dimethyl-$N^5$-[2-({4-[(methylsulfonyl)methyl]phenyl}amino) pyrimidin-4-yl]-1H-benzimidazole-2,5-diamine hydrochloride

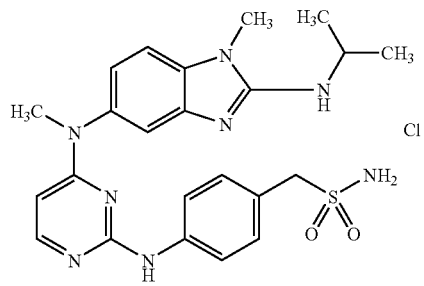

To a solution of $N^5$-(2-chloropyrimidin-4-yl)-$N^2$-isopropyl-$N^5$,1-dimethyl-1H-benzimidazole-2,5-diamine (83 mg, 0.25 mmol) and 1-(4-aminophenyl)methane-sulfonamide (47 mg, 0.25 mmol) in ethanol (2.5 ml) was added a solution of HCl (0.25 ml, 1M in diethyl ether) and the reaction was heated to 70° C. After 20 hours, the reaction mixture was neutralized with the addition of solid $NaHCO_3$. The mixture was filtered and the filtrate was purified with silica gel to give the title compound as a white solid. $^1$H NMR (300 MHz, $d_6$-DMSO) δ 9.16 (s, 1H), 7.78 (m, 3H), 7.19 (d, J=8.1 Hz, 3H), 7.09 (d, J=1.8 Hz, 1H), 6.82 (dd, J=8.1 and 1.8 Hz, 1H), 6.75 (s, 2H), 6.49 (d, J=7.8 Hz, 1H), 5.62 (d, J=6.0 Hz, 1H), 4.15 (s, 2H), 4.02 (m, 1H), 3.51 (s, 3H), 3.44 (s, 3H), 1.24 (d, J=6.6 Hz, 6H) ppm. MS (ESI) m/z=481 $[M+H]^+$.

Example 3

1-{4-[(4-{Methyl[1-methyl-2-(methylamino)-1H-benzimidazol-5-yl]amino}pyrimidin-2-yl)amino]phenyl}methanesulfonamide hydrochloride

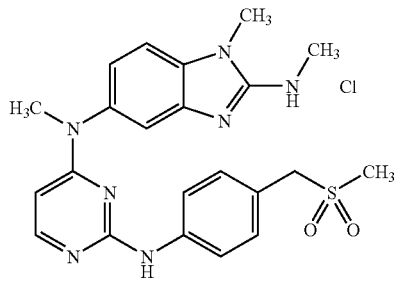

The title compound was prepared following the procedure of Example 1 with $N^5$-(2-chloropyrimidin-4-yl)-$N^2$,$N^5$,1-trimethyl-1H-benzimidazole-2,5-diamine (62 mg, 0.21 mmol) and 4-[(methylsulfonyl)methyl]aniline (39 mg, 0.21 mmol) as a white solid (73 mg, 72%). $^1$H NMR (300 MHz, $d_6$-DMSO) δ 10.22 (s, 1H), 9.32 (d, J=4.5 Hz, 1H), 7.94 (d, J=6.6 Hz, 1H), 7.62 (d, J=8.4 Hz, 3H), 7.43 (d, J=1.8 Hz, 1H), 7.24-7.30 (m, 3H), 5.91 (d, J=5.7 Hz, 1H), 4.40 (s, 2H), 3.69 (s, 3H), 3.49 (s, 3H), 3.07 (d, J=4.5 Hz, 3H), 2.87 (s, 3H). MS (ESI) m/z=452 [M+H]$^+$.

Example 4

$N^2$-benzyl-$N^5$,1-dimethyl-$N^5$-[2-({4-[(methylsulfonyl)methyl]phenyl}amino)pyrimidin-4-yl]-1H-benzimidazole-2,5-diamine hydrochloride

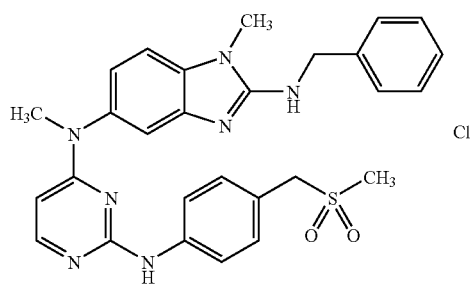

The title compound was prepared following the procedure of Example 1 with $N_2$-benzyl-$N^5$-(2-chloropyrimidin-4-yl)-$N^5$,1-dimethyl-1H-benzimidazole-2,5-diamine (95 mg, 0.25 mmol) and 4-[(methylsulfonyl)methyl]aniline (46 mg, 0.25 mmol) as a white solid (138 mg, 95%). $^1$H NMR (300 MHz, $d_6$-DMSO) δ 9.20 (s, 1H), 7.76-7.80 (m, 3H), 7.38-7.41 (m, 3H), 7.29-7.34 (m, 2H), 7.22-7.24 (m, 4H), 7.08 (d, J=1.8 Hz, 1H), 6.84 (dd, J=8.1 and 1.8 Hz, 1H), 5.63 (d, J=6.0 Hz, 1H), 4.60 (d, J=6.0 Hz, 2H), 4.34 (s, 2H), 3.58 (s, 3H), 3.43 (s, 3H), 2.85 (s, 3H). MS (ESI) m/z=527 [M+H]$^+$.

Example 5

$N^5$,1-Dimethyl-$N^5$-[2-({4-[(methylsulfonyl)methyl]phenyl}amino)pyrimidin-4-yl]-$N^2$-phenyl-1H-benzimidazole-2,5-diamine trifluoroacetic acid

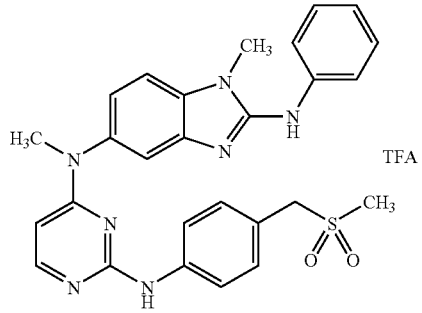

To a solution of tert-butyl 5-[(2-chloropyrimidin-4-yl)(methyl)amino]-1-methyl-1H-benzimidazol-2-yl(phenyl)carbamate (100 mg, 0.22 mmol) and 4-[(methylsulfonyl)methyl]aniline (41 mg, 0.22 mmol) in ethanol (2.5 ml) was added a solution of HCl (1 drop, 1M in diethyl ether) and the reaction was heated to 70° C. After 20 hours, the reaction mixture was neutralized with the addition of solid NaHCO$_3$. The mixture was filtered and the filtrate was purified with silica gel. The collected product was stirred in 5 ml of a 1:1 TFA/methylene chloride solution for 3 h. The reaction was concentrated to give the title compound as a white solid (116 mg, 84%). $^1$H NMR (300 MHz, $d_6$-DMSO) δ 10.6 (s, 1H), 9.83 (br s, 1H), 7.78 (d, J=6.9 Hz, 1H), 7.70 (d, J=8.1 Hz, 2H), 7.57-7.60 (m, 3H), 7.32-7.44 (m, 5H), 7.11-7.21 (m, 2H), 5.93 (br s, 1H), 4.43 (s, 2H), 3.79 (s, 3H), 3.53 (s, 3H), 2.87 (s, 3H). MS (ESI) m/z=514 [M+H]$^+$.

Example 6

5-({4-[[2-(Benzylamino)-1-methyl-1H-benzimidazol-5-yl](methyl)amino]pyrimidin-2-yl}amino)-N-methoxy-2-methylbenzenesulfonamide

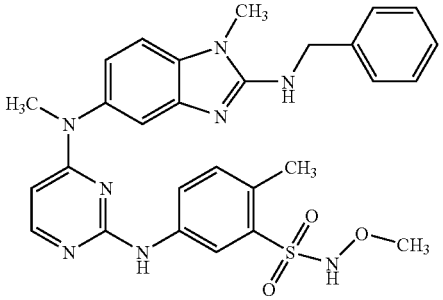

The title compound was prepared following the procedure of Example 2 with $N^2$-benzyl-$N^5$-(2-chloropyrimidin-4-yl)-$N^5$,1-dimethyl-1H-benzimidazole-2,5-diamine (50 mg, 0.13 mmol) and 5-amino-N-methoxy-2-methylbenzenesulfonamide (30 mg, 0.14 mmol) as a white solid (58 mg, 0.10 mmol) after silica gel chromatography with methanol in dichloromethane. $^1$H NMR (300 MHz, $d_6$-DMSO) δ 10.3 (s, 1H), 9.42 (s, 1H), 8.73 (s, 1H), 7.76-7.80 (m, 2H), 7.40-7.23 (m, 8H), 7.09 (br s, 1H), 6.84 (d, J=7.4 Hz, 1H), 5.61 (d, J=5.3 Hz, 1H), 4.60 (br s, 2H), 4.34 (s, 2H), 3.58 (s, 6H), 3.46 (s, 3H). MS (ESI) m/z=559 [M+H]$^+$.

Example 7

3-{4-[(2-Benzylamino-1-methyl-1H-benzoimidazol-5-yl)-methyl-amino]-pyrimidin-2-ylamino}-benzenesulfonamide hydrochloride

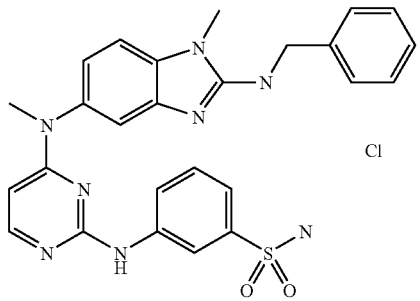

16The title compound was prepared following the procedure of Example 1 with N²-benzyl-N⁵-(2-chloropyrimidin-4-yl)-N⁵,1-dimethyl-1H-benzimidazole-2,5-diamine (95 mg, 0.25 mmol) and 3-amino-benzenesulfonamide (43 mg, 0.25 mmol) as a light pink solid (112 mg, 82%). $^1$H NMR (300 MHz, d$_6$-DMSO+NaHCO$_3$) δ 10.03 (br s, 2H), 9.55 (br s, 1H), 8.48 (s, 1H), 7.89 (d, J=6.3 Hz, 1H), 7.74 (m, 1H), 7.59 (d, J=8.7 Hz, 1H), 7.51 (m, 2H), 7.22-7.41 (m, 8H), 5.76 (d, J=6.3 Hz, 1H), 4.76 (d, J=5.7 Hz, 2H), 3.763 (s, 3H), 3.48 (s, 3H). MS (ESI) m/z=515 [M+H]$^+$.

Example 8

5-{4-[(2-Benzylamino-1-methyl-1H-benzoimidazol-5-yl)-methyl-amino]-pyrimidinylamino}-2-methyl-benzenesulfonamide hydrochloride

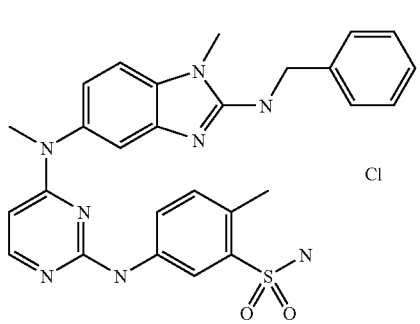

The title compound was prepared following the procedure of Example 1 with N²-benzyl-N⁵-(2-chloropyrimidin-4-yl)-N⁵,1-dimethyl-1H-benzimidazole-2,5-diamine (95 mg, 0.25 mmol) and 5-amino-2-methyl-benzenesulfonamide (47 mg, 0.25 mmol) to give the desired product as a pink solid (114 mg, 81%). $^1$H NMR (300 MHz, d$_6$-DMSO+NaHCO$_3$) δ 10.31 (br s, 2H), 9.61 (br s, 1H), 8.46 (s, 1H), 7.88 (d, J=6.6 Hz, 1H), 7.63 (m, 2H), 7.51 (d, J=7.5 Hz, 2H), 7.23-7.39 (m, 7H), 5.77 (d, J=6.3 Hz, 1H), 4.77 (d, H=6.0 Hz, 2H), 3.74 (s, 3H), 3.50 (s, 3H), 2.52 (s, 3H). MS (ESI) m/z=529 [M+H]$^+$.

Example 9

(4-{4-[(2-Benzylamino-1-methyl-1H-benzoimidazol-5-yl)-methyl-amino]-pyrimidin-2-ylamino}-phenyl)-methanesulfonamide hydrochloride

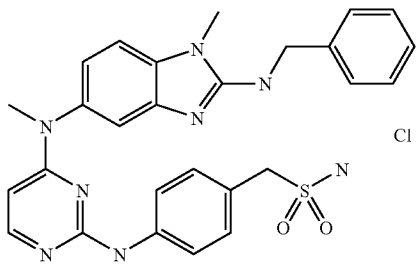

The title compound was prepared following the procedure of Example 1 with N$_2$-benzyl-N⁵-(2-chloropyrimidin-4-yl)-N⁵,1-dimethyl-1H-benzimidazole-2,5-diamine (95 mg, 0.25 mmol) and (4-amino-phenyl)-methanesulfonamide (46 mg, 0.25 mmol) to give the desired product as a white solid (85 mg, 60%). $^1$H NMR (300 MHz, d$_6$-DMSO+NaHCO$_3$) δ 10.17 (brs, 2H), 9.53 (brs, 1H), 7.90 (d, J=6.6 Hz, 1H), 7.61 (d, J=8.4 Hz, 3H), 7.51 (d, J=7.5 Hz, 2H), 7.22-7.39 (m, 6H), 6.82 (s, 2H), 5.87 (d, J=6.0 Hz, 1H), 4.76 (d, J=5.7 Hz, 2H), 4.19 (s, 2H), 3.74 (s, 3H) 3.49 (s, 3H). MS (ESI) m/z=529 [M+H]$^+$.

Example 10

2-(4-{4-[(2-Benzylamino-1-methyl-1H-benzoimidazol-5-yl)-methyl-amino]-pyrimidin-2-ylamino}-phenyl)-ethanesulfonic acid methylamide hydrochloride

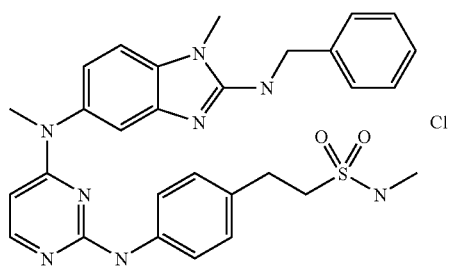

The title compound was prepared following the procedure of Example 1 with N²-benzyl-N⁵-(2-chloropyrimidin-4-yl)-N⁵,1-dimethyl-1H-benzimidazole-2,5-diamine (95 mg, 0.25 mmol) and 2-(4-amino-phenyl)-ethanesulfonic acid methylamide (54 mg, 0.25 mmol) to give the desired product as a white solid (49 mg, 33%). $^1$H NMR (300 MHz, d$_6$-DMSO+ NaHCO$_3$) δ 9.97 (br s, 1H), 9.34 (br s, 1H), 7.85 (d, J=6.6 Hz, 1H), 7.49-7.59 (m, 5H), 7.25-7.37 (m, 4H), 7.17 (d, J=8.1 Hz, 3H), 7.03 (q, J=5.4 Hz, 1H), 5.77 (d, J=6.6 Hz, 1H), 4.74 (d, J=5.1 Hz, 2H), 3.72 (s, 3H), 3.46 (s, 3H), 3.21-3.27 (m, 2H), 2.85-2.91 (m, 2H), 2.58 (d, J=4.8 Hz, 3H). MS (ESI) m/z=557 [M+H]$^+$.

Example 11

3-(4-{[2-(4-Fluoro-benzylamino)-1-methyl-1H-benzoimidazol-5-yl]-methyl-amino}-pyrimidin-2-ylamino)-benzenesulfonamide hydrochloride

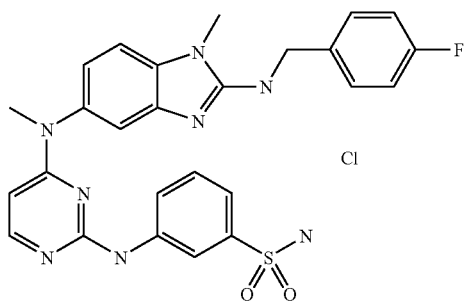

The title compound was prepared following the procedure of example one with $N^5$-(2-chloro-pyrimidin-4-yl)-$N^2$-(4-fluoro-benzyl)-1,$N^5$-dimethyl-1H-benzoimidazole-2,5-diamine (99 mg, 0.25 mmol) and 3-amino-benzenesulfonamide (43 mg, 0.25 mmol) as a white solid (104 mg, 73%). $^1$H NMR (300 MHz, $d_6$-DMSO+NaHCO$_3$) δ 10.08 (br s, 1H), 9.57 (br s, 1H), 8.46 (s, 1H), 7.87 (d, J=1.8 Hz, 1H), 7.73 (m, 1H), 7.55-7.58 (m, 3H), 7.40 (d, J=3.3 Hz, 2H), 7.35 (s, 1H), 7.30 (s, 2H), 7.16-7.23 (m, 3H), 5.74 (d, J=4.5 Hz, 1H), 4.73 (d, J=4.2 Hz, 2H), 3.71 (s, 3H), 3.47 (s, 3H). MS (ESI) m/z=533 [M+H]$^+$.

Example 12

5-(4-{[2-(4-Fluoro-benzylamino)-1-methyl-1H-benzoimidazol-5-yl]-methyl-amino}-pyrimidin-2-ylamino)-2-methyl-benzenesulfonamide hydrochloride

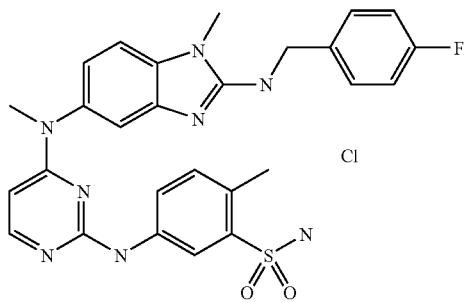

The title compound was prepared following the procedure of example one with $N^5$-(2-chloro-pyrimidin-4-yl)-$N^2$-(4-fluoro-benzyl)-1,$N^5$-dimethyl-1H-benzoimidazole-2,5-diamine (99 mg, 0.25 mmol) and 5-amino-2-methyl-benzenesulfonamide (47 mg, 0.25 mmol) as a white solid (69 mg, 48%). $^1$H NMR (300 MHz, $d_6$-DMSO+NaHCO$_3$) δ10.28 (br s, 1H), 9.61 (br s, 1H), 8.45 (s, 1H), 7.86 (d, J=2.1 Hz, 1H), 7.63 (m, 1H), 7.52-7.59 (m, 3H), 7.37 (s, 1H), 7.31 (s, 2H), 7.13-7.26 (m, 4H), 5.74 (d, J=4.5 Hz, 1H), 4.73 (d, J=4.5 Hz, 2H), 3.71 (s, 3H), 3.48 (s, 3H), 2.50 (s, 3H). MS (ESI) m/z=547 [M+H]$^+$.

Example 13

$N^2$-(4-Fluoro-benzyl)-$N^5$-[2-(4-methanesulfonylmethyl-phenylamino)-pyrimidin-4-yl]-1,$N^5$-dimethyl-1H-benzoimidazole-2,5-diamine hydrochloride

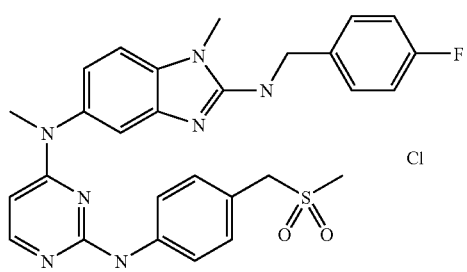

The title compound was prepared following the procedure of example two with $N^5$-(2-chloro-pyrimidin-4-yl)-$N^2$-(4-fluoro-benzyl)-1,$N^5$-dimethyl-1H-benzoimidazole-2,5-diamine (99 mg, 0.25 mmol) and 4-[(methylsulfonyl)methyl] aniline (46 mg, 0.25 mmol) as a white solid (69 mg, 48%). $^1$H NMR (300 MHz, $d_6$-DMSO) δ 9.20 (s, 1H), 7.76-7.80 (m, 3H), 7.41-7.46 (m, 3H), 7.23 (d, J=8.4 Hz, 3H), 7.09-7.17 (m, 3H), 6.84 (dd, J=8.4 and 1.8 Hz, 1H), 5.63 (d, J=6.0 Hz, 1H), 4.57 (d, J=5.7 Hz, 2H), 4.34 (s, 2H), 3.57 (s, 3H), 3.43 (s, 3H), 2.85 (s, 3H). MS (ESI) m/z=546 [M+H]$^+$.

Example 14

[4-(4-{[2-(4-Fluoro-benzylamino)-1-methyl-1H-benzoimidazol-5-yl]-methyl-amino}-pyrimidin-2-ylamino)-phenyl]-methanesulfonamide hydrochloride

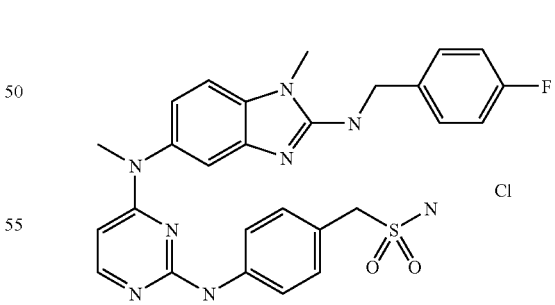

The title compound was prepared following the procedure of example two with $N^5$-(2-chloro-pyrimidin-4-yl)-$N^2$-(4-fluoro-benzyl)-1,$N^5$-dimethyl-1H-benzoimidazole-2,5-diamine (99 mg, 0.25 mmol) and (4-amino-phenyl)-methanesulfonamide (46 mg, 0.25 mmol) as a white solid (50 mg, 34%). $^1$H NMR (300 MHz, $d_6$-DMSO) δ9.16 (S, 1H), 7.75-7.78 (m, 3H), 7.38-7.46 (m, 3H), 7.08-7.24 (m, 6H), 6.84 (dd, J=8.2 and 1.6 Hz, 1H), 6.75 (br s, 2H), 5.61 (d, J=6.0 Hz, 1H), 4.57 (d, J=5.7 Hz, 2H), 4.15 (s, 2H), 3.56 (s, 3H), 3.43 (s, 3H). MS (ESI) m/z=547 [M+H]$^+$.

Example 15

2-[4-(4-{[2-(4-Fluoro-benzylamino)-1-methyl-1H-benzoimidazol-5-yl]-methyl-amino}-pyrimidin-2-ylamino)-phenyl]-ethanesulfonic acid methylamide hydrochloride

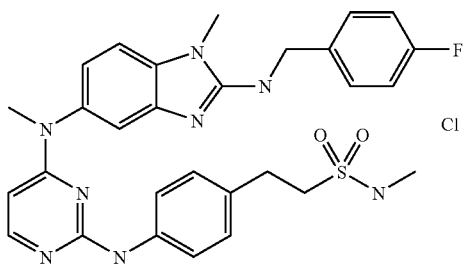

The title compound was prepared following the procedure of example two with N$^5$-(2-chloro-pyrimidin-4-yl)-N$^2$-(4-fluoro-benzyl)-1,N$^5$-dimethyl-1H-benzoimidazole-2,5-diamine (99 mg, 0.25 mmol) and 2-(4-amino-phenyl)-ethanesulfonic acid methylamide (54 mg, 0.25 mmol) to give the desired product as a white solid (90 mg, 59%). $^1$H NMR (300 MHz, d$_6$-DMSO) δ 9.04 (s, 1H), 7.68-7.75 (m, 3H), 7.41-7.46 (m, 3H), 7.23 (d, J=8.1 Hz, 1H), 7.08-7.17 (m, 4H), 6.94 (q, J=5.1 Hz, 1H), 6.83 (dd, J=8.1 and 1.5 Hz, 1H), 5.59 (d, J=6.0 Hz, 1H), 4.57 (d, J=5.4 Hz, 2H), 3.56 (s, 3H), 3.41 (s, 3H), 3.20-3.26 (m, 2H), 2.83-2.88 (m, 2H), 2.59 (d, J=5.1 Hz, 3H). MS (ESI) m/z=575 [M+H]$^+$.

Example 16

3-(4-{[2-(4-Methoxy-benzylamino)-1-methyl-1H-benzoimidazol-5-yl]-methyl-amino}-pyrimidin-2-ylamino)-benzenesulfonamide hydrochloride

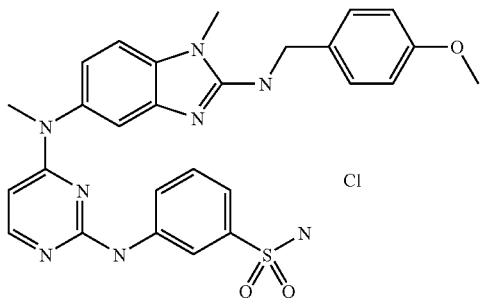

The title compound was prepared following the procedure of example one with N$^5$-(2-chloro-pyrimidin-4-yl)-N$^2$-(4-methoxy-benzyl)-1,N$^5$-dimethyl-1H-benzoimidazole-2,5-diamine (82 mg, 0.20 mmol) and 3-amino-benzenesulfonamide (34 mg, 0.20 mmol) as a white solid (83 mg, 72%). $^1$H NMR (300 MHz, d$_6$-DMSO+NaHCO$_3$) δ10.28 (br s, 2H), 9.53 (br s, 1H), 8.44 (s, 1H), 7.91 (d, J=6.6 Hz, 1H), 7.73 (M, 1H), 7.64 (d, J=8.4 Hz, 1H), 7.43 (d, J=8.4 Hz, 4H), 7.28-7.34 (m, 3H), 6.94 (d, J=8.4 Hz, 2H), 5.81 (m, 1H), 4.67 (d, J=5.7 Hz, 2H), 3.74 (s, 3H), 3.71 (s, 3H), 3.50 (s, 3H). MS (ESI) m/z=545 [M+H]$^+$.

Example 17

5-(4-{[2-(4-Methoxy-benzylamino)-1-methyl-1H-benzoimidazol-5-yl]-methyl-amino}-pyrimidin-2-ylamino)-2-methyl-benzenesulfonamide hydrochloride

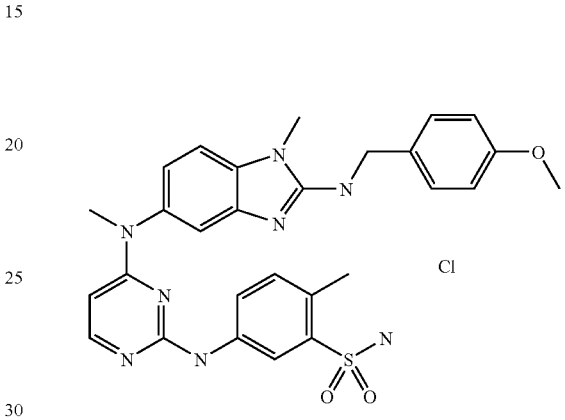

The title compound was prepared following the procedure of example one with N$^5$-(2-chloro-pyrimidin-4-yl)-N$^2$-(4-methoxy-benzyl)-1,N$^5$-dimethyl-1H-benzoimidazole-2,5-diamine (82 mg, 0.20 mmol) and 5-amino-2-methyl-benzenesulfonamide (37 mg, 0.20 mmol) as a white solid (89 mg, 75%). $^1$H NMR (300 MHz, d$_6$-DMSO+NaHCO$_3$). δ 10.25 (br s, 2H), 9.50 (br s, 1H), 8.46 (s, 1H), 7.88 (d, J=6.6 Hz, 1H), 7.60-7.67 (m, 2H), 7.41-7.46 (m, 3H), 7.23-7.32 (m, 4H), 6.93 (d. J=8.7 Hz, 2H), 5.78 (d, J=6.3 Hz, 1H), 6.68 (d, J=5.7 Hz, 2H), 3.74 (s, 3H), 3.71 (s, 3H), 3.51 (s, 3H), 2.53 (s, 3H). MS (ESI) m/z=559 [M+H]$^+$.

Example 18

N$^5$-[2-(4-Methanesulfonylmethyl-phenylamino)-pyrimidin-4-yl]-N$^2$-(4-methoxy-benzyl)-1,N$^5$-dimethyl-1H-benzoimidazole-2,5-diamine hydrochloride

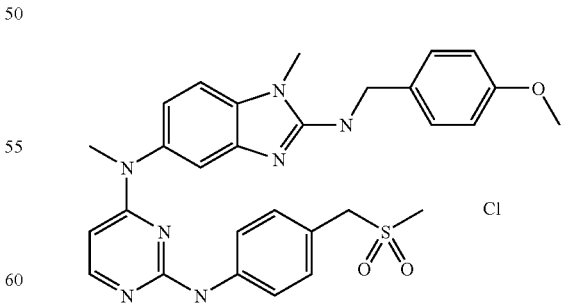

The title compound was prepared following the procedure of example two with N$^5$-(2-chloro-pyrimidin-4-yl)-N$^2$-(4-methoxy-benzyl)-1,N$^5$-dimethyl-1H-benzoimidazole-2,5-diamine (82 mg, 0.20 mmol) and 4-[(methylsulfonyl)methyl]aniline (37 mg, 0.20 mmol) as a white solid (86 mg, 72%). $^1$H NMR (300 MHz, d$_6$-DMSO) δ 9.21 (s, 1H), 7.76-7.81 (m, 3H), 7.29-7.34 (m, 3H), 7.21-7.25 (m, 3H), 7.09 (d, J=1.8 Hz, 1H), 6.82-6.90 (M, 3H), 5.64 (d, J=6.0 Hz, 1H), 4.52 (d, J=5.7 Hz, 2H), 4.35 (s, 2H), 3.72 (s, 3H), 3.56 (s, 3H), 3.43 (s, 3H), 2.85 (s, 3H). MS (ESI) m/z=558 [M+H]$^+$.

Example 19

[4-(4-{[2-(4-Methoxy-benzylamino)-1-methyl-1H-benzoimidazol-5-yl]-methyl-amino}-pyrimidin-2-ylamino)-phenyl]-methanesulfonamide hydrochloride

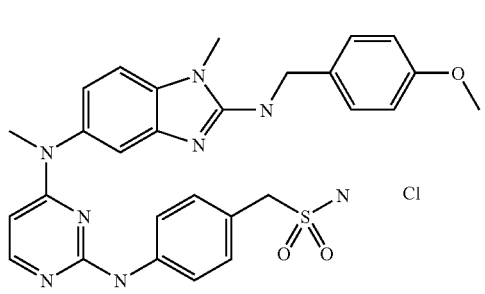

The title compound was prepared following the procedure of example two with N$^5$-(2-chloro-pyrimidin-4-yl)-N$^2$-(4-methoxy-benzyl)-1,N$^5$-dimethyl-1H-benzoimidazole-2,5-diamine (82 mg, 0.20 mmol) and (4-amino-phenyl)-methanesulfonamide (37 mg, 0.20 mmol) as a white solid (49 mg, 41%). $^1$H NMR (300 MHz, d$_6$-DMSO) δ 9.58 (br s, 1H), 9.00 (br s, 1H), 7.85 (d, J=6.0 Hz, 1H), 7.68 (d, J=8.1 Hz, 2H), 7.42-7.50 (M, 3H), 7.29 (s, 1H), 7.12-7.21 (m, 3H), 6.91 (d, J=8.4 Hz, 2H), 6.80 (s, 2H), 5.75 (d, J=5.7 Hz, 1H), 4.64 (d, J=5.1 Hz, 2H), 4.17 (s, 2H), 3.73 (s, 3H), 3.68 (s, 3H), 3.46 (s, 3H). MS (ESI) m/z=559 [M+H]$^+$.

Example 20

2-[4-(4-{[2-(4-Methoxy-benzylamino)-1-methyl-1H-benzoimidazol-5-yl]-methyl-amino}-pyrimidin-2-ylamino)-phenyl]-ethanesulfonic acid methylamide hydrochloride

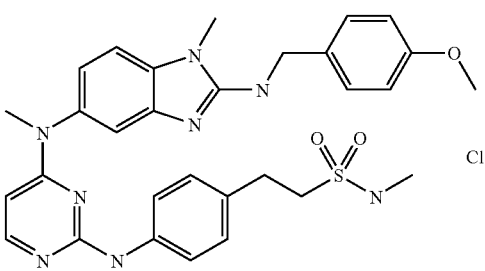

The title compound was prepared following the procedure of example two with N$^5$-(2-chloro-pyrimidin-4-yl)-N$^2$-(4-methoxy-benzyl)-1,N$^5$-dimethyl-1H-benzoimidazole-2,5-diamine (82 mg, 0.20 mmol) and 2-(4-amino-phenyl)-ethanesulfonic acid methylamide (43 mg, 0.20 mmol) as a white solid (105 g, 85%). $^1$H NMR (300 MHz, d$_6$-DMSO) δ 10.18 (br s, 1H), 9.46 (br s, 1H), 7.88 (d, J=6.6 Hz, 1H), 7.54-7.62 (m, 3H), 7.40-7.47 (M, 3H), 7.18-7.26 (M, 3H), 7.01 (M, 1H), 6.92 (d, J=8.4 Hz, 2H), 5.83 (d, J=6.3 Hz, 1H), 4.68 (d, J=5.4 Hz, 2H), 3.73 (s, 3H), 3.72 (s, 3H), 3.48 (s, 3H), 3.23-3.28 (m, 2H), 2.87-2.93 (M, 2H), 2.60 (d, J=4.8 Hz, 3H). MS (ESI) m/z=587 [M+H]$^+$.

Example 21

5-(4-{[2-(3-Fluoro-benzylamino)-1-methyl-1H-benzoimidazol-5-yl]-methyl-amino}-pyrimidin-2-ylamino)-2-methyl-benzenesulfonamide hydrochloride

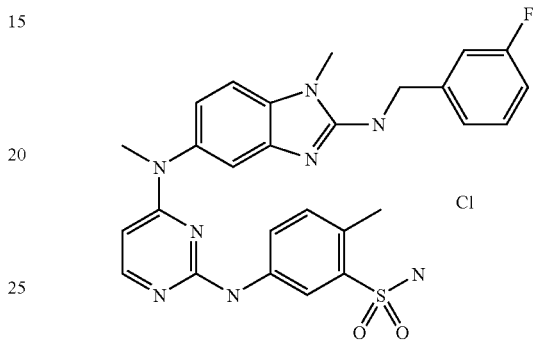

The title compound was prepared following the procedure of example one with N$^5$-(2-chloro-pyrimidin-4-yl)-N$^2$-(3-fluoro-benzyl)-1,N$^5$-dimethyl-1H-benzoimidazole-2,5-diamine (99 mg, 0.25 mmol) and 5-amino-2-methyl-benzenesulfonamide (47 mg, 0.25 mmol) as a white solid (96 mg, 66%). $^1$H NMR (300 MHz, d$_6$-DMSO+NaHCO$_3$) δ10.06 (br s, 1H), 9.34 (br s, 1H), 8.49 (s, 1H), 7.84 (d, J=6.6 Hz, 1H), 7.65 (d, J=6.6 Hz, 1H), 7.56 (d, J=8.4 Hz, 1H), 7.08-7.44 (m, 9H), 5.72 (d, J=6.6 Hz, 1H), 4.75 (d, J=6.6 Hz, 2H), 3.71 (s, 3H), 3.48 (s, 3H), 2.51 (s, 3H). MS (ESI) m/z=547 [M+H]$^+$.

Example 22

3-(4-{[2-(3-Fluoro-benzylamino)-1-methyl-1H-benzoimidazol-5-yl]-methyl-amino}-pyrimidin-2-ylamino)-benzenesulfonamide hydrochloride

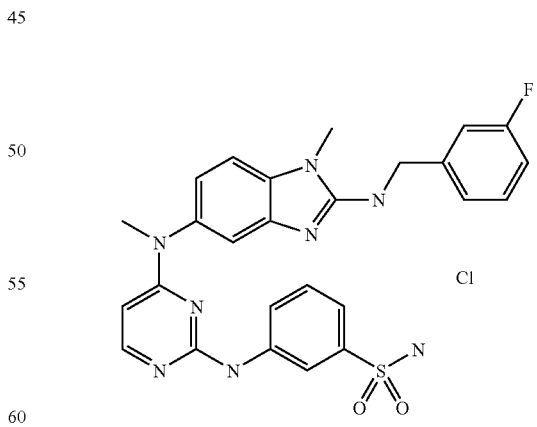

The title compound was prepared following the procedure of example one with N$^5$-(2-chloro-pyrimidin-4-yl)-N$^2$-(3-fluoro-benzyl)-1,N$^5$-dimethyl-1H-benzoimidazole-2,5-diamine (99 mg, 0.25 mmol) and 3-amino-benzenesulfonamide (43 mg, 0.25 mmol) as a white solid (62 mg, 44%). $^1$H NMR (300 MHz, d$_6$-DMSO+NaHCO$_3$) δ 9.70 (s, 2H), 8.53

(s, 1H), 7.83 (d, J=6.0 Hz, 1H), 7.74 (d, J=6.6 Hz, 1H), 7.26-7.50 (M, 8H), 7.10 (m, 2H), 5.69 (d, J=6.0 Hz, 1H), 4.70 (d, J=5.1 Hz, 2H), 3.67 (s, 3H), 3.46 (s, 3H). MS (ESI) m/z=533 [M+H]⁺.

Example 23

N²-(3-Fluoro-benzyl)-N⁵-[2-(4-methanesulfonylmethyl-phenylamino)-pyrimidin-4-yl]-1,N⁵-dimethyl-1H-benzoimidazole-2,5-diamine hydrochloride

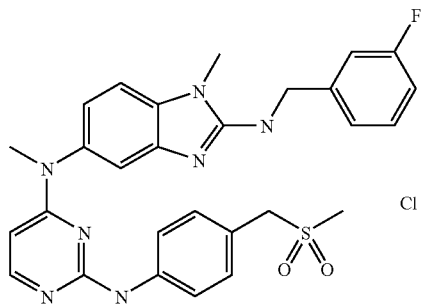

The title compound was prepared following the procedure of example two with N⁵-(2-chloro-pyrimidin-4-yl)-N²-(3-fluoro-benzyl)-1,N⁵-dimethyl-1H-benzoimidazole-2,5-diamine (99 mg, 0.25 mmol) and 4-[(methylsulfonyl)methyl]aniline (46 mg, 0.25 mmol) as a white solid (44 mg, 30%). ¹H NMR (300 MHz, d₆-DMSO) δ 10.64 (s, 1H), 9.82 (s, 1H), 7.93 (d, J=6.9 Hz, 1H), 7.57-7.66 (m, 3H), 7.28-7.43 (m, 7H), 7.12 (m, 1H), 5.94 (s, 1H), 4.80 (d, J=5.7 Hz, 2H), 4.41 (s, 2H), 3.76 (s, 3H), 3.50 (s, 3H), 2.87 (s, 3H). MS (ESI) m/z=546 [M+H]⁺.

Example 24

[4-(4-{[2-(3-Fluoro-benzylamino)-1-methyl-1H-benzoimidazol-5-yl]-methyl-amino}-pyrimidin-2-ylamino)-phenyl]-methanesulfonamide hydrochloride

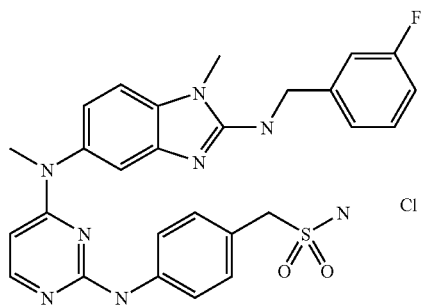

The title compound was prepared following the procedure of example one with N⁵-(2-chloro-pyrimidin-4-yl)-N²-(3-fluoro-benzyl)-1,N⁵-dimethyl-1H-benzoimidazole-2,5-diamine (99 mg, 0.25 mmol) and (4-amino-phenyl)-methanesulfonamide (46 mg, 0.25 mmol) as a white solid (111 mg, 76%). ¹H NMR (300 MHz, dG-DMSO+NaHCO₃) δ 10.03 (br s, 2H), 9.37 (br s, 1H), 7.87 (d, J=6.6 Hz, 1H), 7.54-7.64 (m, 2H), 7.32-7.44 (m, 3H), 7.19-7.24 (M, 3H), 7.08-7.14 (M, 1H), 6.81 (s, 2H), 5.82 (d, J=6.0 Hz, 1H), 4.76 (d, J=5.7 Hz, 2H), 4.18 (s, 2H), 3.72 (s, 3H), 3.47 (s, 3H). MS (ESI) m/z=547 [M+H].

Example 25

2-[4-(4-{[2-(3-Fluoro-benzylamino)-1-methyl-1H-benzoimidazol-S-yl]-methyl-amino}-pyrimidin-2-ylamino)-phenyl]-ethanesulfonic acid methylamide hydrochloride

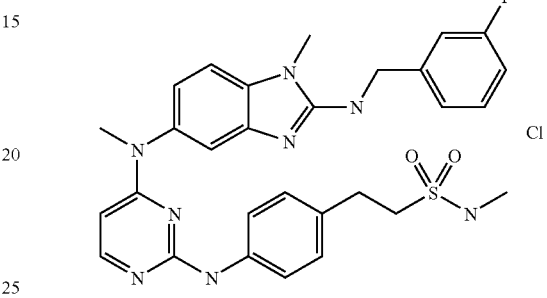

The title compound was prepared following the procedure of example one with N⁵-(2-chloro-pyrimidin-4-yl)-N²-(3-fluoro-benzyl)-1,N⁵-dimethyl-1H-benzoimidazole-2,5-diamine (99 mg, 0.25 mmol) and 2-(4-amino-phenyl)-ethanesulfonic acid methylamide (54 mg, 0.25 mmol) as a white solid (74 mg, 49%). ¹H NMR (300 MHz, d₆-DMSO+ NaHCO₃) δ 9.66 (br s, 1H), 8.73 (br s, 1H), 7.81 (d, J=6.6 Hz, 1H), 7.62 (d, J=8.1 Hz, 2H), 7.36-7.49 (m, 2H), 7.27-7.31 (m, 3), 7.08-7.18 (m, 4H), 6.99 (q, J=4.8 Hz, 1H), 5.73 (d, J=6.3 Hz, 1H), 4.71 (d, J=5.4 Hz, 2H), 3.68 (s, 3H), 3.45 (s, 3H), 3.22-3.27 (m, 2H), 2.86-2.91 (m, 2H), 2.59 (d, J=4.8 Hz, 3H). MS (ESI) m/z=575 [M+H]⁺.

Example 26

3-(4-{[2-(4-Chloro-benzylamino)-1-methyl-1H-benzoimidazol-5-yl]-methyl-amino}-pyrimidin-2-ylamino)-benzenesulfonamide hydrochloride

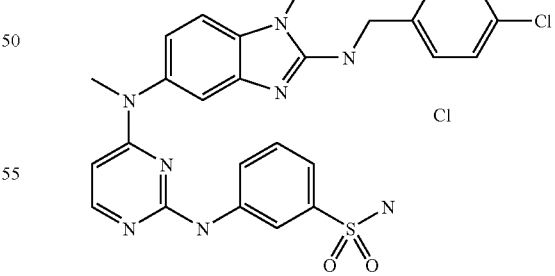

The title compound was prepared following the procedure of example one with N²-(4-Chloro-benzyl)-N⁵-(2-chloro-pyrimidin-4-yl)-1,N⁵-dimethyl-1H-benzoimidazole-2,5-diamine (103 mg, 0.25 mmol) and 3-amino-benzenesulfonamide (43 mg, 0.25 mmol) as a white solid (68 mg, 470%). ¹H NMR (300 MHz, d₆-DMSO+NaHCO₃) δ 9.89 (br s, 1H), 8.49 (s, 1H), 7.86 (d, J=6.3 Hz, 1H), 7.73 (m, 1H), 7.18-7.74

Example 27

5-(4-{[2-(4-Chloro-benzylamino)-1-methyl-1H-benzoimidazol-5-yl]-methyl-amino}-pyrimidin-2-ylamino)-2-methyl-benzenesulfonamide hydrochloride

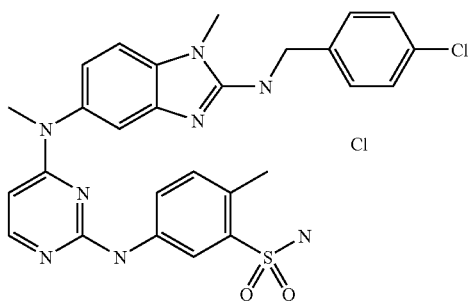

The title compound was prepared following the procedure of example one with $N^2$-(4-Chloro-benzyl)-$N^5$-(2-chloro-pyrimidin-4-yl)-1,$N^5$-dimethyl-1H-benzoimidazole-2,5-diamine (103 mg, 0.25 mmol) and 5-amino-2-methyl-benzenesulfonamide (47 mg, 0.25 mmol) as a white solid (106 mg, 71%). $^1$H NMR (300 MHz, $d_6$-DMSO+NaHCO$_3$) δ 10.17 (br s, 1H), 9.40 (br s, 1H), 8.45 (s, 1H), 7.85 (d, J=6.6 Hz, 1H), 7.62 (m, 2H), 7.49-7.52 (m, 2H), 7.42-7.45 (m, 2H), 7.37 (s, 1H), 7.23-7.31 (m, 4H), 5.75 (m, 1H), 4.72 (d, J=5.7 Hz, 2H), 3.70 (s, 3H), 3.49 (s, 3H), 2.52 (s, 3H). MS (ESI) m/z=561 [M−H]$^−$.

Example 28

2-[4-(4-{[2-(4-Chloro-benzylamino)-1-methyl-1H-benzoimidazol-5-yl]-methyl-amino}-pyrimidin-2-ylamino)-phenyl]-ethanesulfonic acid methylamide hydrochloride

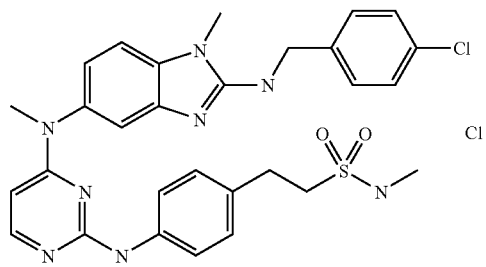

The title compound was prepared following the procedure of example one with $N^2$-(4-Chloro-benzyl)-$N^5$-(2-chloro-pyrimidin-4-yl)-1,$N^5$-dimethyl-1H-benzoimidazole-2,5-diamine (103 mg, 0.25 mmol) and 2-(4-amino-phenyl)-ethanesulfonic acid methylamide (54 mg, 0.25 mmol) as a white solid (96 mg, 64%). $^1$H NMR (300 MHz, $d_6$-DMSO+NaHCO$_3$) δ 10.27 (br s, 1H), 9.34 (br s, 1H), 7.85 (d, J=7.2 Hz, 1H), 7.61 (d, J=8.4 Hz, 1H), 7.49-7.54 (m, 4H), 7.38-7.44 (m, 3H), 7.20-7.26 (m, 3H), 6.99 (q, J=5.1 Hz, 1H), 5.83 (br s, 1H), 4.72 (d, J=5.7 Hz, 2H), 3.71 (s, 3H), 3.48 (s, 3H), 3.22-3.28 (M, 2H), 2.87-2.93 (m, 2H), 2.58 (d, J=4.8 Hz, 3H). MS (ESI) m/z=562 [M+H]$^+$.

Example 29

$N^2$-(4-Chloro-benzyl)-$N^5$-[2-(4-methanesulfonylmethyl-phenylamino)-pyrimidin-4-yl]-1,$N^5$-dimethyl-1H-benzoimidazole-2,5-diamine hydrochloride

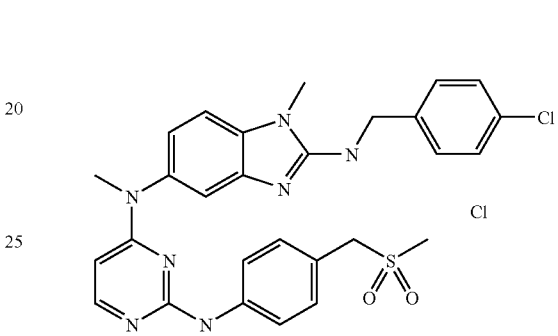

The title compound was prepared following the procedure of example one with $N^2$-(4-Chloro-benzyl)-$N^5$-(2-chloro-pyrimidin-4-yl)-1,$N^5$-dimethyl-1H-benzoimidazole-2,5-diamine (103 mg, 0.25 mmol) and 4-[(methylsulfonyl)methyl] aniline (46 mg, 0.25 mmol) as a white solid (61 mg, 41%). $^1$H NMR (300 MHz, $d_6$-DMSO+NaHCO$_3$) δ 9.20 (s, 1H), 7.76-7.80 (m, 3H), 7.36-7.43 (m, 5H), 7.24 (d, J=8.1 Hz, 2H), 7.08 (d, J=1.8 Hz, 1H), 6.85 (dd, J=8.1 and 1.8 Hz, 1H), 5.63 (d, J=6.0 Hz, 1H), 4.58 (d, J=5.7 Hz, 2H), 4.34 (s, 2H), 3.58 (s, 3H), 3.43 (s, 3H), 2.85 (s, 3H). MS (ESI) m/z=562 [M+H]$^+$.

Example 30

3-{4-[(2-Benzylamino-1-ethyl-1H-benzoimidazol-5-yl)-methyl-amino]-pyrimidin-2-ylamino}-benzenesulfonamide hydrochloride

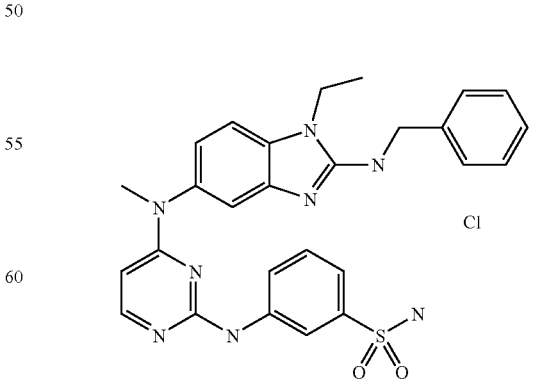

The title compound was prepared following the procedure of example one with $N^2$-Benzyl-$N^5$-(2-chloro-pyrimidin-4- yl)-1-ethyl-N⁵-methyl-1H-benzoimidazole-2,5-diamine (98 mg, 0.25 mmol) and 3-amino-benzenesulfonamide (43 mg, 0.25 mmol) as a white solid (34 mg, 24%). ¹H NMR (300 MHz, d₆-DMSO+NaHCO₃) δ 9.61 (s, 1H), 8.56 (s, 1H), 7.75-7.84 (m, 2H), 7.23-7.45 (m, 11H), 7.04 (d, J=7.2 Hz, 1H), 5.71 (d, J=5.7 Hz, 1H), 4.68 (d, J=5.1 Hz, 2H), 4.21 (m, 2H), 3.46 (s, 3H), 1.28 (m, 3H). MS (ESI) m/z=529 [M+H]⁺.

Example 31

5-{4-[(2-Benzylamino-1-ethyl-1H-benzoimidazol-5-yl)-methyl-amino]-pyrimidin-2-ylamino}-2-methyl-benzenesulfonamide hydrochloride

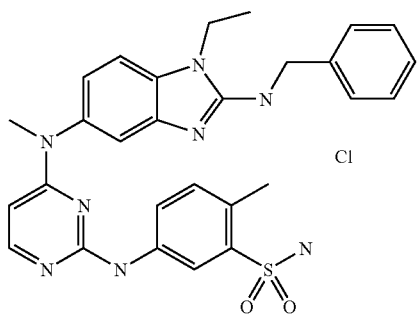

The title compound was prepared following the procedure of example one with N²-Benzyl-N⁵-(2-chloro-pyrimidin-4-yl)-1-ethyl-N⁵-methyl-1H-benzoimidazole-2,5-diamine (98 mg, 0.25 mmol) and 5-amino-2-methyl-benzenesulfonamide (46 mg, 0.25 mmol) as a white solid (83 mg, 58%). ¹H NMR (300 MHz, d₆-DMSO+NaHCO₃) δ 9.54 (s, 1H), 8.56 (s, 1H), 7.80 (d, J=6.3 Hz, 1H), 7.68 (dd, J=8.2 and 1.6 Hz, 1H), 7.15-7.47 (m, 10H), 7.03 (d, J=7.8 Hz, 1H), 5.69 (d, J=6.0 Hz, 1H), 4.68 (d, J=5.7 Hz, 2H), 4.21 (m, 2H), 3.46 (s, 3H), 2.50 (s, 3H), 1.28 (t, J=6.9 Hz, 3H). MS (ESI) m/z=543 [M+H]⁺.

Example 32

N²-Benzyl-1-ethyl-N⁵-[2-(4-methanesulfonylmethyl-phenylamino)-pyrimidin-4-yl]-N⁵-methyl-1H-benzoimidazole-2,5-diamine hydrochloride

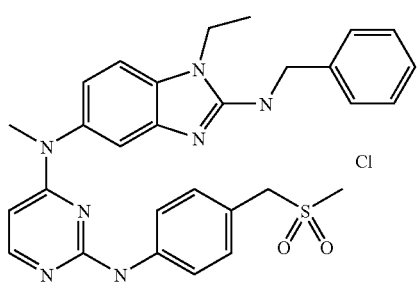

The title compound was prepared following the procedure of example two with N²-Benzyl-N⁵-(2-chloro-pyrimidin-4-yl)-1-ethyl-N⁵-methyl-1H-benzoimidazole-2,5-diamine (98 mg, 0.25 mmol) and 4-[(methylsulfonyl)methyl]aniline (46 mg, 0.25 mmol) as a white solid (65 mg, 45%). ¹H NMR (300 MHz, d₆-DMSO+NaHCO₃) δ 9.53 (s, 1H), 7.75 (m, 3H), 7.19-7.40 (M, 9H), 7.10 (s, 1H), 6.87 (m, 1H), 5.66 (m, 1H), 4.60 (m, 2H), 4.32 (s, 2H), 4.11 (m, 2H), 6.41 (s, 3H), 2.83 (s, 3H), 1.24 (M, 3H).

Example 33

(4-{4-[(2-Benzylamino-1-ethyl-1H-benzoimidazol-5-yl)-methyl-amino]-pyrimidin-2-ylamino}-phenyl)-methanesulfonamide hydrochloride

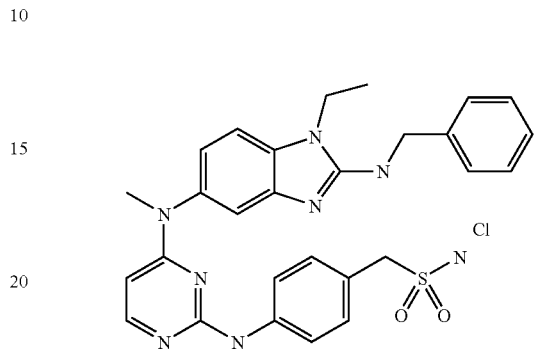

The title compound was prepared following the procedure of example two with N²-Benzyl-N⁵-(2-chloro-pyrimidin-4-yl)-1-ethyl-N⁵-methyl-1H-benzoimidazole-2,5-diamine (98 mg, 0.25 mmol) and (4-amino-phenyl)-methanesulfonamide (46 mg, 0.25 mmol) as a white solid (97 mg, 67%). ¹H NMR (300 MHz, d₆-DMSO+NaHCO₃) δ 9.30 (s, 1H), 7.79 (d, J=6.0 Hz, 1H), 7.75 (d, J=8.7 Hz, 2H), 7.15-7.42 (M, 9H), 6.9+5 (d, J=8.1 Hz, 1H), 6.77 (s, 2H), 5.69 (d, J=6.0 Hz, 1H), 4.65 (d, J=5.7 Hz, 2H), 4.16-4.18 (m, 4H), 3.44 (s, 3H), 1.27 (t, J=7.2 Hz, 3H). MS (ESI) m/z=543 [M+H]⁺.

Example 34

3-(4-{[2-(2-Fluoro-benzylamino)-1-methyl-1H-benzoimidazol-5-yl]-methyl-amino}-pyrimidin-2-ylmethyl)-benzenesulfonamide hydrochloride

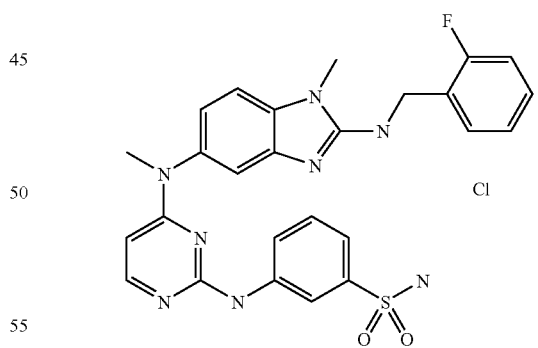

The title compound was prepared following the procedure of example one with N⁵-(2-chloro-pyrimidin-4-yl)-N²-(2-fluoro-benzyl)-1,N⁵-dimethyl-1H-benzoimidazole-2,5-diamine (60 mg, 0.15 mmol) and 3-amino-benzenesulfonamide (26 mg, 0.15 mmol) as a white solid (52 mg, 61%). ¹H NMR (300 MHz, d₆-DMSO+NaHCO₃) δ 9.51 (s, 1H), 8.60 (s, 1H), 7.78 (d, J=6.0 Hz, 2H), 7.62 (br s, 1H), 7.47 (t, J=7.8 Hz, 1H), 7.12-7.41 (M, 9H), 6.89 (d, J=8.1 Hz, 1H), 5.64 (d, J=6.3 Hz, 1H), 4.66 (d, J=5.4 Hz, 2H), 3.61 (s, 3H), 3.45 (s, 3H). MS (ESI) m/z=533 [M+H]⁺.

Example 35

5-(4-{[2-(2-Fluoro-benzylamino)-1-methyl-1H-benzoimidazol-5-yl]-methyl-amino}-pyrimidin-2-ylamino)-2-methyl-benzenesulfonamide hydrochloride

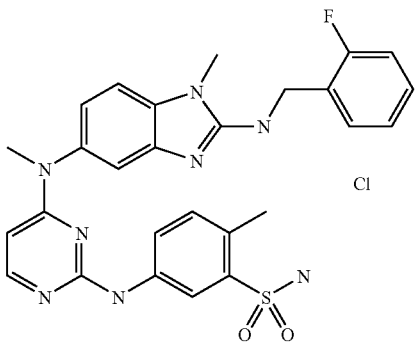

The title compound was prepared following the procedure of example one with N⁵-(2-chloro-pyrimidin-4-yl)-N²-(2-fluoro-benzyl)-1,N⁵-dimethyl-1H-benzoimidazole-2,5-diamine (60 mg, 0.15 mmol) and 5-amino-2-methyl-benzenesulfonamide (28 mg, 0.15 mmol) as a white solid (69 mg, 79%). ¹H NMR (300 MHz, d₆-DMSO+NaHCO₃) δ 9.71 (s, 1H), 8.55 (s, 1H), 7.81 (d, J=6.0 Hz, 1H), 7.68 (dd, J=8.1 and 1.8 Hz, 1H), 7.44-7.54 (m, 2H), 7.16-7.36 (m, 7H), 7.07 (d, J=8.4 Hz, 1H), 5.68 (d, J=6.3 Hz, 1H), 4.73 (d, J=5.1 Hz, 2H), 3.67 (s, 3H), 3.47 (s, 3H), 2.50 (s, 3H). MS (ESI) m/z=547 [M+H]⁺.

Example 36

[4-(4-{[2-(2-Fluoro-benzylamino)-1-methyl-1H-benzoimidazol-5-yl]-methyl-amino}-pyrimidin-2-ylamino)-phenyl]-methanesulfonamide hydrochloride

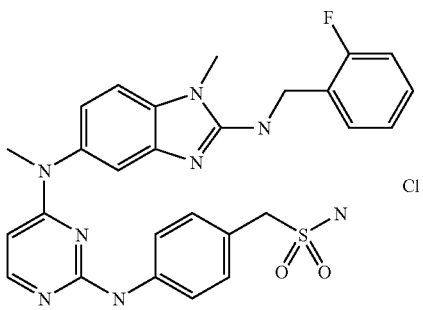

The title compound was prepared following the procedure of example one with N⁵-(2-chloro-pyrimidin-4-yl)-N²-(2-fluoro-benzyl)-1,N⁵-dimethyl-1H-benzoimidazole-2,5-diamine (60 mg, 0.15 mmol) and (4-amino-phenyl)-methanesulfonamide (28 mg, 0.15 mmol) as a white solid (30 mg, 34%). ¹H NMR (300 MHz, d₆-DMSO+NaHCO₃) δ 9.58 (s, 1H), 7.83 (d, J=6.3 Hz, 1H), 7.68 (d, J=8.4 Hz, 2H), 7.49-7.53 (m, 2H), 7.33-7.40 (m, 1H), 7.17-7.27 (m, 4H), 7.09-7.12 (m, 1H), 6.79 (s, 2H), 5.76 (d, J=6.0 Hz, 1H), 4.72 (d, J=5.4 Hz, 2H), 4.18 (s, 2H), 3.67 (s, 3H), 3.46 (s, 3H). MS (ESI) m/z=547 [M+H]⁺.

Example 37

2-(4-{4-[(2-Benzylamino-1-ethyl-1H-benzoimidazol-5-yl)-methyl-amino]-pyrimidin-2-ylamino}-phenyl)-ethanesulfonic acid methylamide hydrochloride

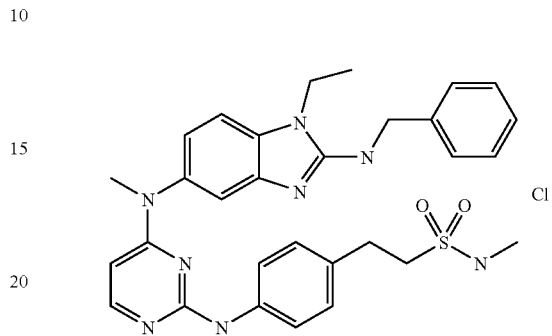

The title compound was prepared following the procedure of example two with N²-Benzyl-N⁵-(2-chloro-pyrimidin-4-yl)-1-ethyl-N⁵-methyl-1H-benzoimidazole-2,5-diamine (98 mg, 0.25 mmol) and 2-(4-amino-phenyl)-ethanesulfonic acid methylamide (54 mg, 0.25 mmol) as a white solid (74 mg, 49%). ¹H NMR (300 MHz, d₆-DMSO+NaHCO₃) δ 9.04 (s, 1H), 7.75 (d, J=6.0 Hz, 1H), 7.69 (d, J=8.4 Hz, 2H), 7.23-7.42 (m, 7H), 7.07-7.12 (m, 3H), 6.94 (q, J=5.1 Hz, 1H), 6.83 (dd, J=8.4 and 2.1 Hz, 1H), 5.63 (d, J=5.7 Hz, 1H), 4.61 (d, J=5.7 Hz, 2H), 4.11 (q, J=6.9 Hz, 2H), 3.41 (s, 3H), 3.32 (s, 3H), 3.20-3.25 (M, 2H), 2.83-2.88 (M, 2H), 2.59 (d, J=4.8 Hz, 3H), 1.26 (t, J=6.9 Hz, 3H). MS (ESI) m/z=571 [M+H]⁺.

Example 38

3-(4-{Methyl-[1-methyl-2-(1-phenyl-ethylamino)-1H-benzoimidazol-5-yl]-amino}-pyrimidin-2-ylamino)-benzenesulfonamide hydrochloride

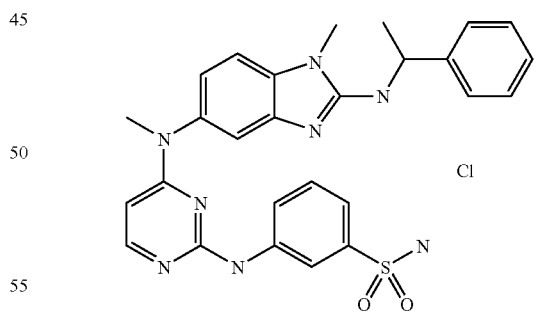

The title compound was prepared following the procedure of example one with N⁵-(2-Chloro-pyrimidin-4-yl)-1,N⁵-dimethyl-N²-(1-phenyl-ethyl)-1H-benzoimidazole-2,5-diamine (98 mg, 0.25 mmol) and 3-amino-benzenesulfonamide (43 mg, 0.25 mmol) as a white solid (65 mg, 46%). ¹H NMR (300 MHz, d₆-DMSO+NaHCO₃) δ 9.58 (s, 2H), 8.57 (s, 1H), 7.75-7.81 (m, 2H), 7.48-7.51 (m, 2H), 7.32-7.41 (m, 5H), 7.17-7.26 (m, 4H), 6.98-7.00 (m, 1H), 5.65 (d, J=6.3 Hz, 1H), 5.17 (m, 1H), 3.67 (s, 3H), 3.44 (s, 3H), 1.58 (d, J=6.9 Hz, 3H). MS (ESI) m/z=529 [M+H]⁺.

Example 39

2-Methyl-5-(4-{methyl-[1-methyl-2-(1-phenyl-ethylamino)-1H-benzoimidazol-5-yl]-amino}-pyrimidin-2-ylamino)-benzenesulfonamide hydrochloride

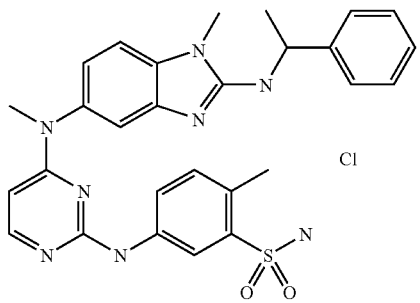

The title compound was prepared following the procedure of example one with $N^5$-(2-Chloro-pyrimidin-4-yl)-1,$N^5$-dimethyl-$N^2$-(1-phenyl-ethyl)-1H-benzoimidazole-2,5-diamine (98 mg, 0.25 mmol) and 5-amino-2-methyl-benzenesulfonamide (46 mg, 0.25 mmol) as a white solid (90 mg, 63%). $^1$H NMR (300 MHz, $d_6$-DMSO+NaHCO$_3$) δ 9.85 (br s, 2H), 8.52 (s, 1H), 7.83 (d, J=6.3 Hz, 1H), 7.65-7.68 (dd, J=8.1 and 1.8 Hz, 1H), 7.51-7.57 (m, 3H), 7.34-7.39 (m, 2H), 7.25-7.30 (m, 4H), 7.15-7.22 (m, 2H), 5.70 (d, J=6.3 Hz, 1H), 5.22 (m, 1H), 3.74 (s, 3H), 3.47 (s, 3H), 2.51 (s, 3H), 1.63 (d, J=6.6 Hz, 3H). MS (ESI) m/z=543 [M+H]$^+$.

Example 40

$N^5$-[2-(4-Methanesulfonylmethyl-phenylamino)-pyrimidin-4-yl]-1,$N^5$-dimethyl-$N^2$-(1-phenyl-ethyl)-1H-benzoimidazole-2,5-diamine hydrochloride

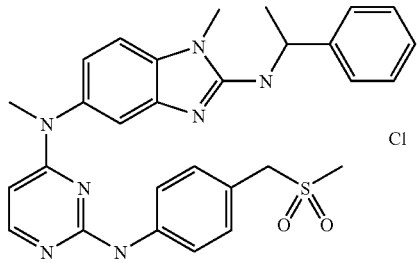

The title compound was prepared following the procedure of example two with $N^5$-(2-Chloro-pyrimidin-4-yl)-1,$N^5$-dimethyl-$N^2$-(1-phenyl-ethyl)-1H-benzoimidazole-2,5-diamine (98 mg, 0.25 mmol) and 4-[(methylsulfonyl)methyl]aniline (46 mg, 0.25 mmol) as a white solid (66 mg, 46%). $^1$H NMR (400 MHz, $d_6$-DMSO) δ 9.18 (s, 1H), 7.72-7.77 (M, 3H), 7.42 (d, J=7.6 Hz, 2H), 7.16-7.21 (m, 4H), 7.10 (d, J=8.0 Hz, 1H), 7.02 (d, J=2.0 Hz, 1H), 6.79 (dd, J=8.4 and 2.0 Hz, 1H), 5.58 (d, J=5.6 Hz, 1H), 5.12 (m, 1H), 4.31 (s, 2H), 3.58 (s, 3H), 3.38 (s, 3H), 2.82 (s, 3H), 1.50 (d, J=6.8 Hz, 3H). MS (ESI) m/z=542 [M+H]$^+$.

Example 41

[4-(4-{Methyl-[1-methyl-2-(1-phenyl-ethylamino)-1H-benzoimidazol-5-yl]-amino}-pyrimidin-2-ylamino)-phenyl]-methanesulfonamide hydrochloride

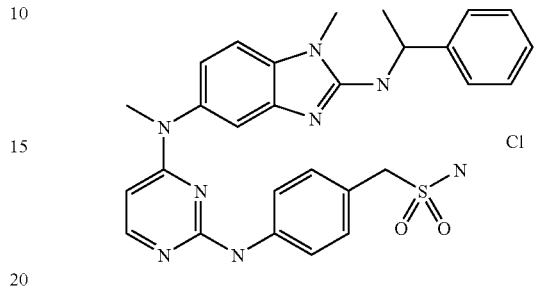

The title compound was prepared following the procedure of example two with $N^5$-(2-Chloro-pyrimidin-4-yl)-1,$N^5$-dimethyl-$N^2$-(1-phenyl-ethyl)-1H-benzoimidazole-2,5-diamine (98 mg, 0.25 mmol) and (4-amino-phenyl)-methanesulfonamide (46 mg, 0.25 mmol) as a white solid (90 mg, 62%). $^1$H NMR (400 MHz, $d_6$-DMSO) δ 9.13 (s, 1H), 7.71-7.75 (m, 3H), 7.42 (d, J=7.6 Hz, 2H), 7.26-7.30 (M, 2H), 7.16-7.19 (m, 4H), 7.11 (d, J=8.0 Hz, 1H), 7.02 (d, J=2.0 Hz, 1H), 6.79 (dd, J=8.4 and 2.0 Hz, 1H), 6.73 (s, 2H), 5.56 (d, J=6.0 Hz, 1H), 5.12 (m, 1H), 4.12 (s, 2H), 3.58 (s, 3H), 3.38 (s, 3H), 1.50 (d, J=7.2 Hz, 3H). MS (ESI) m/z=543 [M+H]$^+$.

Example 42

3-(4-{[2-(3-Chloro-benzylamino)-1-methyl-1H-benzoimidazol-5-yl]-methyl-amino}-pyrimidin-2-ylamino)-benzenesulfonamide hydrochloride

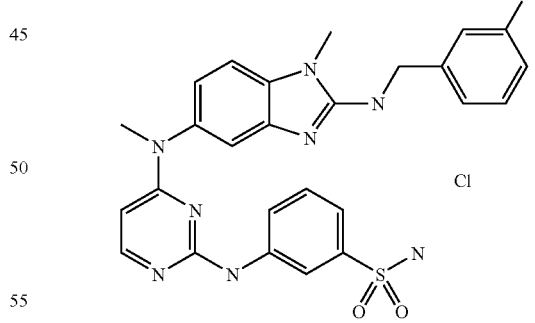

The title compound was prepared following the procedure of example one with $N^2$-(3-Chloro-benzyl)-$N^5$-(2-chloro-pyrimidin-4-yl)-1,$N^5$-dimethyl-1H-benzoimidazole-2,5-diamine (50 mg, 0.12 mmol) and 3-amino-benzenesulfonamide (21 mg, 0.12 mmol) as a white solid (31 mg, 44%). $^1$H NMR (300 MHz, $d_6$-DMSO+NaHCO$_3$) δ 9.51 (s, 1H), 8.60 (s, 1H), 7.76-7.80 (M, 2H), 7.25-7.47 (m, 10H), 7.13 (s, 1H), 6.90 (d, J=7.8 Hz, 1H), 5.64 (d, J=6.0 Hz, 1H), 4.62 (d, J=5.4 Hz, 2H), 3.61 (s, 3H), 3.45 (s, 3H). MS (ESI) m/z=549 [M+H]$^+$.

Example 43

3-(4-{[2-(3-Chloro-benzylamino)-1-methyl-1H-benzoimidazol-5-yl]-methyl-amino}-pyrimidin-2-ylamino)-benzenesulfonamide hydrochloride

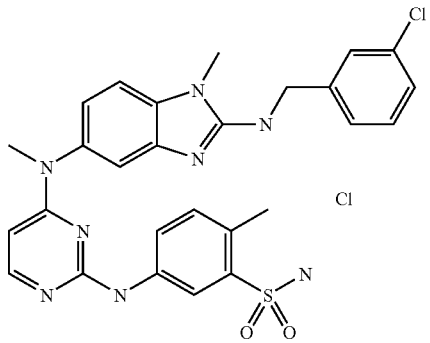

The title compound was prepared following the procedure of example one with $N^2$-(3-Chloro-benzyl)-$N^5$-(2-chloro-pyrimidin-4-yl)-1,$N^5$-dimethyl-1H-benzoimidazole-2,5-diamine (50 mg, 0.12 mmol) and 5-amino-2-methyl-benzenesulfonamide (22 mg, 0.12 mmol) as a white solid (42 mg, 58%). $^1$H NMR (300 MHz, $d_6$-DMSO+NaHCO$_3$) δ 9.79 (s, 1H), 8.54 (s, 1H), 7.81-7.84 (M, 1H), 7.66-7.69 (m, 1H), 7.11-7.56 (m, 11H), 5.69 (d, J=6.0 Hz, 1H), 4.72 (d, J=5.4 Hz, 2H), 3.70 (s, 3H), 3.48 (s, 3H), 2.51 (s, 3H). MS (ESI) m/z=563 [M+H]$^+$.

Example 44

[4-(4-{[2-(4-Chloro-benzylamino)-1-methyl-1H-benzoimidazol-5-yl]-methyl-amino}-pyrimidin-2-ylamino)-phenyl]-methanesulfonamide hydrochloride

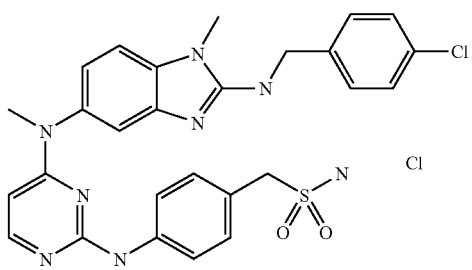

The title compound was prepared following the procedure of example one with $N^2$-(4-Chloro-benzyl)-$N^5$-(2-chloro-pyrimidin-4-yl)-1,$N^5$-dimethyl-1H-benzoimidazole-2,5-diamine (103 mg, 0.25 mmol) and (4-amino-phenyl)-methanesulfonamide (46 mg, 0.25 mmol) as a white solid (90 mg, 60%). $^1$H NMR (300 MHz, $d_6$-DMSO+NaHCO$_3$) δ 9.31 (s, 1H), 8.05 (br s, 1H), 7.72-7.80 (m, 3H), 7.46 (d, J=8.4 Hz, 2H), 7.38 (d, J=8.4 Hz, 2H), 7.32 (d, J=8.4 Hz, 1H), 7.20 (d, J=8.4 Hz, 2H), 7.14 (s, 1H), 6.93 (d, J=8.4 Hz, 1H), 6.78 (s, 2H), 5.66 (d, J=6.0H, 1H), 4.62 (d, J=5.4 Hz, 2H), 4.17 (s, 2H), 3.63 (s, 3H), 3.44 (s, 3H). MS (ESI) m/z=563 [M+H]$^+$.

Example 45

Methanesulfonic acid 3-(4-{[2-(4-chloro-benzylamino)-1-methyl-1H-benzoimidazol-5-yl]-methyl-amino}-pyrimidin-2-ylamino)-phenyl ester hydrochloride

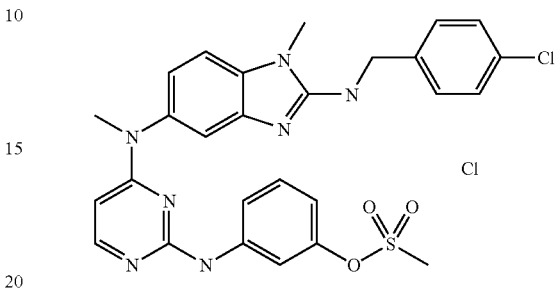

The title compound was prepared following the procedure of example one with $N^2$-(4-Chloro-benzyl)-$N^5$-(2-chloro-pyrimidin-4-yl)-1,$N^5$-dimethyl-1H-benzoimidazole-2,5-diamine (103 mg, 0.25 mmol) and methanesulfonic acid 3-amino-phenyl ester (56 mg, 0.25 mmol) as a white solid (87 mg, 58%). $^1$H NMR (300 MHz, $d_6$-DMSO+NaHCO$_3$) δ 9.40 (s, 1H), 8.00 (s, 1H), 7.79 (d, J=6.0 Hz, 1H), 7.64 (d, J=8.1 Hz, 1H), 7.50 (t, J=5.7 Hz, 1H), 7.36-7.44 (m, 4H), 7.23-7.29 (m, 2H), 7.08 (s, 1H), 6.84 (d, J=8.1 Hz, 2H), 5.65 (d, J=5.7 Hz, 1H), 4.58 (d, J=5.7 Hz, 2H), 3.58 (s, 3H), 3.43 (s, 3H), 3.34 (s, 3H). MS (ESI) m/z=564 [M+H]$^+$.

Example 46

$N^5$-{2-[4-(2-Methanesulfonyl-ethyl)-phenylamino]-pyrimidin-4-yl}-$N^2$-(4-methoxy-benzyl)-1,$N^5$-dimethyl-1H-benzoimidazole-2,5-diamine hydrochloride

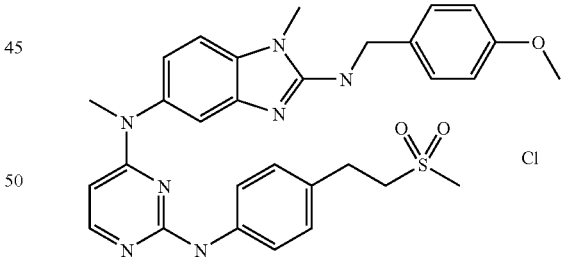

The title compound was prepared following the procedure of example two with $N^5$-(2-chloro-pyrimidin-4-yl)-$N^2$-(4-methoxy-benzyl)-1,$N^5$-dimethyl-1H-benzoimidazole-2,5-diamine (82 mg, 0.20 mmol) and 4-(2-Methanesulfonyl-ethyl)-phenylamine (40 mg, 0.20 mmol) as a white solid (57 mg, 47%). $^1$H NMR (300 MHz, $d_6$-DMSO) δ 9.28 (s, 1H), 7.78 (d, J=6.0 Hz, 1H), 7.67 (d, J=8.4 Hz, 2H), 7.34-7.38 (m, 3H), 7.13-7.18 (m, 3H), 6.94 (d, J=8.4 Hz, 1H), 6.89 (d, J=8.7 Hz, 2H), 5.66 (d, J=6.0 Hz, 1H), 4.57 (d, J=5.4 Hz, 2H), 3.72 (s, 3H), 3.62 (s, 3H), 3.43 (s, 3H), 3.35-3.43 (m, 2H), 2.96 (s, 3H), 2.90-2.96 (m, 2H). MS (ESI) m/z=572 [M+H]$^+$.

Example 47

N[5]-{2-[3-(2-Methanesulfonyl-ethyl)-phenylamino]-pyrimidin-4-yl}-N[2]-(4-methoxy-benzyl)-1,N[5]-dimethyl-1H-benzoimidazole-2,5-diamine hydrochloride

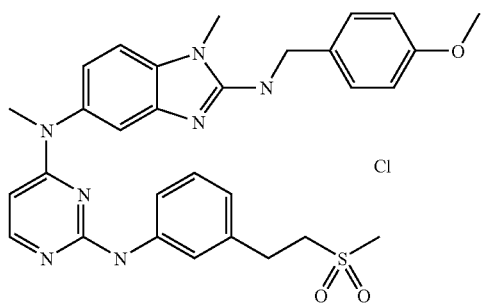

The title compound was prepared following the procedure of example two with N[5]-(2-chloro-pyrimidin-4-yl)-N[2]-(4-methoxy-benzyl)-1,N[5]-dimethyl-1H-benzoimidazole-2,5-diamine (82 mg, 0.20 mmol) and 3-(2-Methanesulfonyl-ethyl)-phenylamine (40 mg, 0.20 mmol) as a white solid (69 mg, 57%). $^1$H NMR (300 MHz, ds-DMSO) δ 9.08 (s, 1H), 7.76 (d, J=6.0 Hz, 2H), 7.59 (d, J=8.4 Hz, 1H), 7.28-7.34 (m, 3H), 7.08-7.23 (m, 3H), 6.79-6.89 (m, 4H), 5.61 (d, J=5.7 Hz, 1H), 4.52 (d, J=5.7 Hz, 2H), 3.72 (s, 3H), 3.55 (s, 3H), 3.43 (s, 3H), 3.35-3.40 (M, 2H), 2.97 (s, 3H), 2.90-2.94 (m, 2H). MS (ESI) m/z=572 [M+H]$^+$.

Example 48

N[5]-{2-[4-(1-Methanesulfonyl-ethyl)-phenylamino]-pyrimidin-4-yl}-N[2]-(4-methoxy-benzyl)-1,N[5]-dimethyl 1H-benzoimidazole-2,5-diamine hydrochloride

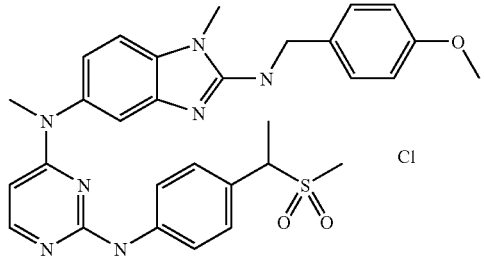

The title compound was prepared following the procedure of example two with N[5]-(2-chloro-pyrimidin-4-yl)-N[2]-(4-methoxy-benzyl)-1,N[5]-dimethyl-1H-benzoimidazole-2,5-diamine (82 mg, 0.20 mmol) and 4-(1-Methanesulfonyl-ethyl)-phenylamine (47 mg, 0.20 mmol) as a white solid (49 mg, 40%). $^1$H NMR (300 MHz, d$_6$-DMSO+NaHCO$_3$) δ 9.24 (s, 1H), 7.75-7.80 (M, 3H), 7.60 (br s, 1H), 7.34 (d, J=8.7 Hz, 2H), 7.26 (d, J=7.8 Hz, 3H), 7.12 (s, 1H), 6.89 (d, J=8.4 Hz, 3H), 5.66 (d, J=6.0 Hz, 1H), 4.53 (d, J=5.7 Hz, 2H), 4.40 (m, 1H), 3.72 (s, 3H), 3.58 (s, 3H), 3.43 (s, 3H), 2.76 (s, 3H), 1.59 (d, J=7.2 Hz, 3H). MS (ESI) m/z=572 [M+H]$^+$.

Example 49

N[5]-[2-(3-Methanesulfonylmethyl-phenylamino)-pyrimidin-4-yl]-N[2]-(4-methoxy-benzyl)-1,N[5]-dimethyl-1H-benzoimidazole-2,5-diamine hydrochloride

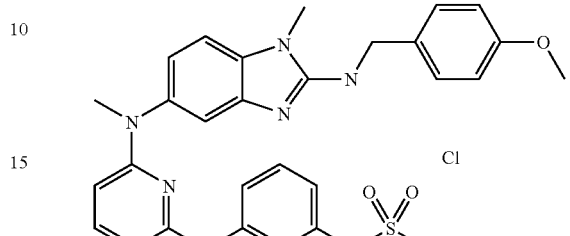

The title compound was prepared following the procedure of example two with N[5]-(2-chloro-pyrimidin-4-yl)-N[2]-(4-methoxy-benzyl)-1,N[5]-dimethyl-1H-benzoimidazole-2,5-diamine (82 mg, 0.20 mmol) and methanesulfonylmethyl-phenylamine (37 mg, 0.20 mmol) as a white solid (105 mg, 88%). $^1$H NMR (300 MHz, d$_6$-DMSO) δ 9.19 (s, 1H), 7.90 (s, 1H), 7.77 (d, J=6.0 Hz, 1H), 7.69 (d, J=8.4 Hz, 1H), 7.28-7.34 (m, 3H), 7.19-7.24 (m, 2H), 7.09 (d, J=1.8 Hz, 1H), 6.81-6.92 (m, 4H), 5.64 (d, J=6.0 Hz, 1H), 4.52 (d, J=5.7 Hz, 2H), 4.32 (s, 2H), 3.72 (s, 3H), 3.55 (s, 3H), 3.43 (s, 3H), 2.88 (s, 3H). MS (ESI) m/z=558 [M+H]$^+$.

Example 50

N[2]-Benzyl-N[5]-[2-(3-methanesulfonylmethyl-phenylamino)-pyrimidin-4-yl]-1,N[5]-dimethyl-1H-benzoimidazole-2,5-diamine hydrochloride

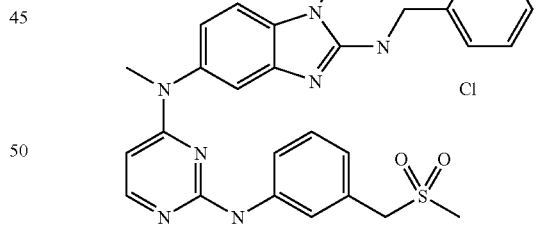

The title compound was prepared following the procedure of Example two with N[2]-benzyl-N[5]-(2-chloropyrimidin-4-yl)-N[5],1-dimethyl-1H-benzimidazole-2,5-diamine (95 mg, 0.25 mmol) and methanesulfonylmethyl-phenylamine (46 mg, 0.25 mmol) to give the desired product as an off-white solid (121 mg, 8601%). $^1$H NMR (300 MHz, d$_6$-DMSO) δ 9.26 (s, 1H), 7.87 (s, 1H), 7.78 (d, J=6.0 Hz, 1H), 7.67 (d, J=8.4 Hz, 1H), 7.42 (m, 1H), 7.21-7.40 (m, 7H), 7.12 (s, 1H), 6.88-6.93 (M, 2H), 5.66 (d, J=5.7 Hz, 1H), 4.62 (d, J=5.4 Hz, 2H), 4.32 (s, 2H), 3.60 (S, 3H), 3.43 (s, 3H), 2.88 (s, 3H). MS (ESI) m/z=528 [M+H]$^+$.

Example 51

N[5]-[2-(3-Methanesulfonylmethyl-phenylamino)-pyrimidin-4-yl]-1,N[5]-dimethyl-N[2]-(1-phenyl-ethyl)-1H-benzoimidazole-2,5-diamine hydrochloride

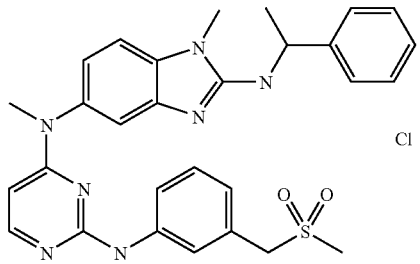

The title compound was prepared following the procedure of example two with N[5]-(2-Chloro-pyrimidin-4-yl)-1,N[5]-dimethyl-N[2]-(1-phenyl-ethyl)-1H-benzoimidazole-2,5-diamine (98 mg, 0.25 mmol) and methanesulfonylmethyl-phenylamine (46 mg, 0.25 mmol) as a white solid (90 mg, 62%). $^1$H NMR (300 MHz, $d_6$-DMSO) δ 9.19 (s, 1H), 7.88 (s, 1H), 7.75 (d, J=6.0 Hz, 1H), 7.68 (d, J=8.1 Hz, 1H), 7.45 (d, J=7.5 Hz, 2H), 7.29-7.34 (m, 2H), 7.16-7.23 (m, 4H), 7.05 (d, J=1.8 Hz, 1H), 6.90 (d, J=7.5 Hz, 1H), 5.62 (dd, J=8.1 and 1.8 Hz, 1H), 5.62 (d, J=6.0 Hz, 1H), 5.15 (m, 1H), 4.31 (s, 2H), 3.61 (s, 3H), 3.41 (s, 3H), 2.87 (s, 3H), 1.53 (d, J=6.9 Hz, 3H). MS (ESI) m/z=542 [M+H]+.

Example 52

N[5]-{2-[3-(2-Methanesulfonyl-ethyl)-phenylamino]-pyrimidin-4-yl}-1,N[5]-dimethyl-N[2]-(1-phenyl-ethyl)-1H-benzoimidazole-2,5-diamine hydrochloride

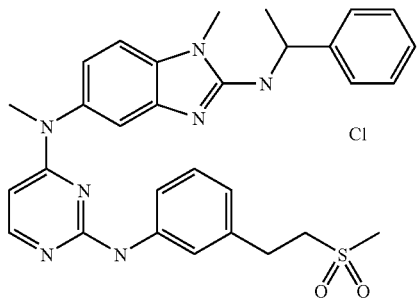

The title compound was prepared following the procedure of example two with N[5]-(2-Chloro-pyrimidin-4-yl)-1,N[5]-dimethyl-N[2]-(1-phenyl-ethyl)-1H-benzoimidazole-2,5-diamine (98 mg, 0.25 mmol) and 3-(2-methanesulfonyl-ethyl)-phenylamine (50 mg, 0.25 mmol) as a white solid (48 mg, 32%). $^1$H NMR (300 MHz, $d_6$-DMSO) δ 9.08 (s, 1H), 7.73-7.77 (m, 2H), 7.58 (d, J=8.4 Hz, 1H), 7.44 (d, J=7.5 Hz, 2H), 7.29-7.34 (m, 2H), 7.12-7.23 (m, 4H), 7.05 (d, J=1.5 Hz, 1H), 6.79-6.84 (m, 2H), 5.59 (d, J=5.7 Hz, 1H), 5.14 (m, 1H), 3.60 (s, 3H), 3.41 (s, 3H), 3.32-3.41 (m, 2H), 2.90-2.96 (m, 5H), 1.53 (d, J=6.9 Hz, 3H). MS (ESI) m/z=556 [M+H]+.

Example 53

N[5]-{2-[4-(2-Methanesulfonyl-ethyl)-phenylamino]-pyrimidin-4-yl}-1,N[5]-dimethyl-N[2]-(1-phenyl-ethyl)-1H-benzoimidazole-2,5-diamine hydrochloride

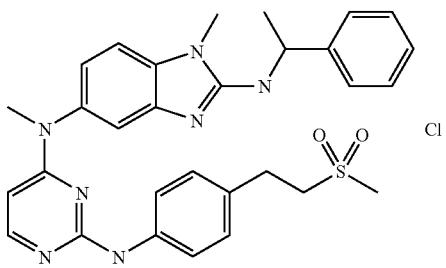

The title compound was prepared following the procedure of example two with N[5]-(2-Chloro-pyrimidin-4-yl)-1,N[5]-dimethyl-N[2]-(1-phenyl-ethyl)-1H-benzoimidazole-2,5-diamine (98 mg, 0.25 mmol) and 4-(2-methanesulfonyl-ethyl)-phenylamine (50 mg, 0.25 mmol) as a white solid (81 mg, 55%). $^1$H NMR (300 MHz, $d_6$-DMSO) δ 10.09 (s, 1H), 8.87 (s, 1H), 7.84 (d, J=6.9 Hz, 1H), 7.48-7.61 (m, 5H), 7.36-7.40 (m, 3H), 7.20-7.31 (m, 4H), 5.82 (d, J=5.7 Hz, 1H), 5.09 (m, 1H), 3.74 (s, 3H), 3.47 (s, 3H), 3.37-3.42 (M, 2H), 2.94-2.99 (M, 5H), 1.63 (d, J=6.6 Hz, 3H). MS (ESI) m/z=556 [M+H]+.

Example 54

2-Methyl-5-(4-{methyl-[1-methyl-2-(4-methyl-benzylamino)-1H-benzoimidazol-5-yl]-amino}-pyrimidin-2-ylamino)-benzenesulfonamide hydrochloride

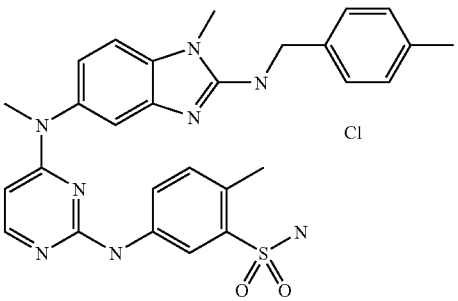

The title compound was prepared following the procedure of example one with N[5]-(2-Chloro-pyrimidin-4-yl)-1,N[5]-dimethyl-N[2]-(4-methyl-benzyl)-1H-benzoimidazole-2,5-diamine (98 mg, 0.25 mmol) and 5-amino-2-methyl-benzenesulfonamide (46 mg, 0.25 mmol) as a white solid (127 mg, 88%). $^1$H NMR (300 MHz, $d_6$-DMSO+NaHCO$_3$) δ 9.34 (s, 1H), 8.62 (s, 1H), 7.70-7.76 (m, 2H), 7.50 (br s, 1H), 7.09-7.30 (m, 9H), 6.85 (d, J=8.1 Hz, 1H), 5.60 (d, J=5.7 Hz, 1H), 4.55 (d, J=5.4 Hz, 1H), 3.58 (s, 3H), 3.44 (s, 3H), 2.50 (s, 3H), 2.26 (s, 3H). MS (ESI) m/z=543 [M+H]+.

Example 55

N⁵-[2-(4-Methanesulfonylmethyl-phenylamino)-pyrimidin-4-yl]-1,N⁵-dimethyl-N²-(4-methyl-benzyl)-1H-benzoimidazole-2,5-diamine hydrochloride

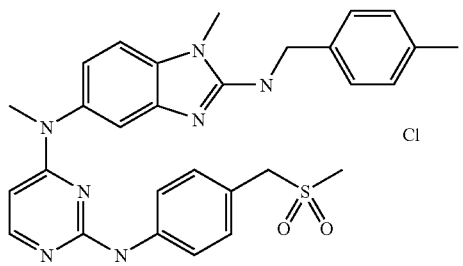

The title compound was prepared following the procedure of example one with N⁵-(2-Chloro-pyrimidin-4-yl)-1,N⁵-dimethyl-N²-(4-methyl-benzyl)-1H-benzoimidazole-2,5-diamine (98 mg, 0.25 mmol) and 4-[(methylsulfonyl)methyl]aniline (46 mg, 0.25 mmol) as a white solid (141 mg, 97%). ¹H NMR (300 MHz, d₆-DMSO+NaHCO₃) δ 9.21 (s, 1H), 7.76-7.79 (M, 3H), 7.50 (br s, 1H), 7.22-7.30 (m, 5H), 7.09-7.14 (M, 3H), 6.86 (d, J=8.4 Hz, 1H), 5.64 (d, J=6.0 Hz, 1H), 4.55 (d, J=5.4 Hz, 2H), 4.34 (s, 2H), 3.58 (s, 3H), 3.43 (s, 3H), 2.85 (s, 3H), 2.26 (s, 3H). MS (ESI) m/z=542 [M+H].

Example 56

N⁵-[2-(3-Methanesulfonylmethyl-phenylamino)-pyrimidin-4-yl]-1,N⁵-dimethyl-N²-(4-methyl-benzyl)-1H-benzoimidazole-2,5-diamine

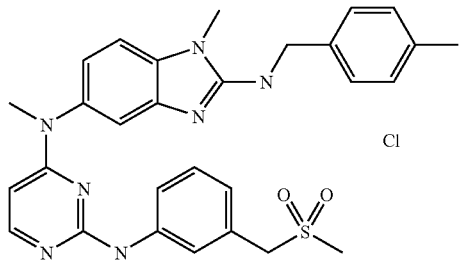

The title compound was prepared following the procedure of example one with N⁵-(2-Chloro-pyrimidin-4-yl)-1,N⁵-dimethyl-N²-(4-methyl-benzyl)-1H-benzoimidazole-2,5-diamine (98 mg, 0.25 mmol) and methanesulfonylmethyl-phenylamine (46 mg, 0.25 mmol) as a white solid (142 mg, 97%). ¹H NMR (300 MHz, d₆-DMSO+NaHCO₃) δ 9.18 (s, 1H), 7.89 (s, 1H), 7.77 (d, J=6.0 Hz, 1H), 7.68 (d, J=8.1 Hz, 1H), 7.36 (t, J=6.0 Hz, 1H), 7.19-7.29 (M, 4H), 7.07-7.13 (M, 3H), 6.91 (d, J=7.5 Hz, 1H), 6.83 (dd, J=8.1 and 1.8 Hz, 1H), 5.64 (d, J=6.0 Hz, 1H), 4.54 (d, J=5.4 Hz, 2H), 4.32-4.35 (m, 2H), 3.57 (s, 3H), 3.42 (S, 3H), 2.88 (s, 3H), 2.26 (s, 3H). MS (ESI) m/z=542 [M+H].

Example 57

N⁵-{2-[4-(2-Methanesulfonyl-ethyl)-phenylamino]-pyrimidin-4-yl}-1,N⁵-dimethyl-N²-(4-methyl-benzyl)-1H-benzoimidazole-2,5-diamine hydrochloride

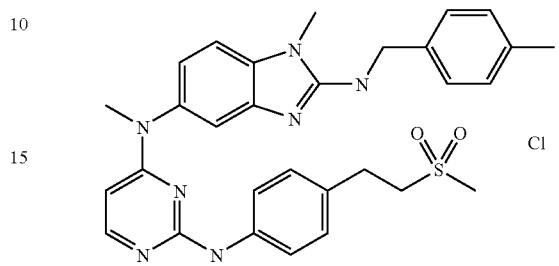

The title compound was prepared following the procedure of example one with N⁵-(2-Chloro-pyrimidin-4-yl)-1,N⁵-dimethyl-N²-(4-methyl-benzyl)-1H-benzoimidazole-2,5-diamine (98 mg, 0.25 mmol) and 4-(2-methanesulfonyl-ethyl)-phenylamine (50 mg, 0.25 mmol) as a white solid (104 mg, 70%). ¹H NMR (300 MHz, d₆-DMSO+NaHCO₃) δ 9.05 (s, 1H), 7.70-7.75 (m, 3H), 7.36 (t, J=5.7 Hz, 1H), 7.20-7.29 (m, 3H), 7.07-7.14 (M, 5H), 6.82 (dd, J=8.1 and 1.5 H. 1H), 5.60 (d, J=5.7 Hz, 1H), 4.54 (d, J=5.4 Hz, 2H), 3.57 (s, 3H), 3.42 (s, 3H), 3.30-3.37 (M, 2H), 2.90-2.95 (m, 5H), 2.26 (s, 3H). MS (ESI) m/z=556 [M+H].

Example 58

N⁵-{2-[3-(2-Methanesulfonyl-ethyl)-phenylamino]-pyrimidin-4-yl}-1,N⁵-dimethyl-N²-(4-methyl-benzyl)-1H-benzoimidazole-2,5-diamine hydrochloride

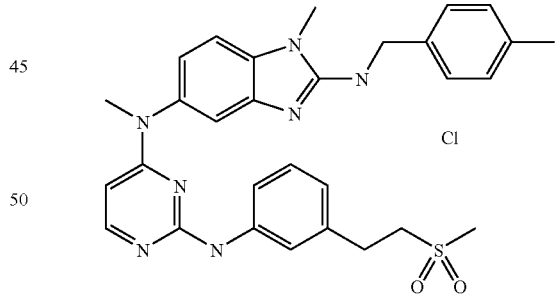

The title compound was prepared following the procedure of example one with N⁵-(2-Chloro-pyrimidin-4-yl)-1,N⁵-dimethyl-N²-(4-methyl-benzyl)-1H-benzoimidazole-2,5-diamine (98 mg, 0.25 mmol) and 3-(2-methanesulfonyl-ethyl)-phenylamine (50 mg, 0.25 mmol) as a white solid (126 mg, 85%). ¹H NMR (300 MHz, d₆-DMSO+NaHCO₃) δ 9.07 (s, 1H), 7.75-7.77 (m, 2H), 7.59 (d, J=8.1 Hz, 1H), 7.36 (t, J=6.0 Hz, 1H), 7.07-7.29 (M, 7H), 6.79-6.85 (M, 2H), 5.61 (d, J=5.7 Hz, 1H), 4.54 (d, J=5.7 Hz, 2H), 3.57 (s, 3H), 3.43 (s, 3H), 3.32-3.40 (m, 2H), 2.97 (s, 3H), 2.90-2.97 (M, 2H), 2.26 (s, 3H). MS (ESI) m/z=556 [M+H].

Example 59

$N^5$-{2-[4-(1-Methanesulfonyl-ethyl)-phenylamino]-pyrimidin-4-yl}-1,$N^5$-dimethyl-$N^2$-(4-methyl-benzyl)-1H-benzoimidazole-2,5-diamine hydrochloride

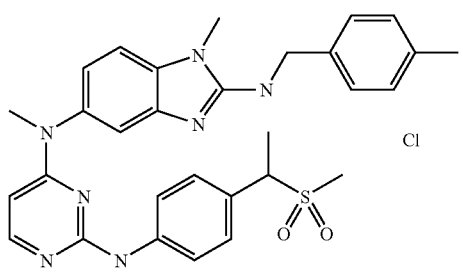

The title compound was prepared following the procedure of example one with $N^5$-(2-Chloro-pyrimidin-4-yl)-1,$N^5$-dimethyl-$N^2$-(4-methyl-benzyl)-1H-benzoimidazole-2,5-diamine (98 mg, 0.25 mmol) and 4-(1-methanesulfonyl-ethyl)-phenylamine (50 mg, 0.25 mmol) as a white solid (151 mg, 97%). $^1$H NMR (300 MHz, $d_6$-DMSO+NaHCO$_3$) δ 9.20 (s, 1H), 7.76-7.79 (M, 3H), 7.38 (m, 1H), 7.21-7.29 (m, 5H), 7.08-7.13 (M, 3H), 6.83 (d, J=8.1 Hz, 1H), 5.64 (d, J=6.0 Hz, 1H), 4.54 (d, J=5.1 Hz, 2H), 4.39 (m, 1H), 3.57 (s, 3H), 3.43 (S, 3H), 2.76 (s, 3H), 2.26 (s, 3H), 1.59 (d, J=7.2 Hz, 3H).

Example 60

(1-Methyl-5-{methyl-[2-(3-sulfamoyl-phenylamino)-pyrimidin-4-yl]-amino}-1H-benzoimidazol-2-yl)-phenyl-carbamic acid tert-butyl ester hydrochloride

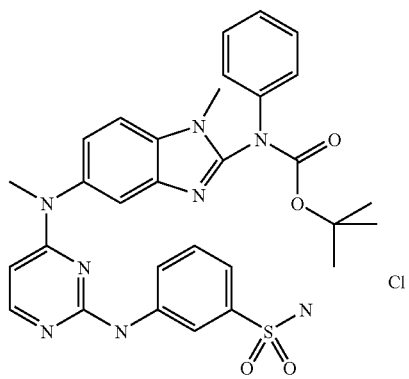

To a solution of {5-[(2-Chloro-pyrimidin-4-yl)-methyl-amino]-1-methyl-1H-benzoimidazol-2-yl}-phenyl-carbamic acid tert-butyl ester (100 mg, 0.22 mmol) and 3-amino-benzenesulfonamide (38 mg, 0.22 mmol) in ethanol was added HCl (1 drop, 1M in diethyl ether), and the reaction was heated to 70° C. After 20 h, the reaction was filtered to give the title compound as a white solid. $^1$H NMR (300 MHz, $d_6$-DMSO+NaHCO$_3$) δ 10.15 (s, 1H), 8.44 (s, 1H), 7.84 (d, J=6.6 Hz, 1H), 7.72 (d, J=8.4 Hz, 2H), 7.61 (s, 1H), 7.27-7.39 (m, 10H), 5.79 (d, J=5.1 Hz, 1H), 3.78 (s, 3H), 3.51 (s, 3H), 1.41 (s, 9H). MS (ESI) m/z=601 [M+H]$^+$.

Example 61

3-{4-[Methyl-(1-methyl-2-phenylamino-1H-benzoimidazol-5-yl)-amino]-pyrimidin-2-ylamino}-benzenesulfonamide trifluoroacetic acid

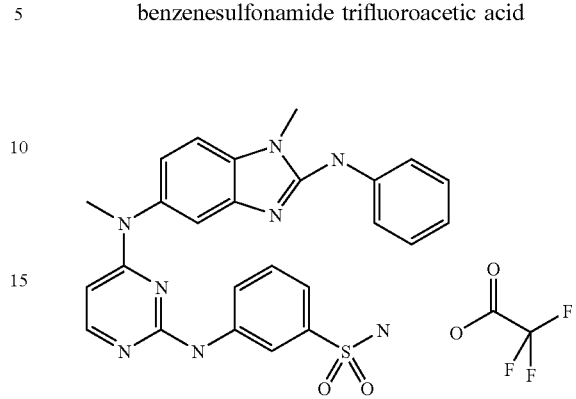

(1-Methyl-5-{methyl-[2-(3-sulfamoyl-phenylamino)-pyrimidin-4-yl]-amino}-1H-benzoimidazol-2-yl)-phenyl-carbamic acid tert-butyl ester hydrochloride was stirred in solution of 50% trifluoroacetic acid and methylene chloride and concentrated to give the title compound as a white solid. $^1$H NMR (300 MHz, $d_6$-DMSO+NaHCO$_3$) δ 10.32 (br s, 1H), 9.54 (br s, 1H), 8.49 (s, 1H), 7.86 (d, J=6.9 Hz, 1H), 7.73-7.78 (m, 3H), 7.47-7.54 (m, 3H), 7.34-7.41 (m, 4H), 7.06-7.14 (m, m 2H), 5.80 (d, J=6.6 Hz, 1H), 3.78 (s, 3H), 3.53 (s, 3H). MS (ESI) m/z=501 [M+H]$^+$.

Example 62

(1-Methyl-5-{methyl-[2-(4-methyl-3-sulfamoyl-phenylamino)-pyrimidin-4-yl]-amino}-1H-benzoimidazol-2-yl)-phenyl-carbamic acid tert-butyl ester hydrochloride

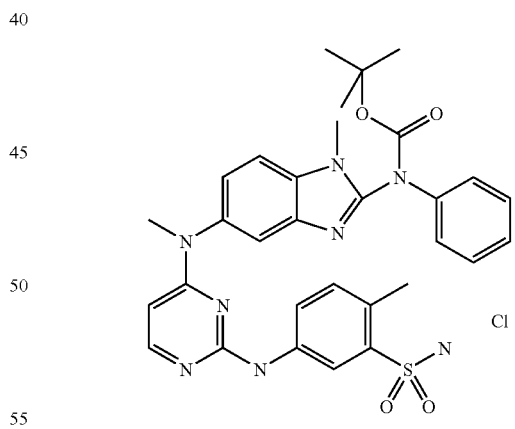

The title compound was prepared following the procedure of example 60 using {5-[(2-Chloro-pyrimidin-4-yl)-methyl-amino]-1-methyl-1H-benzoimidazol-2-yl}-phenyl-carbamic acid tert-butyl ester (100 mg, 0.22 mmol) and 5-amino-2-methyl-benzenesulfonamide (41 mg, 0.22 mmol) to give the desired product as a white solid. $^1$H NMR (300 MHz, $d_6$-DMSO+NaHCO$_3$) δ 9.48 (s, 1H), 8.54 (s, 1H), 7.79 (d, J=6.3 Hz, 1H), 7.66-7.71 (M, 2H), 7.56 (d, J=1.5 Hz, 1H), 7.38 (m, 4H), 7.23-7.29 (m, 4H), 7.12 (m, 1H), 5.68 (d, J=6.0 Hz, 1H), 3.78 (s, 3H), 3.48 (s, 3H), 2.49 (s, 3H), 1.42 (s, 9H). MS (ESI) m/z=615 [M+H]$^+$.

Example 63

N⁵-[2-(3-Methanesulfonyl-4-methyl-phenylamino)-pyrimidin-4-yl]-1,N⁵-dimethyl-N²-phenyl-1H-benzoimidazole-2,5-diamine trifluoroacetic acid

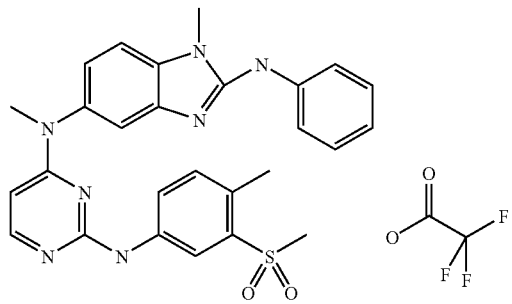

(1-Methyl-5-{methyl-[2-(4-methyl-3-sulfamoyl-phenylamino)-pyrimidin-4-yl]-amino}-1H-benzoimidazol-2-yl)-phenyl-carbamic acid tert-butyl ester hydrochloride was deprotected according to the procedure of example 61 to give the title compound as a white solid. ¹H NMR (300 MHz, d₆-DMSO+NaHCO₃) δ 10.52 (br s, 1H), 9.55 (br s, 1H), 8.45 (s, 1H), 7.83 (d, J=6.9 Hz, 1H), 7.76 (d, J=8.1 Hz, 2H), 7.64 (dd, J=8.1 and 1.5 Hz, 1H), 7.53 (d, J=8.7 Hz, 1H), 7.29-7.40 (m, 5H), 7.04-7.14 (m, 2H), 5.80 (d, J=6.3 Hz, 1H), 3.77 (s, 3H), 3.54 (s, 3H), 2.54 (s, 3H). MS (ESI) m/z=515 [M+H]⁺.

Example 64

N⁵-[2-(4-Methanesulfonylmethyl-phenylamino)-pyrimidin-4-yl]-1,N⁵-dimethyl-N²-phenyl-1H-benzoimidazole-2,5-diamine trifluoroacetic acid

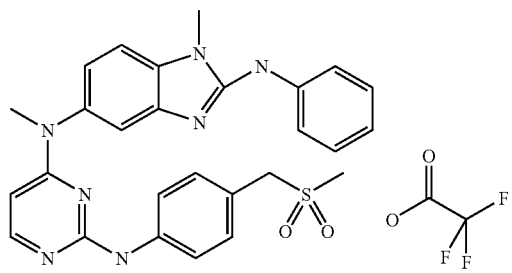

The title compound was prepared following the procedure of example 5 using {5-[(2-Chloro-pyrimidin-4-yl)-methyl-amino]-1-methyl-1H-benzoimidazol-2-yl}-phenyl-carbamic acid tert-butyl ester (100 mg, 0.22 mmol) and 4-[(methylsulfonyl)methyl]aniline (41 mg, 0.22 mmol) to give the desired product as a white solid (116 mg, 84%). ¹H NMR (300 MHz, d₆-DMSO+NaHCO₃) δ 10.55 (s, 1H), 9.83 (br s, 1H), 7.87 (d, J=6.9 Hz, 1H), 7.70 (d, J=8.1 Hz, 2H), 7.57-7.60 (m, 3H), 7.32-7.44 (M, 5H), 7.11-7.21 (M, 2H), 5.93 (br s, 1H), 4.43 (s, 2H), 3.79 (s, 3H), 3.53 (s, 3H), 2.87 (s, 3H). MS (ESI) m/z=514 [M+H]⁺.

Example 65

(4-{4-[Methyl-(1-methyl-2-phenylamino-1H-benzoimidazol-5-yl)-amino]-pyrimidin-2-ylamino}-phenyl)-methanesulfonamide trifluoroacetic acid The title compound was prepared following the procedure of example 5 using {5-[(2-Chloro-pyrimidin-4-yl)-methyl-amino]-1-methyl-1H-benzoimidazol-2-yl}-phenyl-carbamic acid tert-butyl ester (100 mg, 0.22 mmol) and (4-amino-phenyl)-methanesulfonamide (39 mg, 0.22 mmol) to give the desired product as a white solid (53 mg, 40%). ¹H NMR (300 MHz, d₆-DMSO+NaHCO₃) δ 9.47 (s, 1H), 9.10 (s, 1H), 7.73-7.87 (m, 5H), 7.41 (d, J=8.4 Hz, 1H), 7.30-7.36 (m, 3H), 7.23 (d, J=8.4 Hz, 1H), 6.95-7.03 (m, 2H), 6.78 (s, 2H), 5.71 (d, J=6.0 Hz, 1H), 4.18 (s, 2H), 3.76 (s, 3H), 3.49 (s, 3H). MS (ESI) m/z=515 [M+H]⁺.

Example 66

Methanesulfonic acid 4-{4-[methyl-(1-methyl-2-phenylamino-1H-benzoimidazol-5-yl)-amino]-pyrimidin-2-ylamino}-phenyl ester trifluoroacetic acid The title compound was prepared following the procedure of example 5 using {5-[(2-chloro-pyrimidin-4-yl)-methyl-amino]-1-methyl-1H-benzoimidazol-2-yl}-phenyl-carbamic acid tert-butyl ester (100 mg, 0.22 mmol) and sulfamic acid 4-amino-phenyl ester (39 mg, 0.22 mmol) to give the desired product as a white solid (86 mg, 65%). ¹H NMR (300 MHz, d₆-DMSO+NaHCO₃) δ 9.32 (s, 1H), 9.02 (s, 1H), 7.80-7.88 (m, 5H), 7.30-7.41 (M, 4H), 7.18 (d, J=8.7 Hz, 2H), 6.93-7.01 (m, 2H), 5.71 (d, J=6.0 Hz, 1H), 3.76 (s, 3H), 3.47 (s, 3H), 3.30 (s, 3H). MS (ESI) m/z=516 [M+H]⁺.

Example 67

3-(4-{[2-(4-Fluoro-phenylamino)-1-methyl-1H-benzoimidazol-5-yl]-methyl-amino}-pyrimidin-2-ylamino)-benzenesulfonamide trifluoroacetic acid

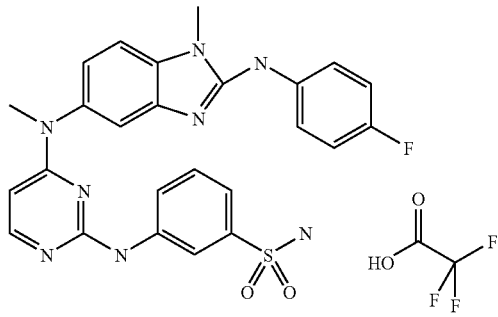

The title compound was prepared following the procedure of example 5 using {5-[(2-Chloro-pyrimidin-4-yl)-methyl-amino]-1-methyl-1H-benzoimidazol-2-yl}-(4-fluoro-phenyl)-carbamic acid tert-butyl ester (120 mg, 0.25 mmol) and 3-amino-benzenesulfonamide (43 mg, 0.25 mmol) to give the desired product as a white solid (76 mg, 48%). $^1$H NMR (300 MHz, $d_6$-DMSO+NaHCO$_3$) δ 9.80 (br s, 1H), 9.21 (br s, 1H), 8.57 (s, 1H), 7.76-7.89 (m, 4H), 7.38-7.45 (m, 3H), 7.29-7.33 (M, 3H), 7.13-7.22 (M, 2H), 7.01-7.05 (M, 1H), 5.71 (d, J=6.0 Hz, 1H), 3.75 (s, 3H), 3.50 (s, 3H). MS (ESI) m/z=519 [M+H]$^+$.

Example 68

5-(4-{[2-(4-Fluoro-phenylamino)-1-methyl-1H-benzoimidazol-5-yl]-methyl-amino}-pyrimidin-2-ylamino)-2-methyl-benzenesulfonamide trifluoroacetic acid

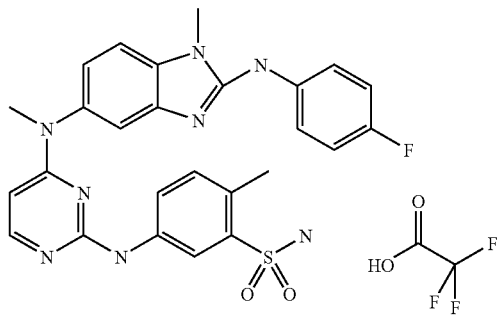

The title compound was prepared following the procedure of example 5 using {5-[(2-Chloro-pyrimidin-4-yl)-methyl-amino]-1-methyl-1H-benzoimidazol-2-yl}-(4-fluoro-phenyl)-carbamic acid tert-butyl ester (120 mg, 0.25 mmol) and 5-amino-2-methyl-benzenesulfonamide (46 mg, 0.25 mmol) to give the desired product as a white solid (150 mg, 93%). $^1$H NMR (300 MHz, $d_6$-DMSO+NaHCO$_3$) δ 10.28 (br s, 1H), 9.36 (br s, 1H), 8.51 (s, 1H), 7.80-7.87 (m, 3H), 7.66 (dd, J=8.4 and 2.1 Hz, 1H), 7.48 (d, J=8.4 Hz, 1H), 7.27-7.37 (m, 4H), 7.17-7.23 (M, 2H), 7.08 (dd, J=8.2 and 1.8 Hz, 1H), 5.76 (d, J=6.3 Hz, 1H), 3.76 (s, 3H), 2.54 (s, 3H). MS (ESI) m/z=533 [M+H]$^+$.

Example 69

$N^2$-(4-Fluoro-phenyl)-$N^5$-[2-(4-methanesulfonylmethyl-phenylamino)-pyrimidin-4-yl]-1,$N^5$-dimethyl-1H-benzoimidazole-2,5-diamine trifluoroacetic acid

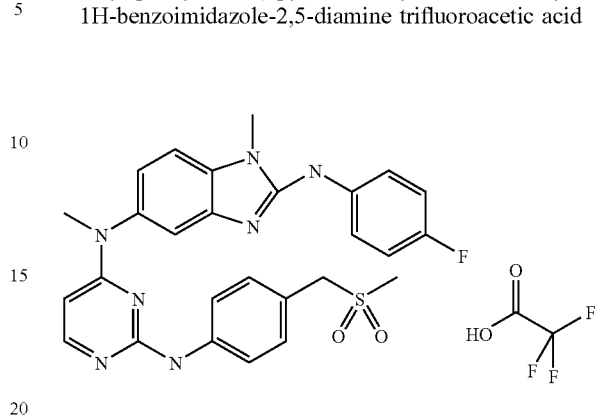

The title compound was prepared following the procedure of example 5 using {5-[(2-Chloro-pyrimidin-4-yl)-methyl-amino]-1-methyl-1H-benzoimidazol-2-yl}-(4-fluoro-phenyl)-carbamic acid tert-butyl ester (100 mg, 0.21 mmol) and 4-(methylsulfonyl)methyl]aniline (39 mg, 0.21 mmol) to give the desired product as a white solid (109 mg, 81%). $^1$H NMR (300 MHz, $d_6$-DMSO+NaHCO$_3$) δ 9.81 (br s, 1H), 9.23 (br s, 1H), 7.81-7.88 (M, 3H), 7.72 (d, J=8.1 Hz, 2H), 7.44 (d, J=8.4 Hz, 1H), 7.28-7.34 (m, 3H), 7.16-7.22 (M, 2H), 7.05 (dd, J=8.2 and 1.6 Hz, 1H), 5.78 (d, J=6.0 Hz, 1H), 4.39 (s, 2H), 3.75 (s, 3H), 3.50 (s, 3H), 2.86 (s, 3H). MS (ESI) m/z=532 [M+H]$^+$.

Example 70

[4-(4-{[2-(4-Fluoro-phenylamino)-1-methyl-1H-benzoimidazol-5-yl]-methyl-amino}-pyrimidin-2-ylamino)-phenyl]-methanesulfonamide trifluoroacetic acid

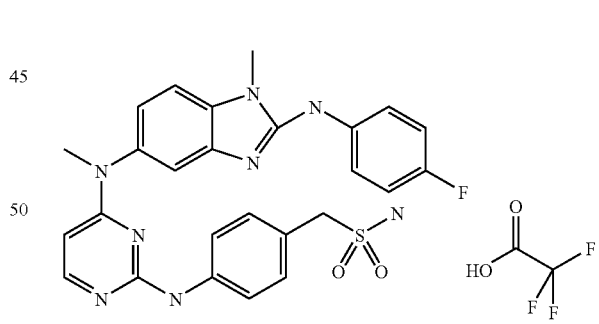

The title compound was prepared following the procedure of example 5 using {5-[(2-Chloro-pyrimidin-4-yl)-methyl-amino]-1-methyl-1H-benzoimidazol-2-yl}-(4-fluoro-phenyl)-carbamic acid tert-butyl ester (100 mg, 0.21 mmol) and (4-amino-phenyl)-methanesulfonamide (39 mg, 0.21 mmol) to give the desired product as a yellow solid (89 mg, 65%). $^1$H NMR (300 MHz, $d_6$-DMSO+NaHCO$_3$) δ 9.54 (br s, 1H), 9.16 (br s, 1H), 7.72-7.90 (m, 5H), 7.41 (d, J=8.4 Hz, 1H), 7.32 (s, 2H), 7.14-7.25 (M, 4H), 7.01 (d, J=8.1 Hz, 1H), 6.78 (s, 2H), 5.71 (d, J=6.0 Hz, 1H), 4.18 (s, 2H), 3.75 (s, 3H), 3.49 (s, 3H). MS (ESI) m/z=533 [M+H]$^+$.

Example 71

Methanesulfonic acid 4-(4-{[2-(4-fluoro-phenylamino)-1-methyl-1H-benzoimidazol-5-yl]-methylamino}-pyrimidin-2-ylamino)-phenyl ester trifluoroacetic acid

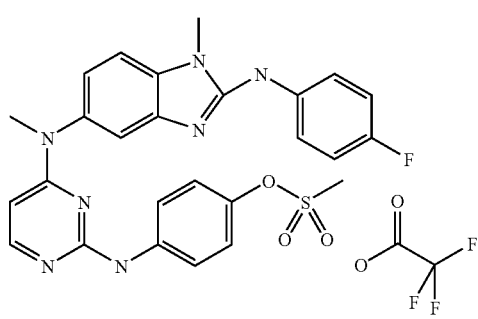

The title compound was prepared following the procedure of example 5 using {5-[(2-chloro-pyrimidin-4-yl)-methylamino]-1-methyl-1H-benzoimidazol-2-yl}-(4-fluoro-phenyl)-carbamic acid tert-butyl ester (96 mg, 0.20 mmol) and sulfamic acid 4-amino-phenyl ester (37 mg, 0.19 mmol) to give the desired product as a yellow solid (66 mg, 51%). $^1$H NMR (300 MHz, $d_6$-DMSO+NaHCO$_3$) δ 9.33 (s, 1H), 9.10 (s, 1H), 7.80-7.92 (M, 5H), 7.39 (d, J=8.4 Hz, 1H), 7.30 (s, 1H), 7.14-7.20 (M, 4H), 6.99 (dd, J=8.4 and 1.6 Hz, 1H), 5.71 (d, J=6.0 Hz, 2H), 3.74 (s, 3H), 3.47 (s, 3H), 2.50 (s, 3H). MS (ESI) m/z=534 [M+H]$^+$.

Example 72

Methanesulfonic acid 3-(4-{[2-(4-fluoro-phenylamino)-1-methyl-1H-benzoimidazol-5-yl]-methylamino}-pyrimidin-2-ylamino)-phenyl ester trifluoroacetic acid

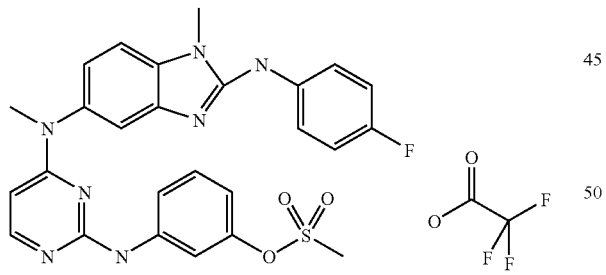

The title compound was prepared following the procedure of example 5 using {5-[(2-chloro-pyrimidin-4-yl)-methylamino]-1-methyl-1H-benzoimidazol-2-yl}-(4-fluoro-phenyl)-carbamic acid tert-butyl ester (92 mg, 0.19 mmol) and Methanesulfonic acid 3-amino-phenylester hydrochloride (42 mg, 0.19 mmol) to give the desired product as a yellow solid (73 mg, 59%). $^1$H NMR (300 MHz, $d_6$-DMSO+NaHCO$_3$) δ 9.46 (s, 1H), 9.10 (s, 1H), 8.00 (m, 1H), 7.87-7.91 (m, 2H), 7.82 (d, J=6.0 Hz, 1H), 7.64 (d, J=8.4 Hz, 1H), 7.40 (d, J=8.1 Hz, 1H), 7.27-7.33 (m, 2H), 7.14-7.20 (m, 2H), 7.00 (dd, J=8.2 and 1.6 Hz, 1H), 6.85 (dd, J=8.1 and 2.1 Hz, 1H), 5.71 (d, J=6.0 Hz, 1H), 3.74 (s, 3H), 3.47 (s, 3H), 3.34 (s, 3H). MS (ESI) m/z=534 [M+H]$^+$.

Example 73

$N^5$-[2-(4-Methanesulfonylmethyl-phenylamino)-pyrimidin-4-yl]-1,$N^5$-dimethyl-$N^2$-p-tolyl-1H-benzoimidazole-2,5-diamine trifluoroacetic acid

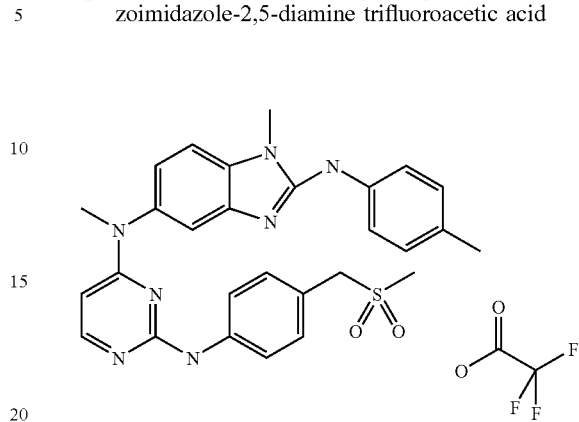

The title compound was prepared following the procedure of example 5 using {5-[(2-Chloro-pyrimidin-4-yl)-methylamino]-1-methyl-1H-benzoimidazol-2-yl}-p-tolyl-carbamic acid tert-butyl ester (66 mg, 0.14 mmol) and 4-(methylsulfonyl)methyl]aniline (26 mg, 0.14 mmol) to give the desired product as a white solid (32 mg, 36%). $^1$H NMR (300 MHz, $d_6$-DMSO+NaHCO$_3$) δ 9.26 (s, 1H), 8.92 (s, 1H), 7.73-7.81 (M, 5H), 7.37 (d, J=8.4 Hz, 1H), 7.29 (d, J=1.5 Hz, 1H), 7.24 (d, J=8.4 Hz, 2H), 7.13 (d, J=8.4 Hz, 2H), 6.98 (dd, J=8.4 and 1.5 Hz, 1H), 5.69 (d, J=6.0 Hz, 1H), 4.35 (s, 2H), 3.74 (s, 3H), 3.47 (s, 3H), 2.85 (s, 3H), 2.26 (s, 3H). MS (ESI) m/z=534 [M+H]$^+$.

Example 74

[4-(4-{[2-(4-tert-Butyl-phenylamino)-1-methyl-1H-benzoimidazol-5-yl]-methyl-amino}-pyrimidin-2-ylamino)-phenyl]-methanesulfonamide trifluoroacetic acid

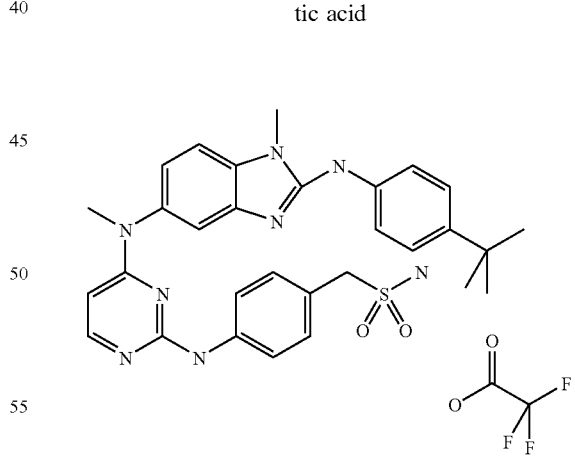

The title compound was prepared following the procedure of example 5 using (4-tert-Butyl-phenyl)-{5-[(2-chloro-pyrimidin-4-yl)-methyl-amino]-1-methyl-1H-benzoimidazol-2-yl}-carbamic acid tert-butyl ester (104 mg, 0.20 mmol) and (4-amino-phenyl)-methanesulfonamide (37 mg, 0.20 mmol) to give the desired product as a white solid. $^1$H NMR (300 MHz, $d_6$-DMSO+NaHCO$_3$) δ 9.42 (s, 1H), 9.04 (s, 1H), 7.80 (d, J=6.0 Hz, 1H), 7.71-7.75 (m, 4H), 7.33-7.41 (m, 3H), 7.29 (s, 1H), 7.22 (d, J=8.4 Hz, 2H), 7.00 (d, J=7.8

Hz, 1H), 6.77 (s, 2H), 5.70 (d, J=6.0 Hz, 1H), 4.17 (s, 2H), 3.74 (s, 3H), 3.48 (s, 3H), 1.28 (m, 9H). MS (ESI) m/z=571 [M+H]+.

Example 75

3-(4-{[2-(4-tert-Butyl-phenylamino)-1-methyl-1H-benzoimidazol-5-yl]-methyl-amino}-pyrimidin-2-ylamino)-benzenesulfonamide trifluoroacetic acid

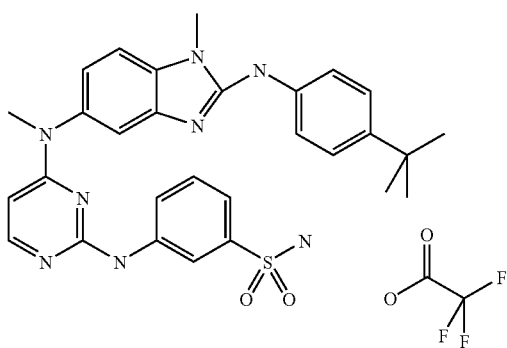

The title compound was prepared following the procedure of example 5 using (4-tert-Butyl-phenyl)-{5-[(2-chloro-pyrimidin-4-yl)-methyl-amino]-1-methyl-1H-benzoimidazol-2-yl}-carbamic acid tert-butyl ester (104 mg, 0.20 mmol) and 3-amino-benzenesulfonamide (34 mg, 0.20 mmol) to give the desired product as a white solid (85 mg, 63%). $^1$H NMR (300 MHz, d$_6$-DMSO+NaHCO$_3$) δ 9.57 (s, 1H), 9.01 (s, 1H), 8.60 (s, 1H), 7.72-7.82 (m, 4H), 7.33-7.42 (m, 5H), 7.26-7.29 (M, 3H), 6.98 (dd, J=8.4 and 1.5 Hz, 1H), 5.68 (d, J=6.0 Hz, 1H), 3.73 (s, 3H), 3.49 (s, 3H), 1.28 (s, 9H). MS (ESI) m/z=557 [M+H]+.

Example 76

5-(4-{[2-(4-tert-Butyl-phenylamino)-1-methyl-1H-benzoimidazol-5-yl]-methyl-amino}-pyrimidin-2-ylamino)-2-methyl-benzenesulfonamide hydrochloric acid

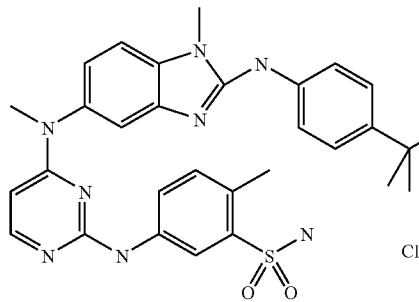

The title compound was prepared following the procedure of example 5 using (4-tert-Butyl-phenyl)-{5-[(2-chloro-pyrimidin-4-yl)-methyl-amino]-1-methyl-1H-benzoimidazol-2-yl}-carbamic acid tert-butyl ester (104 mg, 0.20 mmol) and 5-amino-2-methyl-benzenesulfonamide (37 mg, 0.20 mmol) to give the desired product as a white solid (66 mg, 48%). $^1$H NMR (300 MHz, d$_6$-DMSO+NaHCO$_3$) δ 9.35 (s, 1H), 8.96 (s, 1H), 8.62 (s, 1H), 7.71-7.78 (m, 4H), 7.32-7.38 (M, 3H), 7.27 (s, 1H), 7.17-7.23 (M, 3H), 6.96 (d, J=8.4 Hz, 1H), 5.63 (d, J=6.0 Hz, 1H), 3.74 (s, 3H), 3.48 (s, 3H), 2.50 (s, 3H), 1.28 (s, 9H). MS (ESI) m/z=571 [M+H]+.

Example 77

N$^2$-(4-tert-Butyl-phenyl)-N$^5$-[2-(4-methanesulfonyl-methyl-phenylamino)-pyrimidin-4-yl]-1,N$^5$-dimethyl-1H-benzoimidazole-2,5-diamine trifluoroacetic acid

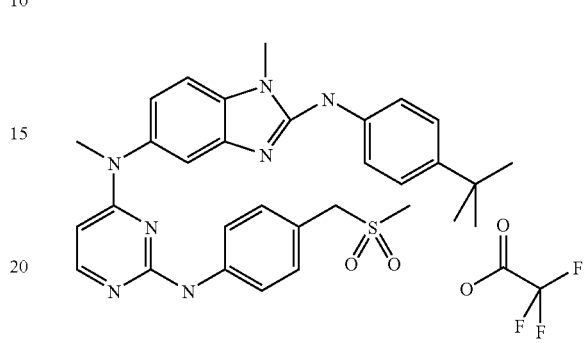

The title compound was prepared following the procedure of example 5 using (4-tert-Butyl-phenyl)-{5-[(2-chloro-pyrimidin-4-yl)-methyl-amino]-1-methyl-1H-benzoimidazol-2-yl}-carbamic acid tert-butyl ester (104 mg, 0.20 mmol) and 4-[(methylsulfonyl)methyl]aniline (37 mg, 0.20 mmol) to give the desired product as a white solid. $^1$H NMR (300 MHz, d$_6$-DMSO+NaHCO$_3$) δ 9.51 (s, 1H), 9.07 (s, 1H), 7.81 (d, J=6.3 Hz, 1H), 7.71-7.77 (m, 4H), 7.24-7.41 (m, 6H), 7.00 (dd, J=8.4 and 1.5 Hz, 1H), 5.72 (d, J=6.0 Hz, 1H), 4.36 (s, 2H), 3.74 (s, 3H), 3.48 (S, 3H), 2.85 (s, 3H), 1.28 (s, 9H). MS (ESI) m/z=570 [M+H]+.

Example 78

(5-{[2-(4-Methanesulfonylmethyl-phenylamino)-pyrimidin-4-y]-methyl-amino}-1-methyl-1H-benzoimidazol-2-yl)-(4-methoxy-phenyl)-carbamic acid tert-butyl ester

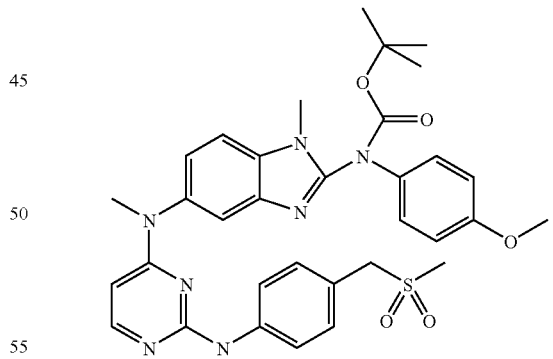

To a solution of {5-[(2-Chloro-pyrimidin-4-yl)-methyl-amino]-1-methyl-1H-benzoimidazol-2-yl}-(4-methoxy-phenyl)-carbamic acid tert-butyl ester (100 mg, 0.20 mmol) and 4-[(methylsulfonyl)methyl]aniline (37 mg, 0.20 mmol) was added cat HCl and the reaction was heated to 70 C overnight. The reaction was neutralized with solid NaHCO$_3$, filtered and concentrated. The crude material as purified through silica gel to give the title compound as a white solid. $^1$H NMR (300 MHz, d$_6$-DMSO) δ 9.24 (s, 1H), 7.82 (d, J=6.0 Hz, 1H), 7.65-7.74 (m, 3H), 7.54 (d, J=1.5 Hz, 1H), 7.35 (d, J=8.7 Hz, 2H), 7.24 (dd, J=8.7 and 1.5 Hz, 1H), 7.18 (d, J=8.4 Hz, 2H), 6.94 (d, J=9.0 Hz, 2H), 5.72 (d, J=5.7 Hz, 1H), 4.32 (s, 2H), 3.78 (s, 3H), 3.74 (s, 3H), 3.46 (s, 3H), 2.84 (s, 3H), 1.41 (s, 9H). MS (ESI) m/z=644 [M+H]⁺.

Example 79

N⁵-[2-(4-Methanesulfonylmethyl-phenylamino)-pyrimidin-4-yl]-N²-(4-methoxy-phenyl)-1,N⁵-dimethyl-1H-benzoimidazole-2,5-diamine

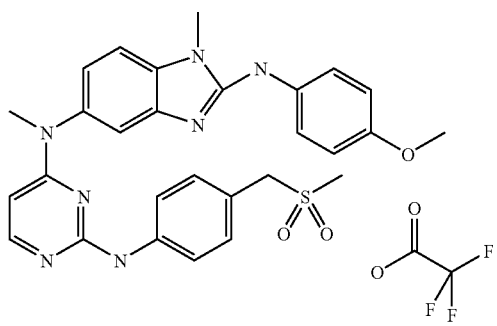

(5-{[2-(4-Methanesulfonylmethyl-phenylamino)-pyrimidin-4-yl]-methyl-amino}-1-methyl-1H-benzoimidazol-2-yl)-(4-methoxy-phenyl)-carbamic acid tert-butyl ester was deprotected according to the procedure of example 61 to give the title compound as a white solid. ¹H NMR (300 MHz, d₆-DMSO+NaHCO₃) δ 9.48 (s, 1H), 9.12 (s, 1H), 7.81 (d, J=6.0 Hz, 1H), 7.69-7.76 (m, 4H), 7.41 (d, J=8.1 Hz, 1H), 7.24-7.27 (m, 3H), 7.02 (d, J=8.1 Hz, 1H), 6.95 (d, J=9.0 Hz, 2H), 5.73 (d, J=6.0 Hz, 1H), 4.36 (s, 2H), 3.74 (s, 3H), 3.73 (s, 3H), 3.47 (s, 3H), 2.86 (s, 3H). MS (ESI) m/z=544 [M+H]⁺.

Example 80

(4-Methoxy-phenyl)-(1-methyl-5-{methyl-[2-(4-sulfamoylmethyl-phenylamino)-pyrimidin-4-yl]-amino}-1H-benzoimidazol-2-yl)-carbamic acid tert-butyl ester

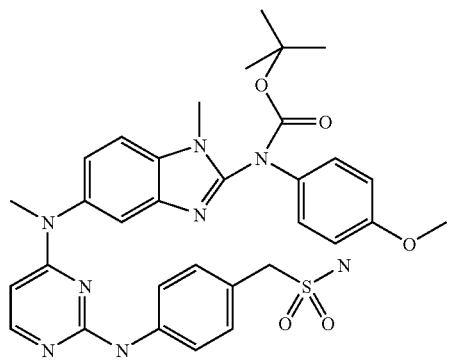

The title compound was prepared following the procedure of example 78 using {5-[(2-Chloro-pyrimidin-4-yl)-methyl-amino]-1-methyl-1H-benzoimidazol-2-yl}-(4-methoxy-phenyl)-carbamic acid tert-butyl ester (100 mg, 0.20 mmol) and (4-amino-phenyl)-methanesulfonamide (37 mg, 0.20 mmol) to give the desired product as a white solid. ¹H NMR (300 MHz, d₆-DMSO) δ 9.20 (s, 1H), 7.81 (d, J=6.0 Hz, 1H), 7.65-7.73 (m, 3H), 7.54 (d, J=1.8 Hz, 1H), 7.34 (d, J=8.7 Hz, 2H), 7.24 (dd, J=8.4 and 1.8 Hz, 1H), 7.16 (d, J=8.4 Hz, 2H), 6.97 (d, J=9.0 Hz, 2H), 6.75 (s, 2H), 5.69 (d, J=6.0 Hz, 1H), 4.14 (s, 2H), 3.78 (s, 3H), 3.74 (s, 3H), 3.46 (s, 3H), 1.41 (s, 9H). MS (ESI) m/z=645 [M+H]⁺.

Example 81

[4-(4-{[2-(4-Methoxy-phenylamino)-1-methyl-1H-benzoimidazol-5-yl]-methyl-amino}-pyrimidin-2-ylamino)-phenyl]-methanesulfonamide trifluoroacetic acid

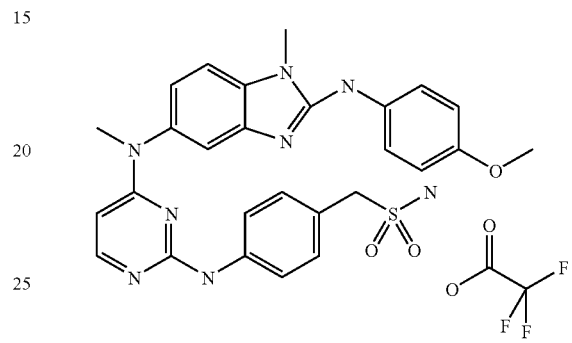

(4-Methoxy-phenyl)-(1-methyl-5-{methyl-[2-(4-sulfamoylmethyl-phenylamino)-pyrimidin-4-yl]-amino}-1H-benzoimidazol-2-yl)-carbamic acid tert-butyl ester was deprotected according to the procedure of example 78 to give the title compound as a white solid. ¹H NMR (300 MHz, d₆-DMSO+NaHCO₃) δ 9.70 (s, 1H), 9.22 (s, 1H), 7.82 (d, J=6.3 Hz, 1H), 7.68-7.71 (m, 4H), 7.43 (d, J=8.1 Hz, 1H), 7.22-7.33 (m, 3H), 7.04 (d, J=8.1 Hz, 1H), 6.95 (d, J=8.7 Hz, 2H), 6.79 (s, 2H), 5.74 (d, J=5.4 Hz, 1H), 4.18 (s, 2H), 3.74 (s, 6H), 3.48 (s, 3H). MS (ESI) m/z=545 [M+H]⁺.

Example 82

(5-{[2-(3-Methanesulfonylmethyl-phenylamino)-pyrimidin-4-yl]-methyl-amino}-1-methyl-1H-benzoimidazol-2-yl)-(4-methoxy-phenyl)-carbamic acid tert-butyl ester

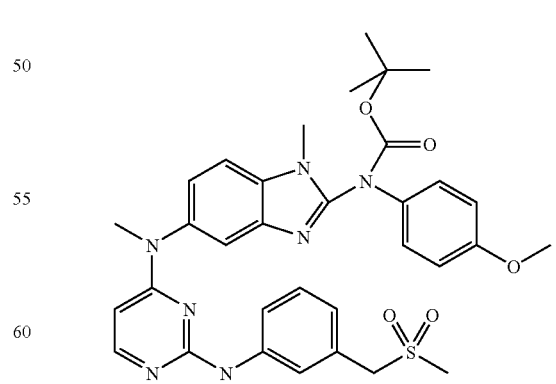

The title compound was prepared following the procedure of example 78 using {5-[(2-Chloro-pyrimidin-4-yl)-methyl-amino]-1-methyl-1H-benzoimidazol-2-yl}-(4-methoxy-phenyl)-carbamic acid tert-butyl ester (100 mg, 0.20 mmol)

and 3-methanesulfonylmethyl-phenylamine (37 mg, 0.20 mmol) to give the desired product as a white solid. $^1$H NMR (300 MHz, d$_6$-DMSO) δ 9.44 (s, 1H), 7.80-7.82 (m, 2H), 7.63-7.70 (M, 2H), 7.56 (d, J=1.5 Hz, 1H), 7.34 (d, J=8.7 Hz, 2H), 7.25 (dd, J=8.6 and 1.2 Hz, 1H), 7.18 (t, J=7.5 Hz, 1H), 6.94 (d, J=9.0 Hz, 2H), 5.75 (d, J=6.0 Hz, 1H), 4.34 (s, 2H), 3.79 (s, 3H), 3.74 (s, 3H), 3.47 (s, 3H), 2.89 (s, 3H), 1.41 (s, 9H). MS (ESI) m/z=644 [M+H]$^+$.

Example 83

N$^5$-[2-(3-Methanesulfonylmethyl-phenylamino)-pyrimidin-4-yl]-N$^2$-(4-methoxy-phenyl)-1,N$^5$-dimethyl-1H-benzoimidazole-2,5-diamine trifluoroacetic acid

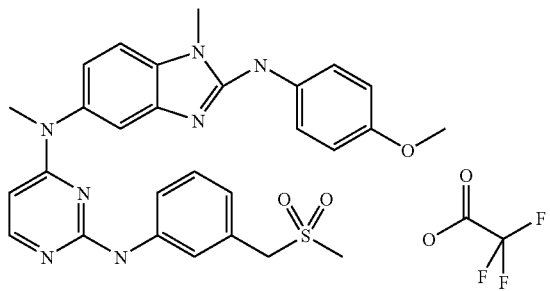

(5-{[2-(3-Methanesulfonylmethyl-phenylamino)-pyrimidin-4-yl]-methyl-amino}-1-methyl-1H-benzoimidazol-2-yl)-(4-methoxy-phenyl)-carbamic acid tert-butyl ester was deprotected according to the procedure of example 61 to give the title compound as a white solid. $^1$H NMR (300 MHz, d$_6$-DMSO+NaHCO$_3$) δ 9.36 (s, 1H), 8.94 (s, 1H), 7.87 (s, 1H), 7.80 (d, J=6.0 Hz, 1H), 7.67-7.75 (m, 3H), 7.21-7.26 (m, 2H), 7.37 (d, J=8.4 Hz, 1H), 6.91-6.99 (m, 4H), 5.70 (d, J=6.0 Hz, 1H), 4.34 (s, 2H), 3.73 (s, 3H), 3.72 (s, 3H), 3.46 (s, 3H), 2.89 (s, 3H). MS (ESI) m/z=544 [M+H]$^+$.

Example 84

[5-({2-[4-(1-Methanesulfonyl-ethyl)-phenylamino]-pyrimidin-4-yl}-methyl-amino)-1-methyl-1H-benzoimidazol-2-yl]-(4-methoxy-phenyl)-carbamic acid tert-butyl ester

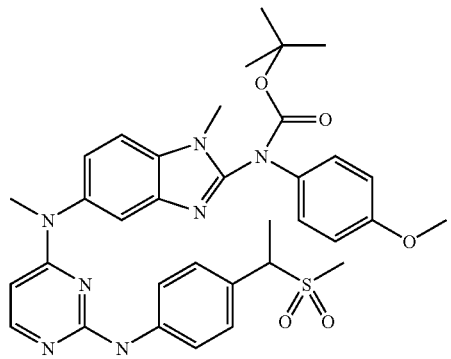

The title compound was prepared following the procedure of example 78 using {5-[(2-Chloro-pyrimidin-4-yl)-methyl-amino]-1-methyl-1H-benzoimidazol-2-yl}-(4-methoxy-phenyl)-carbamic acid tert-butyl ester (100 mg, 0.20 mmol) 4-(1-methanesulfonyl-ethyl)-phenylamine (40 mg, 0.20 mmol) to give the desired product as a white solid. $^1$H NMR (300 MHz, d$_6$-DMSO) δ 9.25 (s, 1H), 7.82 (d, J=6.0 Hz, 1H), 7.65-7.74 (M, 3H), 7.54 (s, 1H), 7.35 (d, J=8.7 Hz, 2H), 7.21-7.25 (m, 3H), 6.94 (d, J=9.0 Hz, 2H), 5.72 (d, J=6.0 Hz, 1H), 4.37 (m, 1H), 3.78 (s, 3H), 3.74 (s, 3H), 3.46 (s, 3H), 2.75 (s, 3H), 1.58 (d, J=7.2 Hz, 3H), 1.41 (s, 9H). MS (ESI) m/z=658 [M+H]$^+$.

Example 85

N$^5$-{2-[4-(1-Methanesulfonyl-ethyl)-phenylamino]-pyrimidin-4-yl}-N$^2$-(4-methoxy-phenyl)-1,N$^5$-dimethyl-1H-benzoimidazole-2,5-diamine trifluoroacetic acid

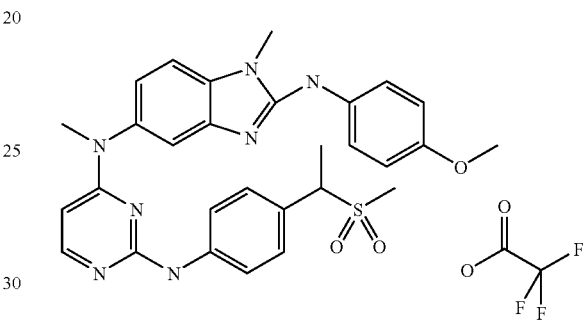

[5-({2-[4-(1-Methanesulfonyl-ethyl)-phenylamino]-pyrimidin-4-yl}-methyl-amino)-1-methyl-1H-benzoimidazol-2-yl]-(4-methoxy-phenyl)-carbamic acid tert-butyl ester was deprotected according to the procedure of example 61 to give the title compound as a white solid. $^1$H NMR (300 MHz, d$_6$-DMSO+NaHCO$_3$) δ 9.38 (s, 1H), 9.00 (s, 1H), 7.81 (d, J=6.0 Hz, 1H), 7.72-7.74 (m, 4H), 7.38 (d, J=8.4 Hz, 1H), 7.26-7.28 (m, 3H), 6.92-7.00 (m, 3H), 5.72 (d, J=5.7 Hz, 1H), 4.40 (m, 1H), 3.73 (s, 6H), 3.47 (s, 3H), 2.76 (s, 3H), 1.59 (d, J=7.2 Hz, 3H). MS (ESI) m/z=558 [M+H]$^+$.

Example 86

N$^5$-{2-[3-(1-Methanesulfonyl-ethyl)-phenylamino]-pyrimidin-4-yl}-N$^2$-(4-methoxy-phenyl)-1,N$^5$-dimethyl-1H-benzoimidazole-2,5-diamine trifluoroacetic acid

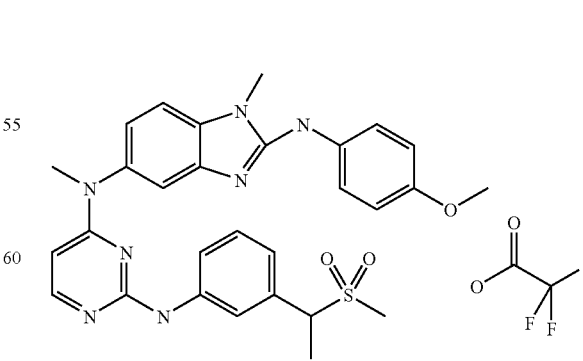

The title compound was prepared following the procedure of example 5 using {5-[(2-Chloro-pyrimidin-4-yl)-methylamino]-1-methyl-1H-benzoimidazol-2-yl}-(4-methoxy-phenyl)-carbamic acid tert-butyl ester (100 mg, 0.20 mmol) and 3-(1-Methanesulfonyl-ethyl)-phenylamine hydrochloride (47 mg, 0.20 mmol) to give the desired product as a white solid. $^1$H NMR (300 MHz, d$_6$-DMSO+NaHCO$_3$) δ9.23 (s, 1H), 8.86 (s, 1H), 7.96 (s, 1H), 7.80 (d, J=6.0 Hz, 1H), 7.75 (d, J=8.7 Hz, 2H), 7.64 (d, J=8.1 Hz, 1H), 7.36 (d, J=8.4 Hz, 1H), 7.19-7.26 (M, 2H), 6.90-6.98 (m, 4H), 5.69 (d, J=5.7 Hz, 1H), 4.28 (m, 1H), 3.73 (s, 3H), 3.72 (s, 3H), 3.47 (s, 3H), 2.77 (s, 3H), 1.59 (d, J=7.2 Hz, 3H). MS (ESI) m/z=558 [M+H]$^+$.

Example 87

3-{4-[(2-Isopropylamino-1-methyl-1H-benzoimidazol-5-yl)-methyl-amino]-pyrimidin-2-ylamino}-benzenesulfonamide hydrochloride

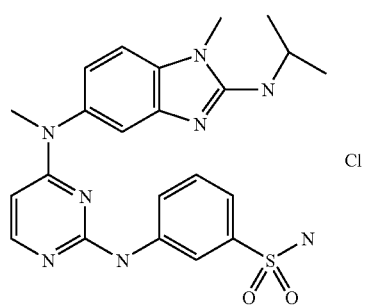

The title compound was prepared following the procedure of example 1 with N$^5$-(2-chloropyrimidin-4-yl)-N$^2$-isopropyl-N$^5$,1-dimethyl-1H-benzimidazole-2,5-diamine (83 mg, 0.25 mmol) and 3-amino-benzenesulfonamide (43 mg, 0.25 mmol) as a white solid (59 mg, 47%). $^1$H NMR (300 MHz, d$_6$-DMSO) δ 11.03 (s, 1H), 8.94 (d, J=8.1 Hz, 1H), 8.35 (s, 1H), 7.97 (d, J=7.2 Hz, 1H), 7.71 (d, J=7.2 Hz, 1H), 7.66 (d, J=8.4 Hz, 1H), 7.48-7.57 (m, 3H), 7.40 (s, 1H), 7.33 (dd, J=8.4 and 1.5 Hz, 1H), 5.90 (s, 1H), 4.12 (m, 1H), 3.70 (s, 3H), 3.54 (s, 3H), 1.33 (d, J=6.3 Hz, 6H) ppm. MS (ESI) m/z=467 [M+H]$^+$.

Example 88

2-Chloro-5-{4-[(2-isopropylamino-1-methyl-1H-benzoimidazol-5-yl)-methyl-amino]-pyrimidin-2-ylamino}-benzenesulfonamide

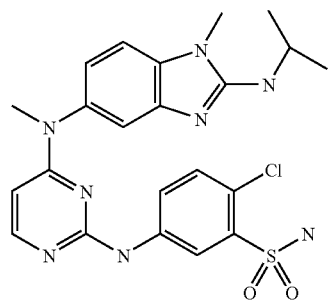

The title compound was prepared following the procedure of example 1 with N$^5$-(2-chloropyrimidin-4-yl)-N$^2$-isopropyl-N$^5$,1-dimethyl-1H-benzimidazole-2,5-diamine (83 mg, 0.25 mmol) and 5-amino-2-chloro-benzenesulfonamide (52 mg, 0.25 mmol) as a white solid (74 mg, 59%). $^1$H NMR (300 MHz, d$_6$-DMSO) δ 9.58 (s, 1H), 8.78 (s, 1H), 7.83 (dd, J=8.7 and 2.1 Hz, 1H), 7.78 (d, J=5.7 Hz, 1H), 7.55 (br s, 1H), 7.40 (d, J=8.7 Hz, 1H), 7.19 (d, J=8.4 Hz, 1H), 7.08 (s, 12H), 6.80 (d, J=8.1 Hz, 1H), 6.61 (d, J=7.5 Hz, 1H), 5.64 (d, J=6.0 Hz, 1H), 4.04 (m, 1H), 3.52 (s, 3H), 3.45 (s, 3H), 1.23 (d, J=6.3 Hz, 6H) ppm. MS (ESI) m/z=501 [M+H]$^+$.

Example 89

5-{4-[(2-Isopropylamino-1-methyl-1H-benzoimidazol-5-yl)-methyl-amino]-pyrimidin-2-ylamino}-2-methyl-benzenesulfonamide hydrochloride

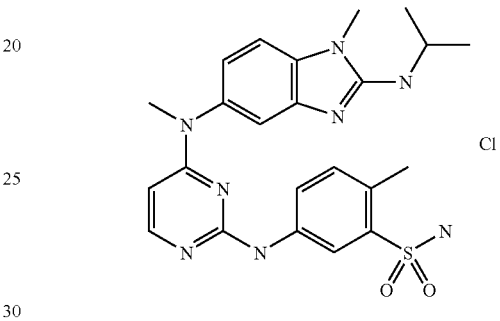

The title compound was prepared following the procedure of example 1 with N$^5$-(2-chloropyrimidin-4-yl)-N$^2$-isopropyl-N$^5$,1-dimethyl-1H-benzimidazole-2,5-diamine (60 mg, 0.18 mmol) and 5-amino-2-methyl-benzenesulfonamide (34 mg, 0.18 mmol) as a white solid (42 mg, 45%). $^1$H NMR (300 MHz, d$_6$-DMSO) δ 9.85 (s, 1H), 8.67 (s, 1H), 8.51 (s, 1H), 7.87 (d, J=6.3 Hz, 1H), 7.67 (d, J=8.1 Hz, 1H), 7.57 (d, J=8.4 Hz, 1H), 7.37 (s, 1H), 7.18-7.27 (m, 3H), 5.73 (d, J=6.0 Hz, 1H), 4.11 (m, 1H), 3.68 (s, 3H), 3.48 (s, 3H), 1.32 (d, J=6.3 Hz 6H) ppm. MS (ESI) m/z=481 [M+H]$^+$.

Example 90

2-(4-{4-[(2-Isopropylamino-1-methyl-1H-benzoimidazol-5-yl)-methyl-amino]-pyrimidin-2-ylamino}-phenyl)-ethanesulfonic acid methylamide hydrochloride

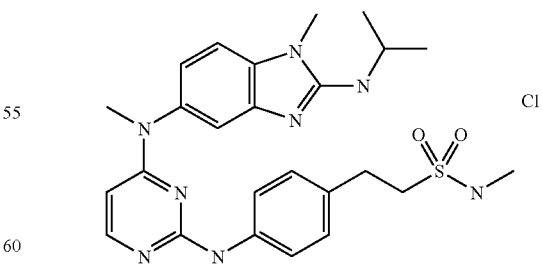

The title compound was prepared following the procedure of example 1 with N$^5$-(2-chloropyrimidin-4-yl)-N$^2$-isopropyl-N$^5$,1-dimethyl-1H-benzimidazole-2,5-diamine (83 mg, 0.25 mmol) and 2-(4-amino-phenyl)-ethanesulfonic acid methylamide (54 mg, 0.25 mmol) as a white solid (71 mg, 52%). ¹H NMR (300 MHz, d₆-DMSO) δ 9.05 (s, 1H), 7.68-7.76 (M, 3H), 7.19 (d, J=8.4 Hz, 1H), 7.08-7.13 (M, 3H), 6.96 (q, J=5.1 Hz, 1H), 6.81 (dd, J=8.1 and 1.8 Hz, 1H), 6.53 (d, J=6.9 Hz, 1H), 5.60 (d, J=5.7 Hz, 1H), 4.04 (m, 1H), 3.51 (s, 3H), 3.42 (s, 3H), 3.21-3.30 (m, 2H), 2.83-2.88 (m, 2H), 2.59 (d, J=5.1 Hz, 3H), 1.23 (d, J=6.6 Hz, 6H) ppm. MS (ESI) m/z=509 [M+H]⁺.

Example 91

Methanesulfonic acid 4-{4-[(2-isopropylamino-1-methyl-1H-benzoimidazol-5-yl)-methyl-amino]-pyrimidin-2-ylamino}-phenyl ester hydrochloride

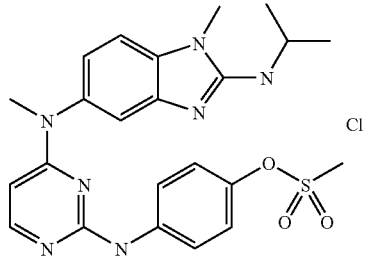

The title compound was prepared following the procedure of example 1 with N⁵-(2-chloropyrimidin-4-yl)-N²-isopropyl-N⁵,1-dimethyl-1H-benzimidazole-2,5-diamine (83 mg, 0.25 mmol) and methanesulfonic acid 4-amino-phenyl ester (47 mg, 0.25 mmol) as a white solid (45 mg, 35%). ¹H NMR (300 MHz, d₆-DMSO) δ 9.30 (s, 1H), 7.78-7.86 (m, 3H), 7.17-7.21 (m, 3H), 7.09 (d, J=1.5 Hz, 1H), 6.82 (dd, J=8.1 and 1.8 Hz, 1H), 6.51 (d, J=7.5 Hz, 1H), 5.67 (d, J=6.0 Hz, 1H), 4.05 (m, 1H), 3.52 (s, 3H), 3.43 (s, 3H), 3.31 (s, 3H), 1.24 (d, J=6.6 Hz, 6H) ppm. MS (ESI) m/z=482 [M+H]⁺.

Example 92

Methanesulfonic acid 3-{4-[(2-isopropylamino-1-methyl-1H-benzoimidazol-5-yl)-ethyl-amino]-pyrimidin-2-ylamino}-phenyl ester hydrochloride

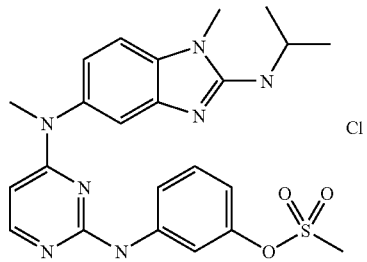

The title compound was prepared following the procedure of example 1 with N⁵-(2-chloropyrimidin-4-yl)-N²-isopropyl-N⁵,1-dimethyl-1H-benzimidazole-2,5-diamine (83 mg, 0.25 mmol) and methanesulfonic acid 3-amino-phenyl ester hydrochloride (56 mg, 0.25 mmol) as a white solid (55 mg, 43%). ¹H NMR (300 MHz, d₆-DMSO) δ 9.41 (s, 1H), 8.02 (s, 1H), 7.79 (d, J=6.0 Hz, 1H), 7.65 (d, J=8.4 Hz, 1H), 7.30 (t, J=8.2 Hz, 1H), 7.20 (d, J=8.1 Hz, 1H), 7.10 (s, 1H), 6.81-6.86 (m, 2H), 6.55 (d, J=7.8 Hz, 1H), 5.46 (d, J=5.7 Hz, 1H), 4.05 (m, 1H), 3.52 (s, 3H), 3.44 (s, 3H), 3.34 (s under H₂O, 3H) ppm. MS (ESI) m/z=482 [M+H]⁺.

Example 93

N²-Isopropyl-N⁵-[2-(3-methanesulfonylmethyl-phenylamino)-pyrimidin-4-yl]-1,N⁵-dimethyl-1H-benzoimidazole-2,5-diamine hydrochloride

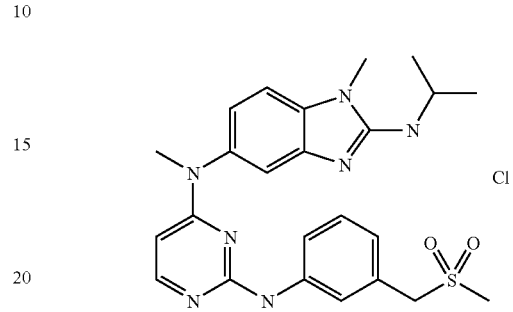

The title compound was prepared following the procedure of example 1 with N⁵-(2-chloropyrimidin-4-yl)-N²-isopropyl-N⁵,1-dimethyl-1H-benzimidazole-2,5-diamine (83 mg, 0.25 mmol) and 3-Methanesulfonylmethyl-phenylamine (46 mg, 0.25 mmol) as a white solid (69 mg, 53%). ¹H NMR (300 MHz, d₆-DMSO) δ 9.20 (s, 1H), 7.90 (s, 1H), 7.77 (d, J=6.0 Hz, 1H), 7.69 (d, J=8.1 Hz, 1H), 7.18-7.25 (m, 2H), 7.09 (d, J=1.8 Hz, 1H), 6.91 (d, J=7.5 Hz, 1H), 6.82 (dd, J=8.1 and 1.8 Hz, 1H), 6.49 (d, J=7.5 Hz, 1H), 5.64 (d, J=6.0 Hz, 1H), 4.34 (s, 2H), 4.03 (m, 1H), 3.51 (s, 3H), 3.43 (s, 3H), 2.89 (s, 3H), 1.24 (d, J=6.6 Hz, 6H) ppm. MS (ESI) m/z=480 [M+H]⁺.

Example 94

3-[4-(1-Methyl-2-phenethylamino-1H-benzoimidazol-5-ylamino)-pyrimidin-2-ylamino]-benzenesulfonamide hydrochloride

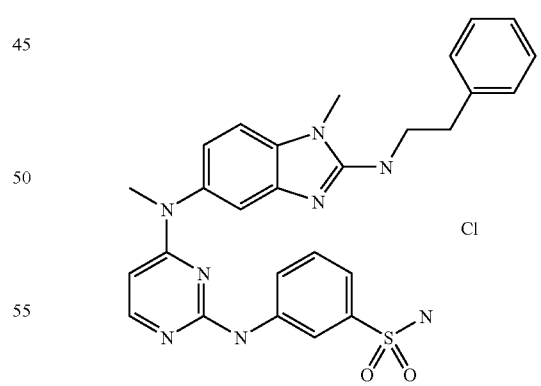

The title compound was prepared following the procedure of example 1 with N⁵-(2-Chloro-pyrimidin-4-yl)-1,N⁵-dimethyl-N²-phenethyl-1H-benzoimidazole-2,5-diamine (98 mg, 0.25 mmol) and 3-amino-benzenesulfonamide (43 mg, 0.25 mmol) as a white solid (95 mg, 67%). ¹H NMR (400 MHz, d₆-DMSO) δ 9.83 (br s, 1H), 9.04 (br s, 1H), 8.49 (s, 1H), 7.87 (d, J=6.0 Hz, 1H), 7.72-7.74 (m, 1H), 7.56 (d, J=8.4 Hz, 1H), 7.18-7.40 (m, 11H), 5.72 (d, J=5.6 Hz, 1H), 3.65-3.71 (m, 2H), 3.64 (s, 3H), 3.46 (s, 3H), 2.96 (m, 2H) ppm. MS (ESI) m/z=529 [M+H]⁺.

Example 95

2-Methyl-5-{4-[methyl-(1-methyl-2-phenethylamino-1H-benzoimidazol-5-yl)-amino]-pyrimidin-2-ylamino}-benzenesulfonamide hydrochloride

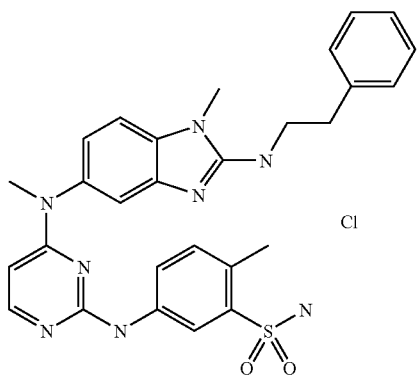

The title compound was prepared following the procedure of example 1 with $N^5$-(2-Chloro-pyrimidin-4-yl)-1,$N^5$-dimethyl-$N^2$-phenethyl-1H-benzoimidazole-2,5-diamine (98 mg, 0.25 mmol) and 5-amino-2-methyl-benzenesulfonamide (46 mg, 0.25 mmol) as a white solid (88 mg, 61%). ¹H NMR (400 MHz, d₆-DMSO) δ 10.25 (br s, 1H), 9.22 (br s, 1H), 8.44 (s, 1H), 7.87 (d, J=6.8 Hz, 1H), 7.58-7.64 (m, 2H), 7.18-7.41 (m, 10H), 5.75 (d, J=5.6 Hz, 1H), 3.68-3.73 (m, 2H), 3.66 (s, 3H), 3.48 (s, 3H), 2.97 (m, 2H), 2.50 (s, 3H) ppm. MS (ESI) m/z=543 [M+H]⁺.

Example 96

(4-{4-[Methyl-(1-methyl-2-phenethylamino-1H-benzoimidazol-5-yl)-amino]-pyrimidin-2-ylamino}-phenyl)-methanesulfonamide hydrochloride

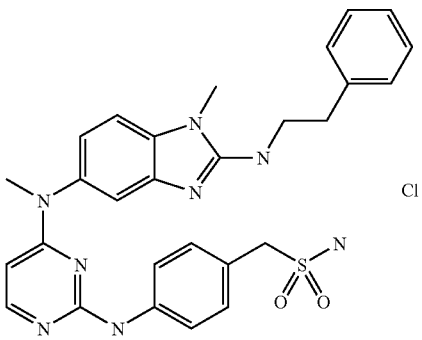

The title compound was prepared following the procedure of example 1 with $N^5$-(2-Chloro-pyrimidin-4-yl)-1,$N^5$-dimethyl-$N^2$-phenethyl-1H-benzoimidazole-2,5-diamine (98 mg, 0.25 mmol) and (4-amino-phenyl)-methanesulfonamide (46 mg, 0.25 mmol) as a white solid (37 mg, 26%). ¹H NMR (300 MHz, d₆-DMSO) δ 9.17 (s, 1H), 7.76-7.78 (m, 3H), 7.21-7.34 (m, 8H), 7.19 (s, 1H), 7.13 (d, J=1.8 Hz, 1H), 7.00 (br s, 1H), 6.84 (dd, J=8.1 and 1.5 Hz, 1H), 6.77 (s, 2H), 5.63 (d, J=6.0 Hz, 1H), 4.16 (s, 2H), 3.54-3.61 (m, 2H), 3.52 (s, 3H), 3.45 (s, 3H), 2.92-2.97 (m, 2H) ppm. MS (ESI) m/z=543 [M+H]⁺.

Example 97

$N^5$-[2-(4-Methanesulfonylmethyl-phenylamino)-pyrimidin-4-yl]-1,$N^5$-dimethyl-$N^2$-phenethyl-1H-benzoimidazole-2,5-diamine

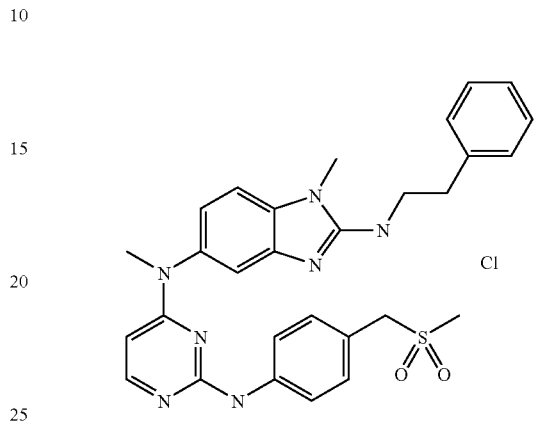

The title compound was prepared following the procedure of example 1 with $N^5$-(2-Chloro-pyrimidin-4-yl)-1,$N^5$-dimethyl-$N^2$-phenethyl-1H-benzoimidazole-2,5-diamine (98 mg, 0.25 mmol) and 4-[(methylsulfonyl)methyl]aniline (46 mg, 0.25 mmol) as a white solid (120 mg, 83%). ¹H NMR (300 MHz, d₆-DMSO) δ 9.21 (s, 1H), 7.77-7.81 (m, 3H), 7.18-7.33 (m, 8H), 7.12 (d, J=1.5 Hz, 1H), 7.00 (t, J=5.7 Hz, 1H), 6.83 (dd, J=8.1 and 1.5 Hz, 1H), 5.65 (d, J=6.0 Hz, 1H), 4.35 (s, 2H), 3.54-3.61 (M, 2H), 3.52 (s, 3H), 3.44 (s, 3H), 2.92-2.97 (m, 2H), 2.86 (s, 3H) ppm. MS (ESI) m/z=542 [M+H]⁺.

Example 98

2-(4-{4-[Methyl-(1-methyl-2-phenethylamino-1H-benzoimidazol-5-yl)-amino]-pyrimidin-2-ylamino}-phenyl)-ethanesulfonic acid methylamide hydrochloride

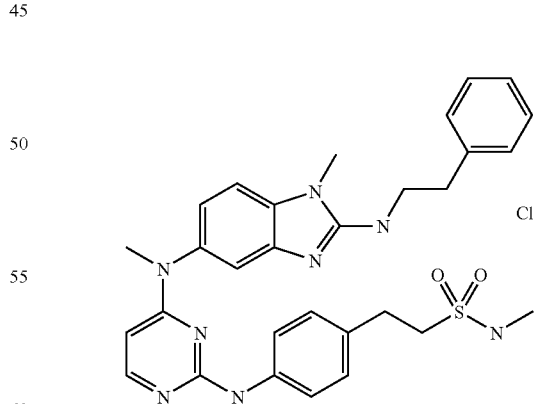

The title compound was prepared following the procedure of example 1 with $N^5$-(2-Chloro-pyrimidin-4-yl)-1,$N^5$-dimethyl-$N^2$-phenethyl-1H-benzoimidazole-2,5-diamine (98 mg, 0.25 mmol) and 2-(4-amino-phenyl)-ethanesulfonic acid methylamide (54 mg, 0.25 mmol) as a white solid (100 mg, 66%). ¹H NMR (300 MHz, d₆-DMSO) δ 9.30 (s, 1H), 7.82 (d, J=6.0 Hz, 1H), 7.65 (d, J=8.4 Hz, 2H), 7.43 (d, J=8.4 Hz, 1H), 7.20-7.33 (m, 5H), 7.06-7.14 (m, 3H), 6.98 (q, J=6.2 Hz, 1H), 5.70 (d, J=6.0 Hz, 1H), 3.65 (m, 2H), 3.60 (s, 3H), 3.45 (s, 3H), 3.21-3.26 (m, 2H), 2.95-3.00 (M, 2H), 2.84-2.90 (m, 2H), 2.59 (d, J=5.1 Hz, 3H) ppm. MS (ESI) m/z=571 [M+H]⁺.

Example 99

N²-tert-Butyl-N⁵-[2-(4-methanesulfonylmethyl-phenylamino)-pyrimidin-4-yl]-1,N⁵-dimethyl-1H-benzoimidazole-2,5-diamine hydrochloride

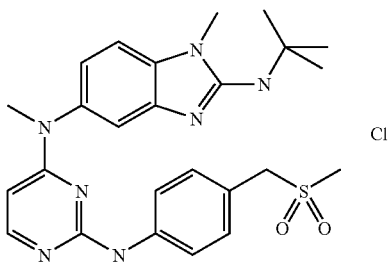

The title compound was prepared following the procedure of example 1 with N²-tert-butyl-N⁵-(2-chloro-pyrimidin-4-yl)-1,N⁵-dimethyl-1H-benzoimidazole-2,5-diamine (69 mg, 0.20 mmol) and 4-[(methylsulfonyl)methyl]aniline (37 mg, 0.20 mmol) as a white solid (111 mg, 95%). ¹H NMR (300 MHz, d₆-DMSO) δ 9.28 (s, 1H), 7.77-7.79 (m, 3H), 7.24 (d, J=8.4 Hz, 3H), 7.16 (d, J=1.5 Hz, 1H), 6.88 (d, J=7.8 Hz, 1H), 6.21 (br s, 1H), 5.67 (d, J=6.0 Hz, 1H), 4.35 (s, 2H), 3.54 (s, 3H), 3.45 (s, 3H), 2.86 (s, 3H), 1.47 (s, 9H) ppm. MS (ESI) m/z=494 [M+H]⁺.

Example 100

N²-Cyclohexyl-N⁵-[2-(4-methanesulfonylmethyl-phenylamino)-pyrimidin-4-yl]-1,N⁵-dimethyl-1H-benzoimidazole-2,5-diamine

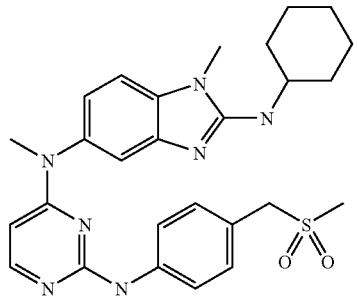

The title compound was prepared following the procedure of example 1 with N⁵-(2-Chloro-pyrimidin-4-yl)-N²-cyclohexyl-1,N⁵-dimethyl-1H-benzoimidazole-2,5-diamine (92 mg, 0.25 mmol) and 4-[(methylsulfonyl)methyl]aniline (46 mg, 0.25 mmol) as a white solid (31 mg, 24%). ¹H NMR (300 MHz, D₆-DMSO) δ 9.20 (s, 1H), 7.77-7.80 (M, 3H), 7.10 (s, 1H), 6.82 (d, J=7.8 Hz, 1H), 6.50 (d, J=7.5 Hz, 1H), 5.64 (d, J=6.0 Hz, 1H), 4.34 (s, 2H), 3.70 (br s, 1H), 3.51 (s, 3H), 3.44 (s, 3H), 2.85 (s, 3H), 2.01 (br s, 2H), 1.74 (br s, 2H), 1.62 (d, J=11.1 Hz, 1H), 1.16-1.32 (m, 5H) ppm. MS (ESI) m/z=520 [M+H]⁺.

Example 101

5-{4-[(2-Cyclohexylamino-1-methyl-1H-benzoimidazol-5-yl)-methyl-amino]-pyrimidin-2-ylamino}-2-methyl-benzenesulfonamide hydrochloride

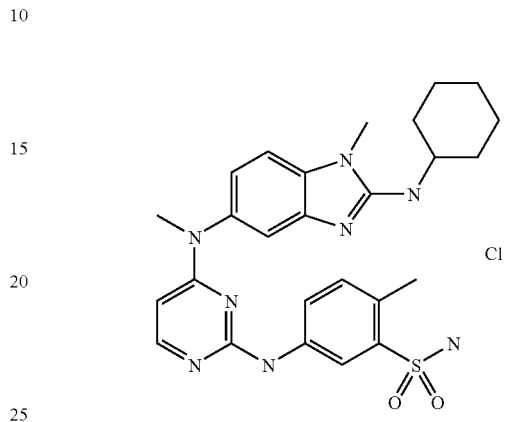

The title compound was prepared following the procedure of example 1 with N⁵-(2-Chloro-pyrimidin-4-yl)-N²-cyclohexyl-1,N⁵-dimethyl-1H-benzoimidazole-2,5-diamine (92 mg, 0.25 mmol) and 5-amino-2-methyl-benzenesulfonamide (46 mg, 0.25 mmol) as a white solid (95 mg, 68%). ¹H NMR (300 MHz, D₆-DMSO) δ 9.51 (s, 1H), 8.56 (s, 1H), 8.18 (br s, 1H), 7.83 (d, J=6.0 Hz, 1H), 7.69 (dd, J=8.4 and 2.1 Hz, 1H), 7.48 (d, J=8.1 Hz, 1H), 7.30 (s, 1H), 7.24 (s, 2H), 7.13-7.18 (M, 2H), 5.69 (d, J=6.0 Hz, 1H), 3.70 (m, 1H), 3.64 (s, 3H), 3.47 (s, 3H), 2.50 (s, 3H), 1.98-2.01 (m, 2H), 1.76-1.79 (m, 2H), 1.62—1.66 (m, 1H), 1.29-1.48 (m, 4H), 1.14-1.17 (m, 1H) ppm. MS (ESI) m/z=521 [M+H]⁺.

Example 102

N²-Cyclohexyl-N⁵-{2-[3-(2-methanesulfonyl-ethyl)-phenylamino]-pyrimidin-4-yl}-1,N⁵-dimethyl-1H-benzoimidazole-2,5-diamine hydrochloride

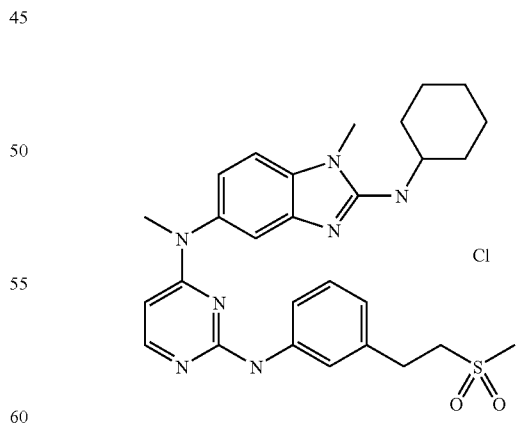

The title compound was prepared following the procedure of example 1 with N⁵-(2-Chloro-pyrimidin-4-yl)-N²-cyclohexyl-1,N⁵-dimethyl-1H-benzoimidazole-2,5-diamine (74 mg, 0.20 mmol) and 3-(2-methanesulfonyl-ethyl)-phenylamine (47 mg, 0.20 mmol) as a white solid (59 mg, 52%). ¹H NMR (300 MHz, D₆-DMSO) δ 9.07 (s, 1H), 7.76-7.78

(m, 2H), 7.60 (d, J=8.4 Hz, 1H), 7.13-7.20 (m, 2H), 7.09 (d, J=1.8 Hz, 1H), 6.79-6.82 (m, 2H), 6.47 (d, J=7.8 Hz, 1H), 5.61 (d, J=6.0 Hz, 1H), 3.70 (m, 1H), 3.51 (s, 3H), 3.44 (s, 3H), 3.35-3.40 (m, 2H), 2.97 (s, 3H), 2.91-2.95 (m, 2H), 2.01 (m, 2H), 1.74 (M, 2H), 1.63 (m, 1H), 1.16-1.31 (m, 5H) ppm. MS (ESI) m/z=534 [M+H]$^+$.

Example 103

N$^2$-Cyclohexyl-N$^5$-{2-[4-(2-methanesulfonyl-ethyl)-phenylamino]-pyridin-4-yl}-1,N$^5$-dimethyl-1H-benzoimidazole-2,5-diamine hydrochloride

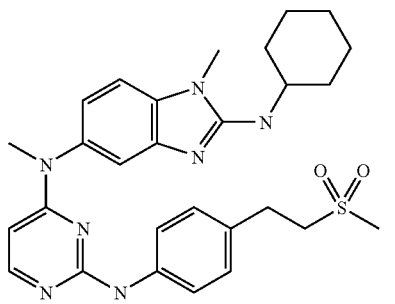

The title compound was prepared following the procedure of example 1 with N$^5$-(2-Chloro-pyrimidin-4-yl)-N$^2$-cyclohexyl-1,N$^5$-dimethyl-1H-benzoimidazole-2,5-diamine (74 mg, 0.20 mmol) and 4-(2-Methanesulfonyl-ethyl)-phenylamine (40 mg, 0.20 mmol) as a white solid (100 mg, 88%). $^1$H NMR (300 MHz, D$_6$-DMSO) δ 9.12 (s, 1H), 7.78 (d, J=6.0 Hz, 1H), 7.69 (d, J=8.4 Hz, 2H), 7.27 (d, J=8.4 Hz, 1H), 7.11-7.14 (m, 3H), 6.90 (d, J=8.1 Hz, 1H), 5.64 (d, J=6.0 Hz, 1H), 3.72 (m, 1H), 3.56 (s, 3H), 3.43 (s, 3H), 3.30-3.43 (m, 2H), 2.90-2.95 (M, 5H), 1.98 (m, 2H), 1.76 (m, 2H), 1.62 (m, 1H), 1.36 (m, 4H), 1.10 (m, 1H) ppm. MS (ESI) m/z=534 [M+H]$^+$.

Example 104

N$^2$-Cyclohexyl-N$^5$-{2-[4-(1-methanesulfonyl-ethyl)-phenylamino]-pyrimidin-4-yl}-1,N$^5$-dimethyl-1H-benzoimidazole-2,5-diamine hydrochloride

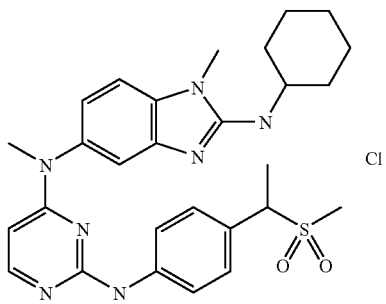

The title compound was prepared following the procedure of example 1 with N$^5$-(2-Chloro-pyrimidin-4-yl)-N$^2$-cyclohexyl-1,N$^5$-dimethyl-1H-benzoimidazole-2,5-diamine (74 mg, 0.20 mmol) and 4-(1-methanesulfonyl-ethyl)-phenylamine (40 mg, 0.20 mmol) as a white solid (104 mg, 91%). $^1$H NMR (300 MHz, D$_6$-DMSO) δ 9.34 (s, 1H), 7.85 (d, J=6.0 Hz, 1H), 7.71 (d, J=8.4 Hz, 2H), 7.43 (d, J=8.1 Hz, 1H), 7.22-7.26 (m, 3H), 7.08 (d, J=8.1 Hz, 1H), 5.76 (d, J=6.0 Hz, 1H), 4.40 (m, 1H), 3.72 (m, 1H), 3.63 (s, 3H), 3.45 (s, 3H), 2.76 (s, 3H), 1.99 (m, 2H), 1.76 (m, 2H), 1.58-1.65 (m, 4H), 1.33-1.43 (m, 4H), 1.15 (m, 1H) ppm. MS (ESI) m/z=534 [M+H]$^+$.

Example 105

2-Methyl-5-{4-[methyl-(1-methyl-2-methylamino-1H-benzoimidazol-5-yl)-amino]-pyrimidin-2-ylamino}-benzenesulfonamide hydrochloride

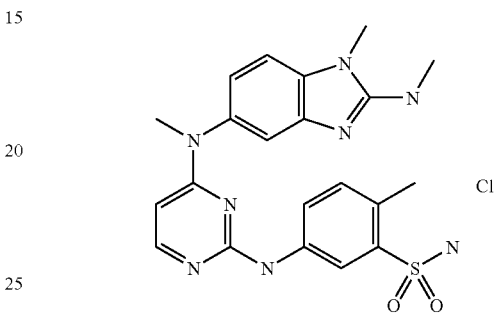

The title compound was prepared following the procedure of Example 1 with N$^5$-(2-chloropyrimidin-4-yl)-N$^2$,N$^5$,1-trimethyl-1H-benzimidazole-2,5-diamine (58 mg, 0.20 mmol) and 5-amino-2-methyl-benzenesulfonamide (35 mg, 0.20 mmol) as a pink solid (78 mg, 84%). $^1$H NMR (300 MHz, d$_6$-DMSO) δ 10.63 (br s, 1H), 9.22 (d, J=4.2 Hz, 1H), 8.40 (br s, 2H), 7.91 (d, J=6.9 Hz, 1H), 7.67 (m, 2H), 7.47 (d, J=1.5 Hz, 1H), 7.28-7.36 (m, 3H), 5.83 (m, 1H), 3.67 (s, 3H), 3.53 (s, 3H), 3.08 (d, J=4.5 Hz, 3H), 2.54 (s, 3H). MS (ESI) m/z=453 [M+H]$^+$.

Example 106

(4-{4-[Methyl-(1-methyl-2-methylamino-1H-benzoimidazol-5-yl)-amino]-pyrimidin-2-ylamino}-phenyl)-methanesulfonamide hydrochloride

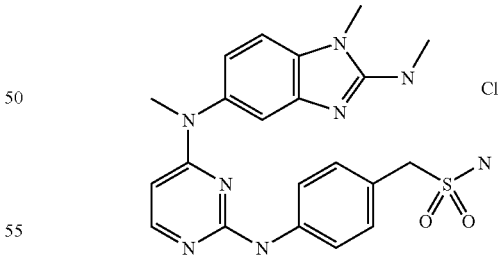

The title compound was prepared following the procedure of Example 1 with N$^6$-(2-chloropyrimidin-4-yl)-N$^2$,N$^5$,1-trimethyl-1H-benzimidazole-2,5-diamine (50 mg, 0.17 mmol) and (4-amino-phenyl)-methanesulfonamide (32 mg, 0.17 mmol) as a white solid (38 mg, 46%). $^1$H NMR (300 MHz, d$_6$-DMSO+NaHCO$_3$) δ 9.71 (br s, 1H), 9.00 (br s, 2H), 7.90 (d, J=6.3 Hz, 1H), 7.61 (m, 3H), 7.39 (s, 1H), 7.26 (d, J=8.4 Hz, 1H), 7.19 (d, J=8.1 Hz, 1H), 6.79 (s, 2H), 5.83 (d, J=5.7 Hz, 1H), 4.17 (s, 2H), 3.66 (s, 3H), 3.48 (s, 3H), 3.06 (d, J=4.5 Hz, 3H). MS (ESI) m/z=453 [M+H]$^+$.

Example 107

3-{4-[Methyl-(1-methyl-2-methylamino-1H-benzoimidazol-5-yl)-amino]-pyrimidin-2-ylamino}-benzenesulfonamide

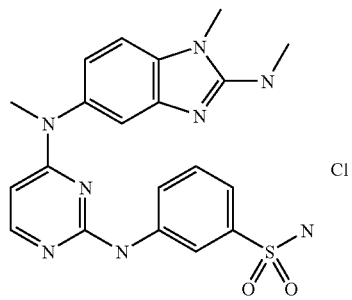

The title compound was prepared following the procedure of Example 1 with $N^5$-(2-chloropyrimidin-4-yl)-$N^2,N^5$,1-trimethyl-1H-benzimidazole-2,5-diamine (60 mg, 0.20 mmol) and 3-amino-benzenesulfonamide (34 mg, 0.20 mmol) as a white solid (40 mg, 42%). $^1$H NMR (300 MHz, $d_6$-DMSO+NaHCO$_3$) δ 9.51 (s, 1H), 8.61 (s, 1H), 7.77-7.82 (M, 2H), 7.26-7.39 (m, 6H), 7.17 (s, 1H), 6.92 (d, J=7.8 Hz, 1H), 5.66 (d, J=6.0 Hz, 1H), 3.55 (s, 3H), 3.47 (s, 3H), 2.95 (d, J=4.2 Hz, 3H). MS (ESI) m/z=439 [M+H]$^+$.

Example 108

$N^5$-[2-(3-Methanesulfonylmethyl-phenylamino)-pyrimidin-4-yl]-1,$N^2,N^5$-trimethyl-1H-benzoimidazole-2,5-diamine

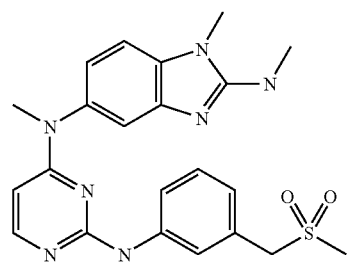

The title compound was prepared following the procedure of Example 1 with $N^5$-(2-chloropyrimidin-4-yl)-$N^2,N^5$,1-trimethyl-1H-benzimidazole-2,5-diamine (48 mg, 0.16 mmol) and 3-methanesulfonylmethyl-phenylamine (30 mg, 0.16 mmol) as a white solid (75 mg, 83%). $^1$H NMR (300 MHz, $d_6$-DMSO) δ 9.23 (s, 1H), 7.89 (s, 1H), 7.79 (d, J=6.0 Hz, 1H), 7.68 (d, J=8.1 Hz, 1H), 7.19-7.27 (m, 3H), 7.13 (s, 1H), 6.87-6.93 (m, 2H), 5.66 (d, J=6.0 Hz, 1H), 4.33 (s, 2H), 3.54 (s, 3H), 3.43 (s, 3H), 2.93 (d, J=4.5 Hz, 3H), 2.89 (s, 3H). MS (ESI) m/z=452 [M+H]$^+$.

Example 109

(4-{4-[(1-Ethyl-2-methylamino-1H-benzoimidazol-5-yl)-methyl-amino]-pyrimidin-2-ylamino}-phenyl)-methanesulfonamide hydrochloride

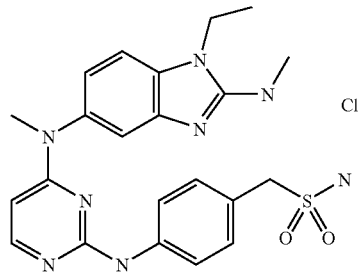

The title compound was prepared following the procedure of Example 1 with $N^5$-(2-Chloro-pyrimidin-4-yl)-1-ethyl-$N^2,N^5$-dimethyl-1H-benzoimidazole-2,5-diamine (79 mg, 0.25 mmol) and (4-amino-phenyl)-methanesulfonamide (46 mg, 0.25 mmol) as a white solid (110 mg, 88%). $^1$H NMR (300 MHz, $d_6$-DMSO) δ 9.24 (s, 1H), 7.81 (d, J=6.0 Hz, 1H), 7.74 (m, 3H), 7.36 (d, J=8.1 Hz, 1H), 7.17-7.20 (M, 3H), 6.96 (d, J=8.4 Hz, 1H), 6.78 (s, 2H), 5.70 (d, J=6.0 Hz, 1H), 4.09-4.16 (m, 4H), 3.45 (s, 3H), 2.97 (d, J=4.5 Hz, 3H), 1.24 (t, J=6.9 Hz, 3H) ppm. MS (ESI) m/z=467 [M+H]$^+$.

Example 110

$N^1$-Methyl-$N^5$-[2-(4-Methanesulfonymethyl-phenylamino)-pyrimidin-4-yl]-$N^5$-methyl-$N^2$-(4-trifluoromethyl-phenyl)-1H-benzoimidazole-2,5-diamine

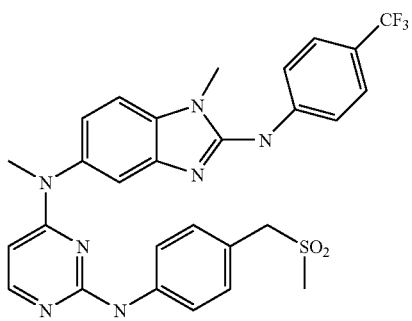

A mixture of $N^4$-(2-Methanesulfonyl-1-methyl-1H-benzoimidazol-5-yl)-$N^2$-(4-methanesulfonylmethyl-phenyl)-$N^4$-methyl-pyrimidine-2,4-diamine (89 mg, 0.18 mmol), 4-(trifluoromethyl)aniline (148 mg, 0.9 mmol) and a catalytic amount of HCl (5 drop, concentrated) in isopropanol was heated in Smith Synthesizer at 150° C. for 10 min. The reaction mixturer was concentrated and purified by prep. HPLC, after concentration the product was treated with HCl (0.1 ml, 1M in ether) to gave the title compound as a pale yellow solid: LC/MS(m/e) 582.2 [M+H]$^+$, Rt at 1.34 min.

The following compounds of Examples 111-125 of Formula I$^α$ were prepared according to the procedure of Example 110.

Iª

| Example | Ar | LC/MS Rt (min) | LC/MS m/z [M + H]+ |
|---|---|---|---|
| 111 | 3-Cl-phenyl, 4-Me | 1.52 | 548.0 |
| 112 | 4-Cl-phenyl, 3-Me | 1.34 | 548.2 |
| 113 | 3,4-diCl-phenyl, 6-Me | 1.52 | 582.2 |
| 114 | 2,5-diCl-phenyl, 3-Me | 1.6 | 582.2 |
| 115 | 3-CF₃, 4-Cl-phenyl, 6-Me | 1.71 | 616.2 |
| 116 | 4-CF₃, 2-Cl-phenyl, 6-Me | 1.59 | 616.2 |

-continued

Iª

| Example | Ar | LC/MS Rt (min) | LC/MS m/z [M + H]+ |
|---|---|---|---|
| 117 | 4-morpholino-phenyl, Me | 1.54 | 597.4 |
| 118 | 3-F-phenyl, 6-Me | 1.92 | 532.2 |
| 119 | 2,4-diF-phenyl, 6-Me | 1.83 | 550.0 |
| 120 | 2-Cl, 4-F-phenyl, 6-Me | 1.77 | 566.2 |
| 121 | 2-F, 4-Cl-phenyl, 6-Me | 1.4 | 566.2 |
| 122 | 2-Cl, 5-F-phenyl, 3-Me | 1.27 | 566.2 |
| 123 | 3-F-phenyl, 2,5-diMe | 1.26 | 546.0 |
| 124 | 2-F-phenyl, 6-Me | 1.55 | 532.2 |
| 125 | 2-F, 5-CF₃-phenyl, 3-Me | 1.7 | 600.0 |

Example 126

4-{4-[Methyl-(1-methyl-2-methylsulfanyl-1H-benzoimidazol-5-yl)-amino]-pyrimidin-2-ylamino}-benzene sulfonamide The procedure of Example 5 was utilized, replacing 4-Methanesulfonylmethyl-phenylamine by 4-Amino-benzenesulfonamide, which gave the title compound as a white solid: LC/MS(m/e) 456.02 [M+H]$^+$, Rt at 1.37 min.

Example 127

4-{4-[(2-Methanesulfinyl-1-methyl-1H-benzoimidazol-5-yl)-methyl-amino]-pyrimidin-2-ylamino}-benzensulfonamide The procedure of Example 6 was utilized, replacing $N^2$-(4-Methanesulfonylmethyl-phenyl)-$N^4$-methyl-$N^4$-(1-methyl-2-methylsulfanyl-1H-benzoimidazol-5-yl)-pyrimidine-2,4-diamine by 4-{4-[Methyl-(1-methyl-2-methylsulfanyl-1H-benzoimidazol-5-yl)-amino]-pyrimidin-2-ylamino}-benzene sulfonamide, which gave the title compound: LC/MS(m/e) 472.2 [M+H]$^+$, Rt at 1.24 min.

Example 128

4-(4-{Methyl-[1-methyl-2-(4-trifluoromethyl-phenylamino)-1H-benzoimidazol-5-yl]-amino}-pyrimidin-2-ylamino)-benzenesulfonamide The procedure of Example 7 was utilized, replacing $N^4$-(2-Methanesulfonyl-1-methyl-1H-benzoimidazol-5-yl)-$N^2$-(4-methanesulfonylmethyl-phenyl)-$N^4$-methyl-pyrimidine-2,4-diaminen by 4-{4-[(2-Methanesulfinyl-1-methyl-1H-benzoimidazol-5-yl)-methyl-amino]-pyrimidin-2-ylamino}-benzensulfonamide, which gave the title compound as a yellow oil: LC/MS(m/e) 569.4 [M+H]$^+$, Rt at 1.41 min.

Example 129

(Methyl-nitro-1H-benzoimidazol-2-yl)-(3-trifluoromethyl-phenyl)-amine

The procedure of Intermediate Example 1B was utilized, replacing isothiocynate by 3-Trifluoromethyl-phenylamine, which gave the title compound as a dark orange solid: LC/MS(m/e) 337.2 [M+H]$^+$.

Example 130

(Methyl-nitro-1H-benzoimidazol-2-yl)-(3-trifluoromethyl-phenyl)-carbamic acid dimethyl-ethyl ester (Methyl-nitro-1H-benzoimidazol-2-yl)-(3-trifluoromethyl-phenyl)-amine (2.34 g) and cesium carbonate (5.61 g, 17.2 mmol) was stirred in DMF for 15 min., then (BOC)$_2$O (2.81 g, 12.9 mmol) was added. The resulting mixture was stirred at room temperature for 4 days, the reaction mixture was then concentrated and the residual was taken into EtOAc and washed by water, then brine, drying and concentration, silica flash, which gave 1.45 g of the title compound as a yellow foam: LC/MS(m/e) 437 [M+H]$^+$, Rt at 2.34 min.

Example 131

(Amino-methyl-1-benzoimidazol-2-yl)-(3-trifluoromethyl-phenyl)-carbamic acid dimethyl-ethyl ester The procedure of Example 3 was utilized, replacing 1-Methyl-2-methylsulfanyl-5-nitro-1H-benzoimidazole by (Methyl-nitro-1H-benzoimidazol-2-yl)-(3-trifluoromethyl-phenyl)-carbamic acid dimethyl-ethyl ester, which gave the title compound as a yellow brownish solid: LC/MS(m/e) 407.4 [M+H]$^+$, Rt at 1.62 min.

Example 132

[(2-Chloro-pyrimidin-4-yl)-methyl-amino]-methyl-1H-benzoimidazol-2-yl}-(3-trifluoromethyl-phenyl)-carbamic acid dimethyl-ethyl ester The procedure of Intermediate Example 1D was utilized, replacing $N^2$-isopropyl-1-methyl-1H-benzoimidazole-2,5-diamine by (Amino-methyl-1-benzoimidazol-2-yl)-(3-trifluoromethyl-phenyl)-carbamic acid dimethyl-ethyl ester, which gave the title compound as a white solid: LC/MS(m/e) 533.2 [M+H]$^+$, Rt at 2.44 min.

Example 133

$N^5$-[2-(4-methanesulfonylmethyl-phenylamino)-pyrimidin-4-yl]-$N^1$,$N^5$-dimethyl-$N^2$-(3-trifluoromethyl-phenyl)-1H-benzoimidazole-2,5-diamine The procedure of Example 7 was utilized, replacing $N^4$-(2-Methanesulfonyl-1-methyl-1H-benzoimidazol-5-yl)-$N^2$-(4-methanesulfonylmethyl-phenyl)-$N^4$-methyl-pyrimidine-2,4-diamine by [(2-Chloro-pyrimidin-4-yl)-methyl-amino]-methyl-1H-benzoimidazol-2-yl}-(3-trifluoromethyl-phenyl)-carbamic acid dimethyl-ethyl este, which gave the title compound as a yellow solid: LC/MS (m/e) 582.0 [M+H]$^+$, Rt at 1.4 min.

Example 134

$N^2$-(5-tert-Butyl-isoxazol-3-yl)-$N^5$[2-(4-methanesulfonylmethyl-phenylamino)-pyrimidin-4-yl]-1,$N^5$-dimethyl-1H-methyl-amino-benzoimidazole-2,5-diamine

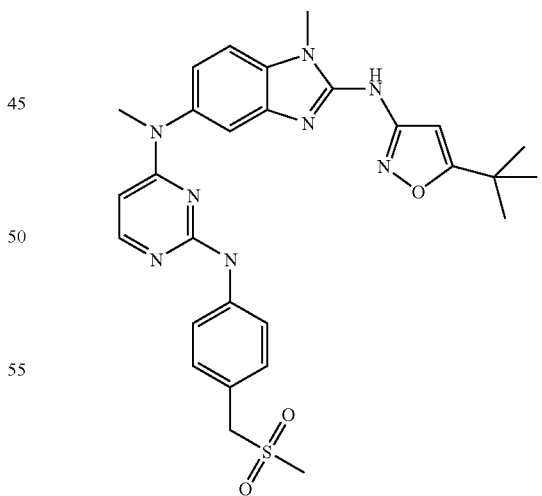

N-(5-tert-Butyl-isoxazol-3-yl)-N-{5-[(2-chloro-pyrimidin-4-yl)-methyl-amino]-1-methyl-1H benzoimidazole-2-yl}-2,2-dimethyl-propionamide (50 mg, 0.10 mmol) and 4-[(methylsulfonyl)methyl]aniline (19 mg, 0.10 mmol) were dissolved in isopropanol (2.5 ml). To this soluton was added a catalytic amount of HCl and the reaction was heated to 70° C. for 12 hours. The solvent was removes and the reaction mixture was purified by RPHPLC and by using CH₃CN:H₂O:0.1% TFA solvent as mobile phase. The solid was dissolved in CH₂Cl₂ and neutralized by a 10% NaHCO₃ solution. The CH₂Cl₂ phase was dyed over Na₂SO₄ and evaporated to give the title compound ¹H NMR (400 MHz, d₆-DMSO) δ11.3 and 10.6 (s, 1H), 9.6 (d, J=10.9 Hz, 1H), 7.85 (d, 5.8 Hz, 1H), 7.75 (m, 2H), 7.45 (d, J=5.8 Hz, 1H), 7.25-7.45 (m, 2H), 7.05-7.10 (m, 2H), 5.75 (m, 1H), 4.35 (s, 2H), 3.52 (s, 3H), 3.51 (d, J=12 Hz, 3H), 2.85 (s, 3H), 1.29 (s, 9H) ppm. MS (ESI) m/z=560 [M+H]⁺.

The following compounds of Examples 135-141 of Formula I$^b$ were prepared according to the procedure of Example 134 with the starting materials indicated in each Example.

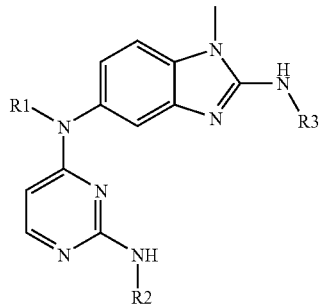

I$^b$

| Example # | R1 | R2 | R3 | LC/MS Rt (min) | LC/MS m/z [M + H]⁺ |
|---|---|---|---|---|---|
| Example 135 | H | 4-methylbenzyl methylsulfonyl | 5-tert-butyl-3-methylisoxazol-4-yl | 1.48 | 547 |
| Example 136 | H | 3-methylbenzyl methylsulfonyl | 5-tert-butyl-3-methylisoxazol-4-yl | 1.56 | 547 |
| Example 137 | CH₃ | 3-methylbenzyl methylsulfonyl | 5-tert-butyl-3-methylisoxazol-4-yl | 1.72 | 561 |
| Example 138 | H | 2,5-dimethylbenzenesulfonamide | 5-tert-butyl-3-methylisoxazol-4-yl | 1.48 | 548 |
| Example 139 | CH₃ | 2,5-dimethylbenzenesulfonamide | 5-tert-butyl-3-methylisoxazol-4-yl | 1.57 | 562 |
| Example 140 | H | 2,5-dimethylbenzenesulfonamide | 8-ethyl-6-fluoro-4H-benzo[d][1,3]dioxine | 1.54 | 604 |

-continued

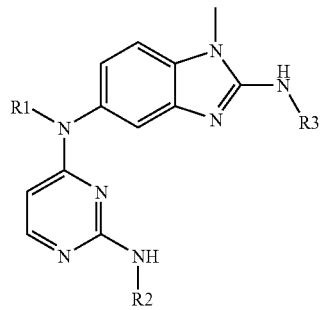

| Example # | R1 | R2 | R3 | LC/MS Rt (min) | LC/MS m/z [M + H]+ |
|---|---|---|---|---|---|
| Example 141 | H | 3-methylphenyl-SO2-morpholine | 5-tert-butyl-3-methylisoxazol-3-yl | 2.43 | 591 |

Example 135

$N^2$-(5-tert-Butyl-isoxazol-3-yl)-$N^5$-[2-(4-methane-sulfonylmethyl-phenylamino)-pyrimidin-4-yl]-1-methyl-1-1H-benzoimidazole-2,5-diamine trifluoroacetate The title compound was prepared following the procedure of Example 134 with $N^2$-(5-tert-Butyl-isoxazol-3-yl)-$N^5$-(2-chloro-pyrimidin-4-yl)-1-methyl-1H benzoimidazole-2,5-diamine (50 mg, 0.126 mmol) and 4-[(methylsulfonyl)methyl]aniline (26 mg, 0.139 mmol) to afford a white solid (36 mg, 0.06 mmol). MS (ESI) m/z=547 [M+H]+.

Example 136

$N^2$-(5-tert-Butyl-isoxazol-3-yl)-$N^5$-[2-(3-methane-sulfonylmethyl-phenylamino)-pyrimidin-4-yl]-1-methyl-1H-benzoimidazole-2,5-diamine The title compound was prepared following the procedure of Example 134 with $N^2$-(5-tert-Butyl-isoxazol-3-yl)-$N^5$-(2-chloro-pyrimidin-4-yl)-1-methyl-1H benzoimidazole-2,5-diamine (50 mg, 0.126 mmol) and 4-[(methylsulfonyl)methyl]aniline (26 mg, 0.139 mmol) to afford a white solid (16 mg, 0.03 mmol). MS (ESI) m/z=547 [M+H]+.

Example 137

$N^2$-(5-tert-Butyl-isoxazol-3-yl)-$N^5$-[2-(3-methane-sulfonylmethyl-phenylamino)-pyrimidin-4-yl]-1,N5-dimethyl-1-H-benzoimidazole-2,5-diamine The title compound was prepared following the procedure of Example 134 with N-(5-tert-Butyl-isoxazol-3-yl)-N-{5-[(2-chloro-pyrimidin-4-yl)-methyl-amino]-1-methyl-1H benzoimidazole-2-yl}-2,2-dimethyl-propionamide (23 mg, 0.045 mmol) and 3-[(methylsulfonyl)methyl]aniline (10 mg, 0.139 mmol) to afford a white solid (5 mg, 0.01 mmol). MS (ESI) m/z=561 [M+H]+.

Example 138

$N^2$-(5-tert-Butyl-isoxazol-3-yl)-$N^5$-[2-(3-methane-sulfonyl-4-methyl-phenylamino)-pyrimidin-4-yl]-1-methyl-1-1H-benzoimidazole-2,5-diamine The title compound was prepared following the procedure of Example 134 with $N^2$-(5-tert-Butyl-isoxazol-3-yl)-$N^5$-(2-chloro-pyrimidin-4-yl)-1-methyl-1H benzoimidazole-2,5-diamine (40 mg, 0.10 mmol) and 5-Amino-2-methyl-benzenesulfonamide (27 mg, 0.11 mmol) to afford an off white solid (26 mg, 0.048 mmol). MS (ESI) m/z=547 [M+H]+.

Example 139

5-(4-{[2-(5-tert-Butyl-isoxazol-3-ylamino)-1-methyl-1-H-benzoimidazol-5-yl]-methyl-amino}-pyrimidin-2-ylamino)-2-methyl-benzenesulfonamide The title compound was prepared following the procedure of Example 134 with N-(5-tert-Butyl-isoxazol-3-yl)-N-{5-[(2-chloro-pyrimidin-4-yl)-methyl-amino]-1-methyl-1H benzoimidazole-2-yl}-2,2-dimethyl-propionamide (50 mg, 0.10 mmol) and 3-[(methylsulfonyl)methyl]aniline (23 mg, 0.10 mmol) to afford an off white solid (20 mg, mmol). MS (ESI) m/z=562 [M+H]+.

Example 140

$N^2$-(6-Fluoro-4-H benzo[1,3]dioxin-8-ylmethyl)-$N^5$-[2-(3-methanesulfonyl-4-methyl-phenylamino)-pyrimidin-4-yl]-1-methyl-1H-benzoimidazole-2,5-diamine The title compound was prepared following the procedure of Example 134 with $N^5$-(2-Chloro-pyrimidin-4-yl)-$N^2$-(6-Fluoro-4-H benzo[1,3]dioxin-8-ylmethyl)-1H-benzoimidazole-2,5-diamine (35 mg, 0.08 mmol) and 3-[(methylsulfonyl)methyl]aniline (16 mg, 0.08 mmol) to give a white solid (12 mg, 0.02 mmol). MS (ESI) m/z=590 [M+H]+.

Example 141

N²-(5-tert-Butyl-isoxazol-3-yl)-1-methyl-N⁵-{2-[3-(morpholine-4-sulfonyl)-phenylamino]-pyrimidin-4-yl}-1H-benzoimidazole-2,5-diamine The title compound was prepared following the procedure of Example I with N²-(5-tert-Butyl-isoxazol-3-yl)-N⁵-(2-chloro-pyrimidin-4-yl)-1-methyl-1H benzoimidazole-2,5-diamine (35 mg, 0.09 mmol) and 3-(Morpholine-4-sulfonyl)-phenylamine (23 mg, 0.10 mmol) to afford an off white solid (32 mg, 005. mmol). MS (ESI) m/z=605 [M+H]⁺.

Example 142

N-(1-methyl-5-{methyl[2-({4-[(methylsulfonyl)methyl]phenyl}amino)pyrimidin-4-yl]amino}-1H-benzimidazol-2-yl)-N'-phenylurea

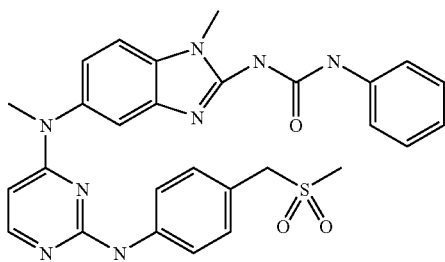

To a solution of N⁵,1-dimethyl-N⁵-[2-({4-[(methylsulfonyl)methyl]phenyl}amino)pyrimidin-4-yl]-1H-benzimidazole-2,5-diamine (150 mg, 0.343 mmol) in N,N-dimethylacetamide (3 ml) was added 1,1'-carbonyldiimidazole (167 mg, 1.03 mmol). The mixture was stirred for 24 h and then aniline (192 mg, 2.06 mmol) was added. The mixture was stirred for 2 h. The reaction was quenched with saturated sodium bicarbonate solution (30 ml) and the product precipitated. The crude product was filtered, washed with water, diethyl ether and air dried to give the desired product without further purification. ¹H NMR (300 MHz, d₆-DMSO) δ 12.14 (s, 1H), 9.26 (s, 1H), 9.12 (s, 1H), 7.86 (d, J=5.8 Hz, 1H), 7.76-7.68 (m, 4H), 7.42 (d, J=8.2 Hz, 1H), 7.30-7.20 (m, 5H), 7.12 (d, J=8.2 Hz, 1H), 6.89 (t, J=7.1 Hz, 1H), 5.75 (d, J=5.7 Hz, 1H), 4.34 (s, 2H), 3.57 (s, 3H), 3.44 (s, 3H), 2.84 (s, 3H). MS (ESI) m/z=557 [M+H]⁺.

Example 143

N-(1-methyl-5-{methyl[2-({4-[(methylsulfonyl)methyl]phenyl}amino)pyrimidin-4-yl]amino}-1H-benzimidazol-2-yl)benzamide

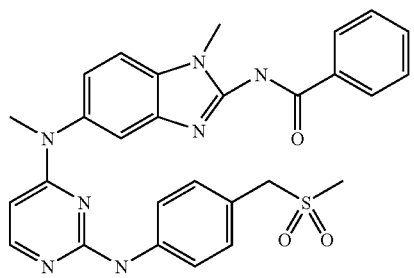

To a solution of benzoic acid (51 mg, 0.402 mmol) in N,N-dimethylformamide (2 ml) was added 1,1'-carbonyldiimidazole (65.2 mg, 0.400 mmol). The mixture was stirred for 30 minutes at room temperature and then a solution of N⁵,1-dimethyl-N⁵-[2-({4-[(methylsulfonyl)methyl] phenyl}amino)pyrimidin-4-yl]-1H-benzimidazole-2,5-diamine (88 mg, 0.201 mmol) and triethylamine (0.03 ml, 0.201 mmol) in N,N-dimethylformamide (2 ml) was added. The reaction mixture was stirred for 16 h, quenched with saturated sodium bicarbonate solution (30 ml) and the product then precipitated. The crude product was filtered, washed with water, diethyl ether and air dried to give the desired product without further purification. ¹H NMR (400 MHz, d₆-DMSO) δ 12.82 (s, 1H), 9.28 (s, 1H), 8.28 (d, J=7.3 Hz, 2H), 7.89 (d, J=6.1 Hz, 1H), 7.74 (d, J=8.2 Hz, 2H), 7.59 (d, J=8.4 Hz, 1H), 7.51-7.44 (m, 4H), 7.25-7.20 (m, 3H), 5.79 (d, J=5.9 Hz, 1H), 4.34 (s, 2H), 3.77 (s, 3H), 3.47 (s, 3H), 2.84 (s, 3H). MS (ESI) m/z=542 [M+H]⁺.

Examples 144-152 following were prepared in a similar manner as Examples 142 or 143.

Example 144

N-(1-methyl-5-{methyl[2-({4-[(methylsulfonyl)methyl]phenyl}amino)pyrimidin-4-yl]amino}-1H-benzimidazol-2-yl)indoline-1-carboxamide

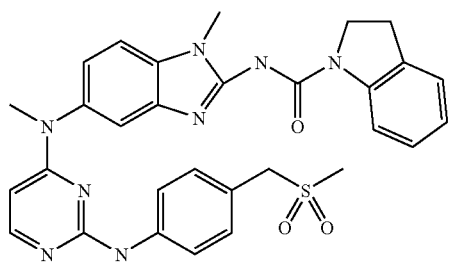

¹H NMR (300 MHz, d₆-DMSO) δ 12.23 (s, 1H), 9.25 (s, 1H), 7.86 (d, J=5.9 Hz, 1H), 7.74 (d, J=8.2 Hz, 2H), 7.65 (d, J=7.4 Hz, 1H), 7.45 (d, J=8.5 Hz, 1H), 7.32 (s, 1H), 7.21-7.12 (m, 5H), 6.85 (m, 1H), 5.75 (d, J=6.1 Hz, 1H), 4.33 (s, 2H), 3.60 (s, 3H), 3.48-3.43 (m, 5H), 3.06 (m, 2H), 2.83 (s, 3H). MS (ESI) m/z=583 [M+H]⁺.

Example 145

N-(5-tert-butylisoxazol-3-yl)-N'-(1-methyl-5-{methyl[2-({4-[(methylsulfonyl) methyl]phenyl}amino) pyrimidin-4-yl]amino}-1H-benzimidazol-2-yl)urea

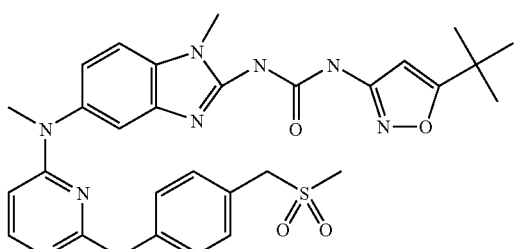

¹H NMR (400 MHz, d₆-DMSO) δ 12.22 (s, 1H), 9.79 (br s, 1H), 9.28 (s, 1H), 7.88 (d, J=5.9 Hz, 1H), 7.75 (d, J=8.2 Hz, 2H), 7.46 (d, J=8.4 Hz, 1H), 7.31 (br s, 1H), 7.22 (d, J=8.4 Hz, 2H), 7.16 (m, 1H), 6.67 (s, 1H), 5.76 (d, J=5.9 Hz, 1H), 4.35 (s, 2H), 3.58 (s, 3H), 3.45 (s, 3H), 2.85 (s, 3H), 1.30 (s, 9H). MS (ESI) m/z=604 [M+H]⁺.

Example 146

N-(1-methyl-5-{methyl[2-({4-[(methylsulfonyl)methyl]phenyl}amino)pyrimidin-4-yl]amino}-1H-benzimidazol-2-yl)-2-phenylacetamide

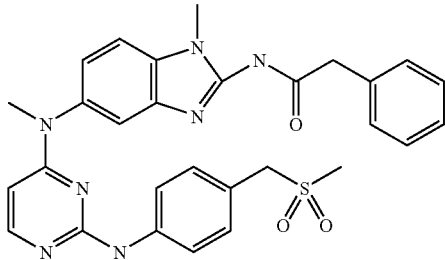

$^1$H NMR (400 MHz, d$_6$-DMSO) δ 10.92 (s, 1H), 9.24 (s, 1H), 7.85 (m, 1H), 7.73 (d, J=8.1 Hz, 2H), 7.59 (d, J=8.3 Hz, 1H), 7.52 (s, 1H), 7.38-7.29 (m, 5H), 7.19 (m, 3H), 5.75 (d, J=4.8 Hz, 1H), 4.34 (s, 2H), 3.81 (s, 3H), 3.58 (s, 3H), 3.48 (s, 3H), 2.84 (s, 3H). MS (ESI) m/z=556 [M+H]$^+$.

Example 147

N-(1-methyl-5-{methyl[2-({4-[(methylsulfonyl)methyl]phenyl}amino)pyrimidin-4-yl]amino}-1H-benzimidazol-2-yl)-1-phenylcyclopropanecarboxamide

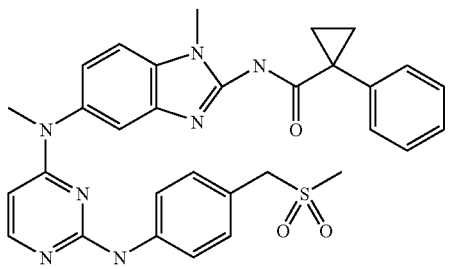

$^1$H NMR (400 MHz, d$_6$-DMSO) δ 12.44 (s, 1H), 9.26 (s, 1H), 7.87 (d, J=6.0 Hz, 1H), 7.72 (d, J=8.3 Hz, 2H), 7.45 (d, J=8.4 Hz, 1H), 7.38 (d, J=7.3 Hz, 2H), 7.31-7.27 (m, 3H), 7.21-7.16 (m, 4H), 5.75 (d, J=5.8 Hz, 1H), 4.34 (s, 2H), 3.43 (s, 6H), 2.84 (s, 3H), 1.60 (m, 2H), 1.10 (m, 2H). MS (ESI) m/z=582 [M+H]$^+$.

Example 148

N-(1-methyl-5-{methyl[2-({4-[(methylsulfonyl)methyl]phenyl}amino)pyrimidin-4-yl]amino}-1H-benzimidazol-2-yl)isonicotinamide

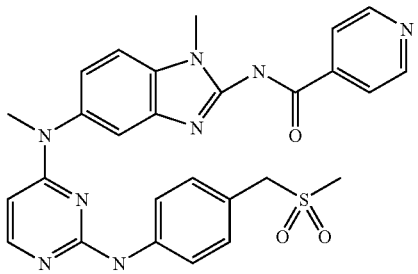

$^1$H NMR (400 MHz, d$_6$-DMSO) δ 12.92 (s, 1H), 9.29 (s, 1H), 8.75 (d, J=5.7 Hz, 2H), 8.11 (d, J=5.7 Hz, 2H), 7.90 (d, J=6.1 Hz, 1H), 7.74 (d, J=8.4 Hz, 2H), 7.64 (d, J=8.4 Hz, 1H), 7.47 (s, 1H), 7.29 (m, 1H), 7.21 (d, J=8.4 Hz, 2H), 5.81 (d, J=5.9 Hz, 1H), 4.34 (s, 2H), 3.80 (s, 3H), 3.48 (s, 3H), 2.85 (s, 3H). MS (ESI) m/z=543 [M+H]$^+$.

Example 149

N-(1-methyl-5-{methyl[2-({4-[(methylsulfonyl)methyl]phenyl}amino)pyrimidin-4-yl]amino}-1H-benzimidazol-2-yl)cyclohexanecarboxamide

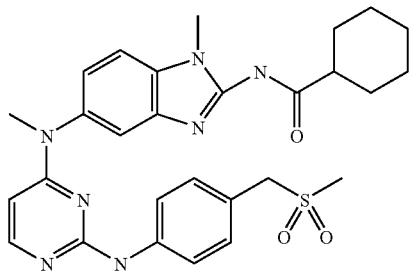

$^1$H NMR (400 MHz, d$_6$-DMSO) δ 10.56 (s, 1H), 9.23 (s, 1H), 7.85 (d, J=5.3 Hz, 1H), 7.85 (d, J=7.3 Hz, 2H), 7.73 (d, J=8.4 Hz, 1H), 7.60 (d, J=8.4 Hz, 1H), 7.51 (s, 1H), 7.19-7.18 (m, 3H), 5.81 (d, J=4.9 Hz, 1H), 4.34 (s, 2H), 3.60 (s, 3H), 3.48 (s, 3H), 2.85 (s, 3H), 1.92 (m, 2H), 1.77 (m, 2H), 1.66 (m, 1H), 1.47 (m, 2H), 1.36-1.20 (m, 4H). MS (ESI) m/z=548 [M+H]$^+$.

Example 150

2-(benzyloxy)-N-(1-methyl-5-{methyl[2-({4-[(methylsulfonyl)methyl]phenyl}amino)pyrimidin-4-yl]amino}-1H-benzimidazol-2-yl)acetamide

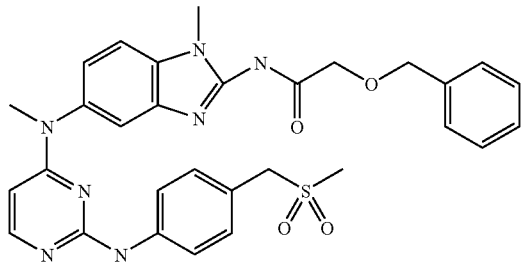

$^1$H NMR (400 MHz, d$_6$-DMSO) δ 8.84 (s, 1H), 7.87 (d, J=5.5 Hz, 1H), 7.73 (d, J=8.6 Hz, 2H), 7.53 (d, J=8.0 Hz, 1H), 7.47-7.18 (m, 10H), 5.81 (d, J=5.4 Hz, 1H), 4.69 (s, 2H), 4.31 (s, 2H), 3.64 (s, 3H), 3.48 (s, 3H), 3.47 (s, 2H), 2.85 (s, 3H). MS (ESI) m/z=586 [M+H]$^+$.

Example 151

2-(3-methylisoxazol-5-yl)-N-(1-methyl-5-{methyl[2-({4-[(methylsulfonyl)methyl]phenyl}amino)pyrimidin-4-yl]amino}-1H-benzimidazol-2-yl)acetamide

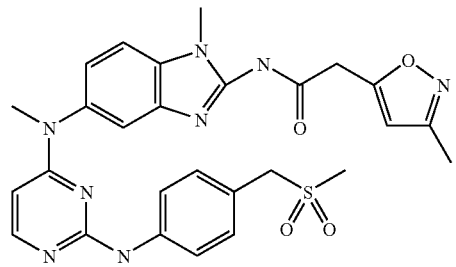

$^1$H NMR (400 MHz, d$_6$-DMSO) δ 8.84 (s, 1H), 7.88 (d, J=6.2 Hz, 1H), 7.72 (d, J=8.4 Hz, 2H), 7.53 (d, J=8.6 Hz, 1H), 7.46 (s, 1H), 7.23-7.19 (m, 3H), 6.23 (s, 1H), 5.82 (d, J=5.7 Hz, 1H), 4.30 (s, 2H), 3.63 (s, 3H), 3.48-3.47 (m, 5H), 2.82 (s, 3H), 2.23 (s, 3H). MS (ESI) m/z=561 [M+H]$^+$.

Example 152

3-[(dimethylamino)methyl]-N-(1-methyl-5-{methyl[2-({4-[(methylsulfonyl)methyl]phenyl}amino)pyrimidin-4-yl]amino}-1H-benzimidazol-2-yl)benzamide

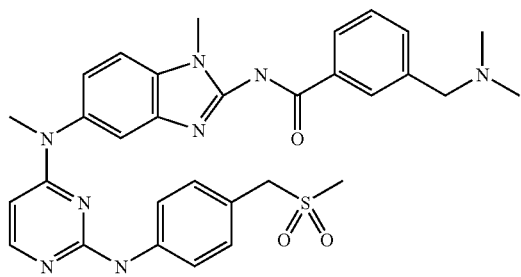

$^1$H NMR (400 MHz, $d_6$-DMSO) δ 8.86 (s, 1H), 8.16-8.14 (m, 2H), 7.89 (d, J=5.8 Hz, 1H), 7.74 (d, J=8.4 Hz, 2H), 7.55-7.41 (m, 4H), 7.24-7.19 (m, 3H), 5.85 (d, J=5.9 Hz, 1H), 4.31 (s, 2H), 3.75 (s, 3H), 3.50 (s, 2H), 3.59 (s, 3H), 2.82 (s, 3H), 2.22 (s, 6H). MS (ESI) m/z=599 [M+H]$^+$.

Example 153

N-({[3-(4-Methanesulfonylmethyl-phenylamino)-phenyl]-methyl-amino}-methyl-1H-benzoimidazol-2-yl)-C-thiophen-2-yl-acetamide

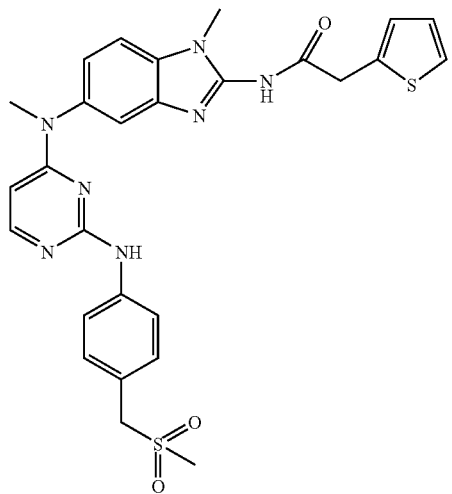

To a solution of {[(2-Chloro-pyrimidin-4-yl)-methyl-amino]-methyl-H-benzoimidazol-2-yl}-carbamic acid tert-butyl ester (3.88 g, 10 mmol) and 4-[(methylsulfonyl)methyl]aniline (1.9 g, 12 mmol) in isopropanol (100 ml) was added a solution of HCl (7 drop, 4 M in dioxane) and the reaction was heated to 85° C. After 48 hours, the reaction mixture was concentrated in vacuo and neutralized with the addition of saturated NaHCO$_3$ solution. The mixture was filtered to give N$^5$-[3-(4-Methanesulfonylmethyl-phenylamino)-phenyl]-1,N$^5$-dimethyl-1H-benzoimidazole-2,5-diamine as an off white solid, which was used to produce the titled compound.

To a solution of thiophen-2-yl-acetic acid (78 mg, 0.58 mmol) and carbonyldiimidazole (88 mg, 0.55 mmol) in DMF, which was stirred at rt for 15 mins, was added a solution of N$^5$-[3-(4-Methanesulfonylmethyl-phenylamino)-phenyl]-1, N$^5$-dimethyl-1H-benzoimidazole-2,5-diamine (120 mg, 0.29 mmol) and triethylamine (40 µl, 0.29 mmol) in DMF. The reaction mixture was stirred at rt for 16 h and N-({[3-(4-Methanesulfonylmethyl-phenylamino)-phenyl]-methyl-amino}-methyl-1H-benzoimidazol-2-yl)-C-thiophen-2-yl-acetamide (54 mg, 17%) was purified with reverse phase HPLC. $^1$H NMR (400 MHz, $d_6$-DMSO) δ 9.23 (s, 1H), 7.74-7.84 (m, 4H), 7.46-6.95 (m, 8H), 5.73 (d, J=5.6 Hz, 1H), 4.35 (s, 2H), 3.91 (s, 2H), 3.60 (s, 3H), 3.46 (s, 3H), 2.85 (s, 3H). MS (ESI) m/z=562 [M+H]$^+$, LC/MS Rt(min) 1.47.

Example 154

C-Fluoro-N-({[3-(3-methanesulfonylmethyl-phenylamino)-phenyl]-methyl-amino}-methyl-1H-benzoimidazol-2-yl)-trifluoromethyl-benzamide

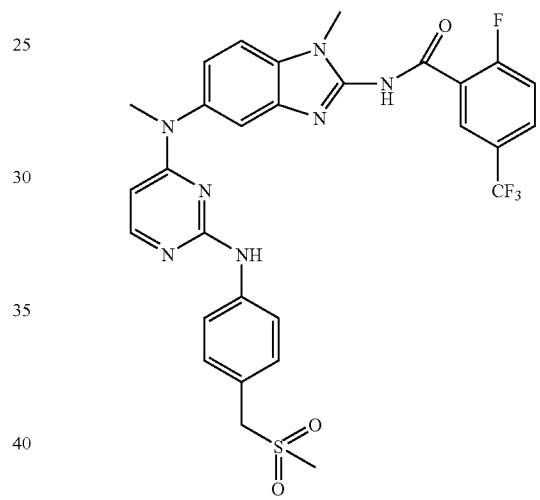

To a solution of {[(2-Chloro-pyrimidin-4-yl)-methyl-amino]-methyl-H-benzoimidazol-2-yl}-carbamic acid tert-butyl ester (2.86 g, 7.4 mmol) and 3-[(methylsulfonyl)methyl]aniline (1.5 g, 8.1 mmol) in isopropanol (70 ml) was added a solution of HCl (1 drop, 4 M in dioxane) and the reaction was heated to 70° C. After 16 hours, the reaction mixture was concentrated in vacuo and neutralized with the addition of saturated NaHCO$_3$ solution. The mixture was filtered to give N$^5$-[3-(3-Methanesulfonylmethyl-phenylamino)-phenyl]-1,N$^5$-dimethyl-1H-benzoimidazole-2,5-diamine as an off white solid, which was used to produce the titled compound.

To the solution of N$^5$-[3-(3-Methanesulfonylmethyl-phenylamino)-phenyl]-1, N$^5$-dimethyl-1H-benzoimidazole-2,5-diamine (36 mg, 0.083 mmol) in NMP was added fluoro-trifluoromethyl-benzoyl chloride (38 µl, 0.25 mmol). The reaction mixture was stirred at rt for 24 hrs and then purified with Gilson HPLC to give C-Fluoro-N-({[3-(3-methanesulfonylmethyl-phenylamino)-phenyl]-methyl-amino}-methyl-1H-benzoimidazol-2-yl)-trifluoromethyl-benzamide (20 mg, 38%). MS (ESI) m/z=628 [M+H]$^+$, LC/MS Rt (min) 2.03.

The following compounds of Examples 155-XXX of Formula I$^c$ were prepared according to the procedures of Examples 153 or 154 with appropriate starting materials.

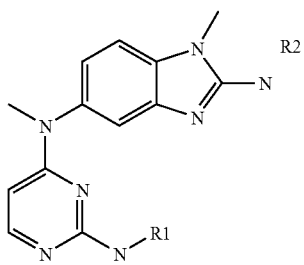

I<sup>c</sup>

| Example | R1 | R2 | LC/MS Rt (min) | LC/MS (m/z) [M + H]$^+$ |
|---|---|---|---|---|
| Example 155 | 3-(methylsulfonylmethyl)phenyl | 1-(3,4-difluorophenyl)ethanone | 2.32 | 578 |
| Example 156 | 3-(methylsulfonylmethyl)phenyl | 1-(3,5-bis(trifluoromethyl)phenyl)ethanone | 2.33 | 678 |
| Example 157 | 3-(methylsulfonylmethyl)phenyl | 1-cyclohexylethanone | 1.43 | 548 |
| Example 158 | 3-(methylsulfonylmethyl)phenyl | 1-(3-methylphenyl)ethanone | 1.80 | 556 |
| Example 159 | 3-(methylsulfonylmethyl)phenyl | 1-(4-methoxyphenyl)ethanone | 1.68 | 572 |
| Example 160 | 3-(methylsulfonylmethyl)phenyl | 1-(2-chloro-5-(trifluoromethyl)phenyl)propan-2-one | 1.81 | 658 |
| Example 161 | 3-(methylsulfonylmethyl)phenyl | 1-(3,5-bis(trifluoromethyl)phenyl)propan-2-one | 1.90 | 692 |

-continued

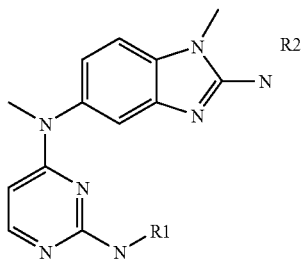

I<sup>c</sup>

| Example | R1 | R2 | LC/MS Rt (min) | LC/MS (m/z) [M + H]+ |
|---|---|---|---|---|
| Example 162 | 3-(methylsulfonylmethyl)phenyl | 1-(3-(trifluoromethylthio)phenyl)propan-2-one | 1.73 | 656 |
| Example 163 | 3-(methylsulfonylmethyl)phenyl | 1-(2,4-bis(trifluoromethyl)phenyl)propan-2-one | 1.88 | 692 |
| Example 164 | 3-(methylsulfonylmethyl)phenyl | 1-(2-fluoro-5-(trifluoromethyl)phenyl)propan-2-one | 1.66 | 642 |
| Example 165 | 3-(methylsulfonylmethyl)phenyl | 1-(1H-benzo[d][1,2,3]triazol-5-yl)ethanone | 1.60 | 583 |
| Example 166 | 3-(methylsulfonylmethyl)phenyl | 1-(1H-benzo[d]imidazol-5-yl)ethanone | 1.38 | 582 |
| Example 167 | 3-(methylsulfonylmethyl)phenyl | 1-(thiophen-2-yl)ethanone | 1.77 | 548 |
| Example 168 | 3-(methylsulfonylmethyl)phenyl | 1-(thiophen-3-yl)ethanone | 1.68 | 548 |
| Example 169 | 3-(methylsulfonylmethyl)phenyl | 1-(thiophen-2-yl)propan-2-one | 1.43 | 562 |

-continued

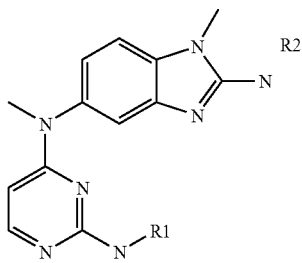

I<sup>e</sup>

| Example | R1 | R2 | LC/MS Rt (min) | LC/MS (m/z) [M + H]+ |
|---|---|---|---|---|
| Example 170 | 4-methylbenzyl-SO2 | 1-(3-methylthiophen-2-yl)ethanone | 1.84 | 562 |
| Example 171 | 4-methylbenzyl-SO2 | 1-(furan-3-yl)ethanone | 1.37 | 532 |
| Example 172 | 4-methylbenzyl-SO2 | 1-(3-methylfuran-2-yl)ethanone | 1.53 | 546 |
| Example 173 | 4-methylbenzyl-SO2 | 1-(3-methylisoxazol-5-yl)propan-2-one | 1.26 | 561 |
| Example 174 | 4-methylbenzyl-SO2 | 1-(2-chloro-5-(trifluoromethyl)phenyl)propan-2-one | 1.70 | 658 |
| Example 175 | 4-methylbenzyl-SO2 | 1-(3-(trifluoromethylthio)phenyl)propan-2-one | 1.74 | 656 |
| Example 176 | 4-methylbenzyl-SO2 | 1-(2-fluoro-5-(trifluoromethyl)phenyl)propan-2-one | 1.54 | 642 |

-continued

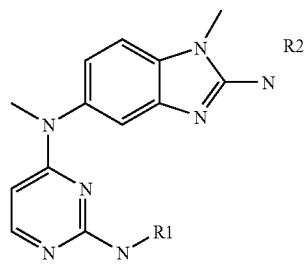

I<sup>c</sup>

| Example | R1 | R2 | LC/MS Rt (min) | LC/MS (m/z) [M + H]+ |
|---|---|---|---|---|
| Example 177 | 4-methylbenzyl-SO2- | tert-butyl-CH2-C(O)- | 1.44 | 536 |
| Example 178 | 4-methylbenzyl-SO2- | dipropyl-CH-C(O)- | 1.59 | 564 |
| Example 179 | 4-methylbenzyl-SO2- | isopropyl-C(O)- | 1.22 | 508 |
| Example 180 | 4-methylbenzyl-SO2- | cyclopropyl-C(O)- | 1.33 | 506 |
| Example 181 | 4-methylbenzyl-SO2- | 4-methoxyphenyl-C(O)- | 1.57 | 572 |
| Example 182 | 4-methylbenzyl-SO2- | 4-methoxyphenyl-C(O)- | 1.66 | 573 |
| Example 183 | 4-methylbenzyl-SO2- | 2-furyl-C(O)- | 1.35 | 532 |
| Example 184 | 2-methyl-5-sulfamoylphenyl- | 2-thienyl-CH2-C(O)- | 1.49 | 563 |

-continued

I<sup>c</sup>

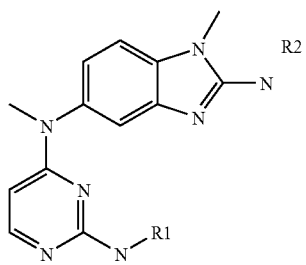

| Example | R1 | R2 | LC/MS Rt (min) | LC/MS (m/z) [M + H]+ |
|---|---|---|---|---|
| Example 185 | 2,5-dimethylphenyl-SO2NH2 | 2-chloro-5-(trifluoromethyl)phenyl acetone | 1.65 | 660 |
| Example 186 | 3-methylphenyl-SO2-morpholine | 4-methoxyphenyl ketone | 1.82 | 629 |
| Example 187 | 3-methylphenyl-SO2-morpholine | 2-thienyl acetone | 1.52 | 619 |
| Example 188 | 3-methylphenyl-SO2-morpholine | 2-thienyl ketone | 1.79 | 605 |
| Example 189 | 3-methylphenyl-SO2-morpholine | 2-furyl ketone | 1.58 | 589 |
| Example 190 | 3-methylphenyl-CH2-SO2-methyl | 3-methylisoxazol-5-yl acetone | 1.42 | 561 |
| Example 191 | 3-methylphenyl-CH2-SO2-methyl | 2-furyl ketone | 1.60 | 532 |

-continued

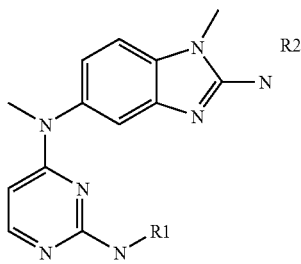

| Example | R1 | R2 | LC/MS Rt (min) | LC/MS (m/z) [M + H]+ |
|---|---|---|---|---|
| Example 192 | 3-(morpholinosulfonyl)phenyl | (3-methylisoxazol-5-yl)acetyl | 1.51 | 618 |
| Example 193 | 3-(methylsulfonylmethyl)phenyl | 3-methylfuran-2-carbonyl | 1.65 | 546 |
| Example 194 | 3-(4-methylpiperazin-1-ylsulfonyl)phenyl | 2-(thiophen-2-yl)acetyl | 1.34 | 632 |
| Example 195 | 3-(4-methylpiperazin-1-ylsulfonyl)phenyl | thiophene-2-carbonyl | 1.53 | 618 |
| Example 196 | 3-(4-methylpiperazin-1-ylsulfonyl)phenyl | furan-2-carbonyl | 1.47 | 602 |
| Example 197 | 3-(4-methylpiperazin-1-ylsulfonyl)phenyl | (3-methylisoxazol-5-yl)acetyl | 1.61 | 631 |
| Example 198 | 3-(methylsulfonylmethyl)phenyl | 3,3-dimethylbutanoyl | 1.36 | 536 |

-continued

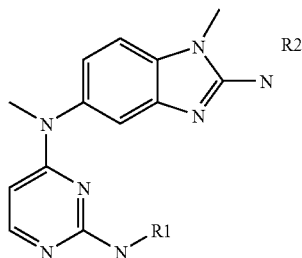

I<sup>c</sup>

| Example | R1 | R2 | LC/MS Rt (min) | LC/MS (m/z) [M + H]<sup>+</sup> |
|---|---|---|---|---|
| Example 199 | 3-(methylsulfonylmethyl)phenyl | propanoyl | 1.36 | 494 |
| Example 200 | 3-(methylsulfonylmethyl)phenyl | hexanoyl | 1.34 | 522 |
| Example 201 | 3-(methylsulfonylmethyl)phenyl | pentanoyl | 1.29 | 508 |
| Example 202 | 4-(methylsulfonylmethyl)phenyl | phenylacetyl | 1.57 | 557.2 |
| Example 203 | 4-(methylsulfonylmethyl)phenyl | 1-phenylcyclopropanecarbonyl | 1.65 | 582.4 |
| Example 204 | 4-(methylsulfonylmethyl)phenyl | 1-(2,5-difluorophenyl)cyclopropanecarbonyl | 1.92 | 618.2 |
| Example 205 | 4-(methylsulfonylmethyl)phenyl | 1-(4-chlorophenyl)cyclopropanecarbonyl | 1.92 | 616.0 |
| Example 206 | 4-(methylsulfonylmethyl)phenyl | (4-fluorophenyl)acetyl | 1.67 | 574.2 |
| Example 207 | 4-(methylsulfonylmethyl)phenyl | [3,5-bis(trifluoromethyl)phenyl]acetyl | 1.90 | 691.8 |

-continued

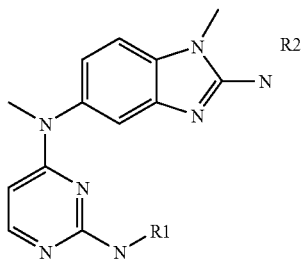

I<sup>e</sup>

| Example | R1 | R2 | LC/MS Rt (min) | LC/MS (m/z) [M + H]+ |
|---|---|---|---|---|
| Example 208 | 4-methylbenzyl methyl sulfone | 1-(3,4-dichlorophenyl)propan-2-one | 1.77 | 624.0 |
| Example 209 | 3-methylbenzyl methyl sulfone | 1-(1-(2,5-difluorophenyl)cyclopropyl)ethanone | 1.77 | 618.2 |
| Example 210 | 3-methylbenzyl methyl sulfone | 1-(2,5-difluorophenyl)propan-2-one | 1.47 | 592.0 |
| Example 211 | 3-methylbenzyl methyl sulfone | 1-(3,4-dichlorophenyl)propan-2-one | 1.67 | 624.2 |
| Example 212 | 4-methoxy-3-methylphenyl ethyl sulfone | 1-(1-(2,5-difluorophenyl)cyclopropyl)ethanone | 1.89 | 648.2 |
| Example 213 | 4-methoxy-3-methylphenyl ethyl sulfone | 1-(2,5-difluorophenyl)propan-2-one | 1.54 | 622.2 |
| Example 214 | 4-methoxy-3-methylphenyl ethyl sulfone | 1-(1-(3,4-dichlorophenyl)cyclopropyl)ethanone | 2.04 | 880.2 |
| Example 215 | 4-methoxy-3-methylphenyl ethyl sulfone | 1-(3,4-dichlorophenyl)propan-2-one | 1.72 | 654.0 |
| Example 216 | 2,5-dimethylbenzene sulfonamide | 1-(1-(2,5-difluorophenyl)cyclopropyl)ethanone | 1.75 | 619.2 |

-continued

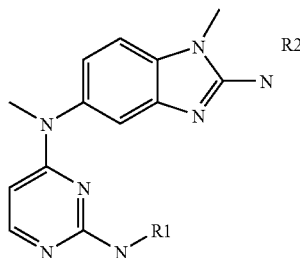

| Example | R1 | R2 | LC/MS Rt (min) | LC/MS (m/z) [M + H]+ |
|---|---|---|---|---|
| Example 217 | 2-methyl-5-SO₂NH₂ phenyl | 1-(3,4-dichlorophenyl)cyclopropyl ketone | 1.90 | 651.2 |
| Example 218 | 2-methyl-5-SO₂NH₂ phenyl | 3,4-dichlorophenylacetone | 1.62 | 625.0 |
| Example 219 | 4-(methylsulfonylmethyl)phenyl | 2,3-dimethoxyphenylacetone | 1.62 | 615.8 |
| Example 220 | 4-(methylsulfonylmethyl)phenyl | 2-methoxyphenylacetone | 1.67 | 586.2 |
| Example 221 | 4-(methylsulfonylmethyl)phenyl | 3-methoxyphenylacetone | 1.65 | 586.2 |
| Example 222 | 4-(methylsulfonylmethyl)phenyl | 4-methoxyphenylacetone | 1.64 | 586.0 |
| Example 223 | 4-(methylsulfonylmethyl)phenyl | 2-fluorophenylacetone | 1.65 | 574.2 |
| Example 224 | 4-(methylsulfonylmethyl)phenyl | 3-fluorophenylacetone | 1.75 | 574.0 |
| Example 225 | 4-(methylsulfonylmethyl)phenyl | 2,6-difluorophenylacetone | 1.69 | 592.0 |

-continued

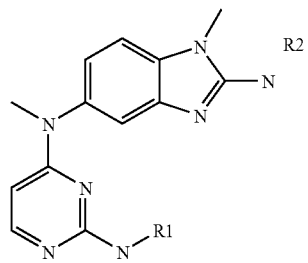

I<sup>c</sup>

| Example | R1 | R2 | LC/MS Rt (min) | LC/MS (m/z) [M + H]+ |
|---|---|---|---|---|
| Example 226 | 4-methylbenzyl-SO2- | 2,3-difluorophenyl ketone | 1.70 | 592.0 |
| Example 227 | 4-methylbenzyl-SO2- | 3,4-dimethoxyphenyl ketone | 1.42 | 616.2 |
| Example 228 | 2,5-dimethylphenyl-SO2NH2 | 2,5-difluorophenyl ketone | 1.95 | 593.2 |
| Example 229 | 3-methylbenzyl-SO2- | 1-(3,4-dichlorophenyl)cyclopropyl ketone | 2.05 | 650.2 |
| Example 230 | 4-methylbenzyl-SO2- | 2-chlorophenyl ketone | 1.64 | 590.0 |
| Example 231 | 4-methylbenzyl-SO2- | 3-chlorophenyl ketone | 1.63 | 590.0 |
| Example 232 | 4-methylbenzyl-SO2- | 4-chlorophenyl ketone | 1.62 | 590.0 |
| Example 233 | 4-methylbenzyl-SO2- | 3,5-dimethoxyphenyl ketone | 1.59 | 616.0 |
| Example 234 | 4-methylbenzyl-SO2- | 2,5-dimethoxyphenyl ketone | 1.54 | 615.8 |

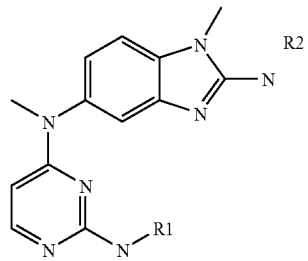

| Example | R1 | R2 | LC/MS Rt (min) | LC/MS (m/z) [M + H]+ |
|---|---|---|---|---|
| Example 235 | 4-methylphenyl-CH2-SO2- | 2-chloro-5-chlorophenyl-CH2-C(O)- | 1.74 | 624.0 |
| Example 236 | 4-methylphenyl-CH2-SO2- | phenyl-CH(iPr)-C(O)- | 1.77 | 596.0 |
| Example 237 | 4-methylphenyl-CH2-SO2- | 2,5-dimethylphenyl-CH2-C(O)- | 1.63 | 583.4 |
| Example 238 | 4-methylphenyl-CH2-SO2- | phenyl-C(CH3)2-C(O)- | 1.74 | 584.0 |
| Example 239 | 4-methylphenyl-CH2-SO2- | 3,4-methylenedioxyphenyl-CH2-C(O)- | 1.45 | 600.2 |

Example 155

Difluoro-N-({[2-(3-methanesulfonylmethyl-phenylamino)-pyrimidin-4-yl]-methyl-amino}-methyl-1H-benzoimidazol-2-yl)-benzamide The titled compound was prepared following the procedure of Example 154 with 3,4-difluoro-benzoyl chloride, 3-[(methylsulfonyl)methyl]aniline and {[(2-Chloro-pyrimidin-4-yl)-methyl-amino]-methyl-H-benzoimidazol-2-yl}-carbamic acid tert-butyl ester. MS (ESI) m/z=578 [M+H]+.

Example 156

N-({[2-(3-methanesulfonylmethyl-phenylamino)-pyrimidin-4-yl]-methyl-amino}-methyl-1H-benzoimidazol-2-yl)-3,5-bis-trifluoromethyl-benzamide The titled compound was prepared following the procedure of Example 154 with Bis-trifluoromethyl-benzoyl chloride, 3-[(methylsulfonyl)methyl]aniline and {[(2-Chloro-pyrimidin-4-yl)-methyl-amino]-methyl-H-benzoimidazol-2-yl}-carbamic acid tert-butyl ester. MS (ESI) m/z=678 [M+H]+.

Example 157

Cyclohexanecarboxylic acid ({[2-(3-methanesulfonylmethyl-phenylamino)-pyrimidin-4-yl]-methyl-amino}-methyl-1H-benzoimidazol-2-yl)-amide The titled compound was prepared following the procedure of Example 154 with Cyclohexanecarboxylic acid chloride, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=548 [M+H]+.

Example 158

N-({[2-(3-Methanesulfonylmethyl-phenylamino)-pyrimidin-4-yl]-methyl-amino}-methyl-1H-benzoimidazol-2-yl)-methyl-benzamide The titled compound was prepared following the procedure of Example 154 with 3-Methyl-benzoyl chloride, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=556 [M+H]$^+$.

Example 159

N-({[2-(3-Methanesulfonylmethyl-phenylamino)-pyrimidin-4-yl]-methyl-amino}-methyl-1H-benzoimidazol-2-yl)-4-methoxy-benzamide The titled compound was prepared following the procedure of Example 153 with 4-Methoxy-benzoic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester. MS (ESI) m/z=572 [M+H]$^+$.

Example 160

C-(Chloro-trifluoromethyl-phenyl)-N-({[2-(3-methanesulfonylmethyl-phenylamino)-pyrimidin-4-yl]-methyl-amino}-methyl-1H-benzoimidazol-2-yl)-acetamide The titled compound was prepared following the procedure of Example 153 with (Chloro-trifluoromethyl-phenyl)-acetic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester. MS (ESI) m/z=658 [M+H]$^+$.

Example 161

(3,5-Bis-trifluoromethyl-phenyl)-N-({[2-(3-methanesulfonylmethyl-phenylamino]-pyrimidin-4-yl]-methyl-amino}-methyl-1H-benzoimidazol-2-yl)-acetamide The titled compound was prepared following the procedure of Example 153 with 3,5-Bis-trifluoromethyl-acetic acid, 3-[(methylsulfonyl)methyl]aniline and {[(2Chloro-pyrimidin-4-yl)-methyl-amino]-methyl-H-benzoimidazol-2-yl}-carbamic acid tert-butyl ester in pyridine. MS (ESI) m/z=692 [M+H]$^+$.

Example 162

N-(5-{[2-(3-Methanesulfonylmethyl-phenylamino)-pyrimidin-4-yl]-methyl-amino}-1-methyl-1H-benzoimidazol-2-yl)-2-(3-trifluoromethylsulfanyl-phenyl)-acetamide The titled compound was prepared following the procedure of Example 153 with (3-Trifluoromethylsulfanyl-phenyl)-aceticacid, 3[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=656 [M+H]$^+$.

Example 163

(2,4-Bis-trifluoromethyl-phenyl)-N-({[2-(3-methanesulfonylmethyl-phenylamino)-pyrimidin-4-yl]-methyl-amino}-methyl-1H-benzoimidazol-2-yl)-acetamide The titled compound was prepared following the procedure of Example 153 with 2,4-Bis-trifluoromethyl-phenyl acetic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=692 [M+H]$^+$.

Example 164

(2-Fluoro-5-trifluoromethyl-phenyl)-N-({[2-(3-methanesulfonylmethyl-phenylamino)-pyrimidin-4-yl]-methyl-amino}-methyl-1H-benzoimidazol-2-yl)-acetamide The titled compound was prepared following the procedure of Example 153 with 2-fluoro-5-trifluoromethyl-phenylaceticacetic, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=642 [M+H]$^+$.

Example 165

3H-Benzotriazole-5-carboxylic acid ({[2-(3-methanesulfonylmethyl-phenylamino)-pyrimidin-4-yl]-methyl-amino}-methyl-1H-benzoimidazol-2-yl)-amide The titled compound was prepared following the procedure of Example 153 with 3H-Benzotriazole-5-carboxylic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=583 [M+H]$^+$.

Example 166

3H-Benzoimidazole-5-carboxylic acid ({[2-(3-methanesulfonylmethyl-phenylamino)-pyrimidin-4-yl]-methyl-amino}-methyl-1H-benzoimidazol-2-yl)-amide The titled compound was prepared following the procedure of Example 153 with 3H-Benzoimidazole-5-carboxylic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=582 [M+H]$^+$.

Example 167

Thiophene-2-carboxylic acid ({[2-(3-methanesulfonylmethyl-phenylamino)-pyrimidin-4-yl]-methyl-amino}-methyl-1H-benzoimidazol-2-yl)-amide The titled compound was prepared following the procedure of Example 153 with Thiophene-2-carboxylic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=548 [M+H]$^+$.

Example 168

Thiophene-3-carboxylic acid ({[2-(3-methanesulfonylmethyl-phenylamino)-pyrimidin-4-yl]-methyl-amino}-methyl-1H-benzoimidazol-2-yl)-amide The titled compound was prepared following the procedure of Example 153 with Thiophene-3-carboxylic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=548 [M+H]$^+$.

Example 169

N-({[2-(3-Methanesulfonylmethyl-phenylamino)-pyrimidin-4-yl]-methyl-amino}-methyl-1H-benzoimidazol-2-yl)-C-thiophen-2-yl-acetamide The titled compound was prepared following the procedure of Example 153 with Thiophen-2-yl-acetic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=562 [M+H]$^+$.

Example 170

3-Methyl-thiophene-2-carboxylic acid ({[2-(4-methanesulfonylmethyl-phenylamino)-pyrimidin-4-yl]-methyl-amino}-methyl-1H-benzoimidazol-2-yl)-amide The titled compound was prepared following the procedure of Example 153 with 3-Methyl-thiophene-2-carboxylic acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=562 [M+H]$^+$.

Example 171

Furan-3-carboxylic acid ({[2-(4-methanesulfonylmethyl-phenylamino)-pyrimidin-4-yl]-methyl-amino}-methyl-1H-benzoimidazol-2-yl)-amide The titled compound was prepared following the procedure of Example 153 with Furan-3-carboxylic acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=532 [M+H]$^+$.

Example 172

3-Methyl-furan-2-carboxylic acid ({[2-(4-methanesulfonylmethyl-phenylamino)-pyrimidin-4-yl]-methyl-amino}-methyl-1H-benzoimidazol-2-yl)-amide The titled compound was prepared following the procedure of Example 153 with 3-Methyl-furan-2-carboxylic acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=546 [M+H]$^+$.

Example 173

N-({[2-(4-Methanesulfonylmethyl-phenylamino)-pyrimidin-4-yl]-methyl-amino}-methyl-1H-benzoimidazol-2-yl)-2-(3-methyl-isoxazol-5-yl)-acetamide The titled compound was prepared following the procedure of Example 153 with 3-methyl-isoxazol-5-yl acetic acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=561 [M+H]$^+$.

Example 174

C-(Chloro-trifluoromethyl-phenyl)-N-({[2-(4-methanesulfonylmethyl-phenylamino)-pyrimidin-4-yl]-methyl-amino}-methyl-1H-benzoimidazol-2-yl)-acetamide The titled compound was prepared following the procedure of Example 153 with 2-Chloro-5-trifluoromethyl-phenyl acetic acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=658 [M+H]$^+$.

Example 175

N-(5-{[2-(4-Methanesulfonylmethyl-phenylamino)-pyrimidin-4-yl]-methyl-amino}-1-methyl-1H-benzoimidazol-2-yl)-2-(3-trifluoromethylsulfanyl-phenyl)-acetamide The titled compound was prepared following the procedure of Example 153 with 3-trifluoromethylsulfanyl-phenyl acetic acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=656 [M+H]$^+$.

Example 176

C-(Fluoro-trifluoromethyl-phenyl)-N-({[2-(4-methanesulfonylmethyl-phenylamino)-pyrimidin-4-yl]-methyl-amino}-methyl-1H-benzoimidazol-2-yl)-acetamide The titled compound was prepared following the procedure of Example 153 with 2-Fluoro-5-trifluoromethyl-phenyl acetic acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=642 [M+H]$^+$.

Example 177

N-({[2-(4-Methanesulfonylmethyl-phenylamino)-pyrimidin-4-yl]-methyl-amino}-methyl-1H-benzoimidazol-2-yl)-dimethyl-butyramide The titled compound was prepared following the procedure of Example 153 with 3,3-Dimethyl-butyric acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=536 [M+H]$^+$.

Example 178

2-Propyl-pentanoic acid ({[2-(4-methanesulfonylmethyl-phenylamino)-pyrimidin-4-yl]-methyl-amino}-methyl-1H-benzoimidazol-2-yl)-amide The titled compound was prepared following the procedure of Example 153 with 2-Propyl-pentanoic acid, 4-[(methylsulfonyl)methyl]aniline and {[(2-Chloro-pyrimidin-4- yl)-methyl-amino]-methyl-H-benzoimidazol-2-yl}-carbamic acid tert-butyl ester in pyridine. MS (ESI) m/z=564 [M+H]⁺.

Example 179

N-({[2-(4-Methanesulfonylmethyl-phenylamino)-pyrimidin-4-yl]-methyl-amino}-methyl-1H-benzoimidazol-2-yl)-isobutyramide The titled compound was prepared following the procedure of Example 153 with isobutyric acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=508 [M+H]⁺.

Example 180

Cyclopropanecarboxylic acid ({[2-(4-methanesulfonylmethyl-phenylamino)-pyrimidin-4-yl]-methyl-amino}-methyl-1H-benzoimidazol-2-yl)-amide The titled compound was prepared following the procedure of Example 153 with Cyclopropanecarboxylic acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=506 [M+H]⁺.

Example 181

N-({[2-(4-Methanesulfonylmethyl-phenylamino)-pyrimidin-4-yl]-methyl-amino}-methyl-1H-benzoimidazol-2-yl)-4-methoxy-benzamide The titled compound was prepared following the procedure of Example 153 with 4-methoxy-benzoic acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=572 [M+H]⁺.

Example 182

4-Methoxy-N-(methyl-{methyl-[2-(4-methyl-3-sulfamoyl-phenylamino)-pyrimidin-4-yl]-amino}-1H-benzoimidazol-2-yl)-benzamide The titled compound was prepared following the procedure of Example 153 with 4-methoxy-benzoic acid, 5-Amino-2-methyl-benzenesulfonamide and {[(2-Chloro-pyrimidin-4-yl)-methyl-amino]-methyl-H-benzoimidazol-2-yl}-carbamic acid tert-butyl ester in pyridine. MS (ESI) m/z=573 [M+H]⁺.

Example 183

Furan-2-carboxylic acid ({[2-(4-methanesulfonylmethyl-phenylamino)-pyrimidin-4-yl]-methyl-amino}-methyl-1H-benzoimidazol-2-yl)-amide The titled compound was prepared following the procedure of Example 153 with Furan-2-carboxylic acid, 4-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=532 [M+H]⁺.

Example 184

N-(Methyl-{methyl-[2-(4-methyl-3-sulfamoyl-phenylamino)-pyrimidin-4-yl]-amino}-1H-benzoimidazol-2-yl)-C-thiophen-2-yl-acetamide The titled compound was prepared following the procedure of Example 153 with thiophen-2-yl-acetic acid, 5-Amino-2-methyl-benzenesulfonamide and {[(2-Chloro-pyrimidin-4-yl)-methyl-amino]-methyl-H-benzoimidazol-2-yl}-carbamic acid tert-butyl ester in pyridine. MS (ESI) m/z=563 [M+H]⁺.

Example 185

C-(Chloro-trifluoromethyl-phenyl)-N-(methyl-{methyl-[2-(4-methyl-3-sulfamoyl-phenylamino)-pyrimidin-4-yl]-amino}-1H-benzoimidazol-2-yl)-acetamide The titled compound was prepared following the procedure of Example 153 with 2-Chloro-5-trifluoromethyl-phenyl acid, 5-Amino-2-methyl-benzenesulfonamide and {[(2-Chloro-pyrimidin-4-yl)-methyl-amino]-methyl-H-benzoimidazol-2-yl}-carbamic acid tert-butyl ester in pyridine. MS (ESI) m/z=660 [M+H]⁺.

Example 186

4-Methoxy-N-[methyl-(methyl-{2-[3-(morpholine-4-sulfonyl)-phenylamino]-pyrimidin-4-yl}-amino)-1H-benzoimidazol-2-yl]-benzamide The titled compound was prepared following the procedure of Example 153 with 4-Methoxy benzoic acid, 3-(Morpholine-4-sulfonyl)-phenylamine and {[(2-Chloro-pyrimidin-4-yl)-methyl-amino]-methyl-H-benzoimidazol-2-yl}-carbamic acid tert-butyl ester in pyridine. MS (ESI) m/z=629 [M+H]⁺.

Example 187

N-[Methyl-(methyl-{2-[3-(morpholine-4-sulfonyl)-phenylamino]-pyrimidin-4-yl}-amino)-1H-benzoimidazol-2-yl]-C-thiophen-2-yl-acetamide The titled compound was prepared following the procedure of Example 153 with thiophen-2-yl-acetic acid, 3-(Morpholine-4-sulfonyl)-phenylamine and {[(2-Chloro-pyrimidin-4-yl)-methyl-amino]-methyl-H-benzoimidazol-2-yl}-carbamic acid tert-butyl ester in pyridine. MS (ESI) m/z=619 [M+H]⁺.

Example 188

Thiophene-2-carboxylic acid [methyl-(methyl-{2-[3-(morpholine-4-sulfonyl)-phenylamino]-pyrimidin-4-yl}-amino)-1H-benzoimidazol-2-yl]-amide The titled compound was prepared following the procedure of Example 153 with Thiophene-2-carboxylic acid, 3-(Morpholine-4-sulfonyl)-phenylamine and {[(2-Chloro-pyrimidin-4-yl)-methyl-amino]-methyl-H-benzoimidazol-2-yl}-carbamic acid tert-butyl ester in pyridine. MS (ESI) m/z=605 [M+H]⁺.

Example 189

Furan-2-carboxylic acid [methyl-(methyl-{2-[3-(morpholine-4-sulfonyl)-phenylamino]-pyrimidin-4-yl}-amino)-1H-benzoimidazol-2-yl]-amide The titled compound was prepared following the procedure of Example 153 with Furan-2-carboxylic acid, 3-(Morpholine-4-sulfonyl)-phenylamine and {[(2-Chloro-pyrimidin-4-yl)-methyl-amino]-methyl-H-benzoimidazol-2-yl}-carbamic acid tert-butyl ester in pyridine. MS (ESI) m/z=589 [M+H]+.

Example 190

N-({[2-(3-Methanesulfonylmethyl-phenylamino)-pyrimidin-4-yl]-methyl-amino}-methyl-1H-benzoimidazol-2-yl)-2-(3-methyl-isoxazol-5-yl)-acetamide The titled compound was prepared following the procedure of Example 153 with 3-methyl-isoxazol-5-yl acetic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=561 [M+H]+.

Example 191

Furan-2-carboxylic acid ({[2-(3-methanesulfonylmethyl-phenylamino)-pyrimidin-4-yl]-methyl-amino}-methyl-1H-benzoimidazol-2-yl)-amide The titled compound was prepared following the procedure of Example 153 with Furan-2-carboxylic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=532 [M+H]+.

Example 192

2-(3-Methyl-isoxazol-5-yl)-N-[methyl-(methyl-{2-[3-(morpholine-4-sulfonyl)-phenylamino]-pyrimidin-4-yl}-amino)-1H-benzoimidazol-2-yl]-acetamide The titled compound was prepared following the procedure of Example 153 with 3-Methyl-isoxazol-5-yl acetic acid, 3-(Morpholine-4-sulfonyl)-phenylamine and {[(2-Chloro-pyrimidin-4-yl)-methyl-amino]-methyl-H-benzoimidazol-2-yl}-carbamic acid tert-butyl ester in pyridine. MS (ESI) m/z=618 [M+H]+.

Example 193

3-Methyl-furan-2-carboxylic acid ({[2-(3-methanesulfonylmethyl-phenylamino)-pyrimidin-4-yl]-methyl-amino}-methyl-1H-benzoimidazol-2-yl)-amide The titled compound was prepared following the procedure of Example 153 with 3-Methyl-furan-2-carboxylic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=546 [M+H]+.

Example 194

N-[Methyl-(methyl-{2-[3-(4-methyl-piperazine-1-sulfonyl)-phenylamino]-pyrimidin-4-yl}-amino)-1H-benzoimidazol-2-yl]-C-thiophen-2-yl-acetamide The titled compound was prepared following the procedure of Example 153 with thiophen-2-yl-acetic acid, 3-(4-Methyl-piperazine-1-sulfonyl)-phenylamine and {[(2-Chloro-pyrimidin-4-yl)-methyl-amino]-methyl-H-benzoimidazol-2-yl}-carbamic acid tert-butyl ester in pyridine. MS (ESI) m/z=632 [M+H]+.

Example 195

Thiophene-2-carboxylic acid [methyl-(methyl-{2-[3-(4-methyl-piperazine-1-sulfonyl)-phenylamino]-pyrimidin-4-yl}-amino)-1H-benzoimidazol-2-yl]-amide The titled compound was prepared following the procedure of Example 153 with Thiophene-2-carboxylic acid, 3-(4-Methyl-piperazine-1-sulfonyl)-phenylamine and {[(2-Chloro-pyrimidin-4-yl)-methyl-amino]-methyl-H-benzoimidazol-2-yl}-carbamic acid tert-butyl ester in pyridine. MS (ESI) m/z=618 [M+H]+.

Example 196

Furan-2-carboxylic acid [methyl-(methyl-{2-[3-(4-methyl-piperazine-1-sulfonyl)-phenylamino]-pyrimidin-4-yl}-amino)-1H-benzoimidazol-2-yl]-amide The titled compound was prepared following the procedure of Example 153 with Furan-2-carboxylic acid, 3-(4-Methyl-piperazine-1-sulfonyl)-phenylamine and {[(2-Chloro-pyrimidin-4-yl)-methyl-amino]-methyl-H-benzoimidazol-2-yl}-carbamic acid tert-butyl ester in pyridine. MS (ESI) m/z=602 [M+H]+.

Example 197

2-(3-Methyl-isoxazol-5-yl)-N-[methyl-(methyl-{2-[3-(4-methyl-piperazine-1-sulfonyl)-phenylamino]-pyrimidin-4-yl}-amino)-1H-benzoimidazol-2-yl]-acetamide The titled compound was prepared following the procedure of Example 153 with 3-Methyl-isoxazol-5-yl acetic acid, 3-(4-Methyl-piperazine-1-sulfonyl)-phenylamine and {[(2-Chloro-pyrimidin-4-yl)-methyl-amino]-methyl-H-benzoimidazol-2-yl}-carbamic acid tert-butyl ester in pyridine. MS (ESI) m/z=631 [M+H]+.

Example 198

N-({[2-(3-Methanesulfonylmethyl-phenylamino)-pyrimidin-4-yl]-methyl-amino}-methyl-1H-benzoimidazol-2-yl)-dimethyl-butyramide The titled compound was prepared following the procedure of Example 153 with 3,3-Dimethyl-butyric acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=536 [M+H]+.

Example 199

N-({[2-(3-Methanesulfonylmethyl-phenylamino)-pyrimidin-4-yl]-methyl-amino}-methyl-1H-benzoimidazol-2-yl)-propionamide The titled compound was prepared following the procedure of Example 153 with propionic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=494 [M+H]$^+$.

Example 200

Pentanoic acid ({[2-(3-methanesulfonylmethyl-phenylamino)-pyrimidin-4-yl]-methyl-amino}-methyl-1H-benzoimidazol-2-yl)-amide The titled compound was prepared following the procedure of Example 153 with Pentanoic acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=522 [M+H]$^+$.

Example 201

N-({[2-(3-Methanesulfonylmethyl-phenylamino)-pyrimidin-4-yl]-methyl-amino}-methyl-1H-benzoimidazol-2-yl)-butyramide The titled compound was prepared following the procedure of Example 153 with Butyric acid, 3-[(methylsulfonyl)methyl]aniline and {[(2-Chloro-pyrimidin-4-yl)-methyl-amino]-methyl-H-benzoimidazol-2-yl}-carbamic acid tert-butyl ester in pyridine. MS (ESI) m/z=508 [M+H]$^+$.

Example 202

Phenyl-N-({[2-(4-methanesulfonylmethyl-phenylamino)-pyrimidin-4-yl]-methyl-amino}-methyl-1H-benzoimidazol-2-yl)-acetamide

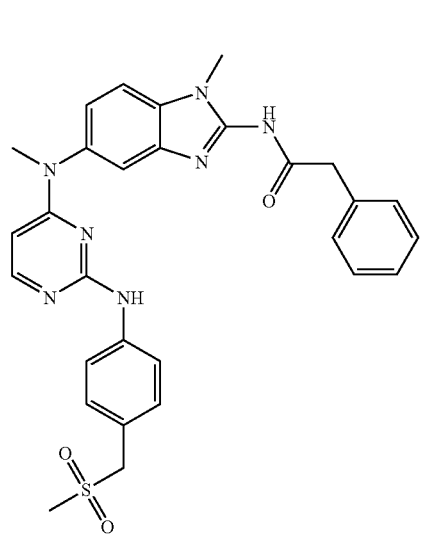

Example 203

Phenylcyclopropanecarboxylic acid ({[2-(4-methanesulfonylmethyl-phenylamino)-pyrimidin-4-yl]-methyl-amino}-methyl-1H-benzoimidazol-2-yl)-amide

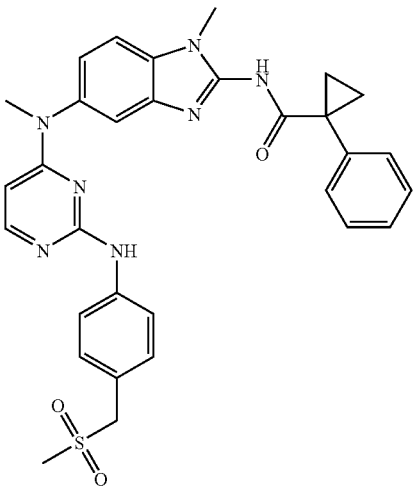

Example 204

1-(2,5-Difluoro-phenyl)-cyclopropanecarboxylic acid ({[2-(4-methanesulfonylmethyl-phenylamino)-pyrimidin-4-yl]-methyl-amino}-methyl-1H-benzoimidazol-2-yl)-amide

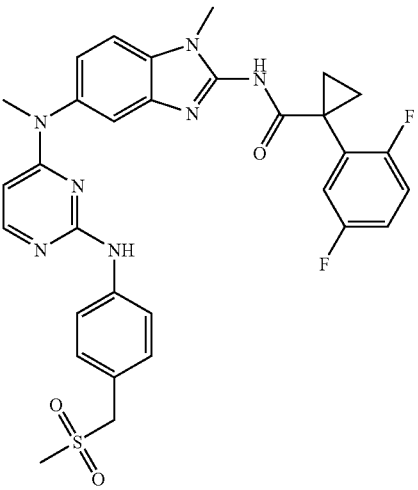

Example 205

1-(4-Chloro-phenyl)-cyclopropanecarboxylic acid ({[2-(4-methanesulfonylmethyl-phenylamino)-pyrimidin-4-yl]-methyl-amino}-methyl-1H-benzoimidazol-2-yl)-amide

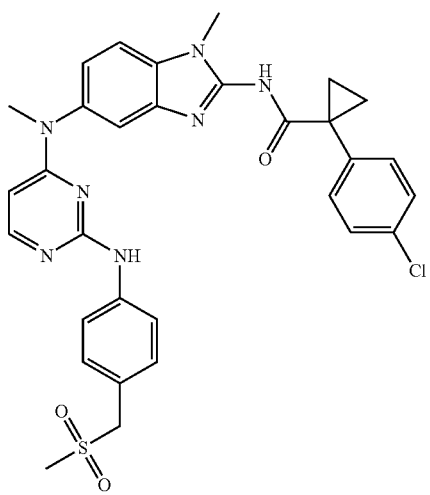

Example 207

(3,5-Bistrifluoromethyl-phenyl)-N-({[2-(4-methanesulfonylmethyl-phenylamino)-pyrimidin-4-yl]-methyl-amino}-methyl-1H-benzoimidazol-2-yl)-acetamide

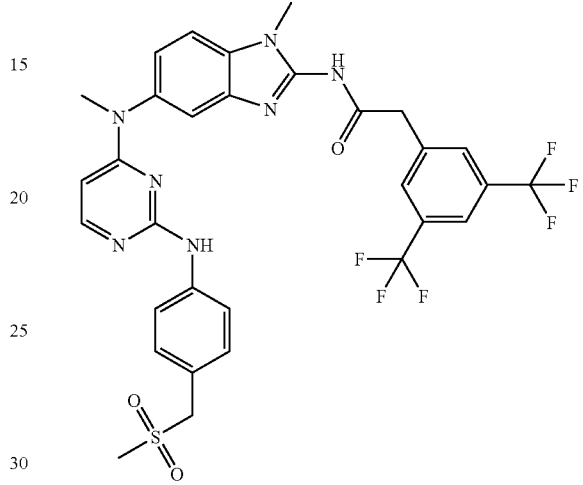

Example 206

2-(4-Fluoro-phenyl)-N-({[2-(4-methanesulfonylmethyl-phenylamino)-pyrimidin-4-yl]-methyl-amino}-methyl-1H-benzoimidazol-2-yl)-acetamide

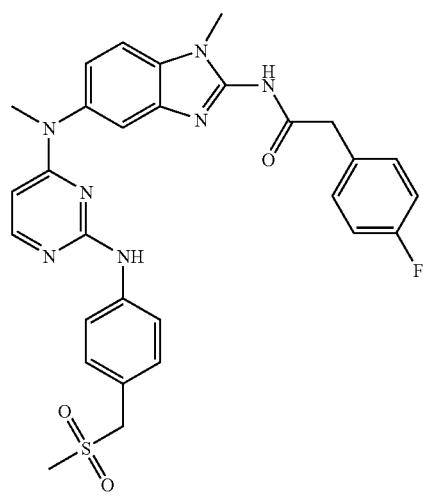

Example 208

(3,4-Dichlorophenyl)-N-({[2-(4-methanesulfonylmethyl-phenylamino)-pyrimidin-4-yl]-methyl-amino}-methyl-1H-benzoimidazol-2-yl)-acetamide

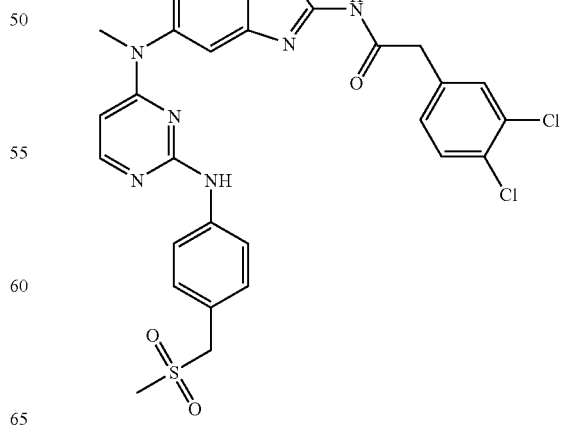

Example 209

1-(2,5-Difluorophenyl)-cyclopropanecarboxylic acid ({[2-(3-methanesulfonylmethyl-phenylamino)-pyrimidin-4-yl]-methyl-amino}-methyl-1H-benzoimidazol-2-yl)-amide

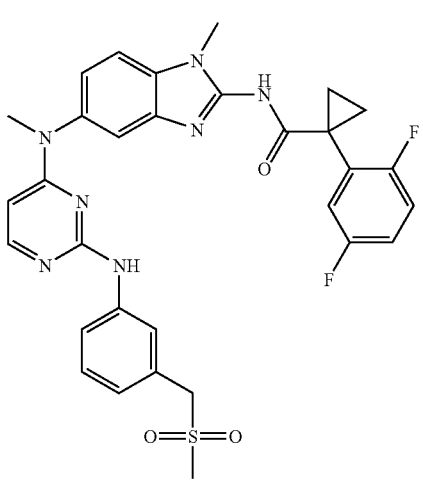

Example 210

(2,5-Difluorophenyl)-N-({[2-(3-methanesulfonylmethyl-phenylamino)-pyrimidin-4-yl]-methyl-amino}-methyl-1H-benzoimidazol-2-yl)-acetamide

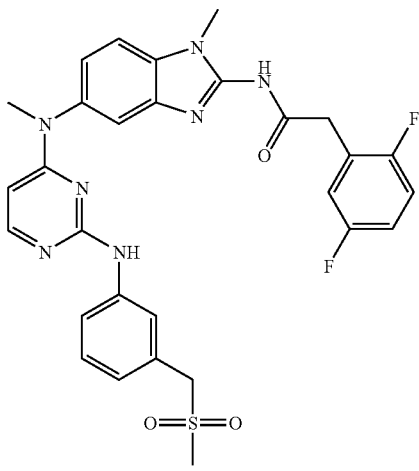

Example 211

(3,4-Dichlorophenyl)-N-({[2-(3-methanesulfonylmethyl-phenylamino)-pyrimidin-4-yl]-methyl-amino}-methyl-1H-benzoimidazol-2-yl)-acetamide

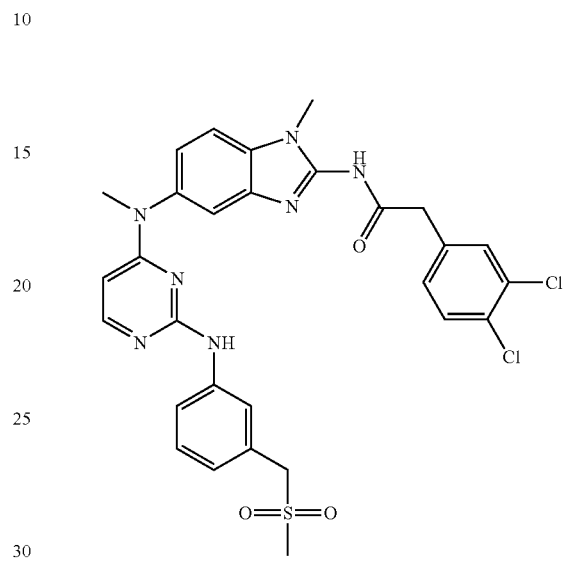

Example 212

1-(2,5-Difluorophenyl)-cyclopropanecarboxylic acid ({[2-(5-ethanesulfonyl-2-methoxy-phenylamino)-pyrimidin-4-yl]-methyl-amino}-methyl-1H-benzoimidazol-2-yl)-amide

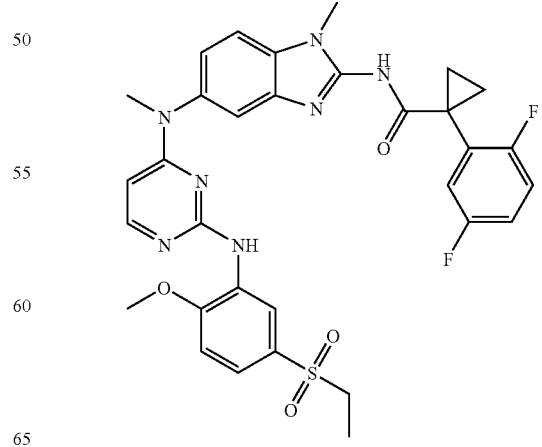

Example 213

(2,5-Difluorophenyl)-N-({[2-(5-ethanesulfonyl-2-methoxy-phenylamino)-pyrimidin-4-yl]-methyl-amino}-methyl-1H-benzoimidazol-2-yl)-acetamide

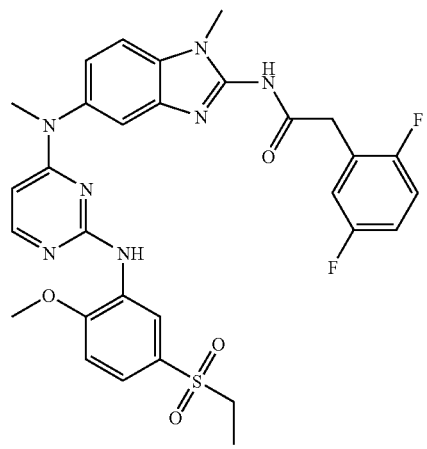

Example 214

1-(3,4-Dichlorophenyl)-cyclopropanecarboxylic acid ({[2-(5-ethanesulfonyl-2-methoxy-phenylamino)-pyrimidin-4-yl]-methyl-amino}-methyl-1H-benzoimidazol-2-yl)-amide

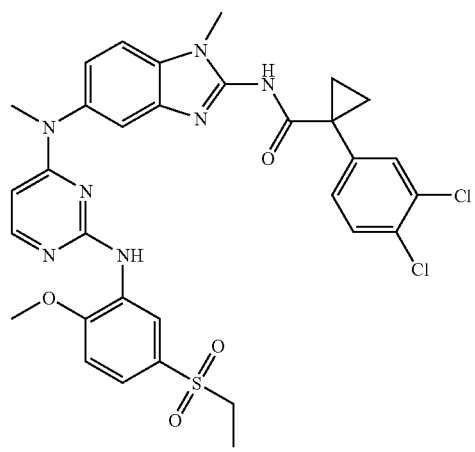

Example 215

3,4-Dichlorophenyl-N-({[2-(5-ethanesulfonyl-2-methoxy-phenylamino)-pyrimidin-4-yl]-methyl-amino}-methyl-1H-benzoimidazol-2-yl)-acetamide

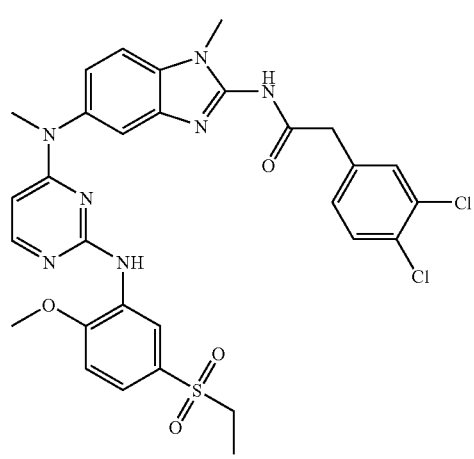

Example 216

1-(2,5-Difluorophenyl)-cyclopropanecarboxylic acid (methyl-{methyl-[2-(4-methyl-3-sulfamoyl-phenylamino)-pyrimidin-4-yl]-amino}-1H-benzoimidazol-2-yl)-amide

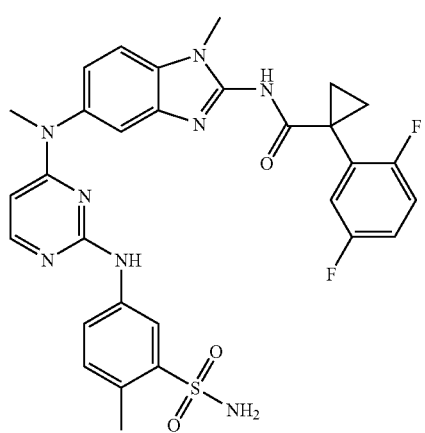

Example 217

1-(3,4-Dichlorophenyl)-cyclopropanecarboxylic acid (methyl-{methyl-[2-(4-methyl-3-sulfamoyl-phenylamino)-pyrimidin-4-yl]-amino}-1H-benzoimidazol-2-yl)-amide

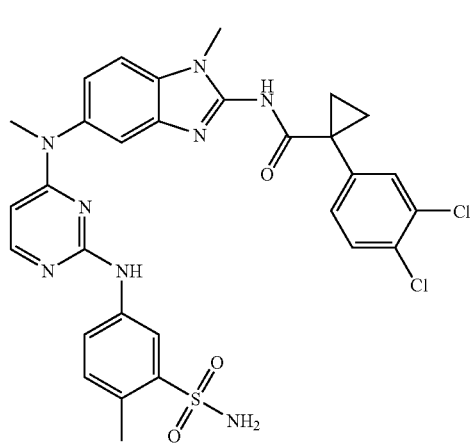

Example 218

(3,4-Dichlorophenyl)-N-(methyl-{methyl-[2-(4-methyl-3-sulfamoyl-phenylamino)-pyrimidin-4-yl]-amino}-1H-benzoimidazol-2-yl)-acetamide

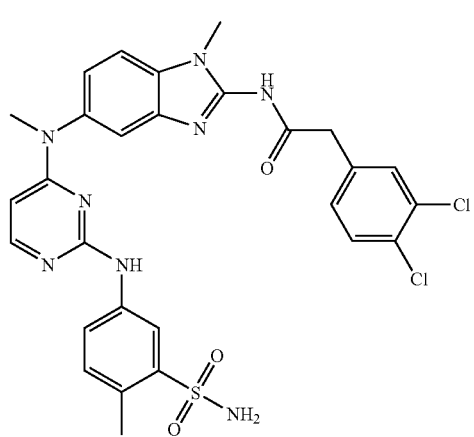

Example 219

2-(2,3-Dimethoxyphenyl)-N-(5-{[2-(4-methanesulfonylmethyl-phenylamino)-pyrimidin-4-yl]-methyl-amino}-1-methyl-1H-benzoimidazol-2-yl)-acetamide

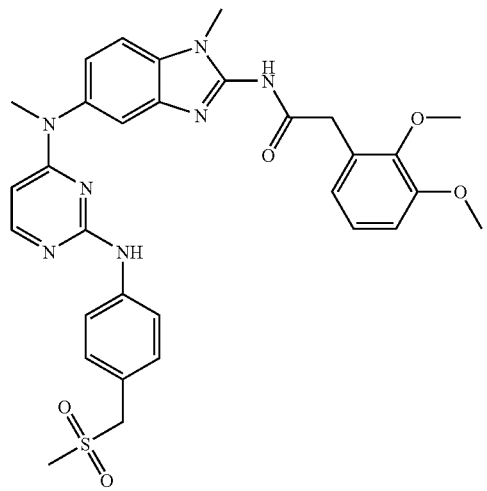

Example 220

2-(2-Methoxyphenyl)-N-(5-{[2-(4-methanesulfonylmethyl-phenylamino)-pyrimidin-4-yl]-methyl-amino}-1-methyl-1H-benzoimidazol-2-yl)-acetamide

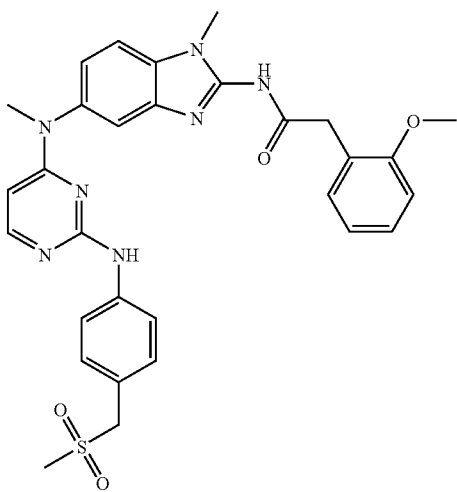

Example 221

2-(3-Methoxyphenyl)-N-(5-{[2-(4-methanesulfonyl-methyl-phenylamino)-pyrimidin-4-yl]-methyl-amino}-1-methyl-1H-benzoimidazol-2-yl)-acetamide

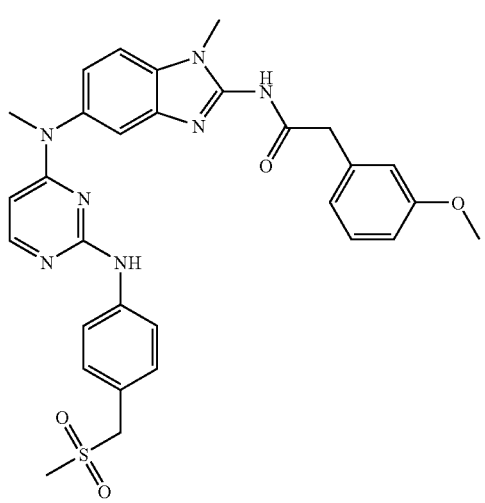

Example 222

2-(3-Methoxyphenyl)-N-(5-{[2-(4-methanesulfonyl-methyl-phenylamino)-pyrimidin-4-yl]-methyl-amino}-1-methyl-1H-benzoimidazol-2-yl)-acetamide

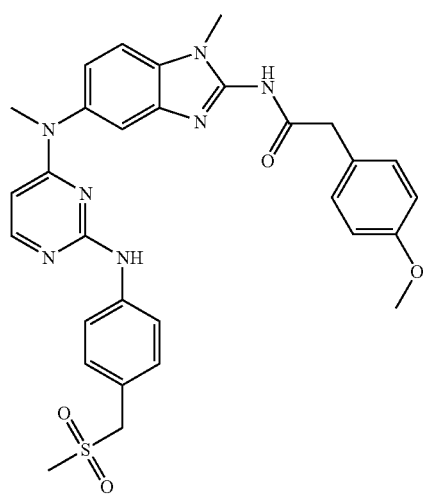

Example 223

2-(2-Fluorophenyl)-N-({[2-(4-methanesulfonylm-ethyl-phenylamino)-pyrimidin-4-yl]-methyl-amino}-methyl-1H-benzoimidazol-2-yl)-acetamide

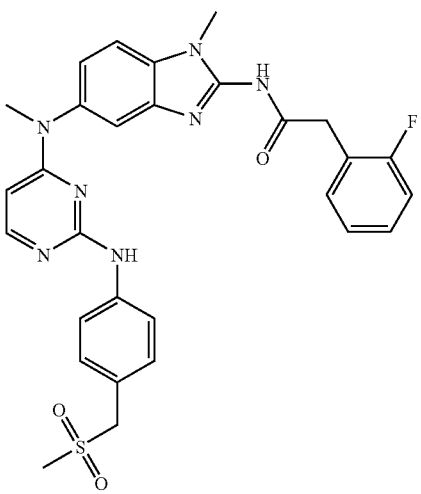

Example 224

2-(3-Fluorophenyl)-N-({[2-(4-methanesulfonylm-ethyl-phenylamino)-pyrimidin-4-yl]-methyl-amino}-methyl-1H-benzoimidazol-2-yl)-acetamide

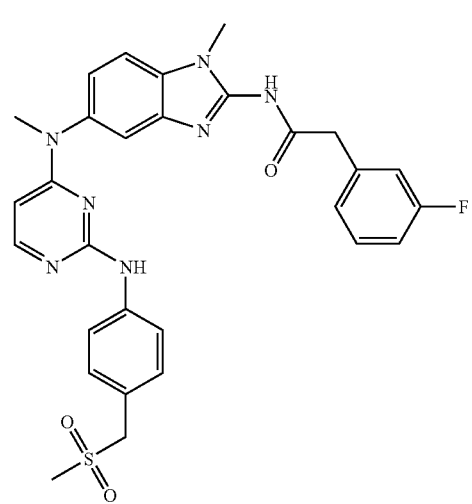

Example 225

(2,5-Difluorophenyl)-N-({[2-(4-methanesulfonylm-ethyl-phenylamino)-pyrimidin-4-yl]-methyl-amino}-methyl-1H-benzoimidazol-2-yl)-acetamide

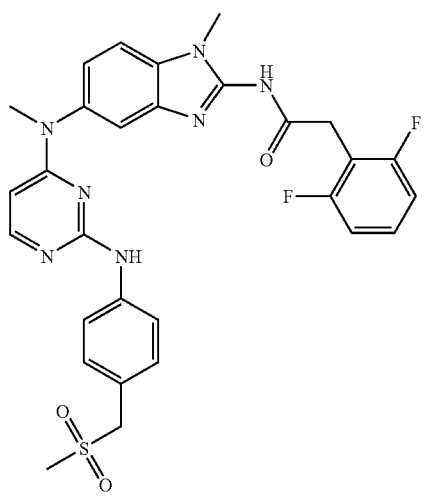

Example 226

(2,3-Difluorophenyl)-N-({[2-(4-methanesulfonylm-ethyl-phenylamino)-pyrimidin-4-yl]-methyl-amino}-methyl-1H-benzoimidazol-2-yl)-acetamide

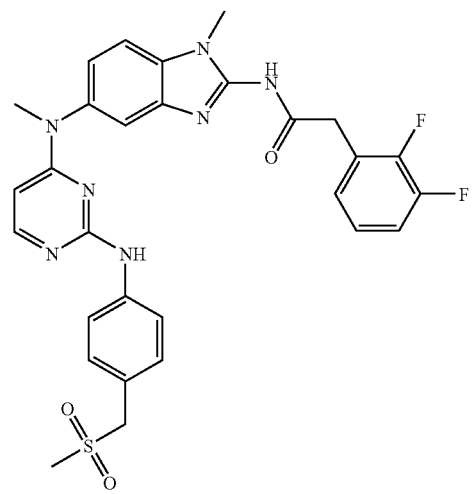

Example 227

2-(3,4-Dimethoxyphenyl)-N-(5-{[2-(4-methane-sulfonylmethyl-phenylamino)-pyrimidin-4-yl]-me-thyl-amino}-1-methyl-1H-benzoimidazol-2-yl)-ac-etamide

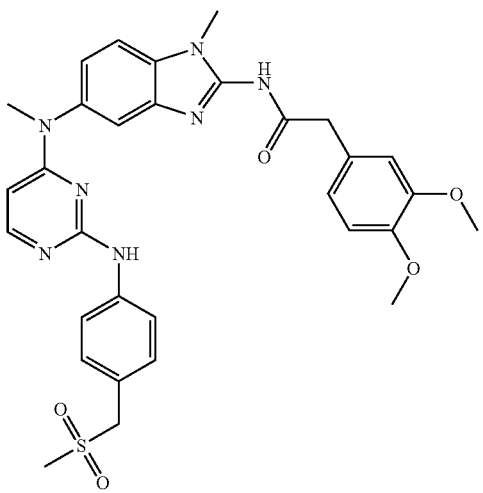

Example 228

(2,5-Difluorophenyl)-N-(methyl-{methyl-[2-(4-me-thyl-3-sulfamoyl-phenylamino)-pyrimidin-4-yl]-amino}-1H-benzoimidazol-2-yl)-acetamide

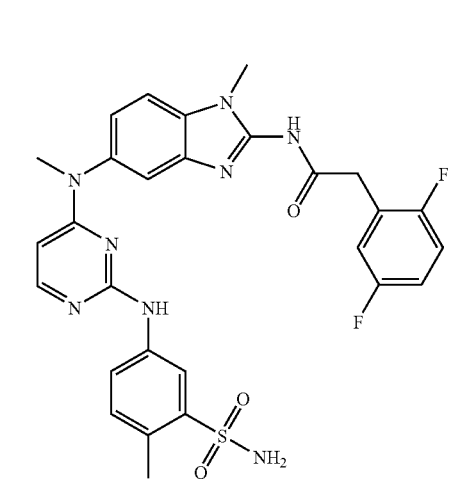

Example 229

1-(3,4-Dichloro-phenyl)-cyclopropanecarboxylic
acid ({[2-(3-methanesulfonylmethyl-phenylamino)-
pyrimidin-4-yl]-methyl-amino}-methyl-1H-ben-
zoimidazol-2-yl)-amide

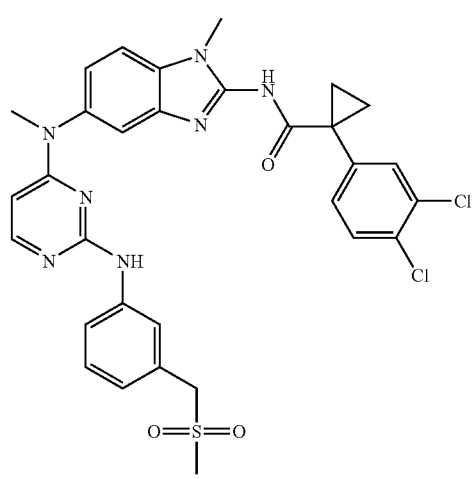

Example 230

2-(2-Chlorophenyl)-N-({[2-(4-methanesulfonylm-
ethyl-phenylamino)-pyrimidin-4-yl]-methyl-amino}-
methyl-1H-benzoimidazol-2-yl)-acetamide

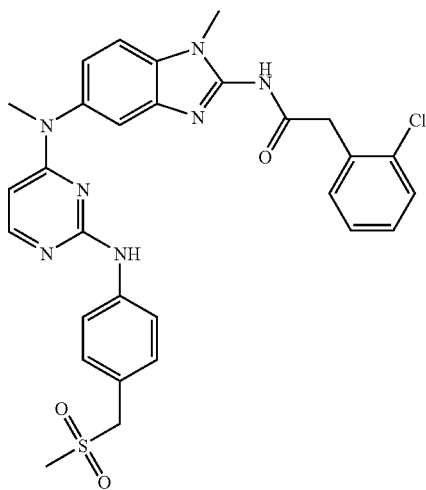

Example 231

2-(3-Chlorophenyl)-N-({[2-(4-methanesulfonylm-
ethyl-phenylamino)-pyrimidin-4-yl]-methyl-amino}-
methyl-1H-benzoimidazol-2-yl)-acetamide

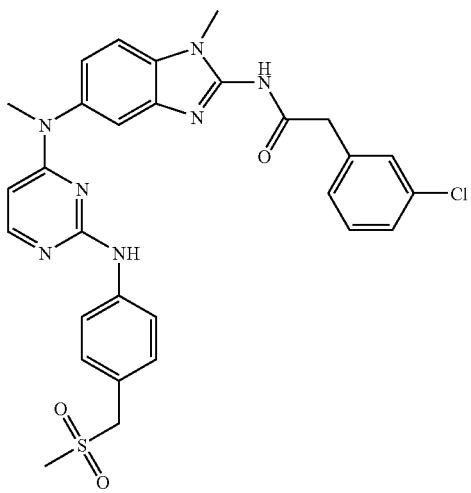

Example 232

2-(4-Chlorophenyl)-N-({[2-(4-methanesulfonylm-
ethyl-phenylamino)-pyrimidin-4-yl]-methyl-amino}-
methyl-1H-benzoimidazol-2-yl)-acetamide

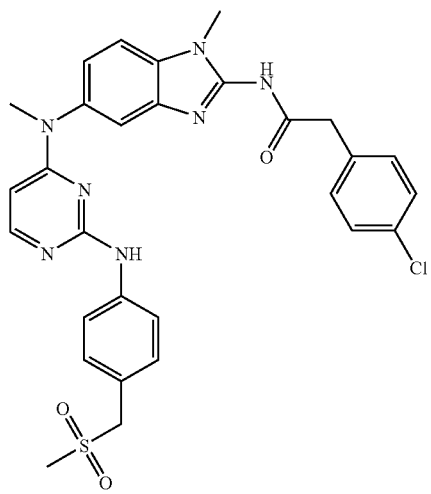

Example 233

2-(3,5-Dimethoxyphenyl)-N-(5-{[2-(4-methane-sulfonylmethyl-phenylamino)-pyrimidin-4-yl]-methyl-amino}-1-methyl-1H-benzoimidazol-2-yl)-acetamide

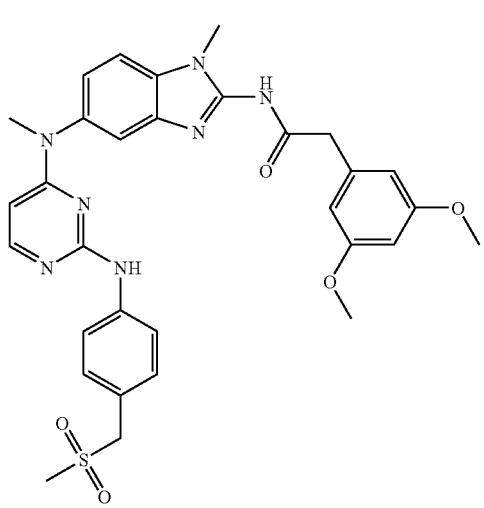

Example 234

2-(2,5-Dimethoxyphenyl)-N-(5-{[2-(4-methane-sulfonylmethyl-phenylamino)-pyrimidin-4-yl]-methyl-amino}-1-methyl-1H-benzoimidazol-2-yl)-acetamide

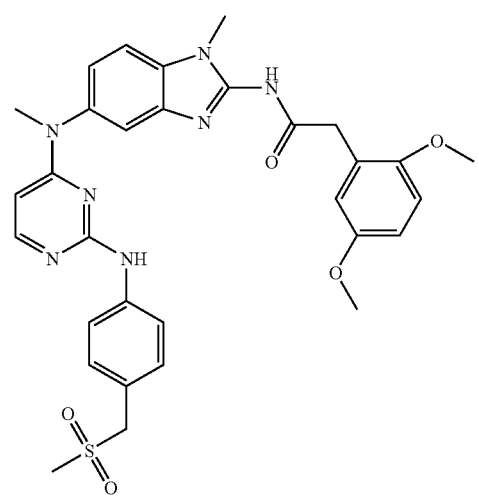

Example 235

(2,5-Dichlorophenyl)-N-({[2-(4-methanesulfonylmethyl-phenylamino)-pyrimidin-4-yl]-methyl-amino}-methyl-1H-benzoimidazol-2-yl)-acetamide

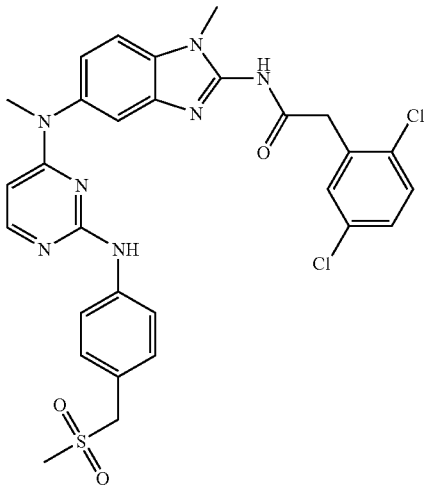

Example 236

N-({[2-(4-Methanesulfonylmethyl-phenylamino)-pyrimidin-4-yl]-methyl-amino}-methyl-1H-benzoimidazol-2-yl)-methyl-C-phenyl-butyramide

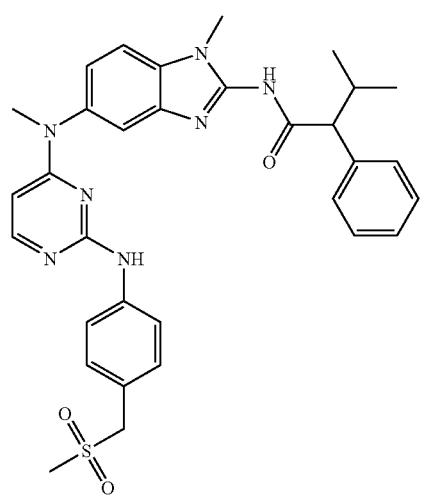

Example 237

(3,5-Dimethylphenyl)-N-({[2-(4-methanesulfonylmethyl-phenylamino)-pyrimidin-4-yl]-methyl-amino}-methyl-1H-benzoimidazol-2-yl)-acetamide

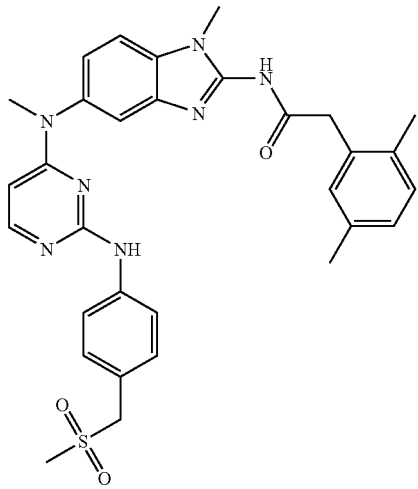

Example 238

N-({[2-(4-Methanesulfonylmethyl-phenylamino)-pyrimidin-4-yl]-methyl-amino}-methyl-1H-benzoimidazol-2-yl)-phenyl-isobutyramide

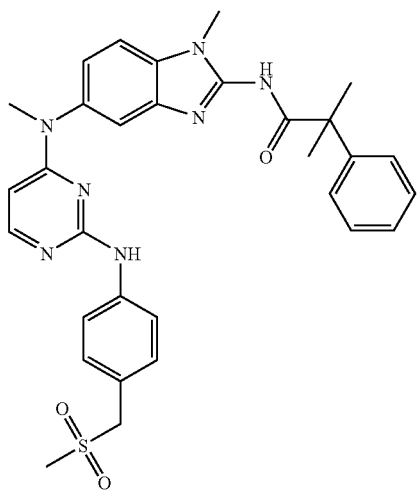

Example 239

Benzo[1,3]dioxol-5-yl-N-({[2-(4-methanesulfonylmethyl-phenylamino)-pyrimidin-4-yl]-methyl-amino}-methyl-1H-benzoimidazol-2-yl)-acetamide

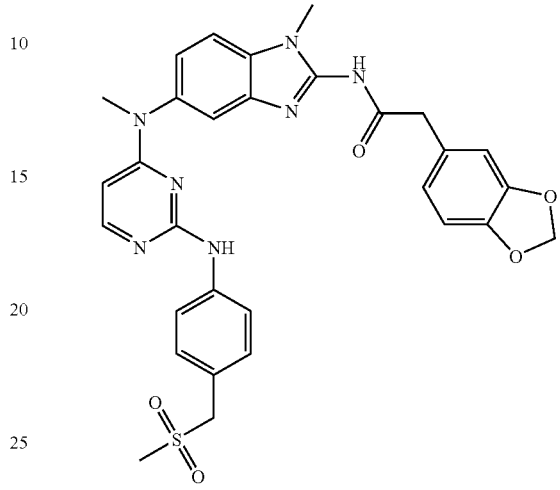

Biological Data

Tie2 Fluorescence Polarization Kinase Activity Assay: (TIE2-FP)

Activation of Recombinant Tie2 Activation:

Recombinant GST-Tie2 was activated by incubating the enzyme in 20 mM Tris-HCl, pH 7.5, 12 mM $MgCl_2$, 100 mM NaCl, 20 μM sodium vanidate, 1 mM DTT and 300 μM ATP at room temperature for 2 hours. The activation mixture was then passed through a NAP-25 desalting column (Pharmacia Biotech cat. no. 17-0852-02) to remove the free ATP. The activated enzyme was stored as aliquots at −80° C. in 20 mM Tris-HCl, pH 7.5 and 100 mM NaCl.

Assay Conditions:

The final assay conditions were 50 mM HEPES, pH 7.5, 5% DMSO (when screening compounds), 200 μM ATP, 5 mM $MgCl_2$, 1 mM DTT, 50 μM sodium vanidate, 1 nM activated enzyme, and 200 μM peptide. $IC_{50}$'s of compounds were measured under subsaturating ATP (200 μM) and varing concentrations of activated Tie2 and peptide substrate (RFWKYEFWR-OH; MW 1873 Da, TFA salt). Panvera Anti-phosphotyrosine antibody (Cat#P2840) and PTK Green Tracer (Cat#P2842) were used to detect the phosphorylated peptide. Polarization was measured on a TECAN Polarion in 138-second cycles for 30 minutes at room temperature. $IC_{50}$'s were then determined from the % polarization using normal calculation methods. Results are indicated below.

VEGF-R2 Enzyme Assay (VEGF-E)

The VEGF enzyme assay used the LANCE method (Wallac) and GST-VEGFR2, baculovirus expressed recombinant constructs of the intracellular domains of human TIE2 tagged by GST. The method measured the ability of the purified enzymes to catalyse the transfer of the γ-phosphate from ATP onto tyrosine residues in a biotinylated synthetic peptide, (biotin-aminohexyl-EEEEYFELVAKKKK-NH2). This peptide phosphorylation was detected using the following procedure: GST-VEGFR2 was incubated for 40-60 mins at room temperature with 75 uM ATP, 5 mM MgCl2, 0.1 mM DTT, 0.1 mg/mL BSA and the test compound (diluted from a 10 mM stock in DMSO for desired concentration) in 100 mM HEPES buffer. The reaction was stopped by the addition of EDTA (final concentration 50 mM). Streptavidin linked-APC (allophycocyanin, Molecular Probe) and Europium-labeled anti-phosphorylated tyrosine antibody (Wallac) were then added at the final concentration of 15 nM and 1 nM, respectively. The APC signal was measured using an ARVO multilabel counter (Wallac Berthold, Japan). The percent inhibition of activity was calculated relative to blank control wells. The concentration of test compound that inhibits 50% of activity ($IC_{50}$) was interpolated using nonlinear regression (Levernberg-Marquardt) and the equation, y=Vmax (1−x/(K+x))+Y2, where "K" was equal to the $IC_{50}$. The $IC_{50}$ values were converted to $pIC_{50}$ values, i.e., −log $IC_{50}$ in Molar concentration. The results are represented in Table 1 below.

VEGF-Driven Cellular Proliferation Assay: BrdU Incorporation Assay (VEGF-C)

Human umbilical cord endothelial cells (HUVEC, Clonetics, CC2519) were passaged in Type I collagen-coated 100-mm petridishes in EGM-MV medium (Clonetics, CC3125) at 37 C in a humidified 5% CO2, 95% air incubator. (HUVEC passaged more than 6 times in vitro were discarded and not subjected to assaying.) The cells were harvested using trypsin/EDTA, counted using a haemocytometer and plated at 5000 cells/well in a Type I-collagen coated 96-well plate (Becton Dickinson, 354407) in M199 medium (Gibco BRL, 12340-030) containing 5% FBS (Hyclone, A 1115-L) and gentamicin (at 50 ug/ml, Gibco BRL). After incubation overnight at 37° C., the media were replaced with 100 ul of M199 serum-free medium containing compounds at various concentrations with 0.6% DMSO and gentamicin. The compounds were diluted in serum-free M199 medium from 10 mM stock solutions prepared in 100% DMSO. After a 30 min incubation at 37° C., the cells were fed with 100 ul of serum-free M199 medium containing gentamicin, 0.2% culture-grade bovine serum albumin (BSA, Sigma A1993) and 20 ng/ml of VEGF (REtD systems, 293-VE) or 0.6 ng/ml of basic FGF (REtD systems, 233-FB), and cultured at 37° C. for another 24 h. The cells were pulsed with bromodeoxyuridine (BrdU at 10 uM in serum-free M199) at 37° C. for an additional 24 h. The incorporation of BrdU into the proliferating HUVEC were analyzed using BrdU Cell Proliferation ELISA (Roche Molecular Biochemicals, 1647229) according to the manufacturer's protocols. The optical density at 450 nm was measured with a multilabel counter (ARVO SX, Wallac). The percent inhibition of cell growth was calculated relative to blank control wells. The concentration of test compound that inhibits 50% of cell growth ($IC_{50}$) was interpolated using nonlinear regression (Levernberg-Marquardt) and the equation, y=Vmax (1−x/(K+x))+Y2, where "K" was equal to the $IC_{50}$. The $IC_{50}$ values were converted to $pIC_{50}$ values, i.e., −log $IC_{50}$ in Molar concentration. The results are represented in Table 1 below.

TABLE I

| Ex. No | TIE2-FP | VEGF-E | VEGF-C |
|---|---|---|---|
| 1 | | +++ | +++ |
| 2 | | +++ | +++ |
| 3 | | +++ | +++ |
| 4 | | +++ | +++ |
| 5 | | +++ | +++ |
| 6 | | +++ | +++ |
| 11 | | +++ | |

TABLE I-continued

| Ex. No | TIE2-FP | VEGF-E | VEGF-C |
|---|---|---|---|
| 90 | | +++ | |
| 92 | + | ++ | |
| 95 | ++ | +++ | |
| 110 | +++ | +++ | |
| 112 | +++ | +++ | |
| 117 | + | +++ | |
| 118 | ++ | +++ | |
| 124 | ++ | +++ | |
| 125 | +++ | +++ | |
| 135 | + | +++ | |
| 136 | + | +++ | |
| 142 | | +++ | |
| 153 | + | +++ | |
| 156 | | ++ | |
| 157 | | +++ | |
| 161 | + | ++ | |
| 162 | + | +++ | |
| 167 | + | +++ | |
| 169 | + | +++ | |
| 173 | + | +++ | |
| 177 | + | +++ | |
| 202 | | +++ | |
| 203 | +++ | +++ | |
| 204 | + | ++ | |
| 206 | + | +++ | |
| 219 | | +++ | |
| 226 | + | +++ | |
| 229 | + | ++ | |
| 230 | + | +++ | |
| 239 | | ++ | |

+ = $pIC_{50}$ of 5.0-6.0;
++ = $pIC_{50}$ of 6.0-7.0;
+++ = $pIC_{50}$ of >7.0;

What is claimed is:
1. A compound of Formula (I):

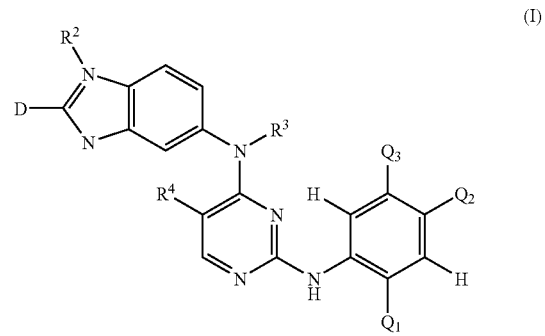

or a salt, thereof:
wherein:
D is —NRR¹, —OR, —SR, —S(O)R, or —S(O)₂R;
R is hydrogen, $C_1$-$C_8$ alkyl, $C_3$-$C_7$ cycloalkyl, aralkyl, aryl, heteroaryl, —C(O)NR¹R¹, —C(O)OR¹, acyl, aroyl, or heteroaroyl;
R¹ is hydrogen, $C_1$-$C_8$ alkyl, $C_3$-$C_7$ cycloalkyl, aralkyl, or aryl;
R² is $C_1$-$C_6$ alkyl or $C_3$-$C_7$ cycloalkyl;
R³ is hydrogen, $C_1$-$C_4$ alkyl, $C_1$-$C_4$ haloalkyl, aralkyl, cyanoalkyl, —(CH₂)$_p$C=CH(CH₂)$_t$H, —(CH₂)$_p$C≡C(CH₂)$_t$H, or $C_3$-$C_7$ cycloalkyl;
p is 1, 2, or 3;
t is 0 or 1;
R⁴ is hydrogen, halo, or cyano;

$Q_1$ is hydrogen, halo, $C_1$-$C_2$ haloalkyl, $C_1$-$C_2$ alkyl, $C_1$-$C_2$ alkoxy, or $C_1$-$C_2$ haloalkoxy;
$Q_2$ is $A^1$ or $A^2$;
$Q_3$ is $A^1$ when $Q_2$ is $A^2$ and $Q_3$ is $A^2$ when $Q_2$ is $A^1$;
wherein
  $A^1$ is hydrogen, halo, $C_1$-$C_3$ alkyl, $C_1$-$C_3$ haloalkyl, —$OR^5$, and
  $A^2$ is the group defined by -$(Z)_m$-$(Z^1)$-$(Z^2)$, wherein
    Z is $CH_2$ and m is 0, 1, 2, or 3, or
    Z is $NR^5$ and m is 0 or 1, or
    Z is oxygen and m is 0 or 1, or
    Z is $CH_2NR^6$ and m is 0 or 1;
  $Z^1$ is $S(O)_2$, S(O), or C(O); and
  $Z^2$ is $C_1$-$C_4$ alkyl, cycloalkyl, heterocyclyl, —$NR^8R^9$, aryl, arylamino, aralkyl, aralkoxy, or heteroaryl;
$R^5$ and $R^6$ are each independently selected from hydrogen, hydroxyl, alkoxy, aryloxy, aralkoxy, $C_1$-$C_4$ alkyl, $C_3$-$C_7$ cycloalkyl, heterocyclyl, —$S(O)_2R^7$, and —$C(O)R^7$;
$R^7$ is $C_1$-$C_4$ alkyl, or $C_3$-$C_7$ cycloalkyl;
$R^8$ is hydrogen, hydroxyl, $C_1$-$C_6$ alkyl, $C_1$-$C_6$ alkoxy, aryloxy, aralkoxy, $C_3$-$C_7$ cycloalkyl, and $C_3$-$C_7$ cycloalkoxy; and
$R^9$ is hydrogen, $C_1$-$C_6$ alkyl, $C_3$-$C_7$ cycloalkyl, aryl, acyl, carbamoyl, or heterocyclyl.

2. A compound of Formula (II):

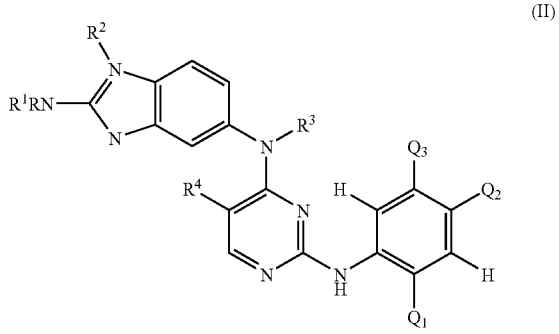

(II)

or a salt, thereof:
wherein:
R is hydrogen, $C_1$-$C_8$ alkyl, $C_3$-$C_7$ cycloalkyl, aralkyl, aryl, heteroaryl, —$C(O)NR^1R^1$, —$C(O)OR^1$, acyl, aroyl, or heteroaroyl;
$R^1$ is hydrogen, $C_1$-$C_8$ alkyl, $C_3$-$C_7$ cycloalkyl, aralkyl, or aryl;
$R^2$ is $C_1$-$C_6$ alkyl or $C_3$-$C_7$ cycloalkyl;
$R^3$ is hydrogen, $C_1$-$C_4$ alkyl, $C_1$-$C_4$ haloalkyl, aralkyl, cyanoalkyl, —$(CH_2)_pC$=$CH(CH_2)_tH$, —$(CH_2)_pC$≡$C(CH_2)_tH$, or $C_3$-$C_7$ cycloalkyl;
p is 1, 2, or 3;
t is 0 or 1;
$R^4$ is hydrogen, halo, or cyano;
$Q_1$ is hydrogen, halo, $C_1$-$C_2$ haloalkyl, $C_1$-$C_2$ alkyl, $C_1$-$C_2$ alkoxy, or $C_1$-$C_2$ haloalkoxy;
$Q_2$ is $A^1$ or $A^2$;
$Q_3$ is $A^1$ when $Q_2$ is $A^2$ and $Q_3$ is $A^2$ when $Q_2$ is $A^1$;
wherein
  $A^1$ is hydrogen, halo, $C_1$-$C_3$ alkyl, $C_1$-$C_3$ haloalkyl, —$OR^5$, and
  $A^2$ is the group defined by -$(Z)_m$-$(Z^1)$-$(Z^2)$, wherein
    Z is $CH_2$ and m is 0, 1, 2, or 3, or
    Z is $NR^5$ and m is 0 or 1, or
    Z is oxygen and m is 0 or 1, or
    Z is $CH_2NR^6$ and m is 0 or 1;
  $Z^1$ is $S(O)_2$, S(O), or C(O); and
  $Z^2$ is $C_1$-$C_4$ alkyl, cycloalkyl, heterocyclyl, —$NR^8R^9$, aryl, arylamino, aralkyl, aralkoxy, or heteroaryl;
$R^5$ and $R^6$ are each independently selected from hydrogen, hydroxyl, alkoxy, aryloxy, aralkoxy, $C_1$-$C_4$ alkyl, $C_3$-$C_7$ cycloalkyl, heterocyclyl, —$S(O)_2R^7$, or —$C(O)R^7$;
$R^7$ is $C_1$-$C_4$ alkyl, or $C_3$-$C_7$ cycloalkyl;
$R^8$ is hydrogen, hydroxyl, $C_1$-$C_6$ alkyl, $C_1$-$C_6$ alkoxy, aryloxy, aralkoxy, $C_3$-$C_7$ cycloalkyl, or $C_3$-$C_7$ cycloalkoxy; and
$R^9$ is hydrogen, $C_1$-$C_6$ alkyl, $C_3$-$C_7$ cycloalkyl, aryl, acyl, carbamoyl, or heterocyclyl.

3. A compound as claimed in claim 1, wherein D is —$NRR^1$.

4. A compound as claimed in claim 1, wherein D is —$NRR^1$ and R is $C_1$-$C_8$ alkyl, aryl, or aralkyl and $R^1$ is hydrogen.

5. A compound as claimed in claim 1, wherein D is —$NRR^1$, wherein R is methyl, isopropyl, benzyl, or phenyl and $R^1$ is hydrogen.

6. A compound as claimed in claim 1, wherein $R^2$ is $C_1$-$C_8$ alkyl.

7. A compound as claimed in claim 1, wherein $R^2$ is methyl.

8. A compound as claimed in claim 1 or 2, wherein $R^3$ is hydrogen, $C_1$-$C_4$ alkyl, cyanoalkyl, or —$(CH_2)_pC$≡$C(CH_2)_tH$.

9. A compound as claimed in claim 1, wherein $R^3$ is hydrogen, methyl, ethyl, isopropyl, cyanomethyl, or —$(CH_2)_pC$≡$C(CH_2)_tH$, wherein p is 1 and t is 0.

10. A compound as claimed in claim 1, wherein $R^3$ is methyl.

11. A compound as claimed in claim 1, wherein $R^4$ is hydrogen or halo.

12. A compound as claimed in claim 1, wherein $R^4$ is hydrogen.

13. A compound as claimed in claim 1, wherein $Q_1$ is hydrogen, halo, $C_1$-$C_2$ alkyl or $C_1$-$C_2$ alkoxy.

14. A compound as claimed in claim 1, wherein $Q_1$ is hydrogen, chloro, methyl, or methoxy.

15. A compound as claimed in claim 1, wherein $Q_2$ is $A^1$ and $Q_3$ is $A^2$.

16. A compound as claimed in claim 1, wherein $Q_2$ is $A^2$ and $Q_3$ is $A^1$.

17. A compound as claimed in claim 1, wherein $Q_2$ is $A^2$ and $Q_3$ is $A^1$, wherein $A^1$ is hydrogen, halo, or $C_1$-$C_3$ haloalkyl and $A^2$ is the group defined by -$(Z)_m$-$(Z^1)$-$(Z^2)$, wherein Z is $CH_2$ and m is 0 or 1; $Z^1$ is $S(O)_2$; and $Z^2$ is $C_1$-$C_4$ alkyl or $NR^8R^9$ and wherein $R^8$ is hydrogen $C_1$-$C_4$alkyl, or alkoxy and $R^9$ is hydrogen, $C_1$-$C_4$alkyl, or alkoxy.

18. A compound as claimed in claim 1, wherein $Q_2$ is $A^2$ and $Q_3$ is $A^1$, wherein $A^1$ is hydrogen or chloro and $A^2$ is the group defined by -$(Z)_m$-$(Z^1)$-$(Z^2)$, wherein Z is $CH_2$ and m is 0 or 1; $Z^1$ is $S(O)_2$; and $Z^2$ is methyl or —$NH_2$.

19. A compound as claimed in claim 1, wherein $Q_2$ is $A^1$ and $Q_3$ is $A^2$, wherein $A^1$ is hydrogen, halo, or $C_1$-$C_3$ alkyl and $A^2$ is the group defined by -$(Z)_m$-$(Z^1)$-$(Z^2)$, wherein Z is $CH_2$ and m is 0 or 1; $Z^1$ is $S(O)_2$; and $Z^2$ is $C_1$-$C_4$ alkyl or $NR^8R^9$, and wherein $R^8$ is hydrogen $C_1$-$C_4$alkyl, or alkoxy and $R^9$ is hydrogen, $C_1$-$C_4$alkyl, or alkoxy.

20. A compound as claimed in claim 1, wherein $Q_2$ is $A^1$ and $Q_3$ is $A^2$, wherein $A^1$ is hydrogen, methyl, or chloro and $A^2$ is the group defined by -$(Z)_m$-$(Z^1)$-$(Z^2)$, wherein Z is $CH_2$ and m is 0 or 1; $Z^1$ is $S(O)_2$; and $Z^2$ is $NR^8R^9$, wherein $R^8$ is methoxy and $R^9$ is hydrogen.

21. A compound as claimed in claim 1, wherein D is —NRR$^1$, where R is $C_1$-$C_8$ alkyl, aryl, or aralkyl and R$^1$ is hydrogen; R$^2$ is $C_1$-$C_8$ alkyl. R$^2$ is methyl; R$^3$ is methyl; R$^4$ is hydrogen; $Q_1$ is hydrogen, chloro, methyl, or methoxy; $Q_2$ is A$^2$ and $Q_3$ is A$^1$, where A$^1$ is hydrogen or chloro and A$^2$ is the group defined by -(Z)$_m$-(Z$^1$)-(Z$^2$), where Z is CH$_2$ and m is 0 or 1; Z$^1$ is S(O)$_2$; and Z$^2$ is methyl or —NH$_2$.

22. A compound as claimed in claim 1, wherein D is —NRR$^1$, where R is $C_1$-$C_8$ alkyl, aryl, or aralkyl and R$^1$ is hydrogen; R$^2$ is $C_1$-$C_8$ alkyl, R$^2$ is methyl; R$^3$ is methyl; R$^4$ is hydrogen; $Q_1$ is hydrogen, chloro, methyl, or methoxy; $Q_2$ is A$^1$ and $Q_3$ is A$^2$, where A$^1$ is hydrogen, methyl, or chloro and A$^2$ is the group defined by -(Z)$_m$-(Z$^1$)-(Z$^2$), where Z is CH$_2$ and m is 0 or 1; Z$^1$ is S(O)$_2$; and Z$^2$ is NR$^8$R$^9$, where R$^8$ is methoxy and R$^9$ is hydrogen.

23. A compound as claimed in claim 1, selected from the group consisting of:
  N$^2$-isopropyl-N$^5$,1-dimethyl-N$^5$-[2-({4-[(methylsulfonyl)methyl]phenyl}amino)pyrimidin-4-yl]-1H-benzimidazole-2,5-diamine;
  N$^2$-isopropyl-N$^5$,1-dimethyl-N$^5$-[2-({4-[(methylsulfonyl)methyl]phenyl}amino)pyrimidin-4-yl]-1H-benzimidazole-2,5-diamine;
  1-{4-[(4-{methyl[1-methyl-2-(methylamino)-1H-benzimidazol-5-yl]amino}pyrimidin-2-yl)amino]phenyl}methanesulfonamide;
  N$^2$-benzyl-N$^5$,1-dimethyl-N$^5$-[2-({4-[(methylsulfonyl)methyl]phenyl}amino)pyrimidin-4-yl]-1H-benzimidazole-2,5-diamine;
  N$^5$,1-dimethyl-N$^5$-[2-({4-[(methylsulfonyl)methyl]phenyl}amino)pyrimidin-4-yl]-N$^2$-phenyl-1H-benzimidazole-2,5-diamine; and
  5-({4-[[2-(benzylamino)-1-methyl-1H-benzimidazol-5-yl](methyl)amino]pyrimidin-2-yl}amino)-N-methoxy-2-methylbenzenesulfonamide;
  or a salt thereof.

24. A compound as claimed in claim 1, selected from the group:
  3-{4-[(2-benzylamino-1-methyl-1H-benzoimidazol-5-yl)-methyl-amino]-pyrimidin-2-ylamino}-benzenesulfonamide;
  5-{4-[(2-benzylamino-1-methyl-1H-benzoimidazol-5-yl)-methyl-amino]-pyrimidinylamino}-2-methyl-benzenesulfonamide;
  (4-{4-[(2-benzylamino-1-methyl-1H-benzoimidazol-5-yl)-methyl-amino]-pyrimidin-2-ylamino}-phenyl)-methanesulfonamide;
  2-(4-{4-[(2-benzylamino-1-methyl-1H-benzoimidazol-5-yl)-methyl-amino]-pyrimidin-2-ylamino}-phenyl)-ethanesulfonic acid methylamide;
  3-(4-{[2-(4-fluoro-benzylamino)-1-methyl-1H-benzoimidazol-5-yl]-methyl-amino}-pyrimidin-2-ylamino)-benzenesulfonamide;
  5-(4-{[2-(4-fluoro-benzylamino)-1-methyl-1H-benzoimidazol-5-yl]-methyl-amino}-pyrimidin-2-ylamino)-2-methyl-benzenesulfonamide;
  N$^2$-(4-fluoro-benzyl)-N$^5$-[2-(4-methanesulfonylmethyl-phenylamino)-pyrimidin-4-yl]-1,N$^5$-dimethyl-1H-benzoimidazole-2,5-diamine;
  [4-(4-{[2-(4-fluoro-benzylamino)-1-methyl-1H-benzoimidazol-5-yl]-methyl-amino}-pyrimidin-2-ylamino)-phenyl]-methanesulfonamide;
  2-[4-(4-{[2-(4-fluoro-benzylamino)-1-methyl-1H-benzoimidazol-5-yl]-methyl-amino}-pyrimidin-2-ylamino)-phenyl]-ethanesulfonic acid methylamide;
  3-(4-{[2-(4-methoxy-benzylamino)-1-methyl-1H-benzoimidazol-5-yl]-methyl-amino}-pyrimidin-2-ylamino)-benzenesulfonamide;
  5-(4-{[2-(4-methoxy-benzylamino)-1-methyl-1H-benzoimidazol-5-yl]-methyl-amino}-pyrimidin-2-ylamino)-2-methyl-benzenesulfonamide;
  N$^5$-[2-(4-methanesulfonylmethyl-phenylamino)-pyrimidin-4-yl]-N$^2$-(4-methoxy-benzyl)-1,N$^5$-dimethyl-1H-benzoimidazole-2,5-diamine;
  [4-(4-{[2-(4-methoxy-benzylamino)-1-methyl-1H-benzoimidazol-5-yl]-methyl-amino}-pyrimidin-2-ylamino)-phenyl]-methanesulfonamide;
  2-[4-(4-{[2-(4-methoxy-benzylamino)-1-methyl-1H-benzoimidazol-5-yl]-methyl-amino}-pyrimidin-2-ylamino)-phenyl]-ethanesulfonic acid methylamide;
  5-(4-{[2-(3-fluoro-benzylamino)-1-methyl-1H-benzoimidazol-5-yl]-methyl-amino}-pyrimidin-2-ylamino)-2-methyl-benzenesulfonamide;
  3-(4-{[2-(3-fluoro-benzylamino)-1-methyl-1H-benzoimidazol-5-yl]-methyl-amino}-pyrimidin-2-ylamino)-benzenesulfonamide;
  N$^2$-(3-fluoro-benzyl)-N$^5$-[2-(4-methanesulfonylmethyl-phenylamino)-pyrimidin-4-yl]-1,N$^5$-dimethyl-1H-benzoimidazole-2,5-diamine;
  [4-(4-{[2-(3-fluoro-benzylamino)-1-methyl-1H-benzoimidazol-5-yl]-methyl-amino}-pyrimidin-2-ylamino)-phenyl]-methanesulfonamide;
  2-[4-(4-{[2-(3-fluoro-benzylamino)-1-methyl-1H-benzoimidazol-5-yl]-methyl-amino}-pyrimidin-2-ylamino)-phenyl]-ethanesulfonic acid methylamide;
  3-(4-{[2-(4-chloro-benzylamino)-1-methyl-1H-benzoimidazol-5-yl]-methyl-amino}-pyrimidin-2-ylamino)-benzenesulfonamide;
  5-(4-{[2-(4-chloro-benzylamino)-1-methyl-1H-benzoimidazol-5-yl]-methyl-amino}-pyrimidin-2-ylamino)-2-methyl-benzenesulfonamide;
  2-[4-(4-{[2-(4-chloro-benzylamino)-1-methyl-1H-benzoimidazol-5-yl]-methyl-amino}-pyrimidin-2-ylamino)-phenyl]-ethanesulfonic acid methylamide;
  N$^2$-(4-chloro-benzyl)-N$^5$-[2-(4-methanesulfonylmethyl-phenylamino)-pyrimidin-4-yl]-1,N$^5$-dimethyl-1H-benzoimidazole-2,5-diamine;
  3-{4-[(2-benzylamino-1-ethyl-1H-benzoimidazol-5-yl)-methyl-amino]-pyrimidin-2-ylamino}-benzenesulfonamide;
  5-{4-[(2-benzylamino-1-ethyl-1H-benzoimidazol-5-yl)-methyl-amino]-pyrimidin-2-ylamino}-2-methyl-benzenesulfonamide;
  N$^2$-benzyl-1-ethyl-N$^5$-[2-(4-methanesulfonylmethyl-phenylamino)-pyrimidin-4-yl]-N$^5$-methyl-1H-benzoimidazole-2,5-diamine;
  (4-{4-[(2-benzylamino-1-ethyl-1H-benzoimidazol-5-yl)-methyl-amino]-pyrimidin-2-ylamino}-phenyl)-methanesulfonamide;
  3-(4-{[2-(2-fluoro-benzylamino)-1-methyl-1H-benzoimidazol-5-yl]-methyl-amino}-pyrimidin-2-ylmethyl)-benzenesulfonamide;
  5-(4-{[2-(2-fluoro-benzylamino)-1-methyl-1H-benzoimidazol-5-yl]-methyl-amino}-pyrimidin-2-ylamino)-2-methyl-benzenesulfonamide;
  [4-(4-{[2-(2-fluoro-benzylamino)-1-methyl-1H-benzoimidazol-5-yl]-methyl-amino}-pyrimidin-2-ylamino)-phenyl]-methanesulfonamide;
  2-(4-{4-[(2-benzylamino-1-ethyl-1H-benzoimidazol-5-yl)-methyl-amino]-pyrimidin-2-ylamino}-phenyl)-ethanesulfonic acid methylamide;

3-(4-{methyl-[1-methyl-2-(1-phenyl-ethylamino)-1H-benzoimidazol-5-yl]-amino}-pyrimidin-2-ylamino)-benzenesulfonamide;

2-methyl-5-(4-{methyl-[1-methyl-2-(1-phenyl-ethylamino)-1H-benzoimidazol-5-yl]-amino}-pyrimidin-2-ylamino)-benzenesulfonamide;

$N^5$-[2-(4-methanesulfonylmethyl-phenylamino)-pyrimidin-4-yl]-1,$N^5$-dimethyl-$N^2$-(1-phenyl-ethyl)-1H-benzoimidazole-2,5-diamine;

[4-(4-{methyl-[1-methyl-2-(1-phenyl-ethylamino)-1H-benzoimidazol-5-yl]-amino}-pyrimidin-2-ylamino)-phenyl]-methanesulfonamide;

3-(4-{[2-(3-chloro-benzylamino)-1-methyl-1H-benzoimidazol-5-yl]-methyl-amino}-pyrimidin-2-ylamino)-benzenesulfonamide;

3-(4-{[2-(3-chloro-benzylamino)-1-methyl-1H-benzoimidazol-5-yl]-methyl-amino}-pyrimidin-2-ylamino)-benzenesulfonamide;

[4-(4-{[2-(4-chloro-benzylamino)-1-methyl-1H-benzoimidazol-5-yl]-methyl-amino}-pyrimidin-2-ylamino)-phenyl]-methanesulfonamide;

methanesulfonic acid-3-(4-{[2-(4-chloro-benzylamino)-1-methyl-1H-benzoimidazol-5-yl]-methyl-amino}-pyrimidin-2-ylamino)-phenyl ester;

$N^5$-{2-[4-(2-methanesulfonyl-ethyl)-phenylamino]-pyrimidin-4-yl}-$N^2$-(4-methoxy-benzyl)-1,$N^5$-dimethyl-1H-benzoimidazole-2,5-diamine;

$N^5$-{2-[3-(2-methanesulfonyl-ethyl)-phenylamino]-pyrimidin-4-yl}-$N^2$-(4-methoxy-benzyl)-1,$N^5$-dimethyl-1H-benzoimidazole-2,5-diamine;

$N^5$-{2-[4-(1-methanesulfonyl-ethyl)-phenylamino]-pyrimidin-4-yl}-$N^2$-(4-methoxy-benzyl)-1,$N^5$-dimethyl-1H-benzoimidazole-2,5-diamine;

$N^5$-[2-(3-methanesulfonylmethyl-phenylamino)-pyrimidin-4-yl]-$N^2$-(4-methoxy-benzyl)-1, $N^5$-dimethyl-1H-benzoimidazole-2,5-diamine;

$N^2$-benzyl-$N^5$-[2-(3-methanesulfonylmethyl-phenylamino)-pyrimidin-4-yl]-1,$N^5$-dimethyl-1H-benzoimidazole-2,5-diamine;

$N^5$-[2-(3-methanesulfonylmethyl-phenylamino)-pyrimidin-4-yl]-1,$N^5$-dimethyl-$N^2$-(1-phenyl-ethyl)-1H-benzoimidazole-2,5-diamine;

$N^5$-{2-[3-(2-methanesulfonyl-ethyl)-phenylamino]-pyrimidin-4-yl}-1,$N^5$-dimethyl-$N^2$-(1-phenyl-ethyl)-1H-benzoimidazole-2,5-diamine;

$N^5$-{2-[4-(2-methanesulfonyl-ethyl)-phenylamino]-pyrimidin-4-yl}-1,$N^5$-dimethyl-$N^2$-(1-phenyl-ethyl)-1H-benzoimidazole-2,5-diamine;

2-methyl-5-(4-{methyl-[1-methyl-2-(4-methyl-benzylamino)-1H-benzoimidazol-5-yl]-amino}-pyrimidin-2-ylamino)-benzenesulfonamide;

$N^5$-[2-(4-methanesulfonylmethyl-phenylamino)-pyrimidin-4-yl]-1,$N^5$-dimethyl-$N^2$-(4-methyl-benzyl)-1H-benzoimidazole-2,5-diamine;

$N^5$-[2-(3-methanesulfonylmethyl-phenylamino)-pyrimidin-4-yl]-1,$N^5$-dimethyl-$N^2$-(4-methyl-benzyl)-1H-benzoimidazole-2,5-diamine;

$N^5$-{2-[4-(2-methanesulfonyl-ethyl)-phenylamino]-pyrimidin-4-yl}-1,$N^5$-dimethyl-$N^2$-(4-methyl-benzyl)-1H-benzoimidazole-2,5-diamine;

$N^5$-{2-[3-(2-methanesulfonyl-ethyl)-phenylamino]-pyrimidin-4-yl}-1,$N^5$-dimethyl-$N^2$-(4-methyl-benzyl)-1H-benzoimidazole-2,5-diamine; and $N^5$-{2-[4-(1-methanesulfonyl-ethyl)-phenylamino]-pyrimidin-4-yl}-1,$N^5$-dimethyl-$N^2$-(4-methyl-benzyl)-1H-benzoimidazole-2,5-diamine;

or a salt thereof.

25. A compound as claimed in claim 1, selected from the group:

(1-methyl-5-{methyl-[2-(3-sulfamoyl-phenylamino)-pyrimidin-4-yl]-amino}-1H-benzoimidazol-2-yl)-phenyl-carbamic acid tert-butyl ester;

3-{4-[methyl-(1-methyl-2-phenylamino-1H-benzoimidazol-5-yl)-amino]-pyrimidin-2-ylamino}-benzenesulfonamide;

(1-methyl-5-{methyl-[2-(4-methyl-3-sulfamoyl-phenylamino)-pyrimidin-4-yl]-amino}-1H-benzoimidazol-2-yl)-phenyl-carbamic acid tert-butyl ester;

$N^5$-[2-(3-methanesulfonyl-4-methyl-phenylamino)-pyrimidin-4-yl]-1,$N^5$-dimethyl-$N^2$-phenyl-1H-benzoimidazole-2,5-diamine;

$N^5$-[2-(4-methanesulfonylmethyl-phenylamino)-pyrimidin-4-yl]-1,$N^5$-dimethyl-$N^2$-phenyl-1H-benzoimidazole-2,5-diamine;

(4-{4-[methyl-(1-methyl-2-phenylamino-1H-benzoimidazol-5-yl)-amino]-pyrimidin-2-ylamino}-phenyl)-methanesulfonamide;

methanesulfonic acid 4-{4-[methyl-(1-methyl-2-phenylamino-1H-benzoimidazol-5-yl)-amino]-pyrimidin-2-ylamino}-phenyl ester;

3-(4-{[2-(4-fluoro-phenylamino)-1-methyl-1H-benzoimidazol-5-yl]-methyl-amino}-pyrimidin-2-ylamino)-benzenesulfonamide;

5-(4-{[2-(4-fluoro-phenylamino)-1-methyl-1H-benzoimidazol-5-yl]-methyl-amino}-pyrimidin-2-ylamino)-2-methyl-benzenesulfonamide;

$N^2$-(4-fluoro-phenyl)-$N^5$-[2-(4-methanesulfonylmethyl-phenylamino)-pyrimidin-4-yl]-1,$N^5$-dimethyl-1H-benzoimidazole-2,5-diamine;

[4-(4-{[2-(4-fluoro-phenylamino)-1-methyl-1H-benzoimidazol-5-yl]-methyl-amino}-pyrimidin-2-ylamino)-phenyl]-methanesulfonamide;

methanesulfonic acid 4-(4-{[2-(4-fluoro-phenylamino)-1-methyl-1H-benzoimidazol-5-yl]-methyl-amino}-pyrimidin-2-ylamino)-phenyl ester;

methanesulfonic acid 3-(4-{[2-(4-fluoro-phenylamino)-1-methyl-1H-benzoimidazol-5-yl]-methyl-amino}-pyrimidin-2-ylamino)-phenyl ester;

$N^5$-[2-(4-methanesulfonylmethyl-phenylamino)-pyrimidin-4-yl]-1,$N^5$-dimethyl-$N^2$-p-tolyl-1H-benzoimidazole-2,5-diamine;

[4-(4-{[2-(4-tert-butyl-phenylamino)-1-methyl-1H-benzoimidazol-5-yl]-methyl-amino}-pyrimidin-2-ylamino)-phenyl]-methanesulfonamide;

3-(4-{[2-(4-tert-butyl-phenylamino)-1-methyl-1H-benzoimidazol-5-yl]-methyl-amino}-pyrimidin-2-ylamino)-benzenesulfonamide;

5-(4-{[2-(4-tert-butyl-phenylamino)-1-methyl-1H-benzoimidazol-5-yl]-methyl-amino}-pyrimidin-2-ylamino)-2-methyl-benzenesulfonamide;

$N^2$-(4-tert-butyl-phenyl)-$N^5$-[2-(4-methanesulfonylmethyl-phenylamino)-pyrimidin-4-yl]-1,$N^5$-dimethyl-1H-benzoimidazole-2,5-diamine;

(5-{[2-(4-methanesulfonylmethyl-phenylamino)-pyrimidin-4-yl]-methyl-amino}-1-methyl-1H-benzoimidazol-2-yl)-(4-methoxy-phenyl)-carbamic acid tert-butyl ester;

$N^5$-[2-(4-methanesulfonylmethyl-phenylamino)-pyrimidin-4-yl]-$N^2$-(4-methoxy-phenyl)-1,$N^5$-dimethyl-1H-benzoimidazole-2,5-diamine;

(4-methoxy-phenyl)-(1-methyl-5-{methyl-[2-(4-sulfamoylmethyl-phenylamino)-pyrimidin-4-yl]-amino}-1H-benzoimidazol-2-yl)-carbamic acid tert-butyl ester;

[4-(4-{[2-(4-methoxy-phenylamino)-1-methyl-1H-benzoimidazol-5-yl]-methyl-amino}-pyrimidin-2-ylamino)-phenyl]-methanesulfonamide;

(5-{[2-(3-methanesulfonylmethyl-phenylamino)-pyrimidin-4-yl]-methyl-amino}-1-methyl-1H-benzoimidazol-2-yl)-(4-methoxy-phenyl)-carbamic acid tert-butyl ester;

$N^5$-[2-(3-methanesulfonylmethyl-phenylamino)-pyrimidin-4-yl]-$N^2$-(4-methoxy-phenyl)-1,$N^5$-dimethyl-1H-benzoimidazole-2,5-diamine;

[5-({2-[4-(1-methanesulfonyl-ethyl)-phenylamino]-pyrimidin-4-yl}-methyl-amino)-1-methyl-1H-benzoimidazol-2-yl]-(4-methoxy-phenyl)-carbamic acid tert-butyl ester;

$N^5$-{2-[4-(1-methanesulfonyl-ethyl)-phenylamino]-pyrimidin-4-yl}-$N^2$-(4-methoxy-phenyl)-1,$N^5$-dimethyl-1H-benzoimidazole-2,5-diamine; and $N^5$-{2-[3-(1-methanesulfonyl-ethyl)-phenylamino]-pyrimidin-4-yl}-$N^2$-(4-methoxy-phenyl)-1,$N^5$-dimethyl-1H-benzoimidazole-2,5-diamine;

or a salt thereof.

26. A compound as claimed in claim 1, selected from the group:

3-{4-[(2-isopropylamino-1-methyl-1H-benzoimidazol-5-yl)-methyl-amino]-pyrimidin-2-ylamino}-benzenesulfonamide;

2-chloro-5-{4-[(2-isopropylamino-1-methyl-1H-benzoimidazol-5-yl)-methyl-amino]-pyrimidin-2-ylamino}-benzenesulfonamide;

5-{4-[(2-isopropylamino-1-methyl-1H-benzoimidazol-5-yl)-methyl-amino]-pyrimidin-2-ylamino}-2-methyl-benzenesulfonamide;

2-(4-{4-[(2-isopropylamino-1-methyl-1H-benzoimidazol-5-yl)-methyl-amino]-pyrimidin-2-ylamino}-phenyl)-ethanesulfonic acid methylamide;

methanesulfonic acid 4-{4-[(2-isopropylamino-1-methyl-1H-benzoimidazol-5-yl)-methyl-amino]-pyrimidin-2-ylamino}-phenyl ester;

methanesulfonic acid 3-{4-[(2-isopropylamino-1-methyl-1H-benzoimidazol-5-yl)-methyl-amino]-pyrimidin-2-ylamino}-phenyl ester;

$N^2$-isopropyl-$N^5$-[2-(3-methanesulfonylmethyl-phenylamino)-pyrimidin-4-yl]-1, $N^5$-dimethyl-1H-benzoimidazole-2,5-diamine;

3-[4-(1-methyl-2-phenethylamino-1H-benzoimidazol-5-ylamino)-pyrimidin-2-ylamino]-benzenesulfonamide;

2-methyl-5-{4-[methyl-(1-methyl-2-phenethylamino-1H-benzoimidazol-5-yl)-amino]-pyrimidin-2-ylamino}-benzenesulfonamide;

(4-{4-[methyl-(1-methyl-2-phenethylamino-1H-benzoimidazol-5-yl)-amino]-pyrimidin-2-ylamino}-phenyl)-methanesulfonamide;

$N^5$-[2-(4-methanesulfonylmethyl-phenylamino)-pyrimidin-4-yl]-1,$N^5$-dimethyl-$N^2$-phenethyl-1H-benzoimidazole-2,5-diamine;

2-(4-{4-[methyl-(1-methyl-2-phenethylamino-1H-benzoimidazol-5-yl)-amino]-pyrimidin-2-ylamino}-phenyl)-ethanesulfonic acid methylamide;

$N^2$-tert-Butyl-$N^5$-[2-(4-methanesulfonylmethyl-phenylamino)-pyrimidin-4-yl]-1, $N^5$-dimethyl-1H-benzoimidazole-2,5-diamine;

$N^2$-cyclohexyl-$N^5$-[2-(4-methanesulfonylmethyl-phenylamino)-pyrimidin-4-yl]-1, $N^5$-dimethyl-1H-benzoimidazole-2,5-diamine;

5-{4-[(2-cyclohexylamino-1-methyl-1H-benzoimidazol-5-yl)-methyl-amino]-pyrimidin-2-ylamino}-2-methyl-benzenesulfonamide;

$N^2$-cyclohexyl-$N^5$-{2-[3-(2-methanesulfonyl-ethyl)-phenylamino]-pyrimidin-4-yl}-1,$N^5$-dimethyl-1H-benzoimidazole-2,5-diamine;

$N^2$-cyclohexyl-$N^5$-{2-[4-(2-methanesulfonyl-ethyl)-phenylamino]-pyridin-4-yl}-1, $N^5$-dimethyl-1H-benzoimidazole-2,5-diamine;

$N^2$-cyclohexyl-$N^5$-{2-[4-(1-methanesulfonyl-ethyl)-phenylamino]-pyrimidin-4-yl}-1,$N^5$-dimethyl-1H-benzoimidazole-2,5-diamine;

2-methyl-5-{4-[methyl-(1-methyl-2-methylamino-1H-benzoimidazol-5-yl)-amino]-pyrimidin-2-ylamino}-benzenesulfonamide;

(4-{4-[methyl-(1-methyl-2-methylamino-1H-benzoimidazol-5-yl)-amino]-pyrimidin-2-ylamino}-phenyl)-methanesulfonamide;

3-{4-[methyl-(1-methyl-2-methylamino-1H-benzoimidazol-5-yl)-amino]-pyrimidin-2-ylamino}-benzenesulfonamide;

$N^5$-[2-(3-methanesulfonylmethyl-phenylamino)-pyrimidin-4-yl]-1,$N^2$,$N^5$-trimethyl-1H-benzoimidazole-2,5-diamine; and (4-{4-[(1-ethyl-2-methylamino-1H-benzoimidazol-5-yl)-methyl-amino]-pyrimidin-2-ylamino}-phenyl)-methanesulfonamide;

or a salt thereof.

27. A compound as claimed in claim 1, selected from the group:

$N^1$-methyl-$N^5$-[2-(4-Methanesulfonymethyl-phenylamino)-pyrimidin-4-yl]-$N^5$-methyl-$N^2$-(4-trifluoromethyl-phenyl)-1H-benzoimidazole-2,5-diamine;

$N^2$-(3-chloro-phenyl)-$N^5$-[2-(4-methanesulfonylmethyl-phenylamino)-pyrimidin-4-yl]-$N^1$,$N^5$-dimethyl-1H-benzoimidazole-2,5-diamine;

$N^2$-(4-chloro-phenyl)-$N^5$-[2-(4-methanesulfonylmethyl-phenylamino)-pyrimidin-4-yl]-$N^1$,$N^5$-dimethyl-1H-benzoimidazole-2,5-diamine;

$N^2$-(2,4-dichloro-phenyl)-$N^5$-[2-(4-methanesulfonylmethyl-phenylamino)-pyrimidin-4-yl]-$N^1$,$N^5$-dimethyl-1H-benzoimidazole-2,5-diamine;

$N^2$-(2,5-dichloro-phenyl)-$N^5$-[2-(4-methanesulfonylmethyl-phenylamino)-pyrimidin-4-yl]-$N^1$,$N^5$-dimethyl-1H-benzoimidazole-2,5-diamine;

$N^2$-(2-chloro-4-trifluoromethyl-phenyl)-$N^5$-[2-(4-methanesulfonylmethyl-phenylamino)-pyrimidin-4-yl]-$N^1$,$N^5$-dimethyl-1H-benzoimidazole-2,5-diamine;

$N^2$-(2-chloro-5-trifluoromethyl-phenyl)-$N^5$-[2-(4-methanesulfonylmethyl-phenylamino)-pyrimidin-4-yl]-$N^1$,$N^5$-dimethyl-1H-benzoimidazole-2,5-diamine;

$N^5$-[2-(4-methanesulfonylmethyl-phenylamino)-pyrimidin-4-yl]-$N^1$,$N^5$-dimethyl-$N^2$-(4-morpholin-4-yl-phenyl)-1H-benzoimidazole-2,5-diamine;

$N^2$-(3-fluoro-phenyl)-$N^5$-[2-(4-methanesulfonylmethyl-phenylamino)-pyrimidin-4-yl]-$N^1$,$N^5$-dimethyl-1H-benzoimidazole-2,5-diamine;

$N^2$-(2,4-difluoro-phenyl)-$N^5$-[2-(4-methanesulfonylmethyl-phenylamino)-pyrimidin-4-yl]-$N^1$,$N^5$-dimethyl-1H-benzoimidazole-2,5-diamine;

$N^2$-(2-chloro-4-fluoro-phenyl)-$N^5$-[2-(4-methanesulfonylmethyl-phenylamino)-pyrimidin-4-yl]-$N^1$,$N^5$-dimethyl-1H-benzoimidazole-2,5-diamine;

$N^2$-(4-chloro-2-fluoro-phenyl)-$N^5$-[2-(4-methanesulfonylmethyl-phenylamino)-pyrimidin-4-yl]-$N^1$,$N^5$-dimethyl-1H-benzoimidazole-2,5-diamine;

$N^2$-(2-chloro-5-fluoro-phenyl)-$N^5$-[2-(4-methanesulfonylmethyl-phenylamino)-pyrimidin-4-yl]-$N^1$,$N^5$-dimethyl-1H-benzoimidazole-2,5-diamine;

$N^2$-(2-fluoro-4-methyl-phenyl)-$N^5$-[2-(4-methanesulfonylmethyl-phenylamino)-pyrimidin-4-yl]-$N^1$,$N^5$-dimethyl-1H-benzoimidazole-2,5-diamine;
$N^2$-(2-fluoro-phenyl)-$N^5$-[2-(4-methanesulfonylmethyl-phenylamino)-pyrimidin-4-yl]-$N^1$,$N^5$-dimethyl-1H-benzoimidazole-2,5-diamine;
$N^2$-(2-fluoro-5-trifluoromethyl-phenyl)-$N^5$-[2-(4-methanesulfonylmethyl-phenylamino)-pyrimidin-4-yl]-$N^1$,$N^5$-dimethyl-1H-benzoimidazole-2,5-diamine;
4-{4-[methyl-(1-methyl-2-methylsulfanyl-1H-benzoimidazol-5-yl)-amino]-pyrimidin-2-ylamino}-benzene sulfonamide;
4-{4-[(2-methanesulfinyl-1-methyl-1H-benzoimidazol-5-yl)-methyl-amino]-pyrimidin-2-ylamino}-benzensulfonamide;
4-(4-{methyl-[1-methyl-2-(4-trifluoromethyl-phenylamino)-1H-benzoimidazol-5-yl]-amino}-pyrimidin-2-ylamino)-benzenesulfonamide;
(methyl-nitro-1H-benzoimidazol-2-yl)-(3-trifluoromethyl-phenyl)-amine;
(methyl-nitro-1H-benzoimidazol-2-yl)-(3-trifluoromethyl-phenyl)-carbamic acid dimethyl-ethyl ester;
(amino-methyl-1-benzoimidazol-2-yl)-(3-trifluoromethyl-phenyl)-carbamic acid dimethyl-ethyl ester;
[(2-chloro-pyrimidin-4-yl)-methyl-amino]-methyl-1H-benzoimidazol-2-yl}-(3-trifluoromethyl-phenyl)-carbamic acid dimethyl-ethyl ester; and
$N^5$-[2-(4-methanesulfonylmethyl-phenylamino)-pyrimidin-4-yl]-$N^1$,$N^5$-dimethyl-$N^2$-(3-trifluoromethyl-phenyl)-1H-benzoimidazole-2,5-diamine;
or a salt thereof.

28. A compound as claimed in claim 1, selected from the group:
$N^2$-(5-tert-butyl-isoxazol-3-yl)-$N^5$[2-(4-methanesulfonylmethyl-phenylamino)-pyrimidin-4-yl]-1,$N^5$-dimethyl-1H-methyl-amino-benzoimidazole-2,5-diamine;
$N^2$-(5-tert-butyl-isoxazol-3-yl)-$N^5$[2-(4-methanesulfonylmethyl-phenylamino)-pyrimidin-4-yl]-1,$N^5$-methyl-1-1H-benzoimidazole-2,5-diamine;
$N^2$-(5-tert-butyl-isoxazol-3-yl)-$N^5$-[2-(3-methanesulfonylmethyl-phenylamino)-pyrimidin-4-yl]-1-methyl-1H-benzoimidazole-2,5-diamine;
$N^2$-(5-tert-butyl-isoxazol-3-yl)-$N^5$-[2-(3-methanesulfonylmethyl-phenylamino)-pyrimidin-4-yl]-1,N5-dimethyl-1-H-benzoimidazole-2,5-diamine;
$N^2$-(5-tert-butyl-isoxazol-3-yl)-$N^5$-[2-(3-methanesulfonyl-4-methyl-phenylamino)-pyrimidin-4-yl]-1-methyl-1-1H-benzoimidazole-2,5-diamine;
5-(4-{[2-(5-tert-butyl-isoxazol-3-ylamino)-1-methyl-1-H-benzoimidazol-5-yl]-methyl-amino}-pyrimidin-2-ylamino)-2-methyl-benzenesulfonamide;
$N^2$-(6-fluoro-4-H benzo[1,3]dioxin-8-ylmethyl)-$N^5$-[2-(3-methanesulfonyl-4-methyl-phenylamino)-pyrimidin-4-yl]-1-methyl-1H-benzoimidazole-2,5-diamine; and
$N^2$-(5-tert-butyl-isoxazol-3-yl)-1-methyl-$N^5$-{2-[3-(morpholine-4-sulfonyl)-phenylamino]-pyrimidin-4-yl}-1H-benzoimidazole-2,5-diamine;
or a salt thereof.

29. A compound as claimed in claim 1, selected from the group:
N-(1-methyl-5-{methyl[2-({4-[(methylsulfonyl)methyl]phenyl}amino)pyrimidin-4-yl]amino}-1H-benzimidazol-2-yl)-N'-phenylurea;
N-(1-methyl-5-{methyl[2-({4-[(methylsulfonyl)methyl]phenylamino)pyrimidin-4-yl]amino}-1H-benzimidazol-2-yl)benzamide;
N-(1-methyl-5-{methyl[2-({4-[(methylsulfonyl)methyl]phenyl}amino)pyrimidin-4-yl]amino}-1H-benzimidazol-2-yl)indoline-1-carboxamide;
N-(5-tert-butylisoxazol-3-yl)-N'-(1-methyl-5-{methyl[2-({4-[(methylsulfonyl)methyl]phenyl}amino)pyrimidin-4-yl]amino}-1H-benzimidazol-2-yl)urea;
N-(1-methyl-5-{methyl[2-({4-[(methylsulfonyl)methyl]phenyl}amino)pyrimidin-4-yl]amino}-1H-benzimidazol-2-yl)-2-phenylacetamide;
N-(1-methyl-5-{methyl[2-({4-[(methylsulfonyl)methyl]phenyl}amino)pyrimidin-4-yl]amino}-1H-benzimidazol-2-yl)-1-phenylcyclopropanecarboxamide;
N-(1-methyl-5-{methyl[2-({4-[(methylsulfonyl)methyl]phenyl}amino)pyrimidin-4-yl]amino}-1H-benzimidazol-2-yl)isonicotinamide;
N-(1-methyl-5-{methyl[2-({4-[(methylsulfonyl)methyl]phenyl}amino)pyrimidin-4-yl]amino}-1H-benzimidazol-2-yl)cyclohexanecarboxamide;
2-(benzyloxy)-N-(1-methyl-5-{methyl[2-({4-[(methylsulfonyl)methyl]phenyl}amino)pyrimidin-4-yl]amino}-1H-benzimidazol-2-yl)acetamide;
2-(3-methylisoxazol-5-yl)-N-(1-methyl-5-{methyl[2-({4-[(methylsulfonyl)methyl]phenyl}amino)pyrimidin-4-yl]amino}-1H-benzimidazol-2-yl)acetamide; and
3-[(dimethylamino)methyl]-N-(1-methyl-5-{methyl[2-({4-[(methylsulfonyl)methyl]phenyl}amino)pyrimidin-4-yl]amino}-1H-benzimidazol-2-yl)benzamide;
or a salt thereof.

30. A compound as claimed in claim 1, selected from the group:
N-({[3-(4-methanesulfonylmethyl-phenylamino)-phenyl]-methyl-amino}-methyl-1H-benzoimidazol-2-yl)-C-thiophen-2-yl-acetamide;
C-fluoro-N-({[3-(3-methanesulfonylmethyl-phenylamino)-phenyl]-methyl-amino}-methyl-1H-benzoimidazol-2-yl)-trifluoromethyl-benzamide;
difluoro-N-({[2-(3-methanesulfonylmethyl-phenylamino)-pyrimidin-4-yl]-methyl-amino}-methyl-1H-benzoimidazol-2-yl)-benzamide;
N-({[2-(3-methanesulfonylmethyl-phenylamino)-pyrimidin-4-yl]-methyl-amino}-methyl-1H-benzoimidazol-2-yl)-3,5-bis-trifluoromethyl-benzamide;
cyclohexanecarboxylic acid ({[2-(3-methanesulfonylmethyl-phenylamino)-pyrimidin-4-yl]-methyl-amino}-methyl-1H-benzoimidazol-2-yl)-amide;
N-({[2-(3-methanesulfonylmethyl-phenylamino)-pyrimidin-4-yl]-methyl-amino}-methyl-1H-benzoimidazol-2-yl)-methyl-benzamide;
N-({[2-(3-methanesulfonylmethyl-phenylamino)-pyrimidin-4-yl]-methyl-amino}-methyl-1H-benzoimidazol-2-yl)-4-methoxy-benzamide;
C-(chloro-trifluoromethyl-phenyl)-N-({[2-(3-methanesulfonylmethyl-phenylamino)-pyrimidin-4-yl]-methyl-amino}-methyl-1H-benzoimidazol-2-yl)-acetamide;
(3,5-bis-trifluoromethyl-phenyl)-N-({[2-(3-methanesulfonylmethyl-phenylamino)-pyrimidin-4-yl]-methyl-amino}-methyl-1H-benzoimidazol-2-yl)-acetamide;
N-(5-{[2-(3-methanesulfonylmethyl-phenylamino)-pyrimidin-4-yl]-methyl-amino}-1-methyl-1H-benzoimidazol-2-yl)-2-(3-trifluoromethylsulfanyl-phenyl)-acetamide;
(2,4-bis-trifluoromethyl-phenyl)-N-({[2-(3-methanesulfonylmethyl-phenylamino)-pyrimidin-4-yl]-methyl-amino}-methyl-1H-benzoimidazol-2-yl)-acetamide;
(2-fluoro-5-trifluoromethyl-phenyl)-N-({[2-(3-methanesulfonylmethyl-phenylamino)-pyrimidin-4-yl]-methyl-amino}-methyl-1H-benzoimidazol-2-yl)-acetamide;

3H-benzotriazole-5-carboxylic acid ({[2-(3-methanesulfonylmethyl-phenylamino)-pyrimidin-4-yl]-methyl-amino}-methyl-1H-benzoimidazol-2-yl)-amide;
3H-benzoimidazole-5-carboxylic acid ({[2-(3-methanesulfonylmethyl-phenylamino)-pyrimidin-4-yl]-methyl-amino}-methyl-1H-benzoimidazol-2-yl)-amide;
thiophene-2-carboxylic acid ({[2-(3-methanesulfonylmethyl-phenylamino)-pyrimidin-4-yl]-methyl-amino}-methyl-1H-benzoimidazol-2-yl)-amide;
thiophene-3-carboxylic acid ({[2-(3-methanesulfonylmethyl-phenylamino)-pyrimidin-4-yl]-methyl-amino}-methyl-1H-benzoimidazol-2-yl)-amide;
N-({[2-(3-methanesulfonylmethyl-phenylamino)-pyrimidin-4-yl]-methyl-amino}-methyl-1H-benzoimidazol-2-yl)-C-thiophen-2-yl-acetamide;
3-methyl-thiophene-2-carboxylic acid ({[2-(4-methanesulfonylmethyl-phenylamino)-pyrimidin-4-yl]-methyl-amino}-methyl-1H-benzoimidazol-2-yl)-amide;
furan-3-carboxylic acid ({[2-(4-methanesulfonylmethyl-phenylamino)-pyrimidin-4-yl]-methyl-amino}-methyl-1H-benzoimidazol-2-yl)-amide;
3-methyl-furan-2-carboxylic acid ({[2-(4-methanesulfonylmethyl-phenylamino)-pyrimidin-4-yl]-methyl-amino}-methyl-1H-benzoimidazol-2-yl)-amide;
N-({[2-(4-methanesulfonylmethyl-phenylamino)-pyrimidin-4-yl]-methyl-amino}-methyl-1H-benzoimidazol-2-yl)-2-(3-methyl-isoxazol-5-yl)-acetamide;
C-(chloro-trifluoromethyl-phenyl)-N-({[2-(4-methanesulfonylmethyl-phenylamino)-pyrimidin-4-yl]-methyl-amino}-methyl-1H-benzoimidazol-2-yl)-acetamide;
N-(5-{[2-(4-methanesulfonylmethyl-phenylamino)-pyrimidin-4-yl]-methyl-amino}-1-methyl-1H-benzoimidazol-2-yl)-2-(3-trifluoromethylsulfanyl-phenyl)-acetamide;
C-(fluoro-trifluoromethyl-phenyl)-N-({[2-(4-methanesulfonylmethyl-phenylamino)-pyrimidin-4-yl]-methyl-amino}-methyl-1H-benzoimidazol-2-yl)-acetamide;
N-({[2-(4-methanesulfonylmethyl-phenylamino)-pyrimidin-4-yl]-methyl-amino}-methyl-1H-benzoimidazol-2-yl)-dimethyl-butyramide;
2-propyl-pentanoic acid ({[2-(4-methanesulfonylmethyl-phenylamino)-pyrimidin-4-yl]-methyl-amino}-methyl-1H-benzoimidazol-2-yl)-amide;
N-({[2-(4-methanesulfonylmethyl-phenylamino)-pyrimidin-4-yl]-methyl-amino}-methyl-1H-benzoimidazol-2-yl)-isobutyramide;
cyclopropanecarboxylic acid ({[2-(4-methanesulfonylmethyl-phenylamino)-pyrimidin-4-yl]-methyl-amino}-methyl-1H-benzoimidazol-2-yl)-amide;
N-({[2-(4-methanesulfonylmethyl-phenylamino)-pyrimidin-4-yl]-methyl-amino}-methyl-1H-benzoimidazol-2-yl)-4-methoxy-benzamide;
4-methoxy-N-(methyl-{methyl-[2-(4-methyl-3-sulfamoyl-phenylamino)-pyrimidin-4-yl]-amino}-1H-benzoimidazol-2-yl)-benzamide;
furan-2-carboxylic acid ({[2-(4-methanesulfonylmethyl-phenylamino)-pyrimidin-4-yl]-methyl-amino}-methyl-1H-benzoimidazol-2-yl)-amide;
N-(methyl-{methyl-[2-(4-methyl-3-sulfamoyl-phenylamino)-pyrimidin-4-yl]-amino}-1H-benzoimidazol-2-yl)-C-thiophen-2-yl-acetamide;
C-(chloro-trifluoromethyl-phenyl)-N-(methyl-{methyl-[2-(4-methyl-3-sulfamoyl-phenylamino)-pyrimidin-4-yl]-amino}-1H-benzoimidazol-2-yl)-acetamide;
4-methoxy-N-[methyl-(methyl-{2-[3-(morpholine-4-sulfonyl)-phenylamino]-pyrimidin-4-yl}-amino)-1H-benzoimidazol-2-yl]-benzamide;
N-[methyl-(methyl-{2-[3-(morpholine-4-sulfonyl)-phenylamino]-pyrimidin-4-yl}-amino)-1H-benzoimidazol-2-yl]-C-thiophen-2-yl-acetamide;
thiophene-2-carboxylic acid [methyl-(methyl-(2-[3-(morpholine-4-sulfonyl)-phenylamino]-pyrimidin-4-yl}-amino)-1H-benzoimidazol-2-yl]-amide;
furan-2-carboxylic acid [methyl-(methyl-{2-[3-(morpholine-4-sulfonyl)-phenylamino]-pyrimidin-4-yl}-amino)-1H-benzoimidazol-2-yl]-amide;
N-({[2-(3-methanesulfonylmethyl-phenylamino)-pyrimidin-4-yl]-methyl-amino}-methyl-1H-benzoimidazol-2-yl)-2-(3-methyl-isoxazol-5-yl)-acetamide;
furan-2-carboxylic acid ({[2-(3-methanesulfonylmethyl-phenylamino)-pyrimidin-4-yl]-methyl-amino}-methyl-1H-benzoimidazol-2-yl)-amide;
2-(3-methyl-isoxazol-5-yl)-N-[methyl-(methyl-{2-[3-(morpholine-4-sulfonyl)-phenylamino]-pyrimidin-4-yl}-amino)-1H-benzoimidazol-2-yl]-acetamide;
3-methyl-furan-2-carboxylic acid ({[2-(3-methanesulfonylmethyl-phenylamino)-pyrimidin-4-yl]-methyl-amino}-methyl-1H-benzoimidazol-2-yl)-amide;
N-[methyl-(methyl-{2-[3-(4-methyl-piperazine-1-sulfonyl)-phenylamino]-pyrimidin-4-yl}-amino)-1H-benzoimidazol-2-yl]-C-thiophen-2-yl-acetamide;
thiophene-2-carboxylic acid [methyl-(methyl-{2-[3-(4-methyl-piperazine-1-sulfonyl)-phenylamino]-pyrimidin-4-yl}-amino)-1H-benzoimidazol-2-yl]-amide;
furan-2-carboxylic acid [methyl-(methyl-{2-[3-(4-methyl-piperazine-1-sulfonyl)-phenylamino]-pyrimidin-4-yl}-amino)-1H-benzoimidazol-2-yl]-amide;
2-(3-methyl-isoxazol-5-yl)-N-[methyl-(methyl-{2-[3-(4-methyl-piperazine-1-sulfonyl)-phenylamino]-pyrimidin-4-yl}-amino)-1H-benzoimidazol-2-yl]-acetamide;
N-({[2-(3-methanesulfonylmethyl-phenylamino)-pyrimidin-4-yl]-methyl-amino}-methyl-1H-benzoimidazol-2-yl)-dimethyl-butyramide;
N-({[2-(3-methanesulfonylmethyl-phenylamino)-pyrimidin-4-yl]-methyl-amino}-methyl-1H-benzoimidazol-2-yl)-propionamide;
pentanoic acid ({[2-(3-methanesulfonylmethyl-phenylamino)-pyrimidin-4-yl]-methyl-amino}-methyl-1H-benzoimidazol-2-yl)-amide;
N-({[2-(3-methanesulfonylmethyl-phenylamino)-pyrimidin-4-yl]-methyl-amino}-methyl-1H-benzoimidazol-2-yl)-butyramide;
phenyl-N-({[2-(4-methanesulfonylmethyl-phenylamino)-pyrimidin-4-yl]-methyl-amino}-methyl-1H-benzoimidazol-2-yl)-acetamide;
phenylcyclopropanecarboxylic acid ({[2-(4-methanesulfonylmethyl-phenylamino)-pyrimidin-4-yl]-methyl-amino}-methyl-1H-benzoimidazol-2-yl)-amide;
1-(2,5-difluoro-phenyl)-cyclopropanecarboxylic acid ({[2-(4-methanesulfonylmethyl-phenylamino)-pyrimidin-4-yl]-methyl-amino}-methyl-1H-benzoimidazol-2-yl)-amide;
1-(4-chloro-phenyl)-cyclopropanecarboxylic acid ({[2-(4-methanesulfonylmethyl-phenylamino)-pyrimidin-4-yl]-methyl-amino}-methyl-1H-benzoimidazol-2-yl)-amide;
2-(4-fluoro-phenyl)-N-({[2-(4-methanesulfonylmethyl-phenylamino)-pyrimidin-4-yl]-methyl-amino}-methyl-1H-benzoimidazol-2-yl)-acetamide;
(3,5-bistrifluoromethyl-phenyl)-N-({[2-(4-methanesulfonylmethyl-phenylamino)-pyrimidin-4-yl]-methyl-amino}-methyl-1H-benzoimidazol-2-yl)-acetamide;

(3,4-dichlorophenyl)-N-({[2-(4-methanesulfonylmethyl-phenylamino)-pyrimidin-4-yl]-methyl-amino}-methyl-1H-benzoimidazol-2-yl)-acetamide;

1-(2,5-difluorophenyl)-cyclopropanecarboxylic acid ({[2-(3-methanesulfonylmethyl-phenylamino)-pyrimidin-4-yl]-methyl-amino}-methyl-1H-benzoimidazol-2-yl)-amide;

(2,5-difluorophenyl)-N-({[2-(3-methanesulfonylmethyl-phenylamino)-pyrimidin-4-yl]-methyl-amino}-methyl-1H-benzoimidazol-2-yl)-acetamide;

(3,4-dichlorophenyl)-N-({[2-(3-methanesulfonylmethyl-phenylamino)-pyrimidin-4-yl]-methyl-amino}-methyl-1H-benzoimidazol-2-yl)-acetamide;

1-(2,5-difluorophenyl)-cyclopropanecarboxylic acid ({[2-(5-ethanesulfonyl-2-methoxy-phenylamino)-pyrimidin-4-yl]-methyl-amino}-methyl-1H-benzoimidazol-2-yl)-amide;

(2,5-difluorophenyl)-N-({[2-(5-ethanesulfonyl-2-methoxy-phenylamino)-pyrimidin-4-yl]-methyl-amino}-methyl-1H-benzoimidazol-2-yl)-acetamide;

1-(3,4-dichlorophenyl)-cyclopropanecarboxylic acid ({[2-(5-ethanesulfonyl-2-methoxy-phenylamino)-pyrimidin-4-yl]-methyl-amino}-methyl-1H-benzoimidazol-2-yl)-amide;

3,4-dichlorophenyl-N-({[2-(5-ethanesulfoyl-2-methoxy-phenylamino)-pyrimidin-4-yl]-methyl-amino}-methyl-1H-benzoimidazol-2-yl)-acetamide;

1-(2,5-difluorophenyl)-cyclopropanecarboxylic acid (methyl-{methyl-[2-(4-methyl-3-sulfamoyl-phenylamino)-pyrimidin-4-yl]-amino}-1H-benzoimidazol-2-yl)-amide;

1-(3,4-dichlorophenyl)-cyclopropanecarboxylic acid (methyl-{methyl-[2-(4-methyl-3-sulfamoyl-phenylamino)-pyrimidin-4-yl]-amino}-1H-benzoimidazol-2-yl)-amide;

(3,4-dichlorophenyl)-N-(methyl-{methyl-[2-(4-methyl-3-sulfamoyl-phenylamino)-pyrimidin-4-yl]-amino}-1H-benzoimidazol-2-yl)-acetamide;

2-(2,3-dimethoxyphenyl)-N-(5-{[2-(4-methanesulfonyl-methyl-phenylamino)-pyrimidin-4-yl]-methyl-amino}-1-methyl-1H-benzoimidazol-2-yl)-acetamide;

2-(2-methoxyphenyl)-N-(5-{[2-(4-methanesulfonylm-ethyl-phenylamino)-pyrimidin-4-yl]-methyl-amino}-1-methyl-1H-benzoimidazol-2-yl)-acetamide;

2-(3-methoxyphenyl)-N-(5-{[2-(4-methanesulfonylm-ethyl-phenylamino)-pyrimidin-4-yl]-methyl-amino}-1-methyl-1H-benzoimidazol-2-yl)-acetamide;

2-(3-methoxyphenyl)-N-(5-{[2-(4-methanesulfonylm-ethyl-phenylamino)-pyrimidin-4-yl]-methyl-amino}-1-methyl-1H-benzoimidazol-2-yl)-acetamide;

2-(2-fluorophenyl)-N-({[2-(4-methanesulfonylmethyl-phenylamino)-pyrimidin-4-yl]-methyl-amino}-methyl-1H-benzoimidazol-2-yl)-acetamide;

2-(3-fluorophenyl)-N-({[2-(4-methanesulfonylmethyl-phenylamino)-pyrimidin-4-yl]-methyl-amino}-methyl-1H-benzoimidazol-2-yl)-acetamide;

(2,5-difluorophenyl)-N-({[2-(4-methanesulfonylmethyl-phenylamino)-pyrimidin-4-yl]-methyl-amino}-methyl-1H-benzoimidazol-2-yl)-acetamide;

(2,3-difluorophenyl)-N-({[2-(4-methanesulfonylmethyl-phenylamino)-pyrimidin-4-yl]-methyl-amino}-methyl-1H-benzoimidazol-2-yl)-acetamide;

2-(3,4-dimethoxyphenyl)-N-(5-{[2-(4-methanesulfonyl-methyl-phenylamino)-pyrimidin-4-yl]-methyl-amino}-1-methyl-1H-benzoimidazol-2-yl)-acetamide;

(2,5-difluorophenyl)-N-(methyl-{methyl-[2-(4-methyl-3-sulfamoyl-phenylamino)-pyrimidin-4-yl]-amino}-1H-benzoimidazol-2-yl)-acetamide;

1-(3,4-dichloro-phenyl)-cyclopropanecarboxylic acid ({[2-(3-methanesulfonylmethyl-phenylamino)-pyrimidin-4-yl]-methyl-amino}-methyl-1H-benzoimidazol-2-yl)-amide;

2-(2-chlorophenyl)-N-({[2-(4-methanesulfonylmethyl-phenylamino)-pyrimidin-4-yl]-methyl-amino}-methyl-1H-benzoimidazol-2-yl)-acetamide;

2-(3-chlorophenyl)-N-({[2-(4-methanesulfonylmethyl-phenylamino)-pyrimidin-4-yl]-methyl-amino}-methyl-1H-benzoimidazol-2-yl)-acetamide;

2-(4-chlorophenyl)-N-({[2-(4-methanesulfonylmethyl-phenylamino)-pyrimidin-4-yl]-methyl-amino}-methyl-1H-benzoimidazol-2-yl)-acetamide;

2-(3,5-dimethoxyphenyl)-N-(5-{[2-(4-methanesulfonyl-methyl-phenylamino)-pyrimidin-4-yl]-methyl-amino}-1-methyl-1H-benzoimidazol-2-yl)-acetamide;

2-(2,5-dimethoxyphenyl)-N-(5-{[2-(4-methanesulfonyl-methyl-phenylamino)-pyrimidin-4-yl]-methyl-amino}-1-methyl-1H-benzoimidazol-2-yl)-acetamide;

(2,5-dichlorophenyl)-N-({[2-(4-methanesulfonylmethyl-phenylamino)-pyrimidin-4-yl]-methyl-amino}-methyl-1H-benzoimidazol-2-yl)-acetamide;

N-({[2-(4-methanesulfonylmethyl-phenylamino)-pyrimidin-4-yl]-methyl-amino}-methyl-1H-benzoimidazol-2-yl)-methyl-C-phenyl-butyramide;

(3,5-dimethylphenyl)-N-({[2-(4-methanesulfonylmethyl-phenylamino)-pyrimidin-4-yl]-methyl-amino}-methyl-1H-benzoimidazol-2-yl)-acetamide;

N-({[2-(4-methanesulfonylmethyl-phenylamino)-pyrimidin-4-yl]-methyl-amino}-methyl-1H-benzoimidazol-2-yl)-phenyl-isobutyramide; and benzo[1,3]dioxol-5-yl-N-({[2-(4-methanesulfonylm-ethyl-phenylamino)-pyrimidin-4-yl]-methyl-amino}-methyl-1H-benzoimidazol-2-yl)-acetamide;

or a salt thereof.

31. A pharmaceutical composition, comprising: a therapeutically effective amount of a compound as claimed claim 1, or a salt thereof and one or more of pharmaceutically acceptable carriers, diluents and excipients.

32. The pharmaceutical composition of claim 31, further comprising at least one additional anti-neoplastic agent.

33. The pharmaceutical composition of claim 31, further comprising an additional agent which inhibits angiogenesis.

* * * * *